(12) United States Patent
Takayama

(10) Patent No.: US 7,204,139 B2
(45) Date of Patent: Apr. 17, 2007

(54) ANALYTICAL CHIP, ANALYTICAL-CHIP UNIT, AND ANALYSIS APPARATUS

(75) Inventor: Hidehito Takayama, Kanagawa (JP)

(73) Assignee: Mitsubishi Chemical Corporation, Tokyo (JP)

(*) Notice: Subject to any disclaimer, the term of this patent is extended or adjusted under 35 U.S.C. 154(b) by 80 days.

(21) Appl. No.: 11/034,458

(22) Filed: Jan. 12, 2005

(65) Prior Publication Data

US 2005/0229696 A1 Oct. 20, 2005

Related U.S. Application Data

(63) Continuation of application No. PCT/JP03/08851, filed on Jul. 11, 2003.

(30) Foreign Application Priority Data

Jul. 12, 2002 (JP) .............................. 2002-204677

(51) Int. Cl.
*G01F 1/68* (2006.01)
(52) U.S. Cl. .................................. 73/204.26
(58) Field of Classification Search ................. 438/10; 425/116, 542; 435/6; 73/204.22, 204.26
See application file for complete search history.

(56) References Cited

U.S. PATENT DOCUMENTS

| 6,117,643 | A | 9/2000 | Simpson et al. | |
|---|---|---|---|---|
| 6,192,168 | B1 | 2/2001 | Feldstein et al. | |
| 6,511,857 | B1* | 1/2003 | Kono et al. | 438/10 |
| 2002/0115225 | A1 | 8/2002 | Wagner et al. | |
| 2004/0071805 | A1* | 4/2004 | Boyaud et al. | 425/116 |
| 2004/0121356 | A1 | 6/2004 | Yamagata et al. | |
| 2004/0146874 | A1* | 7/2004 | Inami et al. | 435/6 |

FOREIGN PATENT DOCUMENTS

| JP | 7-506430 | 7/1995 |
|---|---|---|
| JP | 10-221249 | 8/1998 |
| JP | 2001-252897 | 9/2001 |
| JP | 2001-524667 | 12/2001 |
| JP | 2002-31638 | 1/2002 |
| JP | 2002/122597 | 4/2002 |
| JP | 2002-520621 | 7/2002 |
| WO | WO 00/04390 | 1/2000 |
| WO | WO 00/62105 | 10/2000 |
| WO | WO 01/02093 | 1/2001 |
| WO | WO 01/13096 | 2/2001 |
| WO | WO 02/065138 | 8/2002 |

OTHER PUBLICATIONS

Hye Jin Lee, et al. SPR Imaging Measurements of 1-d and 2-d DNA Microarrays Created from Microfluidic Channels on Gold Thin Films. Analytical Chemistry, vol. 73, No. 22, Nov. 15, 2001.

* cited by examiner

*Primary Examiner*—Jewel Thompson
(74) *Attorney, Agent, or Firm*—Katten Muchin Rosenman LLP

(57) ABSTRACT

An analytical chip is provided with a flow channel (5), whose section is in a closed shape and through which a fluid sample (Fs) is made to flow, for carrying out analysis regarding the fluid sample (Fs) based on interaction between a predetermined substance and a specific substance (61), which is placed facing said flow channel (5). The chip further has a projection member (9b) attached to said flow channel (5). With this arrangement, it becomes possible to analyze the fluid sample (Fs) efficiently with high precision.

34 Claims, 67 Drawing Sheets

FLOW DIRECTION →

F I G. 15 (a)
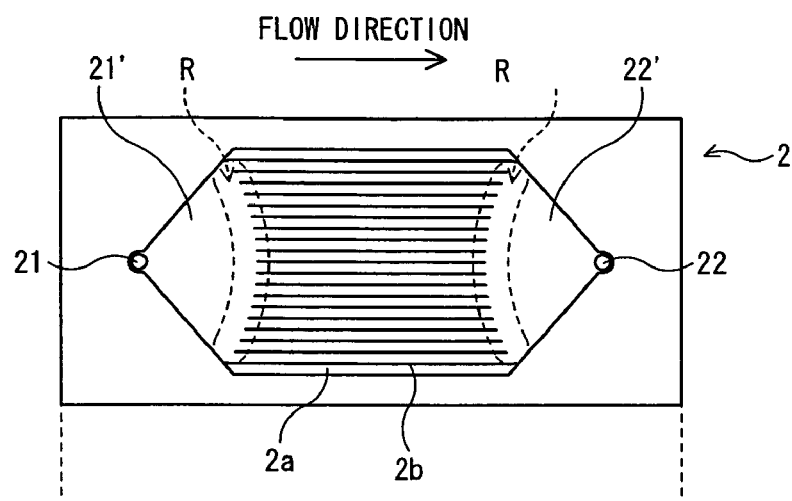
F I G. 15 (b)
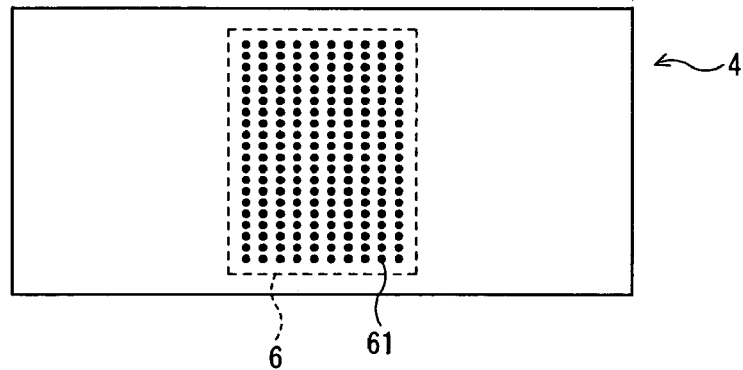

FLOW DIRECTION →

FLOW DIRECTION →

F I G. 5 1 (a)
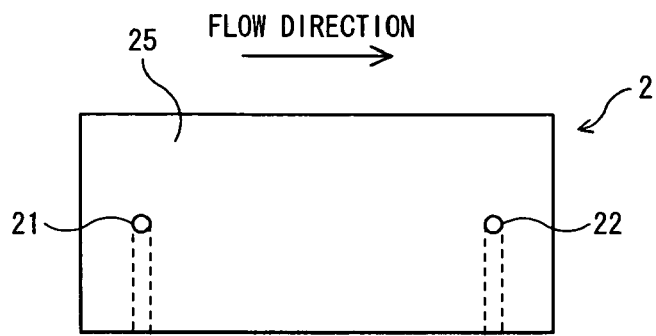
F I G. 5 1 (b)
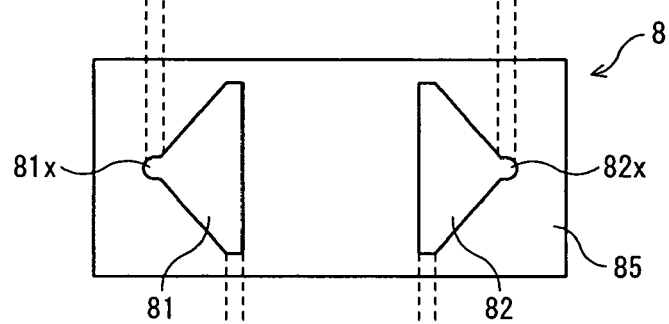
F I G. 5 1 (c)
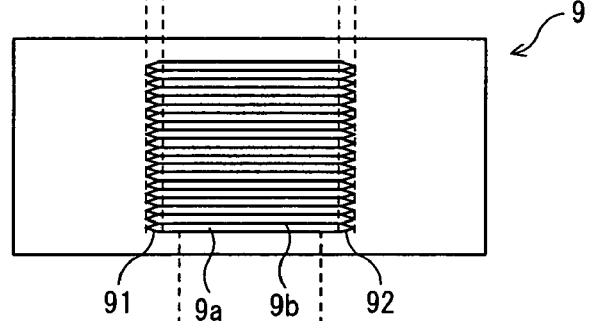
F I G. 5 1 (d)
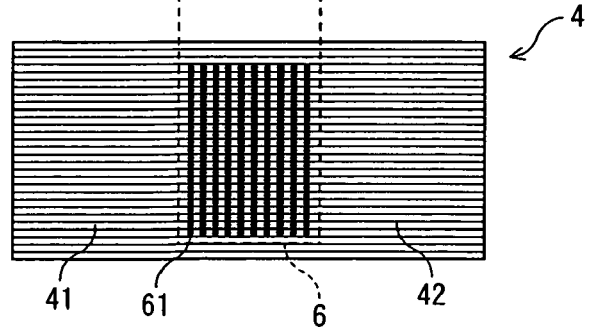

F I G. 53 (a)
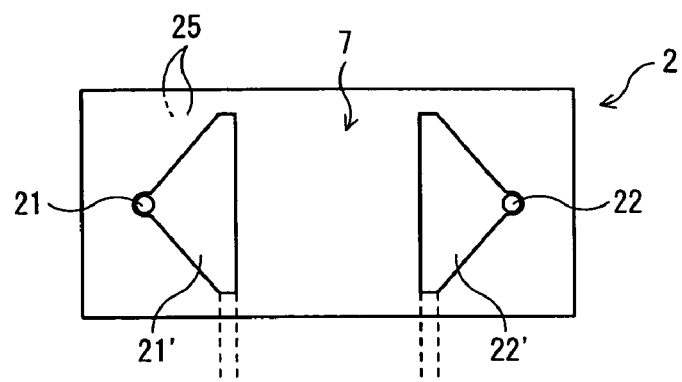
F I G. 53 (b)
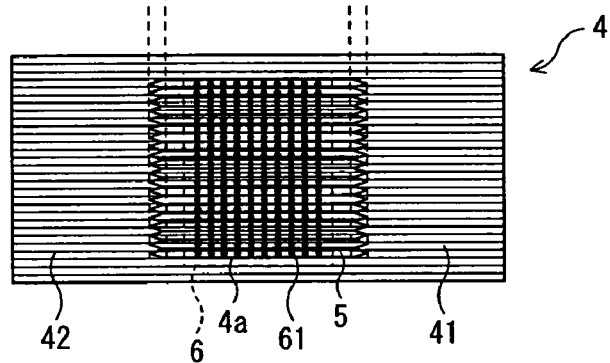

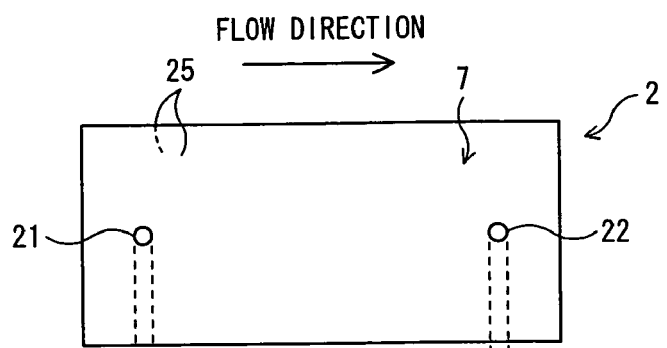
F I G. 5 4 (a)
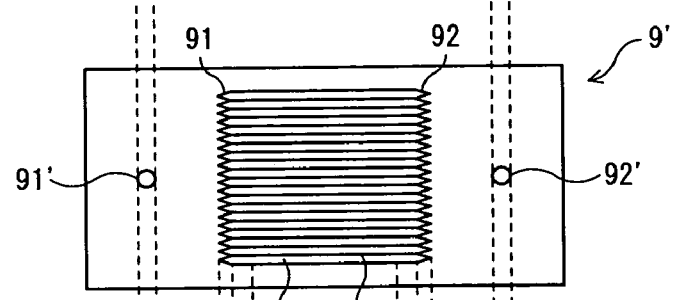
F I G. 5 4 (b)
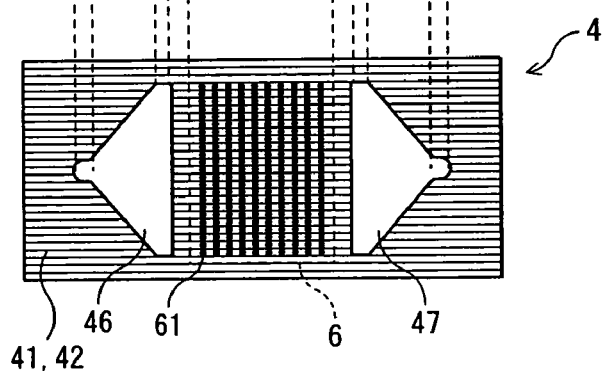
F I G. 5 4 (c)

F I G. 6 6 (a)
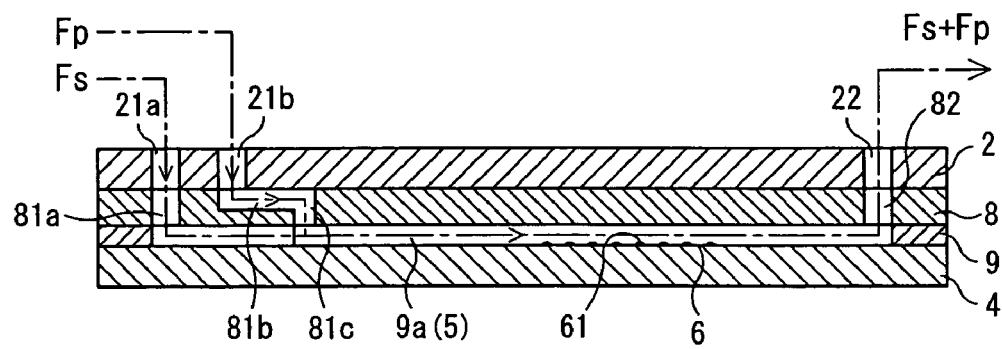
F I G. 6 6 (b)
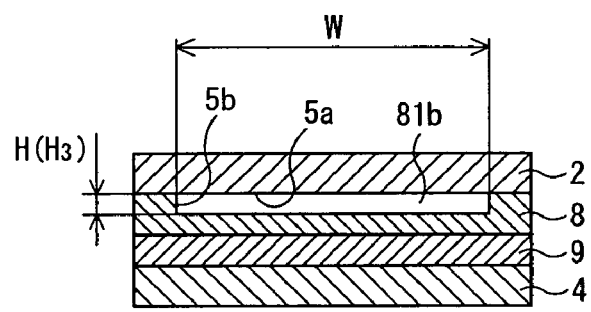
F I G. 6 6 (c)
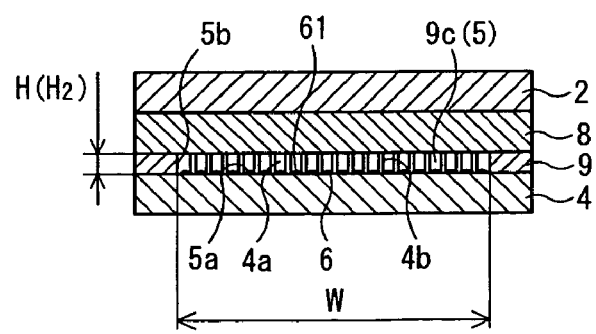

F I G. 70 (a)
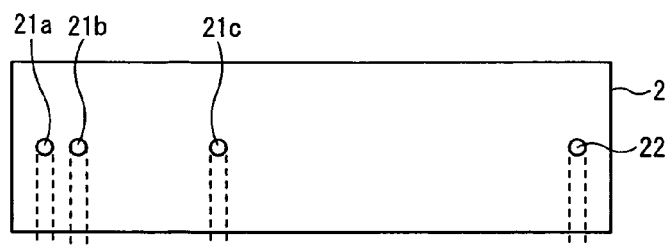
F I G. 70 (b)
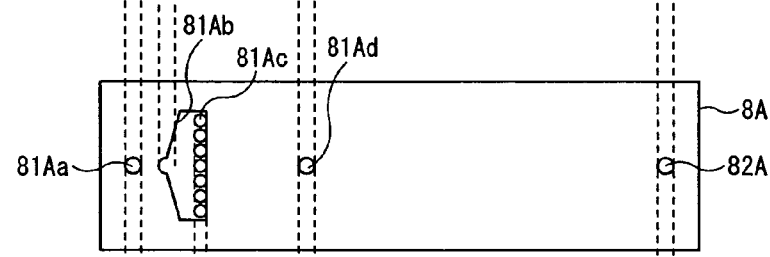
F I G. 70 (c)
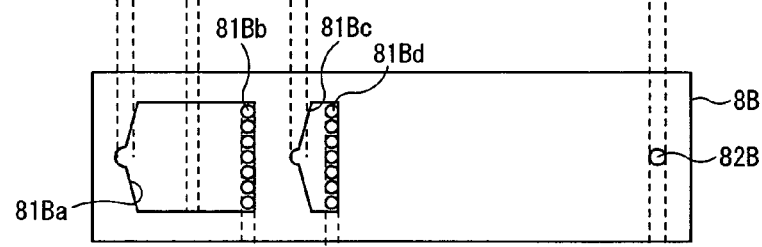
F I G. 70 (d)
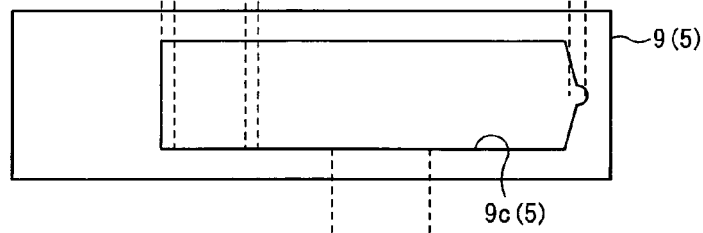
F I G. 70 (e)
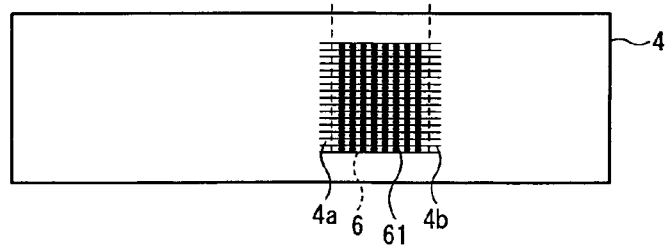

F I G. 74 (a)
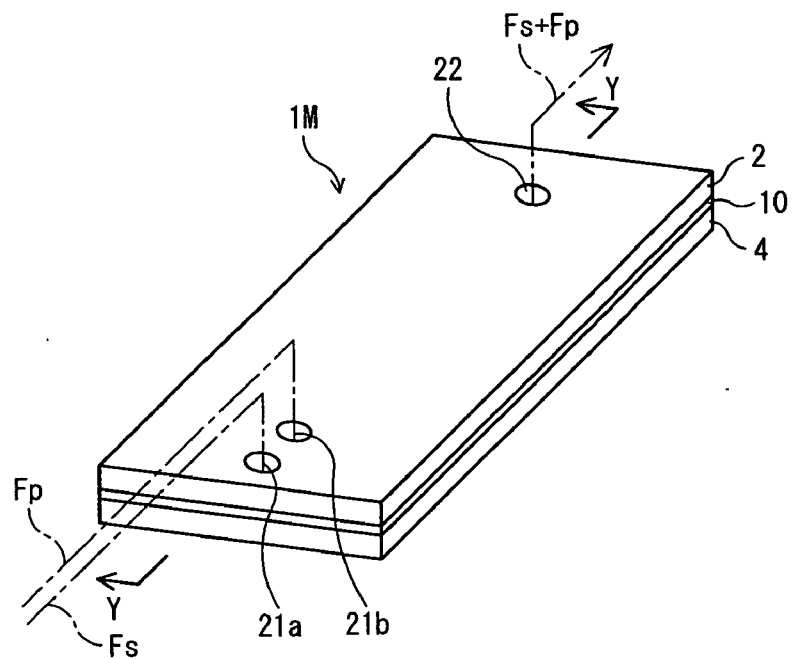
F I G. 74 (b)
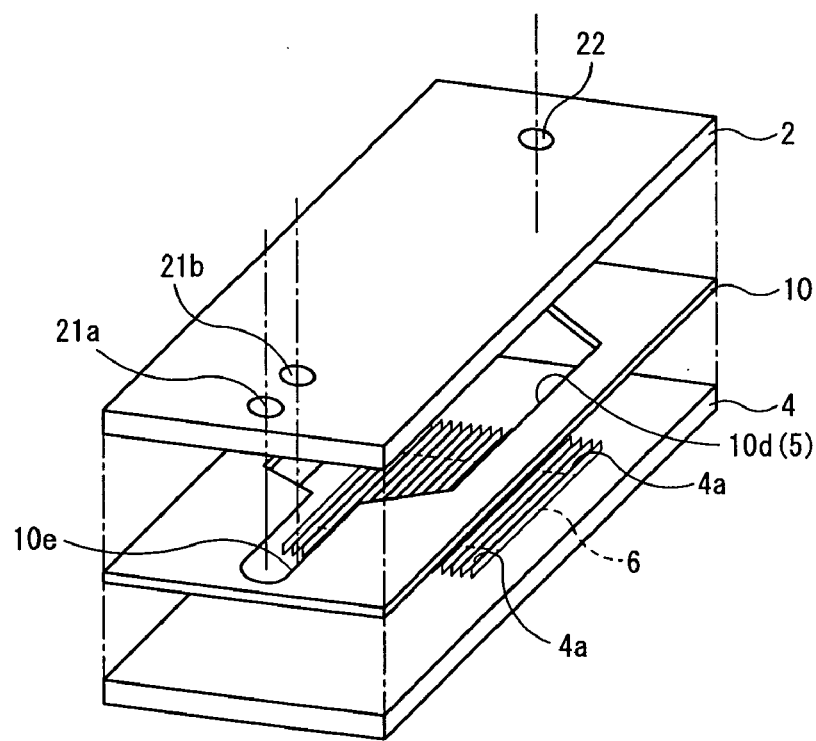

FIG. 75
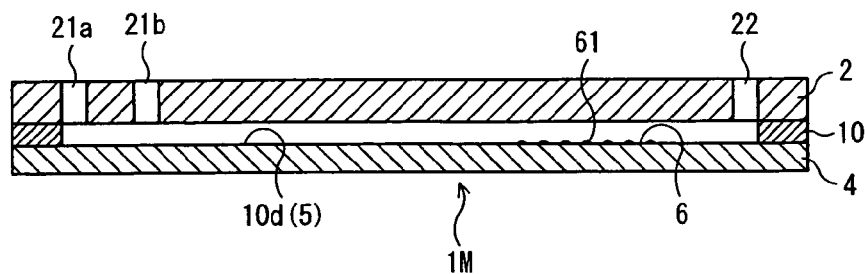
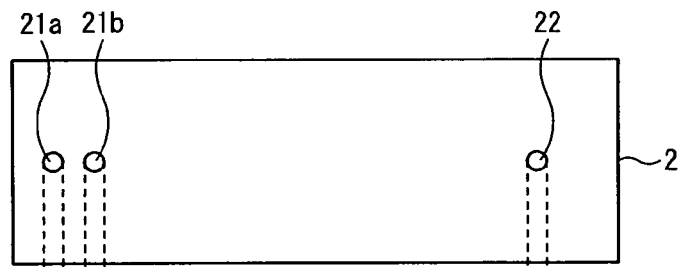
FIG. 76 (a)
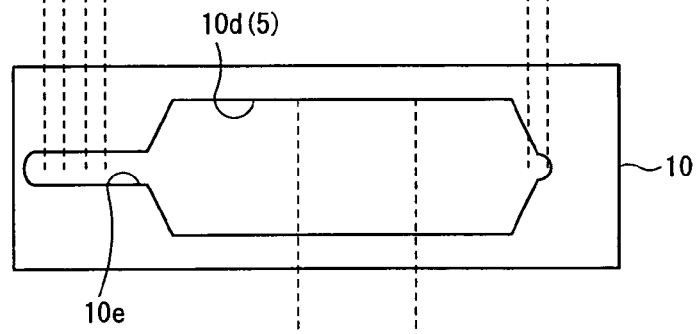
FIG. 76 (b)
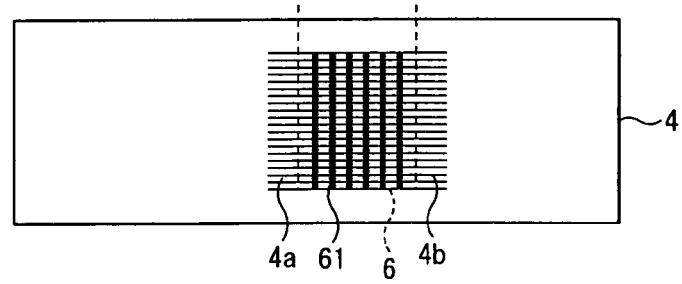
FIG. 76 (c)

ANALYTICAL CHIP, ANALYTICAL-CHIP UNIT, AND ANALYSIS APPARATUS

CROSS-REFERENCE TO RELATED APPLICATION

This application is a continuation of International Application PCT/JP2003/08851 filed on Jul. 11, 2003, now pending and claims priority from Japanese Patent Application 2002-204677 filed on Jul. 12, 2002, the contents of which are herein wholly incorporated by reference.

TECHNICAL FIELD

The present invention relates to a chip provided with a flow channel, through which a fluid sample is made to flow, and used for analyzing the fluid sample, and also relates to a chip unit, an analysis apparatus and method using the chip, and a method of making the chip.

BACKGROUND ART

Various techniques have been proposed until now for detecting the reaction or binding between a fluid sample and a substance fixed to a chip and for carrying out different kinds of analyses rapidly within a limited time, and some of those have been already put into practical use as high throughput analysis systems.

Among those techniques, attention has been given in recent years especially to the flow-through type analytical chips (microchannel chips) such as DNA chip and protein chip.

Some microchannel chips belong to the type that has a flow channel with a minute cross section formed on a chip body. The substance (specific substance) causing interaction with a predetermined chemical substance is fixed to the wall surfaces defining the flow channel. The fluid sample is made flow through the flow channel to pass along the specific substance on the wall surfaces, or to remain at the specific substance for a while, so that the fluid sample touches the specific substance. If a predetermined chemical substance (target substance for measurement) is included in the fluid sample, it is detectable based on its interaction with the specific substance.

There are known several techniques for fixing a specific substance to a chip such as a DNA chip or a protein chip with high density. One example is the technique of spotting, wherein a target substance to be fixed (specific substance) is held at the tip of a pin in advance and then spotted to a chip by a spotter (e.g. Affymetrix47$^R$ Arrayer). Another example is the technique of spraying, wherein a target substance to be fixed is sprayed on a chip by an ink jet or a dispenser (e.g. Tango$^R$ Liquid Handling System).

Besides, combining such a microchannel chip with an SPR (surface plasmon resonance) based analytical method (e.g. Biacore$^R$), it becomes possible to detect online the process of binding and dissociation between the target substance for measurement and the specific substance.

In the meantime, there are cases where analysis with a microchannel chip must be carried out using a fluid sample that is limited in amount. In analysis using a chip such as a DNA chip or a protein chip, a fluid sample can be taken from all kinds of products (DNA, RNA, PNA, peptide, protein, etc.), including both natural products extracted from diverse creatures and various biochemically synthetic products. Some of these products can be extracted or synthesized only in a restricted amount, or require a great deal of labor for extraction or synthesis. It is therefore strongly desired to reduce the amount of a sample used for analysis to a minimum.

On using an analytical chip as mentioned above, e.g. a DNA chip or a protein chip, a number of specific substances in general are placed on a plane along the bottom face of the flow channel, and then the fluid sample is made flow through the flow channel so that the fluid sample comes into contact with the specific substances. In order to achieve efficient analysis using such an analytical chip, it is necessary to fix a large number of specific substances to a single analytical chip. Accordingly, a reaction area (area in which the specific substances are to be fixed) is not localized in a small area but occupies a relatively large area.

For this reason, the flow channel generally has a large area of bottom face so that a large number of specific substances can be fixed thereon. In contrast, the fluid sample diffuse in the flow channel with the passage of time as the distribution of concentration becomes uniform. Part of the fluid sample failing to touch the specific substances at first can thus come into touch with the specific substances later at some point in time. It may take a long time, however, until the whole fluid sample has come into contact with the specific substances. For this reason, the flow channel generally has a little height (or depth) in order to efficiently make the whole fluid sample flowing through the flow channel come into touch with the specific substances fixed to the bottom face of the flow channel, that is, in order to reduce the volume of fluid sample that does not touch the specific substances fixed to the bottom face of the flow channel. Consequently, the flow channel of such an analytical chip has a quite high value of size ratio [(long-side size)/(short-side size)], namely, ratio of the width to the height of the flow channel. Hence the flow channel is generally in a sheet-like shape, whose size along its width directions is large while whose size along its height direction is small. The flow channel made in a sheet-like shape as mentioned-above allows that even a sample fluid in a small amount fully comes into contact with a large number of specific substances while flowing once. As a result, it improves the throughput of analysis and thereby enables to carry out analysis efficiently.

Regarding analytical chips of the flow-through type as mentioned above, a number of techniques have been proposed in recent years. Anal. Chem. 73, 22, pp. 5525, 2001 (hereinafter called nonpatent document 1), for example, discloses a chip having a basal plate and a sheet member on which plural slits are formed in parallel. According to the technique, the sheet member is set on the basal plate so that the slits arranged in parallel serve as parallel flow channels on the basal plate.

Next, different kinds of fluid materials are made to flow through the parallel flow channels, respectively, to fix these materials to the bottom face (namely, the basal plate) in their respective flow channels. And then the sheet member is set again on the basal plate with altering its orientation in such a manner that the parallel flow channels newly formed on the basal plate and the previous parallel flow channels cross each other. Other different kinds of fluid materials are again made to flow through the new flow channels, respectively, to make these materials come into touch with each of the materials previously fixed to the basal plate. Put another way, the technique is intended to form on a single chip a binding area in the form of a matrix, based on the combinations of a number of fluid materials, in order to realize the densification (tighter packaging) of analysis points.

Besides, International Publication No. WO 00/04390 (hereinafter called patent document 1) discloses a chip for analyzing different fluid samples simultaneously using a single microreactor chip, by arranging plural flow channels in parallel on the chip and making plural fluid samples flow through the plural channels, respectively.

As mentioned above, several techniques have been suggested for making modifications to the arrangement of a conventional analytical chip to reduce the amount of fluid sample required for analysis and to realize analysis with high efficiency. Nevertheless, there still remains a large demand for a technique to carry out analysis more efficiently.

From another viewpoint, improving the precision of analysis leads to reducing the necessary number of times that analysis is carried out, which enables to reduce the necessary amount of fluid sample and to carry out analysis efficiently. It is therefore desired strongly to provide an analytical chip that enables to improve the precision of analysis.

The present invention has been made in view of the problems mentioned above. An object of the present invention is to provide an analytical chip, an analytical-chip unit, an analysis apparatus, an analysis method, and a method of making an analytical chip that enable to carry out analysis regarding a fluid sample efficiently with high precision.

DISCLOSURE OF THE INVENTION

According to an aspect of the present invention, there is provided an analytical chip comprising: a flow channel, whose section is in a closed shape and through which a fluid sample is made to flow, for carrying out analysis regarding the fluid sample based on interaction between a predetermined substance and a specific substance, which is fixed facing said flow channel; and a projection member attached to said flow channel As a preferred feature, said flow channel is formed as a sheet-shaped space.

As a still preferred feature, an injection port connected to the upstream end of said flow channel, through which port the fluid sample is to be injected; and a drain port connected to the downstream end of said flow channel, through which port the fluid sample is to be drained.

In a preferred variant of the above analytical chip, said projection member is in the form of one or more partition members dividing said flow channel across the width directions, and said flow channel has two or more inner flow channels divided by said one or more partition members.

It is advantageous that the analytical chip further comprises: a basal plate; a cover member; and at least one intermediate plate being interposed between said basal plate and said cover member and, together with at least either of said basal plate and said cover member, defining a sheet-shaped space that has said flow channel.

As a preferred feature, one or more inner openings are formed through said intermediate plate, and said cover member is overlaid on said basal plate with said intermediate plate between in such a manner that the inner openings for said inner flow channels.

As a still preferred feature, the surface of said intermediate plate on the side opposite to said basal plate is made from a material having a lower affinity for a fluid containing the specific substance than that of at least either of the wall surface of the inner openings in said intermediate plate and the surface of said basal plate on the side facing said flow channel. Using the analytical chip, it becomes possible to easily make an analytical chip with a fixed specific substance according to a method comprising the steps of: fixing the intermediate plate on the basal plate; topping a fluid containing the specific substance on the basal plate through the inner openings of the intermediate plate to thereby fix the specific substance on the basal plate as spots; and fixing the cover member on the intermediate plate.

It is also advantageous that the analytical chip further comprises: a basal plate; and a cover member being disposed so as to face said basal plate and, together with said basal plate, defining a sheet-shaped space that has said flow channel.

As a preferred feature, said cover member is overlaid on said basal plate, and said inner flow channels are formed on at least either of the confronting surfaces of said basal plate and said cover member.

In another preferred variant of the above analytical chip, each of said inner flow channels has a contraction part an the downstream end, in which pan each said inner flaw channel contracts gradually.

As a preferred feature, said inner flow channels extend from said injection port to said drain port.

As another preferred feature, said partition members are in the form of partition walls, said inner flow channels are slit-form flow channels divided from each other by said partition walls round a middle part of said flow channel along a flow direction, and said analytical chip further comprises a flow-channel confluence part disposed at each of the upstream and downstream ends of said flow channel along the flow direction, in which part the fluid sample flows unitedly.

As a further preferred feature, the flow-channel confluence part at the upstream end is formed in such a mariner as to become gradually broad from said injection port toward the middle part, and the flow-channel confluence part at the downstream end is formed in such a manner as to become gradually narrow from the middle part toward said drain port.

As a still further preferred feature, the flow-channel confluence part at each of the upstream and downstream ends is formed on either of said basal plate and said cover member As another preferred feature, each of said slit-form flow channels has a cross sectional area of 5 mm$^2$ or smaller.

As a further preferred feature, the cross section of each said slit-form flow channel has an aspect ratio of between 0.005 and 100.

As still another preferred feature, the specific substance is fixed as a plurality of spots, which are arranged with regular intervals, in such a manner as to face said inner flow channels.

In another preferred variant of the above analytical chip, said projection member is in the form of a prop member interposed between the confronting interior surfaces of said flow channel.

It is advantageous that the above analytical chip comprises: a basal plate; a cover member; and at least one intermediate plate being interposed between said basal plate and said cover member and, together wit at least either of said basal plate and said cover member, defining a sheet-shaped space that has said flow channel; wherein, in said flow channel of the sheet-shaped spare, said prop member is interposed between the confronting surfaces of said intermediate plate and at least either of said basal plate and said cover member.

It is also advantageous that the above analytical chip comprises: a basal plate; and a cover member being disposed so as to face said basal plate and, together with said basal plate, defining a sheet-shaped space that has said flow channel; wherein, in said flow channel of the sheet-shaped space, said prop member is interposed between the confronting surfaces of said basal plate and said cover member.

As a preferred feature, the sheet-shaped space is defined by the floor surface, the ceiling surface, the left-side surface, the right-side surface, the upstream-end surface, and the downstream-end surface of said flow channel, and said prop member is interposed at least either of between the left-side and right-side surfaces and between the upstream-end and downstream-end surfaces.

As a still preferred feature, said prop member adjoins directly each of the confronting surfaces.

As another preferred feature, a part of said prop member adjoins directly one of the confronting surfaces, and the opposite end of said prop member is joined by a fluid with the other of the confronting surfaces when the fluid is made to flow through said flow channel.

As a further preferred feature, an adhesion-reducing layer is formed on the surface of said prop member.

In a preferred variant of the above analytical chip, the specific substance is fixed to said flow channel.

In another preferred variant of the above analytical chip, said flow channel has a first affinity part and a second affinity part, whose affinity for the fluid sample is lower than that of the first affinity part.

As a preferred feature, the specific substance is fixed to a part of the surface of said flow channel, and both of the first affinity part and the second affinity part are disposed upstream, along the flow direction, of the part to which the specific substance is fixed.

As another preferred feature, each of the first affinity part and the second affinity part is in a belt shape that spreads along a line crossing the flow direction of said flow channel.

As another preferred feature, more than one first affinity part and more than one second affinity part are provided and arranged alternately.

As another preferred feature, the first affinity part is a hydrophilic part, and the second affinity part is a hydrophobic part.

As another preferred feature, the first affinity part is a rough-surfaced part, and the second affinity part is a smooth-surfaced part.

In a preferred variant of the above analytical chip, said flow channel has an area to which the specific substance is fixed, and said area has a diffraction grating that can generate an evanescent wave upon light irradiation, and a metal layer along which a surface plasmon wave can be induced.

As a preferred feature, the above analytical chip is made from a material having a Young's modulus that is not lower than 60 GPa and not higher than 1000GPa.

According to another aspect of the present invention, there is provided an analytical chip comprising: a flow channel, to which the specific substance is fixed and through which a fluid sample containing a predetermined substance is made to flow, for carrying out analysis regarding the fluid sample based on interaction between the predetermined substance in the fluid sample and the specific substance; an injection port through which the fluid sample is to be injected; and a drain port through which the fluid sample is to be drained; wherein said flow channel has a cross section whose aspect ratio is between 0.005 and 100 and whose area is 5 $mm^2$ or below, and more than one flow channel is disposed in parallel between said injection port and said drain port According to another aspect of the present invention, there is provided an analytical-chip unit comprising: a unit base having a plurality of sides; and a plurality of unit chips disposed on the sides of said unit base, respectively, each of said unit chips being the above analytical chip.

According to another aspect of the present invention, there is provided an analytical-chip unit comprising: a unit base; a plurality of unit chips disposed on said unit base, each of said unit chips being the above analytical chip; and a connection flow channel that connects two or more associated unit chips among said unit chips.

According to another aspect of the present invention, there is provided an analytical chip comprising: a flow channel, to which a specific substance is fixed and through which a fluid sample is made to flow, for carrying out analysis regarding the fluid sample based on interaction between a predetermined substance and the specific substance; an optically transparent part being incorporated as at least part of said analytical chip and allowing light to pass through between the exterior surface of said analytical chip and the surface of said analytical chip on the side of said flow channel; and a protective layer, formed on the surface of said optically transparent part, for protecting the surface of said optically transparent part while allowing light to pass through.

As a preferred feature, said protective layer is disposed to at least either of the exterior surface and the surface on the side of said flow channel.

It is advantageous that the above analytical chip comprises: a basal plate; a cover member; and at least one intermediate plate being interposed between said basal plate and said cover member and, together with at least either of said basal plate and said cover member, defining a sheet-shaped space that has said flow channel; wherein said optically transparent part is incorporated in each of said cover member and said intermediate plate.

It is also advantageous that the above analytical chip comprises: a basal plate; and a cover member being disposed so as to face said basal plate and, together with said basal plate, defining a sheet-shaped space that has said flow channel; wherein said optically transparent part is incorporated in said cover member.

In a preferred variant of the above analytical chip, said protective layer has an anti-reflection layer preventing the reflection of light.

As a preferred feature, said anti-reflection layer is a layer whose refractive index is different from that of said optically transparent part. It is also preferable that said anti-reflection layer has a plurality of layers whose refractive indexes are different from each other.

As a further preferred feature, said anti-reflection layer is a nonglare layer.

It is advantageous that said protective layer has an abrasion resistance layer.

As a preferred feature, said protective layer is composed of said anti-reflection layer, formed on the surface of said analytical chip, and said abrasion resistance layer, formed on the surface of said anti-reflection layer.

It is also advantageous tat said flow channel has an area to which the specific substance is fixed, and said area has a diffraction grating that can generate an evanescent wave upon light irradiation, and a metal layer along which a surface plasmon wave can be induced.

According to another aspect of the present invention, there is provided an analytical chip comprising: a flow channel, to which a specific substance is fixed and through which a fluid sample is made to flow, for carrying out analysis regarding the fluid sample based on interaction between a predetermined substance and the specific substance; and a plurality of injection ports, each of which is connected to an upstream portion of said flow channel and through each of which the fluid is to be injected into said flow channel. In the analytical chip, the fluid to be injected through the injection port into the flow channel is not limited to the fluid sample, but any kinds of fluid is usable according to the analysis using the analytical chip of the present invention.

It is advantageous that said injection ports include a group of injection ports that are arranged in a row along the width directions of said flow channel, and that said injection ports include a slotted hole continuously formed along the width directions of said flow channel.

As a preferred feature, at least part of the upstream portion of said flow channel has a width narrower than that of said flow channel.

As another preferred feature, the upstream portion is in the form of a chaotic mixer.

In a preferred variant of the above analytical chip, said flow channel has an area to which the specific substance is fixed, and said area has a diffraction grating that can generate an evanescent wave upon light irradiation, and a metal layer along which a surface plasmon wave can be induced.

According to another aspect of the present invention, there is provided an analysis method using the above analytical chip, comprising the steps of; assigning a plurality of fluid samples one to each of the plural injection ports; injecting each of the fluid samples to the upstream portion through the respective injection port so that the fluid samples are mixed in the upstream portion; and making the mixed fluid samples flow through the flow channel to carry out analysis.

According to another aspect of the present invention, there is provided an analysis apparatus comprising: either of the above analytical chip and the above analytical-chip unit; and an analysis section for analyzing the fluid sample.

As a preferred feature, said analysis section is operable to carry out analysis by an analytical method using at least one technique selected from the group consisting of surface plasmon resonance, chemiluminescence, bioluminescence, electrochemiluminescence, fluorescence, and radioactive isotope analyses.

In a preferred variant, the above analysis apparatus further comprises a separation section for separating the fluid sample by a physical and/or chemical action before introducing the fluid sample into either of said analytical chip and said analytical-chip unit.

In another preferred variant, the above analysis apparatus further comprises an after-analysis section for analyzing the fluid sample drained from at least either of said analytical chip and said analytical-chip unit.

According to the analytical chip, analytical-chip unit, analysis apparatus, and analysis method of the present invention, it becomes possible to analyze a fluid sample efficiently with high precision.

Also, according to the method of making an analytical chip of the present invention, the surface of the intermediate plate on the side opposite to the basal plate is made from a material having a lower affinity for a fluid containing the specific substance than that of at least either of the wall surface of the inner openings in the intermediate plate and the surface of the basal plate on the side facing the flow channel. After the intermediate plate is fixed on the basal plate, a fluid containing the specific substance is dropped on the basal plate through the inner openings of the intermediate plate to thereby fix the specific substance on the basal plate as spots, and than the cover member is fixed on the intermediate plate. Even when the fluid containing specific substance happen to be spilled over the partition walls of the intermediate plate, it spontaneously runs (namely, is guided) toward the basal plate along the wall surface of the inner openings in the intermediate plate and/or the surface of the basal plate on the side facing the flow channel, which is made from a material having a higher affinity for the fluid containing the specific substance than that of the surface of the intermediate plate on the side opposite to the basal plate. Namely, since the specific substance can thus be placed securely to target positions on the basal plate, it becomes possible to make an analytical chip with a fixed specific substance easily with high precision.

BRIEF DESCRIPTION OF THE DRAWINGS

FIG. 15(a) is a diagrammatic bottom view of a cover member of an analytical chip according to the first modification of the third embodiment of the present invention, and FIG. 15(b) is a diagrammatic top view of a basal plate of the analytical chip according to the first modification of the third embodiment of the present invention;

FIG. 51(a) is a diagrammatic top view of a cover member of an analytical chip according to the eleventh embodiment of the present invention, FIG. 51(b) is a diagrammatic bottom view of a first plate of an analytical chip according to the eleventh embodiment of the present invention, FIG. 51(c) is a diagrammatic top view of a second plate of an analytical chip according to the eleventh embodiment of the present invention, and FIG. 51(d) is a diagrammatic top view of a basal plate of an analytical chip according to the eleventh embodiment of the present invention;

FIG. 53(a) is a diagrammatic bottom view of a cover member according to the second modification of the eleventh embodiment of the present invention, and FIG. 53(b) is a diagrammatic top view of a basal plate according to the second modification of the eleventh embodiment of the present invention;

FIG. 54(a) is a diagrammatic top view of a cover member according to the third modification of the eleventh embodiment of the present invention, FIG. 54(b) is a diagrammatic top view of an intermediate plate according to the third modification of the eleventh embodiment of the present invention, and FIG. 54(c) is a diagrammatic top view of a basal plate according to the third modification of the eleventh embodiment of the present invention;

FIG. 66(a) is a diagrammatic sectional view taken on line Y—Y of FIG. 65(a), FIG. 66(b) is a diagrammatic sectional view taken on line X1—X1 of FIG. 65(a), and FIG. 66(c) is a diagrammatic sectional view taken on line X2—X2 of FIG. 65(a);

FIG. 70(a) is a diagrammatic top view of a cover member of an analytical chip according to the second modification of the thirteenth embodiment of the present invention, FIG. 70(b) is a diagrammatic top view of a plate of an analytical chip according to the second modification of the thirteenth embodiment of the present invention, FIG. 70(c) is a diagrammatic top view of a plate of an analytical chip according to the second modification of the thirteenth embodiment of the present invention, FIG. 70(d) is a diagrammatic top view of a plate of an analytical chip according to the second modification of the thirteenth embodiment of the present invention, and FIG. 70(e) is a diagrammatic top view of a basal plate of an analytical chip according to the second modification of the thirteenth embodiment of the present invention;

Figure 72:
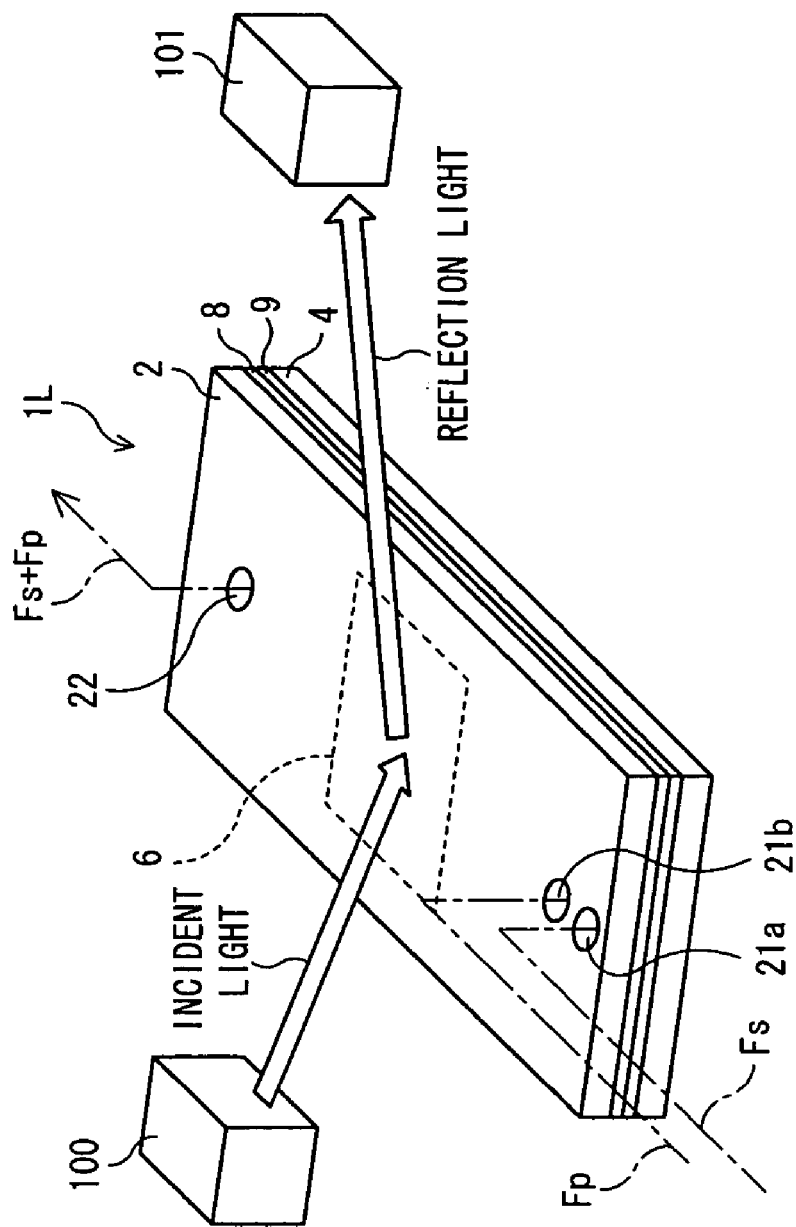
Figure 73:
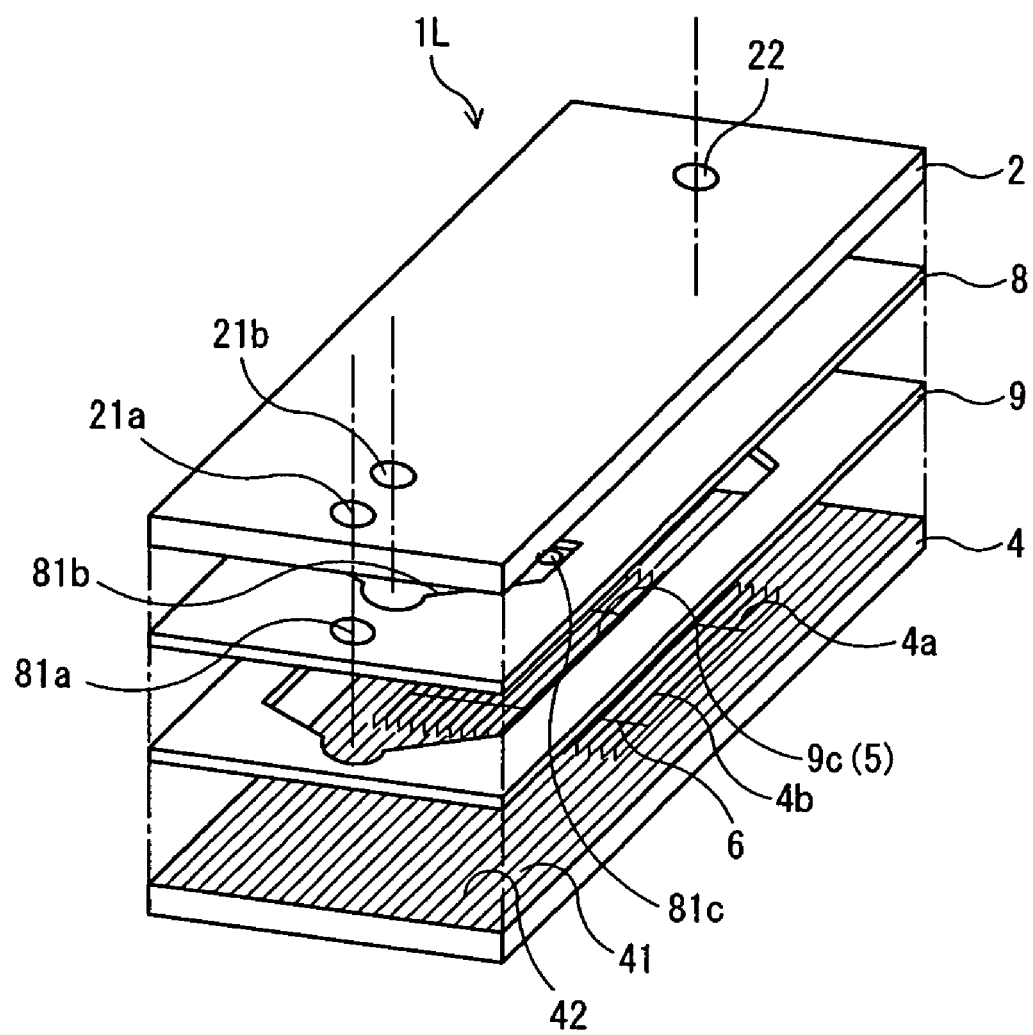
Figure 77:
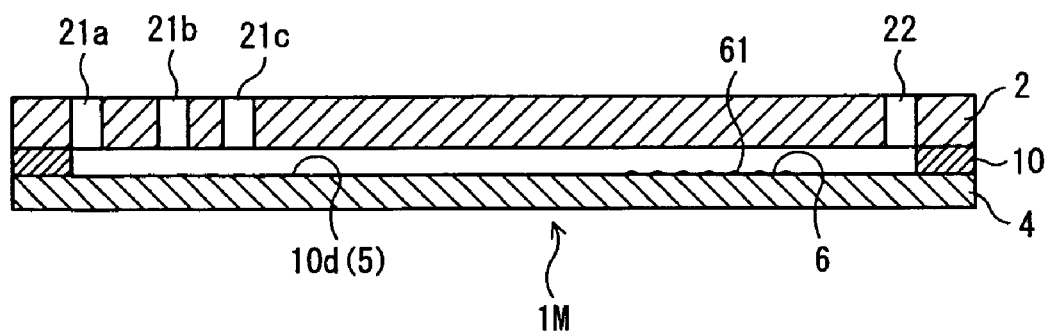
Figure 77:
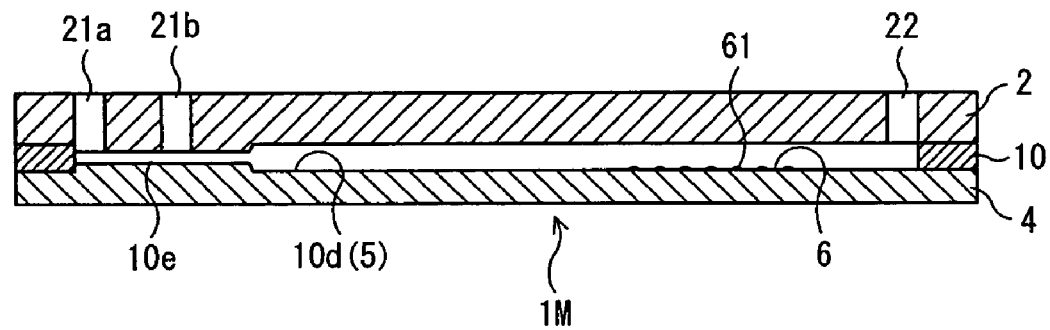
Figure 78:
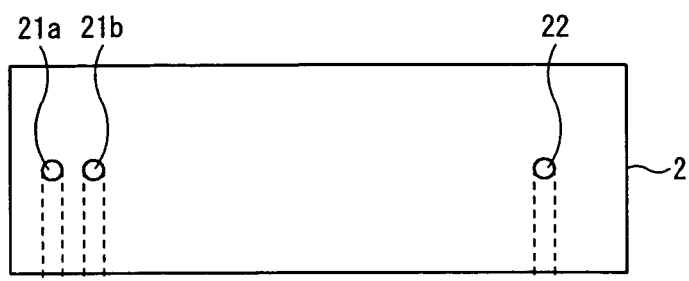
Figure 78:
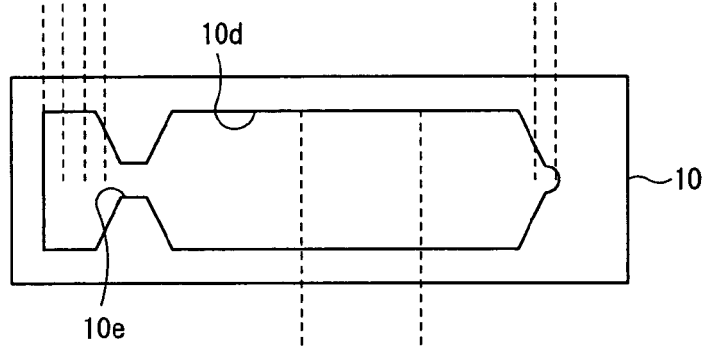
Figure 78:
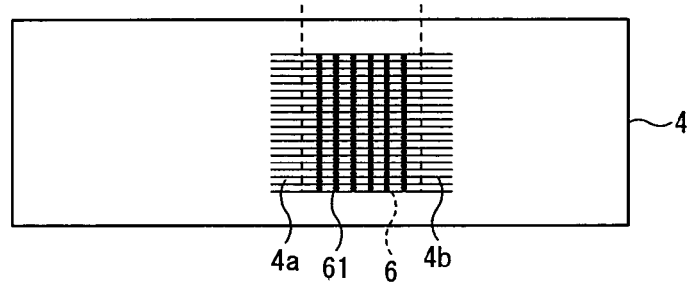
Figure 79:
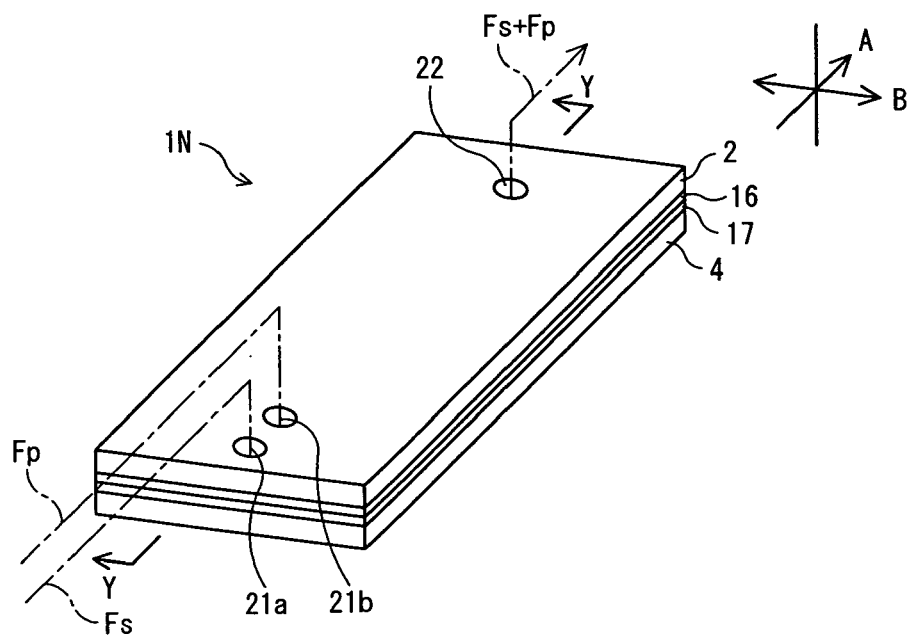
Figure 79:
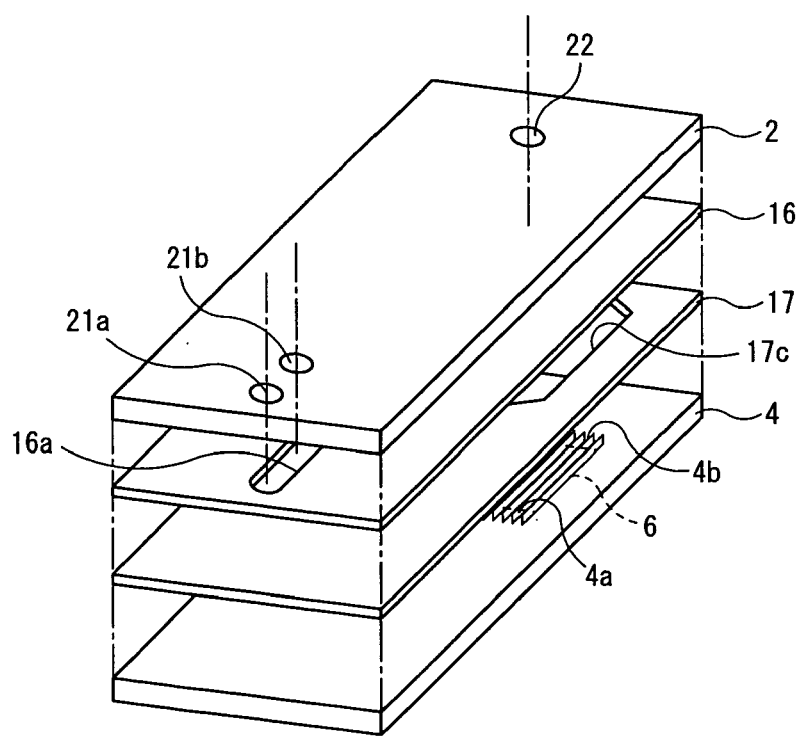
Figure 80:
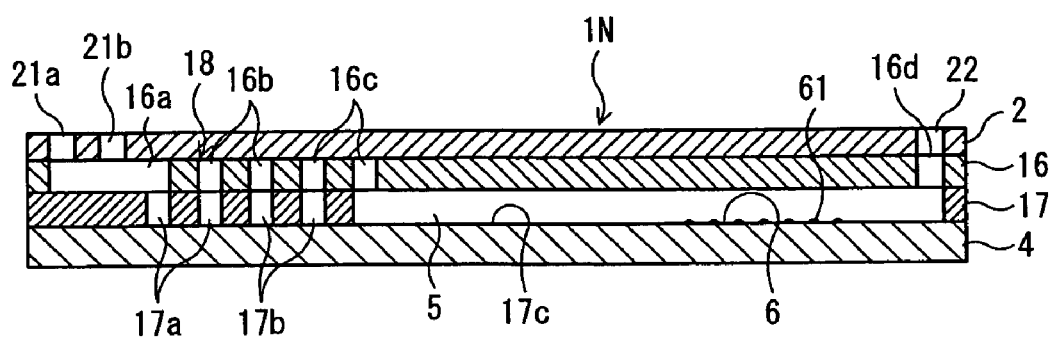
Figure 81:
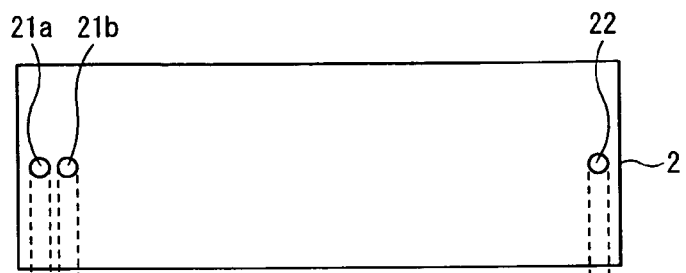
Figure 81:
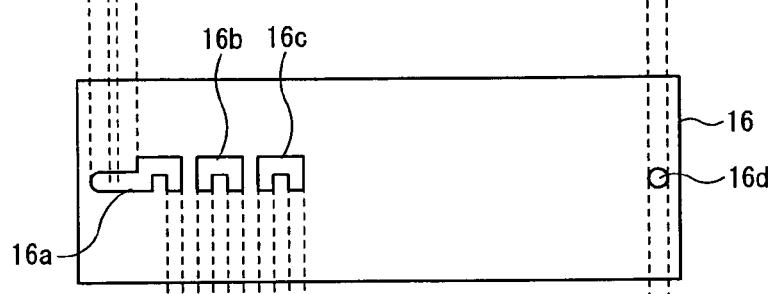
Figure 81:
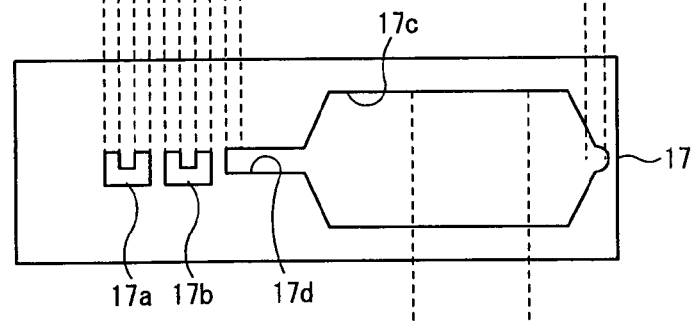
Figure 81:
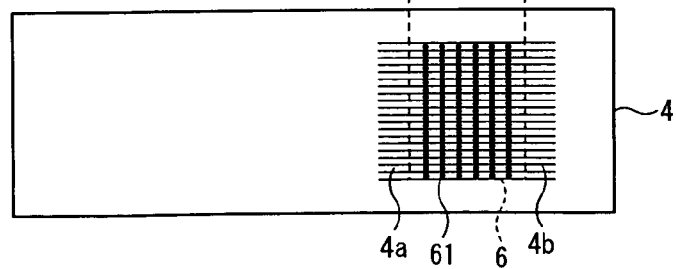
Figure 82:
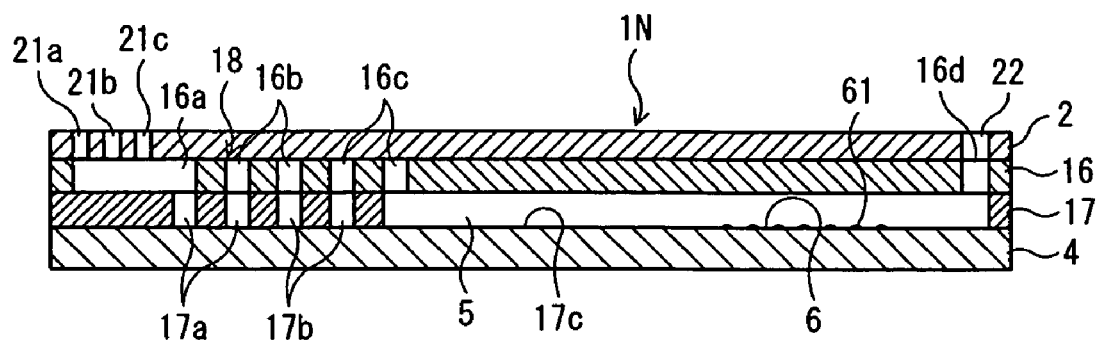
Figure 83:
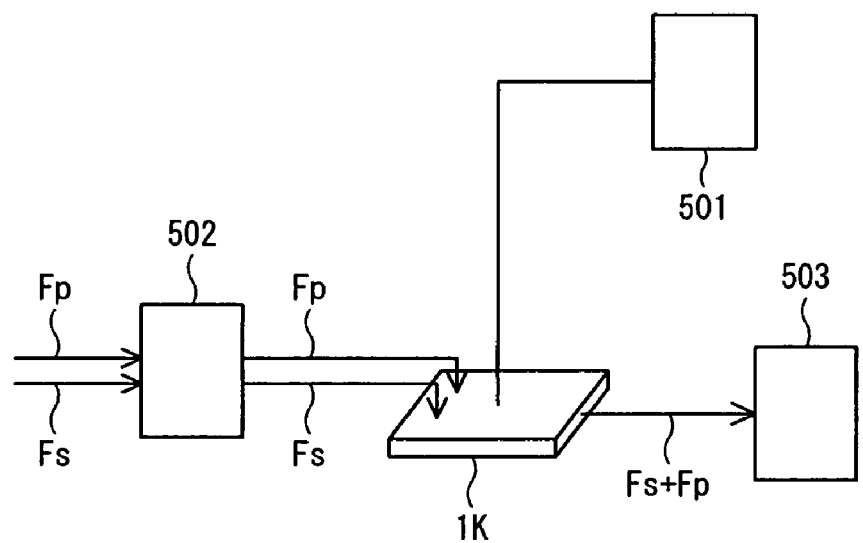
Figure 84:
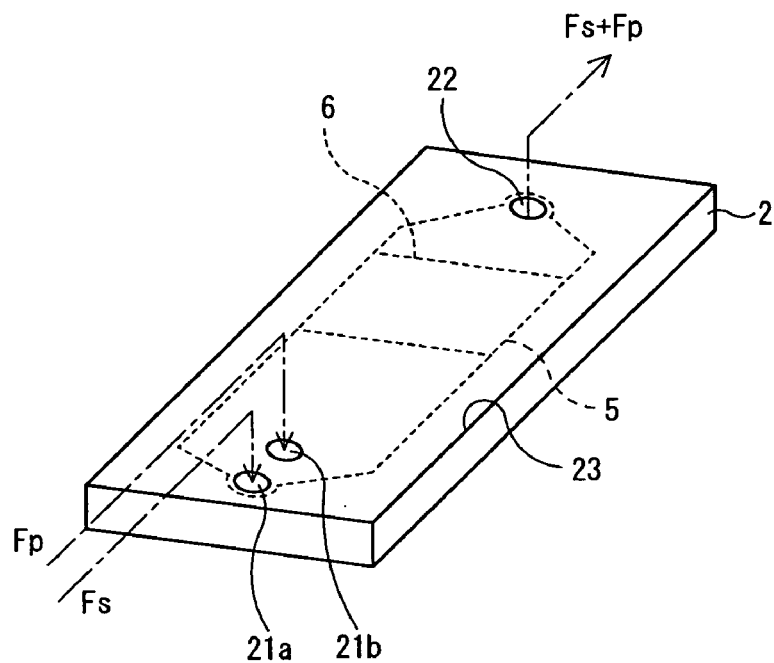
Figure 85:
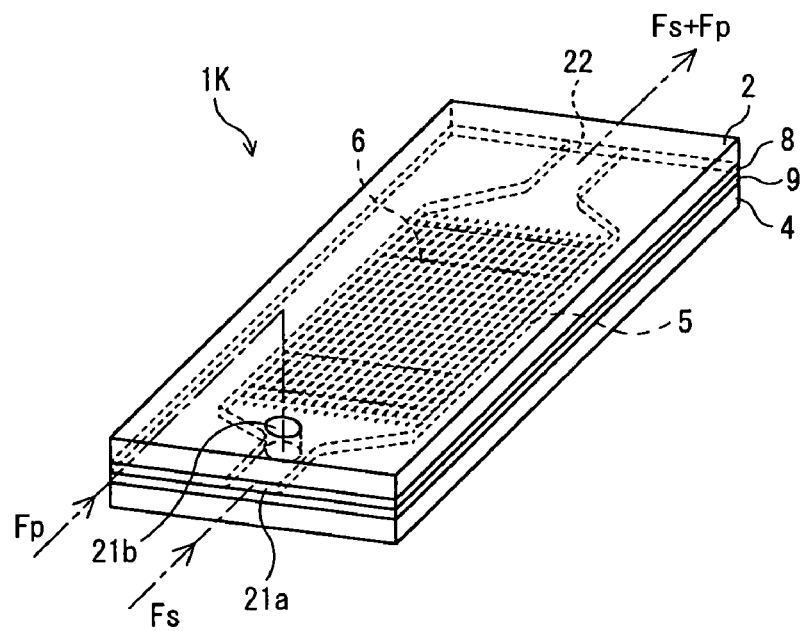
Figure 86:
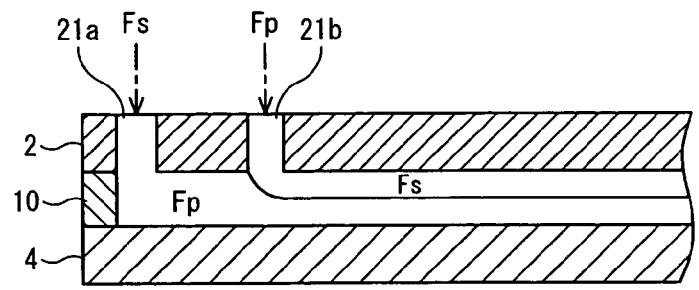
Figure 86:
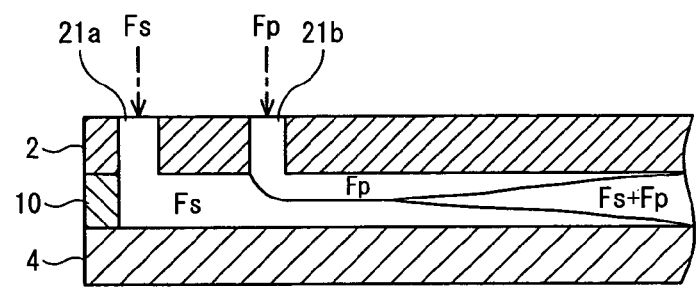
Figure 87:
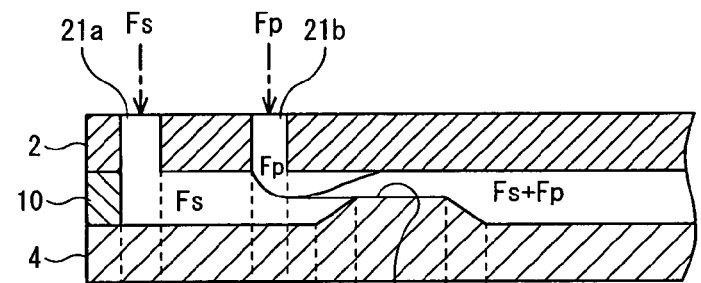
Figure 87:
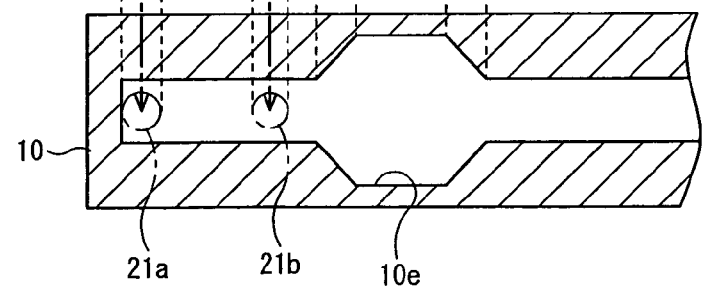
Figure 88A:
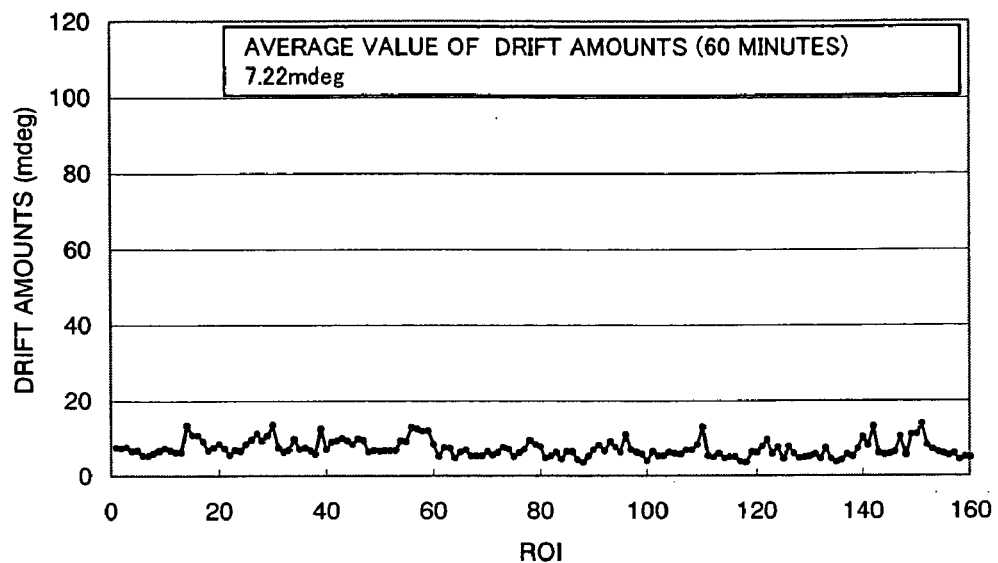
Figure 88B:
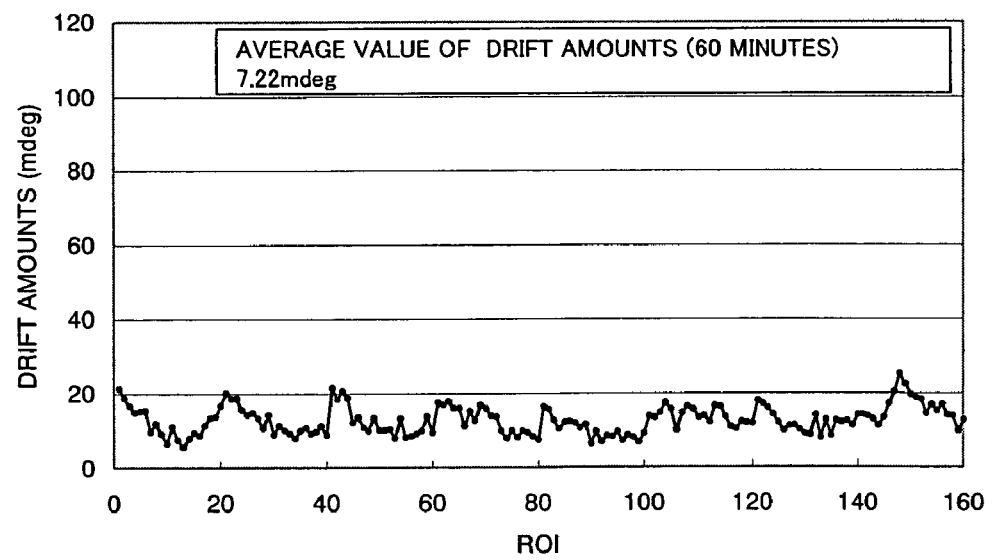

71(*b*) is a diagrammatic top view of a plate of an analytical chip according to the fourth modification of the thirteenth embodiment of the present invention;

FIG. 72 is a diagrammatic perspective view showing the whole constitution of an SPR sensor according to the fourteenth embodiment of the present invention;

FIG. 73 is a diagrammatic exploded perspective view showing the constitution of an analytical chip according to the fourteenth embodiment of the present invention;

FIG. 74(*a*) is a diagrammatic assembled perspective view of an analytical chip according to the fifteenth embodiment of the present invention, and FIG. 74(*b*) is a diagrammatic exploded perspective view of an analytical chip according to the fifteenth embodiment of the present invention;

FIG. 75 is a diagrammatic sectional view taken on line Y—Y of FIG. 74(*a*), illustrating an analytical chip according to the fifteenth embodiment of the present invention;

FIG. 76(*a*) is a diagrammatic top view of a cover member of an analytical chip according to the fifteenth embodiment of the present invention, FIG. 76(*b*) is a diagrammatic top view of a plate of an analytical chip according to the fifteenth embodiment of the present invention, and FIG. 76(*c*) is a diagrammatic top view of a basal plate of an analytical chip according to the fifteenth embodiment of the present invention;

FIG. 77(*a*) is a diagrammatic sectional view of an analytical chip according to the first modification of the fifteenth embodiment of the present invention, and FIG. 77(*b*) is a diagrammatic sectional view of an analytical chip according to the second modification of the third embodiment of the present invention;

FIG. 78(*a*) is a diagrammatic top view of a cover member of an analytical chip according to the third modification of the fifteenth embodiment of the present invention, FIG. 78(*b*) is a diagrammatic top view of a plate of an analytical chip according to the third modification of the fifteenth embodiment of the present invention, and FIG. 78(*c*) is a diagrammatic top view of a basal plate of an analytical chip according to the third modification of the fifteenth embodiment of the present invention;

FIG. 79(*a*) is a diagrammatic assembled perspective view of an analytical chip according to the sixteenth embodiment of the present invention, FIG. 79(*b*) is a diagrammatic exploded perspective view of an analytical chip according to the sixteenth embodiment of the present invention;

FIG. 80 is a diagrammatic sectional view taken on line Y—Y of FIG. 79(*a*), showing an analytical chip according to the sixteenth embodiment of the present invention;

FIG. 81(*a*) is a diagrammatic top view of a cover member of an analytical chip according to the sixteenth embodiment of the present invention, FIG. 81(*b*) is a diagrammatic top view of a plate of an analytical chip according to the sixteenth embodiment of the present invention, FIG. 81(*c*) is a diagrammatic top view of a plate of an analytical chip according to the sixteenth embodiment of the present invention, and FIG. 81(*d*) is a diagrammatic top view of a basal plate of an analytical chip according to the sixteenth embodiment of the present invention;

FIG. 82 is a diagrammatic sectional view of an analytical chip according to a modification of the sixteenth embodiment of the present invention;

FIG. 83 is a diagram of assistance in explaining an analysis apparatus according to the seventeenth embodiment of the present invention;

FIG. 84 is a diagram showing another embodiment of the present invention;

FIG. 85 is a diagram showing another embodiment of the present invention;

FIG. 86(*a*), FIG. 86(*b*) are sectional views of assistance in explaining the diffusion of fluid in the flow channel;

FIG. 87(*a*) is a sectional view of assistance in explaining the diffusion in the flow channel of a modification of the fifteenth embodiment of the present invention, and FIG. 87(*b*) is a sectional view of the flow channel shown from the side of the cover member; and FIG. 88(*a*) is a graph showing the results of an experimental embodiment of the present invention, and FIG. 88(*b*) is a graph showing the results using a conventional analytical chip.

BEST MODE FOR CARRYING OUT THE INVENTION

Preferred embodiments of the present invention will be described hereinafter with reference to the drawings. Throughout the following embodiments, description will be given on the assumption that a fluid sample being the target for analysis is water-soluble (or hydrophilic, provided that the solvent is water). It is a matter of course, however, that even if the fluid sample is hydrophobic, it can be analyzed using an analytical chip according the present invention in a similar manner. Further, the fluid sample of the present invention is to contain one or more substances that can cause any interaction such as antigen-antibody reaction, complementary DNA binding, receptor-ligand interaction, or enzyme-substrate interaction. Specifically, the sample is selectable from various liquids (and disperse systems, such as suspensions and colloids) that contain (or may contain) one or more target substances for measurement, for example, protein, nucleic acid, DNA, RNA, PNA, peptide, hormone, antigen, antibody, ligand, receptor, enzyme, substrate, low molecular organic compound, cell, ion, etc., and complex thereof. These target substances may be labeled, if necessary, with any other substance such as a fluorescence substance, a luminescence substance, a radioactive substance, etc.

Moreover, the term light of the present invention does not limitedly mean light in the visible region, unless otherwise indicated, but may be include non-visible light in the long-wavelength region or the short-wavelength region, such as ultraviolet rays, infrared rays, and X-rays.

In the following description, like or corresponding components are designated by like reference characters throughout the drawings.

(1) First Embodiment

Figure 1A:
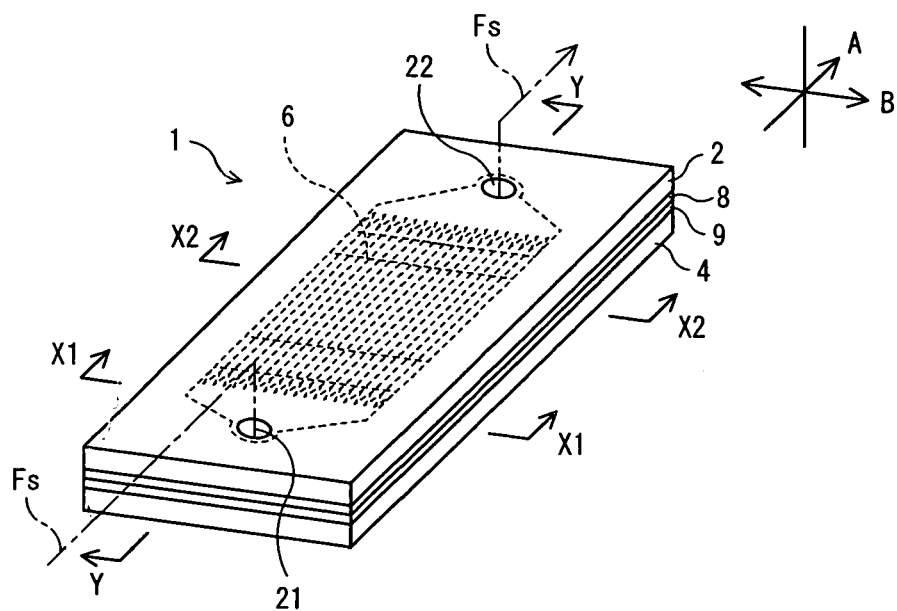
FIG. 1(a) is a diagrammatic assembled perspective view of an analytical chip according to the first embodiment of the present invention.
Figure 1B:
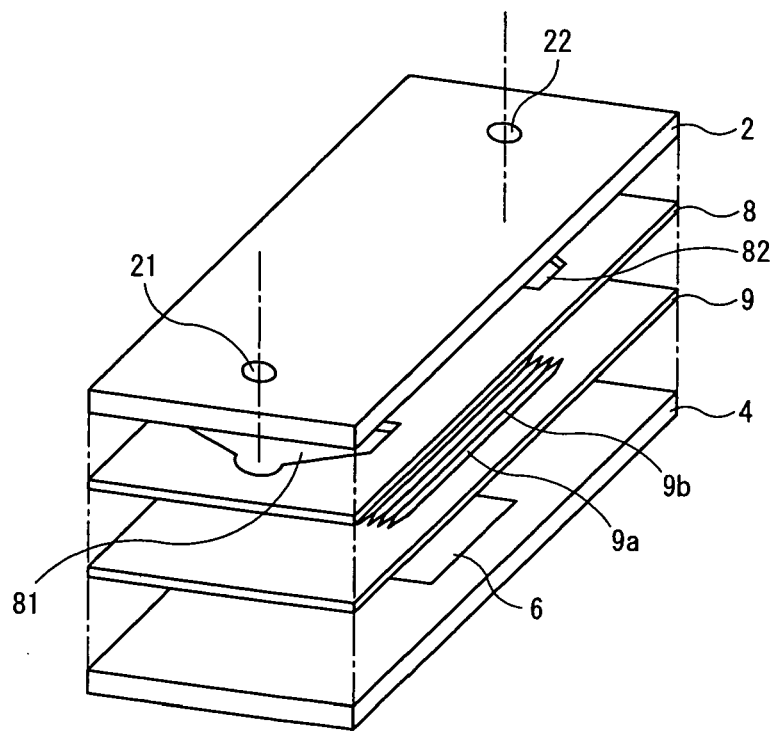
FIG. 1(b) is a diagrammatic exploded perspective view of the analytical chip according to the first embodiment of the present invention.
Figure 2A:
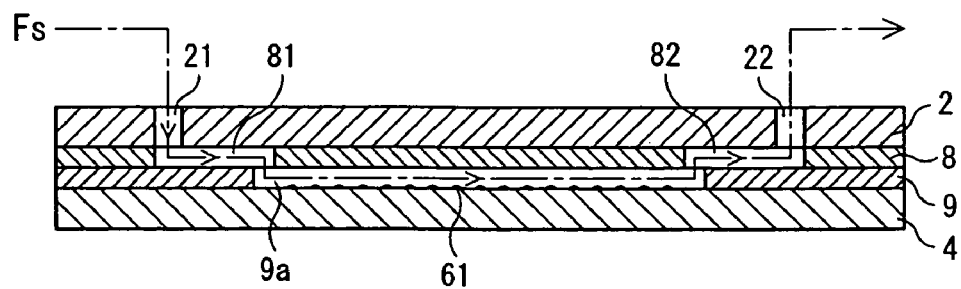
FIG. 2(a) is a diagrammatic sectional view taken on line Y—Y of FIG. 1(a)
Figure 2B:
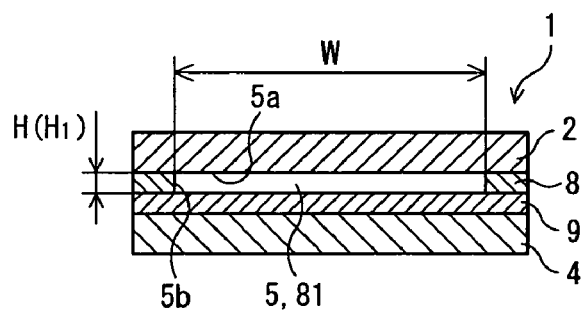
FIG. 2(b) is a diagrammatic sectional view taken on line X1—X1 of FIG. 1(a)
Figure 2C:
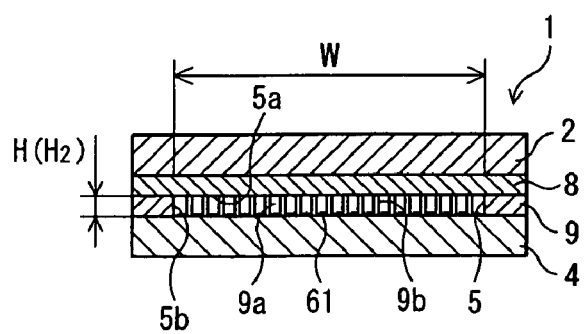
FIG. 2(c) is a diagrammatic sectional view taken on line X2—X2 of FIG. 1(a)

FIGS. 1–3 show analytical chip according to the first embodiment of the present invention. Specifically, FIG. 1(*a*) is a diagrammatic assembled perspective view of the chip, FIG. 1(*b*) is a diagrammatic exploded perspective view of the chip, FIG. 2(*a*) is a sectional view taken along line Y—Y of FIG. 1(*a*), FIG. 2(*b*) is a sectional view taken along line X1—X1 of FIG. 1(*a*), FIG. 2(*c*) is a sectional view taken along line X2—X2 of FIG. 1(*a*), FIG. 3(*a*) is a top view of the cover member of the chip, FIG. 3(*b*) is a top view of the first plate of the chip, FIG. 3(*c*) is a top view of the second plate of the chip, and FIG. 3(*d*) is a top view of the basal plate of the chip. In the following description, flow direction A of fluid sample Fs is defined as the major direction in which most of the fluid sample Fs flows through the flow channel. To take FIG. 4 as an example, the flow direction of flow channel 5' is defined as the direction indicated by the arrow in solid line.

As shown in FIGS. 1(a), (b), the present analytical chip (hereinafter called simply "the chip") 1 is composed of cover member 2, which is flat-plate shaped, first plate (hereinafter called simply "the plate") 8, which is of small thickness, second plate (an intermediate plate, hereinafter called simply "the plate") 9, which is of small thickness as with the plate 8, and basal plate 4. In carrying out analysis, as shown in FIG. 1(a), these components 2, 8, 9, 4 are piled in the listed order from above downward, and fastened together as a unit by a joining holder, not shown in the drawings. The plates 8, 9 are thus interposed between the cover member 2 and the basal plate 4.

It is preferable that the holder has a protection device for securing accurate alignment and preventing scratches. Examples of the protection device include a locking part, attached to the holder so as to lock the analytical chip 1, and a hollow, formed on the holder so that an observation part (reaction area 6, which will be described later) of the analytical chip 1 does not touch the holder.

As shown in FIG. 2(a), fluid sample Fs is to be injected into opening 21 (an injection port at the upstream end of flow channel 5, which will be described later) of the cover member 2, and to flow through opening 81 (a flow-channel confluence part on the upstream side) of the plate 8, then through each of slit-form openings 9a (inner flow channels) of the plate 9. Subsequently, the fluid sample Fs is to flow through opening 82 (a flow-channel confluence part on the downstream side) of the plate 8, and to be finally drained from opening 22 (a drain port at the downstream end of flow channel 5, which will be described later) of the cover member 2. While passing through the slit-form openings 9a of the plate 9, the fluid sample Fs is to be in contact with one or more specific substances 61, which are fixed to reaction area 6 of the basal plate 4.

The fluid sample Fs is to flow through the flow channel 5, whose section (orthogonal to the flow direction A of the fluid sample Fs) is in a slit shape elongated horizontally, as shown in FIGS. 2(b), (c). Put another way, the flow channel 5 is formed as a sheet-shaped space having closed-section structure.

In the present invention, the "flow channel formed as a sheet-shaped space" generally means a flow channel whose long side 5a has a size W of between 500 μm and 100 mm inclusive, and whose short side 5b has a size H of between 5 μm and 2 mm inclusive. The "long side" means the longest side among all the sides of both sections orthogonal to the flow direction of the flow channel 5 and sections orthogonal to width directions, generally being a side along either the width of the flow channel 5 or the length of the flow channel 5 in the flow direction (in the present embodiment, a side along the width of the flow channel 5). The "short side" means a side along the height of flow channel 5. The size ratio between the long side 5a and the short side 5b (=[long side size W]/[short side size H]) is generally 1.5 or above, preferably 10 or above, and generally 20000 or below, preferably 100 or below. When the flow channel 5 is, as will be described later, divided into two or more inner flow channels 9a with one or more partition walls 9b (which serve as projection member, partition members, or prop members), at least the sizes of the whole flow channel 5 (the sizes of the whole of the plural inner flow channels 9a joined together) have to meet the above range of size ratio. In the present embodiment, the length W of the long side 5a is set at 20 mm, while the length of the short side 5b of each of the plates 8, 9 (in X1—X1 section, thickness $H_1$ of the plate 8; in X2—X2 section, thickness $H_2$ of the plate 9) is set at 250 μm.

Also, the "closed-section structure" means that the flow channel's section orthogonal to the flow direction of the flow channel 5 is in a closed shape. The flow channel 5 is regarded to having closed-section structure even when the bottom face, the ceiling surface, the wall surface, etc. of the flow channel 5 are made of a porous material having minute pores, such as a membrane filter or a gas-permeable membrane, as long as the fluid sample Fs flowing through the flow channel 5 does not pass through the minute pores during analysis. The descriptions in the present specification are made on the assumption that, unless otherwise indicated, the flow channel 5 is formed as a sheet-shaped space having closed-section structure.

Hereafter, each of the above components of the present analytical chip 1 will be described in detail.

Each of the cover member 2, the plate 8, the plate 9, and the basal plate 4 can be made from any kinds of materials, examples of which include, but are not limited to, resins, ceramics, glasses, and metals. However, when measuring any interaction (such as reaction or binding) between target species and the specific substances 61 optically based on fluorescence, luminescence, color change, or phosphorescence, etc., it is desired to make each of the cover member 2 and the plates 8, 9 from one or more transparent materials; as an exception, when measurement can be carried out with the analytical chip 1 being disassembled, the cover member 2 and the plates 8, 9 are not necessarily required to have transparency. Examples of transparent materials are: resins, such as acrylic resin, polycarbonate, polystyrene, polydimethylsiloxane, and polyolefin; and glasses, such as Pyrex$^R$ (i.e., borosilicate glass) and quartz glass.

In the present embodiment, it is allowed to make the analytical chip 1 using low-strength materials (whose Young's modulus is 1 GPa or above and 60 GPa or below), because the deformation of the chip can be prevented by adopting such an arrangement as will be described later. Still, making the analytical chip 1 from high-strength materials enables analysis with higher precision. It is therefore preferable to make the components of the analytical chip 1, namely the cover member 2, the plate 8, the plate 9, and the basal plate 4, from one or more high-strength materials. Specifically, each of the cover member 2, the plate 8, the plate 9, and the basal plate 4 is made from at least one material whose Young's modulus is preferably 60 GPa or more. In the embodiment, it is assumed that every component of the analytical chip 1 is made from a strong material whose Young's modulus is 60 GPa or more.

Figure 3A:
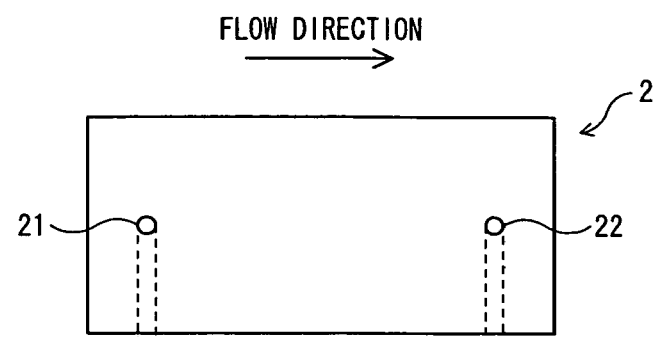
FIG. 3(a) is a diagrammatic top view of a cover member of the analytical chip according to the first embodiment of the present invention.

As shown in FIG. 3(a), opening (injection port) 21 is formed at the upstream end of the cover member 2, while another opening (drain port) 22 is formed at the downstream end of the cover member 2.

The injection port 21 is connected to an injection pump (e.g. syringe pump) using a connector and a tube (not shown in the drawings), while the drain port 22 is connected to a waste liquid tank using a connector and a tube (not shown in the drawings). Operating the above injection pump, it is possible to inject the fluid sample Fs via the injection port 21 into the chip 1 and drain it from the chip 1.

Figure 3B:
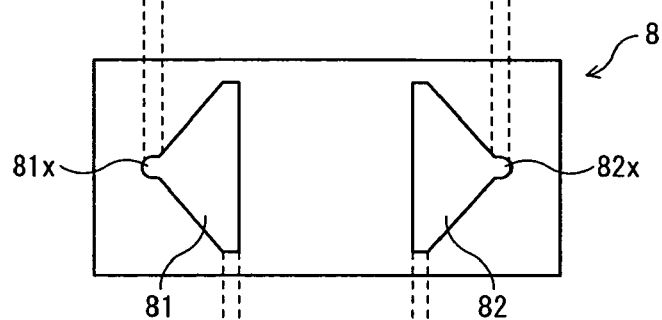
FIG. 3(b) is a diagrammatic top view of an intermediate plate of the analytical chip according to the first embodiment of the present invention.

As shown in FIG. 3(b), opening 81 is formed at the upstream side of the plate 8, while opening 82 is formed at the downstream side of the plate 8.

The upstream end 81x of the opening 81 is located in such a manner as to be aligned, and communicate, with the injection port 21 of the cover member 2 when the chip 1 is in the assembled state. The opening 81 is also formed in such a manner that its width gradually becomes broader from the upstream end 81x along the flow direction toward a middle part of the plate 8 (toward the downstream side along the flow direction of the fluid sample Fs).

On the other hand, the downstream end 82x of the opening 82 is located in such a manner as to be aligned, and communicate, with the drain port 22 of the cover member 2 when the chip 1 is in the assembled state. The opening 82 is also formed in such a manner that its width gradually becomes narrower from the middle part of the plate 8 along the flow direction toward the downstream end 82x (toward the downstream side along the flow direction of the fluid sample Fs).

When the chip 1 is in the assembled state, the top and under faces of the plate 8 are blocked by the cover member 2 and the plate 9, respectively, and each of the openings 81, 82 forms a part of the flow channel in which the fluid sample Fs flows unitedly. The part of the flow channel, formed by each the openings 81, 82 of the plate 8, is also called flow-channel confluence part 81, 82. Although in FIGS. 1(a) and 2(a), (b) the whole top surface and the whole under surface of the plate 8 are blocked by the cover member 2 and the plate 9, respectively, yet it is allowable that at least the parts of the top and under surfaces of the plate 8 corresponding to the openings 81, 82 is blocked.

Figure 3C:
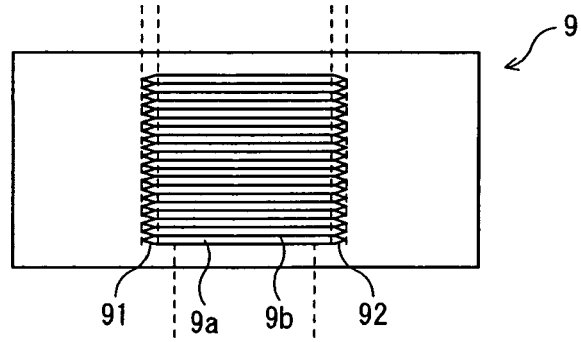
FIG. 3(c) is a diagrammatic top view of an intermediate plate of the analytical chip according to the first embodiment of the present invention.

As shown in FIG. 3(c), around the middle part of the plate 9 along the flow direction, projection member is formed as one or more partition walls (partition members) 9b, dividing two or more slit-form openings (or inner openings. hereinafter called the slit-form openings) 9a one from another across the width directions. When the chip 1 is in the assembled state, the slit-form openings 9a form slit-form inner flow channels (hereinafter also called slit-form flow channels), which are divided with the partition walls 9b one from another around the middle part of the flow channel 5. The term "inner flow channels" means flow channels that are divided with the partition members across the width directions. The partition walls 9b adjoin directly the basal plate 4 and the plate 8 so that the fluid sample Fs is shut out from both between the partition walls 9b and the basal plate 4 and between the partition walls 9b and the plate 8, thereby the flow channel 5 being divided into plural inner flow channels. Meanwhile, when the chip 1 is in the assembled state, the top and under faces of the slit-form openings are blocked by the plate 8 and the basal plate 4 to thereby define the slit-form flow channels. Since the slit-form openings, the slit-form flow channels, and the inner flow channels are thus equivalent to each other, they are all designated by the same reference character 9a.

It is usually preferable to form each of the slit-form flow channels 9a such that its cross section has an aspect ratio {[length size]/[width size]} of between 0.005 (e.g., 5 μm in length and 1 mm in width) and 100 (e.g., 10 mm in length and 100 μm in width) inclusive. Also, it is generally preferred that each of the slit-form flow channels 9a has a cross sectional area of 5 mm$^2$ or below. Specifically, the sectional area of each slit-form flow channel 9a is usually 100 μm$^2$ or above, preferably 2000 μm$^2$ or above, and usually 5 mm$^2$ or below, preferably 0.3 mm$^2$ or below.

Also, when the chip 1 is in the assembled state, the upstream end 91 of each slit-form opening 9a is located such as to communicate with the downstream end of the opening 81 of the plate 8, while the downstream end 92 of each slit-form opening 9a is located such as to communicate with the upstream end of the opening 82 of the plate 8.

With the above arrangement, the fluid sample Fs injected from the flow-channel confluence part 81 of the plate 8 flows through the upstream end 91 of each slit-form flow channel 9a into each slit-form flow channel 9a of the plate 9, finally going out of the downstream end 92 of each slit-form flow channel 9a to gather into one volume in the flow-channel confluence part 82 of the plate 8.

According to the present analytical chip 1 as described above, it becomes possible to prevent running ahead of the fluid sample Fs by providing the conventionally-formed, sheet-shaped flow channel with one or more partition walls 9b to divide the flow channel 5 into two or more inner flow channels 9a with minute section (namely, by decreasing the cross sectional area of the individual flow channel).

In the meanwhile, as shown in FIGS. 1(a), (b), reaction area 6 is disposed around the middle part of the basal plate 4 along the flow direction so as to face the flow channel 5.

Figure 3D:
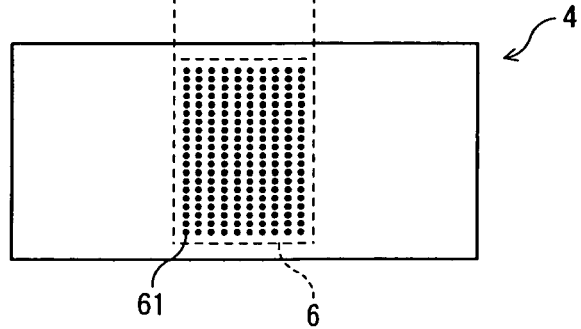
FIG. 3(d) is a top view of a basal plate of the analytical chip according to the first embodiment of the present invention.

Illustrated in a simplified form in FIGS. 1(a), (b), the reaction area 6 is an area where, as shown in FIG. 3(d), at least one specific substance 61 that can cause interaction specifically or nonspecifically with one or more predetermined substances (target species) is fixed, as plural spots, to the surface of the basal plate 4 on the side of the flow channel 5. In order to fix the specific substance 61 securely to the basal plate 4, it is preferable to previously form on the surface of the basal plate 4 an immobilized film (organic film) that can bind with the specific substance 61.

The sizes {[length size]×[width size]} of the reaction area 6 are usually between 3 mm×3 mm through 20 mm×20 mm inclusive. In the area, the specific substance 61 are disposed as generally 9 through 40000 spots in such a matrix that 3 through 200 spots are aligned along every row of each direction at intervals of between 100 μm and 1 mm inclusive.

It is assumed that as the specific substance 61, the embodiment uses plural kinds of specific substances (different from each other) each of which can cause any interaction, such as reaction or binding, specifically or nonspecifically with different kinds of substances.

Each of the predetermined substance and the specific substance can be selected from substances that can cause any interaction, such as antigen-antibody reaction, complementary DNA binding, receptor-ligand interaction, enzyme-substrate interaction, etc., and is selectable from various substances, for examples, protein, nucleic acid, DNA, RNA, PNA, peptide, hormone, antigen, antibody, ligand, receptor, enzyme, substrate, low molecular organic compound, cell, etc., and complex thereof. These substances may be labeled, if necessary, with any other substance such as a fluorescence substance, luminescence substance, radioactive substance, etc.

Meanwhile, the following point is to be noted (although it is restated in the description of the production method of the present analytical chip 1, as will be described later). When the present analytical chip 1 is assembled, the plate 9 is first fixed on the basal plate 4, after which the specific substances 61 are fixed to the basal plate 4 from above the plate 9 through the slit-form openings 9a of the plate 9. Hence, the reaction area 6 (the area where the plural specific substances 61 are fixed) shown in FIG. 3(d) is not actually formed in the early stage of assembling: in FIG. 3(d), the specific substances 61 fixed to the basal plate 4 are illustrated for convenience in explaining the arrangement of the spots of the specific substances 61 with respect to the basal plate 4 intelligibly. Accordingly, FIG. 3(d) illustrates the positions and the number of the spots of the specific substances 61 along the width directions in such a manner that they correspond to the positions and the number of the slit-form openings 9a of the intermediate plate 9 along the width directions.

The fluid sample Fs flowing through the slit-form flow channels 9a comes into contact with these specific substances 61 during the process of the flowing, after which analysis is carried out regarding the fluid sample Fs, based on the state of reaction at each spot of the specific substances 61.

Specifically, if the occurrence of reaction is detected at any spot of the specific substances 61, it is possible to determine that the fluid sample Fs contains a kind of substance corresponding to the specific substance 61 fixed at the spot where the reaction is detected.

The specific substances 61 are fixed to the chip 1 as plural spots arranged at regular intervals so as not to be contaminated with the specific substance 61 at the neighboring spots. The term "regular intervals" means the intervals between the centers of the spots where the specific substances are fixed, to which intervals the pitch of the partition walls 9b is set to be substantially identical. In the present invention, it is not necessary to reduce the number of spots of the specific substance 61 per unit area than in the conventional chip in return for disposing the partition walls 9b; on the contrary, since the disposition of the partition walls 9b enables to prevent the contamination as described above, the pitch of the specific substances 61 along the width directions (the directions orthogonal to the flow direction) can be minimized, so that it becomes possible to rather increase the number of spots per unit area.

It is not necessary to use different kinds of specific substances 61 at different spots; the same specific substance 61 can be used at two or more different spots. In any event, what kinds of specific substances 61 are used should be determined as appropriate, depending on the object of analysis.

Figure 5:
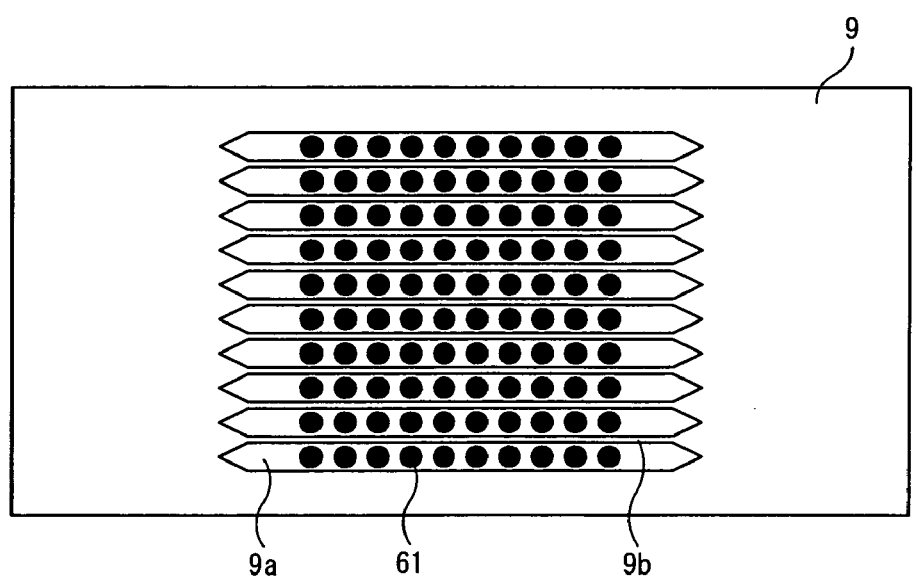
FIG. 5 is a diagrammatic top view of assistance in explaining a method of making an analytical chip according to the first and eleventh embodiments of the present invention.

The following description is made on a production method of the present analytical chip 1. The plate 9 is bonded to the basal plate 4, after which the specific substance 61 is fixed to the basal plate 4. Specifically, the specific substance 61 is dispersed or dissolved in a liquid to form a dispersion liquid or solution of the specific substance 61. The dispersion liquid or solution is dripped through the slit-form openings 9a of the plate 9 in such a manner that the drops are aligned at regular intervals, as shown in FIG. 5, using a injector or a spotter (not shown in the drawings) that is capable of positioning operation. In the following description, the above dispersion liquid or solution, which is obtained by dispersing or dissolving the specific substance 61 into a liquid, is called the "fluid containing specific substance". Although not limiting the kind of the liquid in which the specific substance 61 is dispersed or dissolved, it is assumed that in the present embodiment, the fluid containing specific substance is an aqueous solution obtained by dissolving the specific substance 61 in water. FIG. 5 is a top view of the chip, illustrating the state where the plate 9 is bonded to the basal plate 4 and the fluid containing specific substance is dripped so that the specific substance 61 is fixed.

Subsequently, the plate 8 is mounted on the plate 9, and the cover member 2 is further mounted on the plate 8.

In the above production method of the present analytical chip 1, it is preferable that the plate 9 is made of a material having lower affinity for the fluid containing specific substance than that of the basal plate 4. In the present embodiment, because the fluid containing specific substance is the aqueous solution of the specific substance 61, it is preferable to use a material having hydrophobicity as a preferred example of the member having lower affinity. With this arrangement, the surface of the plate 9 on the side of the plate 8 (the side opposite to the basal plate 4) has a lower affinity for the fluid containing specific substance than that of the surface of the basal plate 4 on the side of the flow channel 5. When dripping from an injector the fluid containing specific substance, in which the specific substance 61 is dispersed or dissolved, there may arise the case where drops of the fluid containing specific substance deviate from the desired positions due to environmental disturbances or equipment factors and fall over the partition walls 9b of the plate 9. Even in such a case, the fluid containing specific substance spontaneously runs (namely, is guided) toward the basal plate 4, which has a higher affinity for the specific substance 61 than the plate 9, and is guided securely onto the basal plate 4. Consequently, it becomes possible to fix the specific substance 61 correctly at target positions on the basal plate 4.

It is also preferable to make only the partition walls 9b of the plate 9 from a material having a lower affinity for the fluid containing specific substance than that of the basal plate 4, or to form, on the surface of the partition walls 9b of the plate 9, a layer having a lower affinity for the fluid containing specific substance than that of the basal plate 4. Also preferably, the plate 8 and the cover member 2 can be bonded and joined together as a unit.

Alternatively, it is also preferable to make the surface of the plate 9 on the side of the plate 8 (the side opposite to the basal plate 4) from a material having a lower affinity for the fluid containing specific substance than the wall surface of the slit-form openings 9a of the plate 9. With this arrangement, as is the case described above, even when the fluid containing specific substance has fallen over the surface of the partition walls 9b of the plate 9 on the side of the plate 8, the specific substance 61 runs toward the slit-form openings 9a, which has a higher affinity for the fluid containing specific substance than the surface of the plate 9 opposite to the basal plate 4. Consequently, the fluid containing specific substance is guided securely onto the slit-form openings 9a, so that it becomes possible to fix the specific substance 61 correctly at target positions on the basal plate 4.

In the present specification, the term "affinity" of a certain substance means broadly a property of tending to bind with or adsorb another substance, and therefore should not be interpreted as limitedly designating hydrophilicity or hydrophobicity.

Besides, although in the present embodiment the components are joined together by fastening physically with a holder so that the chip 1 can be disassembled, it is also possible to use any other measures for joining the components. Examples of the joining measures include, although not limited thereto, adhesion with an adhesive agent, resin bonding with a primer, diffusion bonding, anodic bonding, eutectic bonding, heat sealing, ultrasonic bonding, laser fusing, dissolution with a resolvent or a solvent, etc. It is also possible to use a sticky tape, an adhesive tape, or a self-adsorbent. Alternatively, it is also preferable to adopt pressure bonding, or form concavities and convexities on the components so as to be engageable with each other. With these measures, the components can be easily assembled. It is also allowable to use any two or more of the above joining measures in combination.

Because the analytical chip according to the first embodiment of the present invention is constituted as described above, the fluid sample Fs injected via the injection port 21 of the cover member 2 flows into the flow-channel confluence part 81 of the plate 8, as shown in FIGS. 2(a) and 3(a)–(d).

After then, the fluid sample Fs flows from the upstream ends 91 of the slit-form flow channels 9a into the individual slit-form flow channels 9a, and comes into touch with the specific substance 61.

Subsequently, the flows of the fluid sample Fs run out of the downstream ends 92 of the slit-form flow channels 9a to join together in the flow-channel confluence part 82 and be drained from the drain port 22 of the cover member 2 toward outside the chip 1.

As described above, according to the present analytical chip 1, the plural slit-form flow channels 9a share the single injection port 21 and the single drain port 22. Hence, compared to the above-described conventional technique, in which plural flow channels are simply arranged in parallel and the fluid is injected into and drained from each of the flow channels separately, the present analytical chip has the advantage that it needs fewer connectors and tubes for injection and drainage, simplifying the installation work of such connectors and tubes to the chip 1.

Further, using the present analytical chip 1, it becomes possible to make different kinds of fluid samples Fs flow serially to measure them successively. With this feature, there is no need to prepare a different analytical chip 1 for each kind of fluid sample Fs, so that analysis can be carried out easily within a short time.

Furthermore, since the flow-channel confluence part 81 becomes gradually broader from the upstream end 81x toward the middle part along the flow direction, the fluid sample Fs can be guided smoothly toward the middle part of the flow direction. On the other hand, since the flow-channel confluence part 82 becomes gradually narrower from the middle part toward the downstream end 82x along the flow direction, the fluid sample Fs can be guided smoothly toward the downstream end 82x.

Besides, using the present analytical chip 1, it is possible to prevent the occurrence of air bubbles due to enclosing flow of the fluid sample Fs. The following description is given on the advantage that the occurrence of air bubbles is preventable compared with a conventional problem.

In the conventional microchannel chip, a fluid sample is generally made flow into a flow channel that is initially filled with gas (mostly air), so that the interface between the three phases of solid-gas-liquid arises to move on through the flow channel. However, since the flow channel has a cross section that is elongated along its width directions, various trifle matters (non-uniformity of wettability along the wall surface of the flow channel, vibrations due to unstable equipment, adhesion of foreign particles to the surface of the flow channel, etc.) may bring about the state shown in FIG. 36(a): namely, the interface between the three phases of solid-gas-liquid S (the front end of the fluid sample Fs) becomes a non-linear, non-uniform shape along the width directions B of the flow channel, which is perpendicular to the flow direction A.

Figure 36:
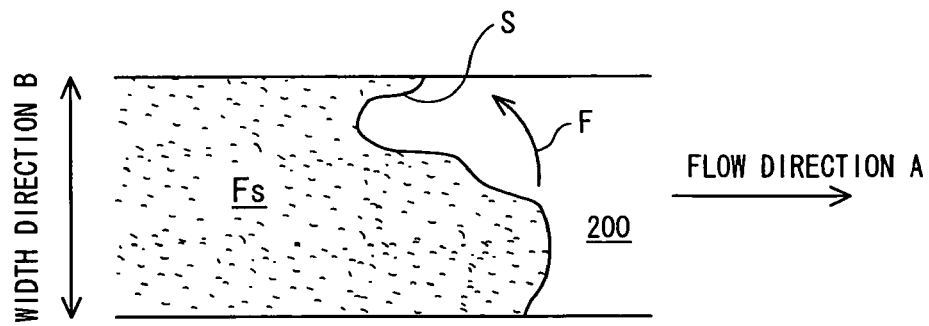
FIG. 36(a), FIG. 36(b) are diagrammatic views of assistance in explaining a conventional analytical chip.
Figure 36:
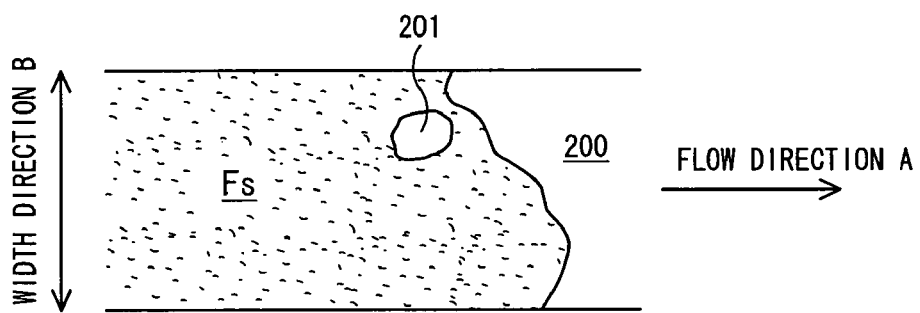

Subsequent to the state shown in FIG. 36(a), as the fluid sample Fs flows, a part of the interface between the three phases of solid-gas-liquid S runs ahead of the remaining part to gradually spread out as indicated by arrow F and finally, as shown in FIG. 36(b), completely encloses a small amount of gas 200, thereby an air bubble 201 being produced in the fluid sample Fs. In addition, in such a sheet-shaped flow channel as described above, since such an air bubble 201 adjoins the wall surface of the flow channel with a large interfacial area, it is difficult to carry away and remove the air bubble 201 toward the downstream direction by keeping the fluid flowing, so that in many cases the air bubble 201 remains dwelling.

Another conceivable idea is to apply high pressure to inside the flow channel to thrust out forcibly the air bubble 201 from the flow channel. However, depending on the constitution of the analytical chip, the materials of the analytical chip, or the measures used for joining the analytical chip, it may cause damage to the flow channel due to acute increase of the pressure. As long as the flow channel is made from a solid material, the flow channel does not receive a critical influence even when high pressure is applied to the flow channel. Even if the flow channel structure is made from a combination of plural materials, as long as these materials are strongly bonded together, the flow channel does not receive a critical influence due to high pressure applied to the flow channel. Also, even when piping (tube) or a connector is joined to the flow channel, as long as they are bound firmly to the flow channel, the flow channel still does not receive a critical influence due to high pressure applied to the flow channel. However, under circumstances where for some reason any restrictions are imposed on the conditions applied to the analytical chip, such as materials, measures for joining, piping installation, etc., there are assumable cases where it is undesirable to apply high pressure to inside the flow channel to thrust out forcibly the air bubble 201 from the flow channel. For example, when the analytical chip needs be made from a combination of plural materials, it is preferable that compared to the combination of materials selected from different material groups (for example, the combination of a metal and a glass, the combination of a resin and a glass, etc.), a combination of materials selected from the same material group is used in view of waste treatment. Further, in order to reduce the weight of the analytical chip, it is preferable that the analytical chip is made from a lightweight material such as a resin. Also, when using a processing method with high precision such as injection molding or compression molding from the viewpoint of formability, it is preferable that the analytical chip is made from a resin. Further, in the case where exposure to high-temperature circumstances is assumed during the stage of producing the analytical chip, the preliminary stage toward the analysis using the analytical chip, and/or the stage of analysis using the analytical chip, it is preferable that the analytical chip is made from a material such as a glass or a metal. Thus, materials from which the analytical chip is made should be selected as appropriate, according to the demands of a designer, a manufacturer, a user, etc.

When an air bubble 201 remains dwelling as described above, there arise such defects as illustrated by FIG. 37 through FIGS. 39(a), (b).

For example, an air bubble 201 that remains dwelling in the reaction area 204 can prevent, as shown in FIG. 39(a), the specific substance fixed to the reaction area 204 from coming into touch with the fluid sample.

In addition, if an air bubble 201 remains dwelling in the measurement area 205, as shown in FIG. 39(b), accurate analysis can be prevented. Especially when optical measurement is being carried out while the air bubble 201 stays dwelling in the measurement area 205, the measurement may become even impossible. It is therefore necessary to remove the fluid sample from the flow channel and then carry out prearrangement again before resuming the measurement, so that the efficiency of analytical work is decreased markedly.

Figure 37:
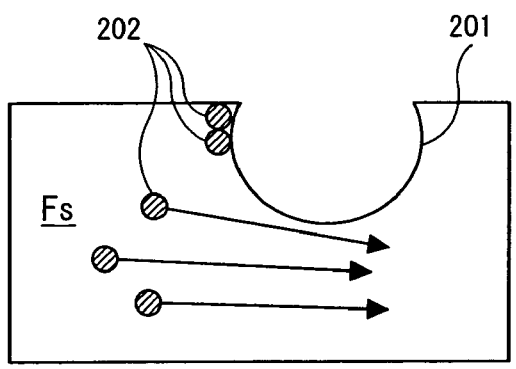
FIG. 37 is a diagrammatic view of assistance in explaining a conventional analytical chip.
Figure 38:
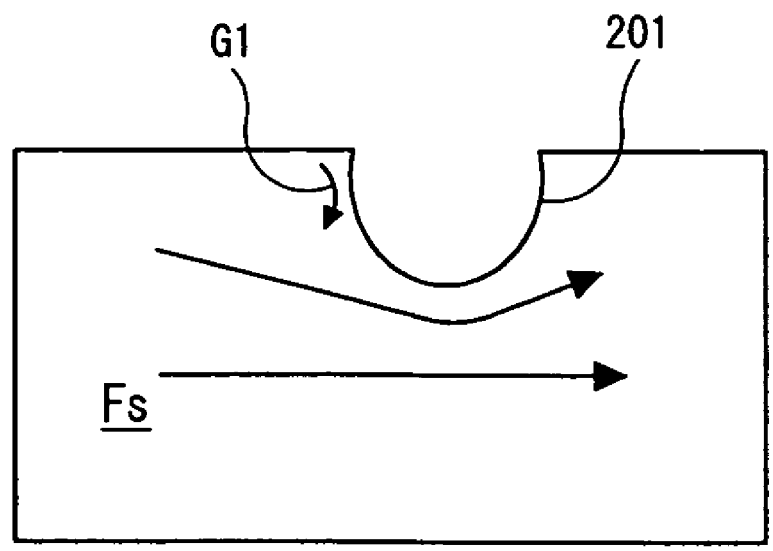
FIG. 38(a), FIG. 38(b) are diagrammatic views of assistance in explaining a conventional analytical chip.
Figure 38:
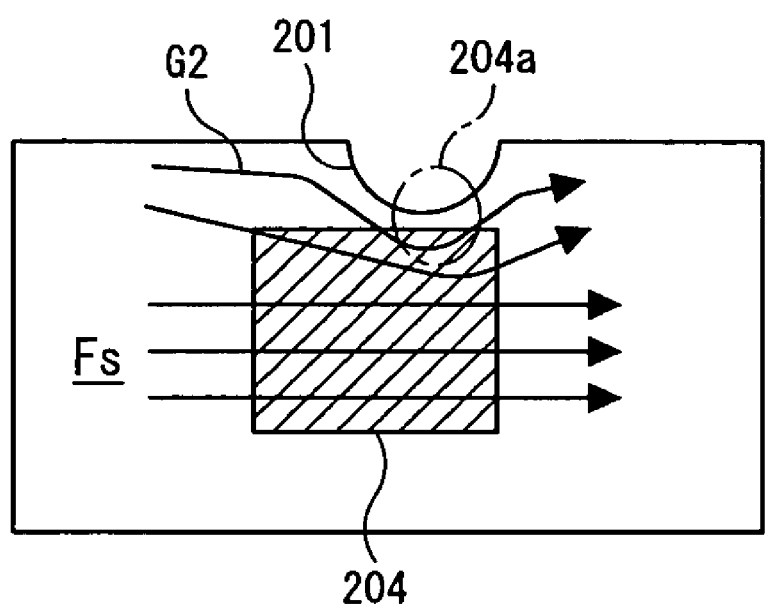
Figure 39:
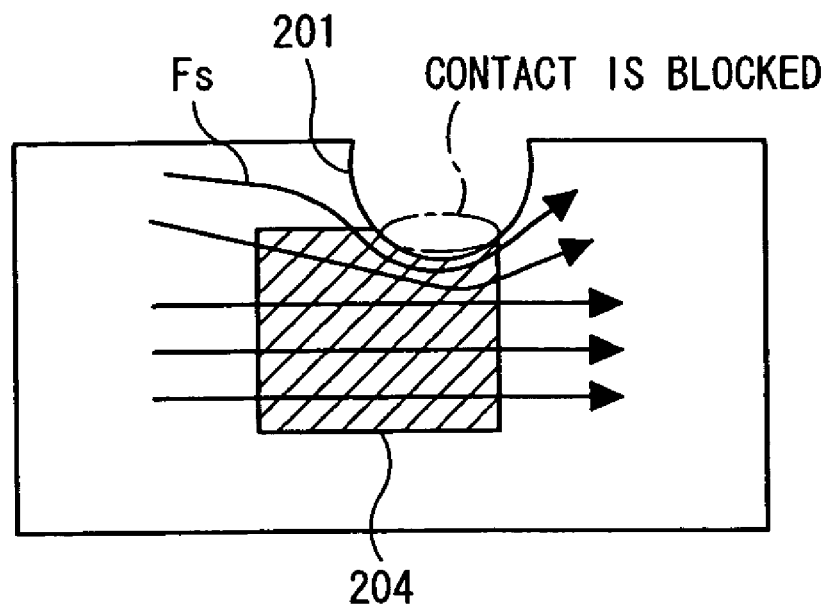
FIG. 39(a), FIG. 39(b) are diagrammatic views of assistance in explaining a conventional analytical chip.
Figure 39:
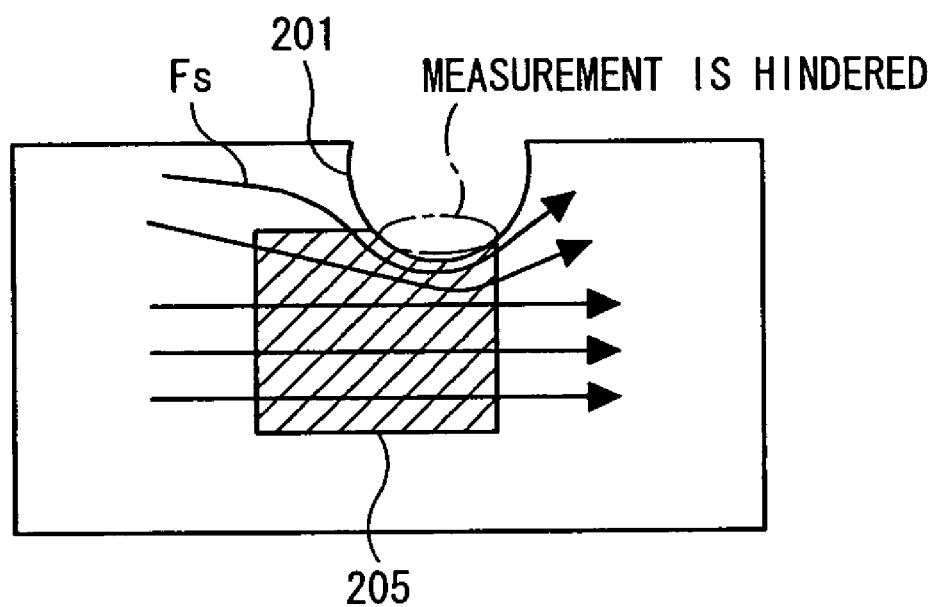

Besides, as shown in FIG. 37, particulate substances 202 contained in the fluid sample Fs tend to aggregate and be accumulated specifically around the upstream side of the air bubble 201, thereby exerting an influence upon the subsequent processes such as flowing process, mixing process, and reaction process.

In addition, when the air bubble 201 remains dwelling to make the surrounding flow non-uniform, as indicated by arrow G1 of FIG. 38(a), back-flow arises in extreme cases between the upstream side of the air bubble 201 and the flow channel wall surface, occasionally exerting an influence upon analysis. Further, at a constant pressure and a constant velocity, the fluid sample Fs in the vicinity of the air bubble 201 flows along the exterior surface of the air bubble 201, as indicated by arrow G2 of FIG. 38(b), and therefore runs faster than the other.

Hence, in the reaction area 204 to which the specific substance is fixed, the subarea 204a in the vicinity of the air bubble 201 comes in touch with a larger number of molecules in the fluid sample (namely, is passed along by a larger volume of fluid sample) than the other subarea. Consequently, interactions proceed under various conditions depending on the positions in the reaction area 204, so that it is difficult to accurately analyze the fluid sample based on the interactions occurring in the reaction area 204, such as binding or dissociation.

Furthermore, when an air bubble 201 remains dwelling in the fluid sample, the difference of heat transfer coefficient between the fluid sample Fs and the air bubble 201 can bring about non-uniformity of temperature in the system of measurement, thereby exerting an influence upon the results of analysis.

By contrast, according to the analytical chip 1 of the present embodiment, since the flow channel 5 formed as a sheet-shaped space is divided into the minute (narrow-width) inner flow channels (slit-form flow channels) 9a with the partition walls 9b, it becomes possible to prevent the occurrence of air bubbles due to enclosing flow of the fluid sample Fs.

Figure 6A:
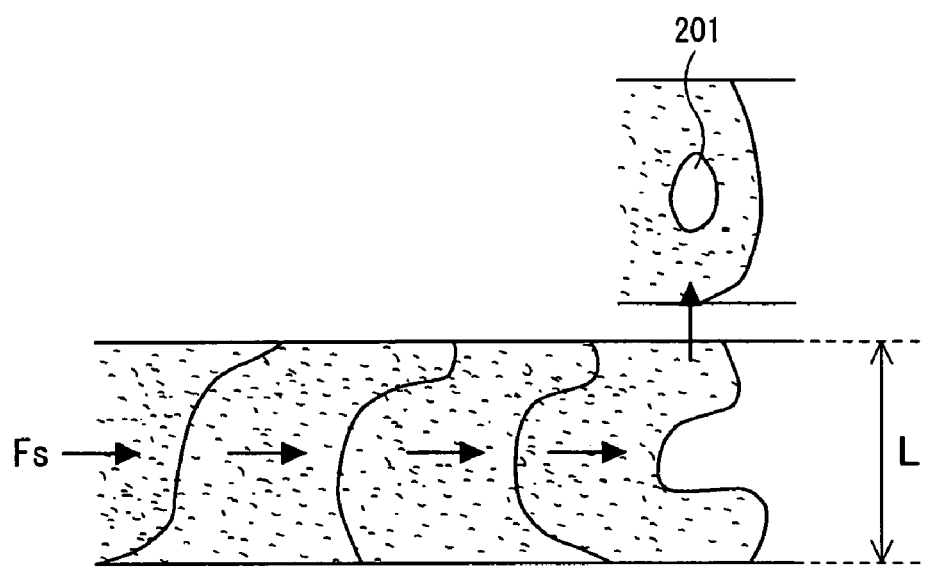
FIG. 6(a) is a plan view diagrammatically showing a conventional flow channel formed in a sheet-shaped space.
Figure 6B:
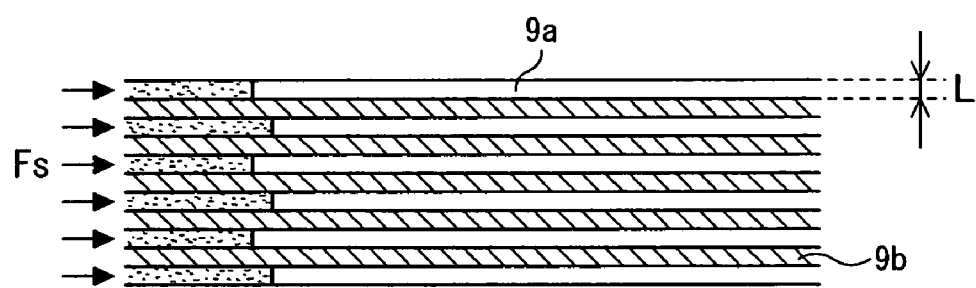
FIG. 6(b) is a plan view diagrammatically showing a slit-form flow channel of analytical chips according to the first, eleventh, and thirteenth embodiments of the present invention.

Specifically speaking, in the conventional sheet-shaped flow channel, since the interface between the three phases of solid-gas-liquid has a long front line as shown in FIG. 6(a), part of the fluid sample Fs runs ahead due to non-uniformity of wettability, so that enclosing flow of the fluid sample Fs occurs to result in generation of the enclosure of gas (air bubble 201). In the present invention, since the flow channel 5 is divided into the separate, minute inner flow channels (the slit-form flow channels 9a), the length of line segment L (flow channel width) perpendicular to the main flow in the flow channel becomes small as shown in FIG. 6(b), so that the occurrence rate of the enclosing flow decreases significantly. Besides, since the cross sectional area of the flow channel becomes small, it is possible to apply backing pressure efficiently to the interior of each slit-form flow channel 9a, thereby making air bubbles hard to remain dwelling.

Consequently, according to the present analytical chip 1, it becomes possible to remove various adverse effects arising from the dwelling of air bubbles (such as the blockage of the normal flow of the fluid sample Fs, the hindering of the contact between the specific substance 61 and the fluid sample Fs, the non-uniformity of temperature in the system of measurement caused by the difference of heat transfer coefficient between the liquid Fs and the air bubble 201, the inhibition of the measurement during the analysis using an optical system because of the air bubble 201 dwelling in the optical path, etc.), resulting in the advantage that the reliability of analysis is improved. Besides, since it eliminates the need for extra work of getting rid of air bubbles, there is the advantage that analytical work can be carried out efficiently.

Meanwhile, other techniques of preventing air bubbles in the fluid sample Fs are disclosed in, for example, Japanese Patent Laid-Open Publication (Koukai) No. 2001-162817 (hereinafter called patent document 2) and Japanese Patent Laid-Open Publication (Koukoku) No. HEI 11-508360 (hereinafter called patent document 3).

Patent document 2 discloses a recording-liquid supply pipe for supplying a recording liquid (ink) to an ink jet head. According to the art, by imparting lyophilicity to the interior surface of the supply pipe, air bubbles can be prevented from adhering to the interior surface of the supply pipe. Besides, even if having adhered to the interior surface of the supply pipe, the air bubbles can easily desorb from the interior surface of the supply pipe and be removed together with the flow of the liquid through the supply pipe.

However, the art is not intended for a sheet-shaped flow channel with minute section, and therefore does not enable to prevent enclosing flow of a fluid sample in such a flow channel.

Patent document 3 discloses a flow-through sampling cell with a flow channel through which a fluid sample is made flow, the corners of which flow channel are rounded so that the adhesion of air bubbles to the corners can be prevented.

However, the art is also not intended to prevent the very occurrence of air bubbles due to enclosing flow of the fluid sample, and does not have much effect because it can prevent only the adhesion of air bubbles to the corners.

In addition, the art disclosed by the above nonpatent document 1 is not intended to make a fluid sample flow in a sheet-shaped space and thereby make the fluid sample bind with a number of specific substances during the single flow, failing to pay any attention to the occurrence of air bubbles due to enclosing flow of the interface between the three phases of solid-gas-liquid.

Besides, the art disclosed by the above patent document 1, like the art disclosed by the above nonpatent document 1, is not intended to make a single fluid sample flow in a sheet-shaped space and thereby make the fluid sample come in touch with a number of specific substances, failing to pay any attention to the occurrence of air bubbles due to enclosing flow of the fluid sample.

In addition, in the conventional flow channel formed in the sheet-shaped space, the non-uniformity of flow occurs over a wide area. Specifically, when a liquid fluid is fed at a flow rate within the normal range, the velocity of the liquid fluid is zero at the wall surface of the flow channel while being the highest at the center of the flow channel, and becomes lower as being closer to the wall surface both longitudinally and latitudinally, thus causing the non-uniformity.

By contrast, according to the present analytical chip 1, the separate, minute inner flow channels (slit-form flow channels 9a) are formed. When the spots of the specific substance 61 are aligned, for example, in two rows along the width directions of the slit-form flow channels 9a, it becomes possible to make the fluid sample Fs be in contact with the spots of the specific substance 61 aligned in each row along the width directions during the same period, thereby improving the precision of the analysis results.

Figure 40:
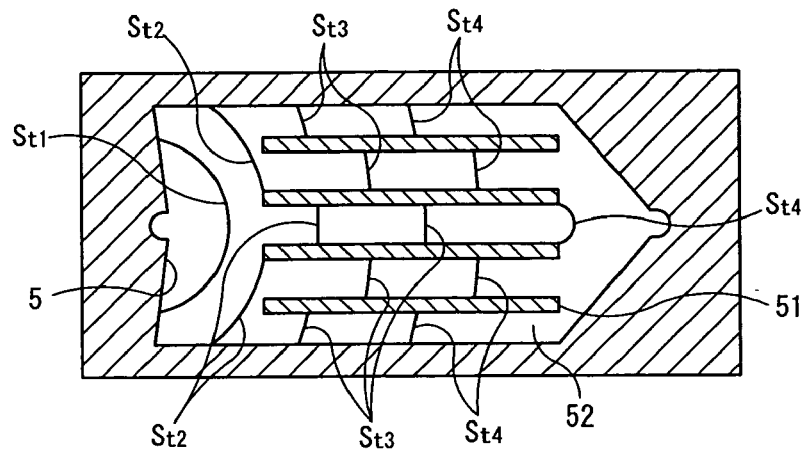
FIG. 40 is a diagram of assistance in explaining running ahead of the fluid sample.
Figure 41:
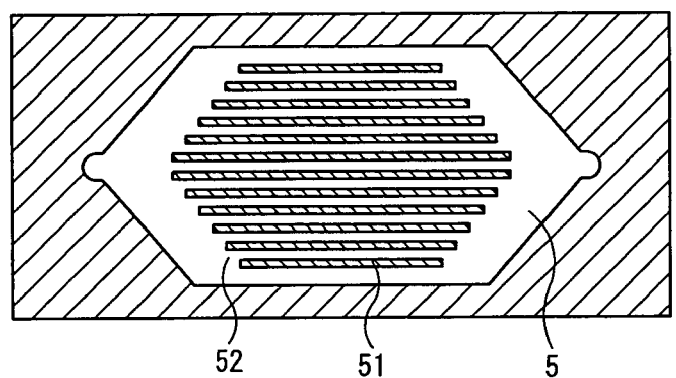
FIG. 41 is a diagram of assistance in explaining a constitution of the flow channel for preventing the running ahead of the fluid sample.

Moreover, when the lengths Fs of main flow of the fluid sample vary among the inner flow channels 9a, a flow of the fluid sample Fs through an inner flow channel 9a near the center of the flow channel 5 forms the interface between the three phases of solid-gas-liquid that precedes the one formed by a flow of the fluid sample Fs through an inner flow channel 9a near the border of the flow channel 5. Therefore, the flow of the fluid sample Fs through the inner flow channel 9a near the center of the flow channel 5 "arrives ahead" of the flow through the other inner flow channels 9a to the flow-channel confluence part at downstream side, causing the dwelling of air bubbles around the border of the flow channel 5. FIG. 40 illustrates the occurrence of such a state. In FIG. 40, reference character 51 designates a partition wall, reference character 52 designates an inner flow channel, reference characters St1, St2, St3, St4 each designate the positions of the interface between the three phases of solid-gas-liquid after the lapses of different time periods since the fluid sample Fs starts flowing through the flow channel 5, the interface passing in the order of St1, St2, St3, St4.

Figure 26:
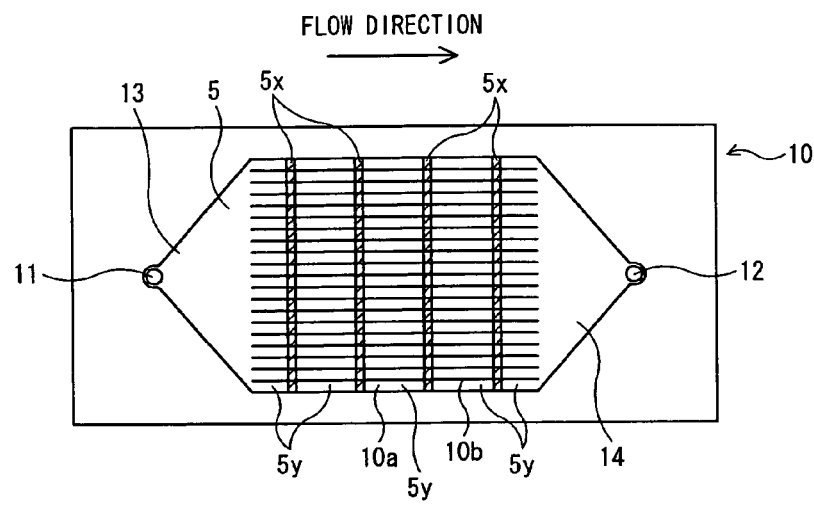
FIG. 26(a), FIG. 26(b), FIG. 26(c) are diagrammatic bottom views intermediate plate according to the third through fifth modifications of the seventh embodiment of the present invention.
Figure 26:
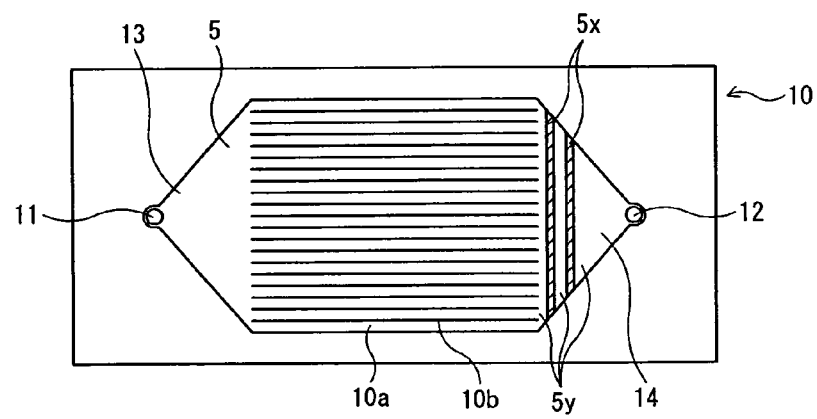
Figure 26:
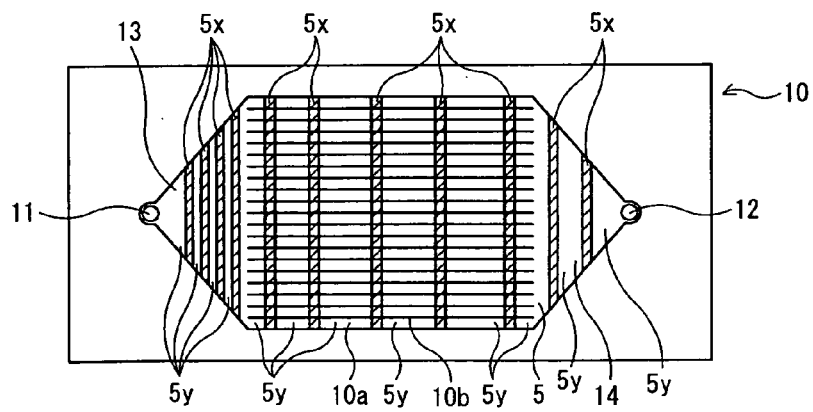
Figure 42:
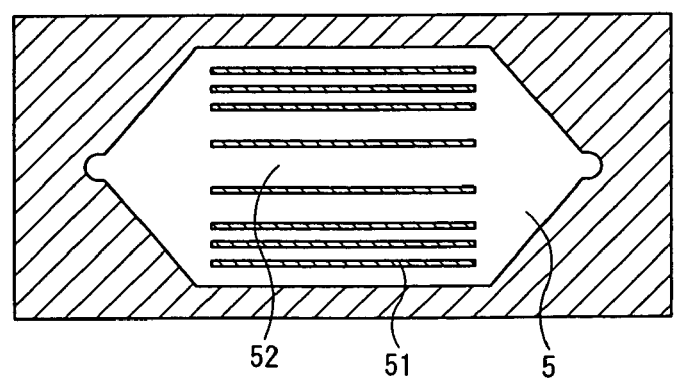
FIG. 42 is a diagram of assistance in explaining a constitution of the flow channel for preventing the running ahead of the fluid sample.
Figure 43:
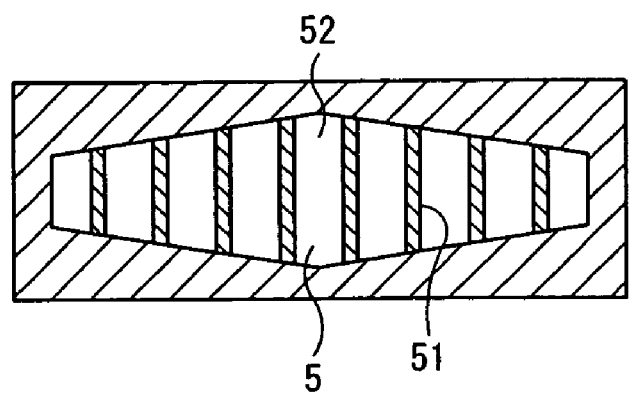
FIG. 43 is a transverse sectional view of a flow channel for assistance in explaining a constitution of the flow channel for preventing the running ahead of the fluid sample.
Figure 44:
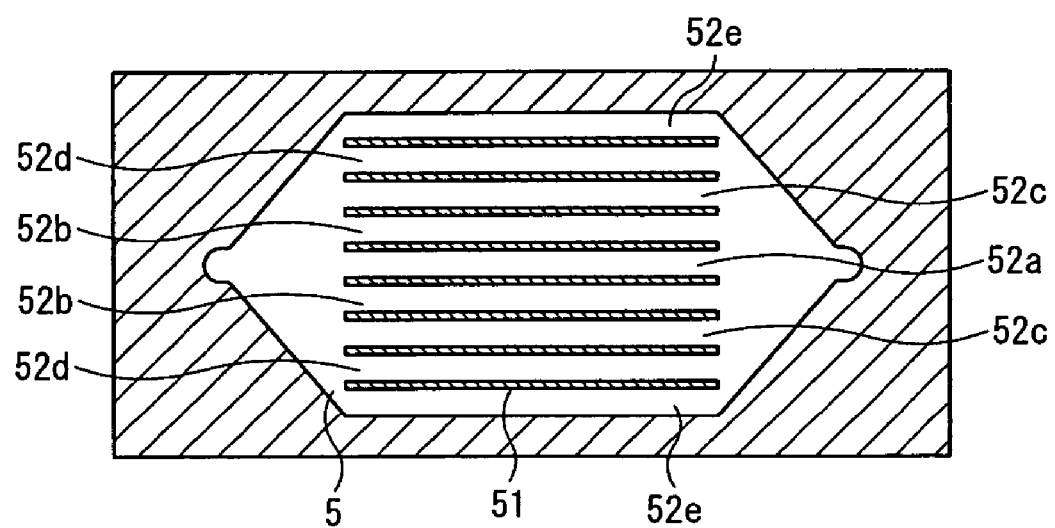
FIG. 44 is a diagram of assistance in explaining a constitution of the flow channel for preventing the running ahead of the fluid sample.

It is therefore preferable to level the lengths of the inner flow channels in such a manner that the "arriving ahead" does not occur (refer to FIG. 41), or to adjust the velocity of the fluid sample Fs in each of the inner flow channels by forming the first and second affinity parts explained in the seventh embodiment, which will be described later {refer to FIG. 26(c)}. Alternatively, as shown in FIG. 42, it is also desirable to make the sectional areas of the inner flow channels 52 gradually narrower from the center toward either of the edges of the flow channel 5 along the width directions, thereby adjusting the linear velocity of the fluid sample Fs. As another option, it is also preferable to adjust the sectional areas of the inner flow channels 52 by varying the heights of the inner flow channels 52 (refer to FIG. 43) or adjust the relative roughness of the surface of the partition wall 51 or the flow channel 5 (refer to FIG. 44) so as to regulate the pressure loss of the fluid sample Fs flowing through each of the inner flow channels 9a, thereby adjusting the velocity of the fluid sample Fs flowing through each inner flow channel 9a. The constitution of FIG. 44 is based on the fact that the pressure loss of the fluid sample Fs flowing through the flow channel 5 generally becomes larger as the relative roughness of the surface of the partition wall 51 or the flow channel 5 is higher. In FIGS. 41 through 44, the reference characters also used in FIG. 40 designate the like components. Moreover, in FIG. 44, the relative roughnesses of the wall surfaces of the inner flow channels 52a-52e are adjusted in such a manner as to be in the order of, from roughest to smoothest, 52a, 52b, 52c, 52d, and 52e.

Moreover, even when the chip 1 fastened together with the holder is subjected to a pressure, since it is provided with the plural partition walls 9b formed across the width directions of the chip 1, the pressure resistance of the chip 1 can be improved and the chip 1 can be prevented from undergoing shape distortion, specifically shape distortion along the thickness direction. This feature offers the advantage that the occurrence of non-uniformity in velocity distribution due to bending of the chip 1 can be prevented. It also offers the advantage that even when the analysis is carried out using an optical system, since the unevenness in length of the optical paths and the alteration of the optical axis can be prevented, it becomes possible to carry out analysis under the favorable conditions, thereby the precision of analysis results being improved.

The following description will be made on the present embodiment focusing on the shape distortion resistance in contrast with the conventional problem.

According to the conventional analytical chips such as DNA chip and protein chip, in order to allow a number of specific substances to be arranged in a plane and then made in contact with the fluid sample, the reaction area is not limited to a local area but occupies a relatively large area. In addition, the conventional analytical chip generally has a sheet-like shape in which the flow channel has a large size along width directions and a small height, the request to reduce the amount of fluid sample. With this arrangement, the analytical chip is subjected to holding or drawing force along the thickness of the chip applied for joining the chip and to internal pressure from the fluid sample flowing through the flow channel in the analytical chip, which force and pressure cause compressive stress and tensile stress. As a result, the shape of the analytical chip can become deformed from the initial, ideal shape (in most cases, rectangular parallelepiped shapes or similar shapes), causing unevenness in height of the flow channel along the width directions. Although the initial, ideal shape is most typified by a rectangular parallelepiped shape, it can partially have a curved surface or an inclined plane surface.

The shape deformation is notable especially in the case where the analytical chip has a high size ratio (=[long side size]/[short side size]) or the analytical chip is made from a material whose strength (various elasticity coefficients) is low.

When the analytical chip is deformed from the initial, ideal shape, compared to the state where the analytical chip remains in the initial, ideal shape, the height distribution of the flow channel become varied along the width directions of the flow channel, so that the velocity distribution of the fluid sample flowing through the flow channel is altered from the initial velocity distribution. Further, when analysis is carried out using an optical system, the optical path length of a light beam passing through the flow channel may deviate from the initial optical path length due to the deformation of the analytical chip, or the orientation of the optical axis may shift due to a small amount of displacement in the part of the analytical chip through which the light beam passes. Of the cases where analysis is carried out using an optical system, especially in the case where the light beam is reflected by the surface of the analytical chip or the surface of the flow channel during analysis, the optical axis may be shifted from that of the initial, ideal shape. Thus, if any change takes place in the velocity of the fluid sample, the optical path length of the light beam, the orientation or the position of the optical axis, etc., there arises a possibility that accurate analysis is impossible.

Additionally, in the case where any parameter regarding the sample liquid, such as the species, the velocity, or the pressure of the sample liquid, changes with passage of time, in the case where the force for joining the analytical chip changes with passage of time, in the case where fluctuations in humidity or temperature cause change with time in parameters such as force for joining the analytical chip and the viscosity of the fluid sample, and in other similar cases, the shape deformation of the analytical chip also changes with passage of time accordingly and may hinder accurate analysis.

By contrast, in the analytical chip 1 according to the present embodiment, the partition walls 9b of the plate 9 divide the flow channel 5 across the width directions. The partition walls 9b serves as prop members interposed between the confronting surfaces of the flow channel 5, namely, between the surface of the basal plate 4 on the side facing the flow channel 5 and the surface of the plate 8 on the side facing the flow channel 5.

Being attached perpendicularly to the basal plate 4 while connecting the basal plate 4 with the plate 8, the partition walls 9b serve as the prop members for supporting the plate 8. With this arrangement, even if any force is exerted along the thickness of the chip 1, it is possible to prevent the deformation of the chip 1.

Alternatively, the state where the partition walls 9b are interposed in the flow channel 5 as prop members can also be explained as follows. The surface of the basal plate 4 on the side of the flow channel 5 (which defines the floor surface of the flow channel 5), the surface of the plate 8 on the side of flow channel 5 (which defines the ceiling surface of the flow channel 5), and the surfaces of the plate 9 facing the slit-form flow channels 9a (which define the left-side surface, the right-side surface, the upstream-end surface, and the downstream-end surface of the flow channel 5, respectively) collectively define the flow channel 5 as the sheet-shaped space. The partition walls 9b, which serves as prop members, are interposed at least either of between the left-side surface and the right-side surface flow channel 5 and between the upstream-end surface and the downstream-end surface of the flow channel 5 (in the present embodiment, between the upstream-end surface and the downstream-end surface).

With this arrangement, since the partition walls 9b are connected with the plate 9 at the upstream end of the flow channel 5 and the downstream end of the flow channel 5, it is possible to prevent the deformation of the chip 1 even when force is applied along the interposed directions of the partition walls 9b in the chip 1 {in the present embodiment, along the long sides, i.e., flow direction A}. However, since the shape distortion along the long sides of the analytical chip 1 is generally not as high as the shape distortion along the thickness, it is usually preferred to form the partition walls 9b in such a manner that the shape distortion along the thickness can be prevented.

Besides, although in the above description, the pressure exerted by the holder for joining the chip 1 is taken as an instance of the force applied to the chip 1, the partition walls 9b can be also arranged so as to prevent the occurrence of shape deformation due to other kinds of force. Specifically, it is possible to prevent the occurrence of shape deformation due to various kinds of force applied to the chip 1, such as the force resulting from pressure fluctuation of the fluid sample Fs in the flow channel 5 or changes in barometric pressure.

In addition, although in the present embodiment, the holder is used for joining the basal plate 4, the plates 8, 9, and the cover member 2 together to form the chip 1, it is also possible to fasten the confronting surfaces of the basal plate 4, the plates 8, 9, and the cover member 2 to each other using an adhesive or the like, thereby preventing not only the occurrence of deformation due to the force in compressive movement but also the occurrence of deformation due to the force in tensile movement or slide movement.

Since the deformation of the chip 1 can be prevented owing to the partition walls 9b being the prop members, as described above, it is possible to carry out analysis accurately without being disturbed by changes in the velocity distribution of the fluid sample Fb flowing through the flow channel 5, the optical path length of the light beam passing through the flow channel 5, the orientation of the optical axis, etc., as is in the conventional chip. Besides, even in the case where any parameter regarding the sample liquid Fs, such as the species, the velocity, or the pressure, changes with passage of time, in the case where the force for joining the analytical chip changes with passage of time, in the case where fluctuations in humidity or temperature cause change with time in parameters such as force for joining the analytical chip and the viscosity of the fluid sample, and in other similar cases, when the shape deformation of the analytical chip 1 fluctuates with the passage of time, it is possible to prevent the deformation of the chip 1 due to the fluctuation with time and to carry out analysis accurately.

Moreover, since the pitch of the spots of the specific substance 61 can be reduced to increase the number of the spots per unit area than in the conventional chip, as described above, it is possible to carry out analysis efficiently with only a small amount of fluid sample Fs. In other words, it is possible to achieve reduction in the necessary amount of the fluid sample Fs. Besides, by contrast to the conventional chip, in which the fluid sample Fs flows also through the space in the flow channel 5 being not faced by the specific substance 61, in the present embodiment, since at least part of the space in the flow channel 5 being not faced by the specific substance 61 is occupied by the partition wall 9b, it is possible to further reduce the amount of the fluid sample Fs by the volume occupied by the partition walls 9b.

In other words, without reducing the area to which the specific substance 61 is fixed, it is possible to reduce the area of a section of the flow channel 5 taken along a plane orthogonal to the flow direction of the fluid sample Fs through the flow channel 5 (hereinafter called the flow channel section). Consequently, the area where the fluid sample Fs touches the specific substance 61 can be increased than in the conventional chip, while the amount of the fluid sample Fs made flow through the flow channel 5 can be reduced than in the conventional chip. As a result, even when only a small amount of fluid sample Fs is usable, it becomes possible to make the fluid sample Fs in touch with plural spots of the specific substance 61 to realize high-throughput analysis, so that analysis can be carried out efficiently.

Besides, since the chip 1 is made from a high-strength material, the deformation of the chip 1 can be prevented. Moreover, such a high-strength material used for the chip 1 also prevent the flow channel 5 from breaking even when the flow channel 5 is subjected to a high pressure. As a result, even when any air bubbles 201 have occurred in the flow channel 5, it is possible to apply high pressure to the fluid sample Fs flowing through the flow channel 5 to thereby drain the air bubbles 201 forcibly.

The present invention also offers the advantage that it enables to reduce various wastes resulting from the occurrence of air bubbles 201, such as the number of times analytical work must be carried out and the amount of fluid sample Fs to be used accordingly, thereby enabling efficient analysis.

On the other hand, according to the production method of the present analytical chip 1, the plate 9 made from a material with a lower affinity for the fluid sample Fs than that of the basal plate 4 is fixed to the basal plate 4, and then the fluid containing specific substance is dropped through the slit-form openings 9a in the state where their upper parts are opened. Since in this process the fluid sample Fs is guided to the basal plate 4, it becomes possible to place the specific substance 61 securely within the slit-form flow channels 9a.

As is evident from the above description, the term "projection member" in the present specification means a member that can divide the flow channel 5 or a member formed as a projection that is interposed between confronting surfaces of the flow channel 5 and can support the confronting surfaces.

Figure 7A:
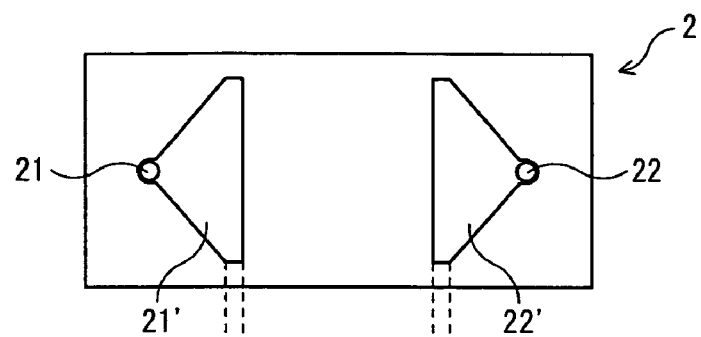
FIG. 7(a) is a diagrammatic bottom view of a cover member according to the first modification of the first embodiment of the present invention.
Figure 7B:
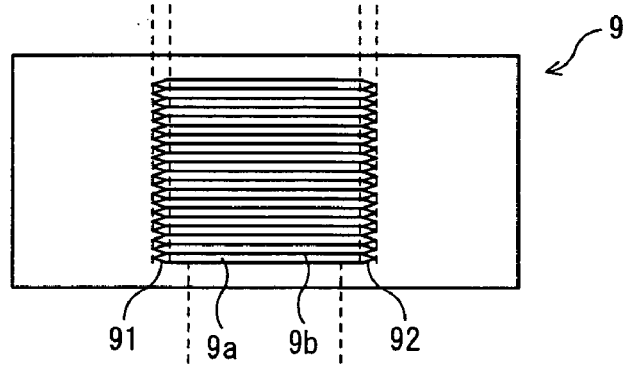
FIG. 7(b) is a diagrammatic top view of an intermediate plate according to the first modification of the first embodiment of the present invention.
Figure 7C:
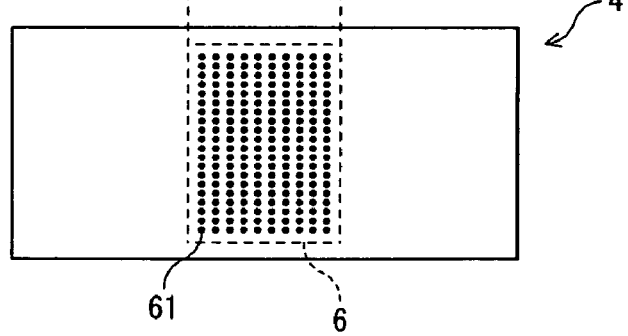
FIG. 7(c) is a diagrammatic top view of a basal plate according to the first modification of the first embodiment of the present invention.
Figure 8A:
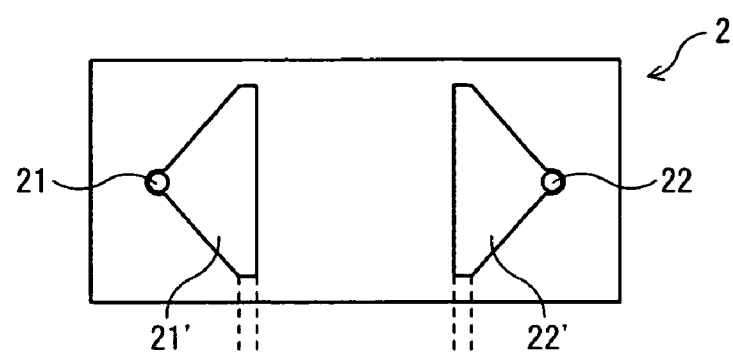
FIG. 8(a) is a diagrammatic bottom view of a cover member of the second modification of the first embodiment of the present invention.
Figure 8B:
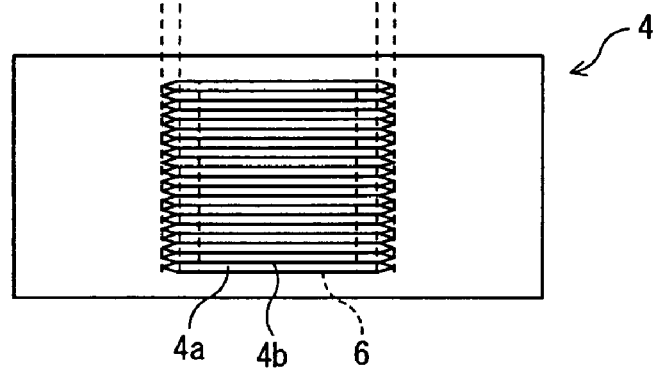
FIG. 8(b) is a diagrammatic top view of a basal plate according to the second modification of the first embodiment of the present invention.

Furthermore, although in the present embodiment the plate 8 and the plate 9 are sandwiched between the basal plate 4 and the cover member 2 to thereby form the chip 1, it is also preferable that as shown in FIGS. 7(a)–(c), the openings 81, 82 of the plate 8 defining the flow-channel confluence parts are incorporated into the cover member 2. In the modification, the cover member 2 has groove parts (concavity parts) 21', 22', which are formed directly on the under surface of the cover member 2 and have the shapes corresponding to the openings 81, 82 so as to define the flow-channel confluence parts. With this arrangement, since it is necessary only that the plate 9 be sandwiched between the basal plate 4 and the cover member 2, it is possible to make the chip 1 easily. Alternatively, it is also preferable that as shown in FIGS. 8(a), (b), in addition to the groove parts (concavity parts) 21', 22' formed directly on the under surface of the cover member 2 and having the shapes corresponding to the openings 81, 82 so as to define the flow-channel confluence parts, the slit-form grooves are formed directly on the basal plate 4 the slit-form flow channels 4a so as to eliminate the need for the plate 9. With this arrangement, since it is necessary only that the cover member 2 is laid on the basal plate 4, it is possible to make the chip 1 more easily. In the modification, the partition walls 4b between the slit-form grooves 4a function as projection member and prop members.

Figure 9A:
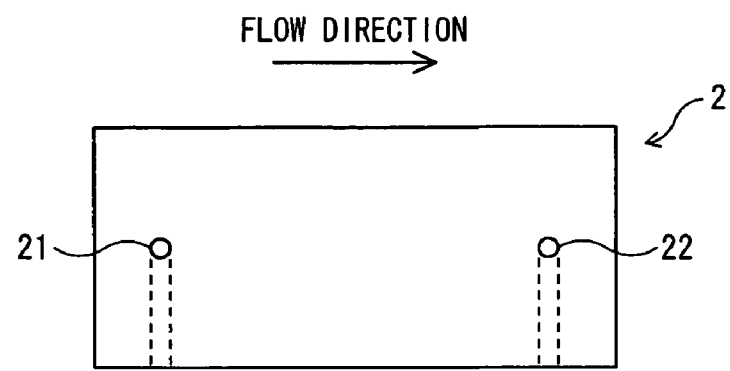
FIG. 9(a) is a diagrammatic top view of a cover member according to the third modification of the first embodiment of the present invention.
Figure 9B:
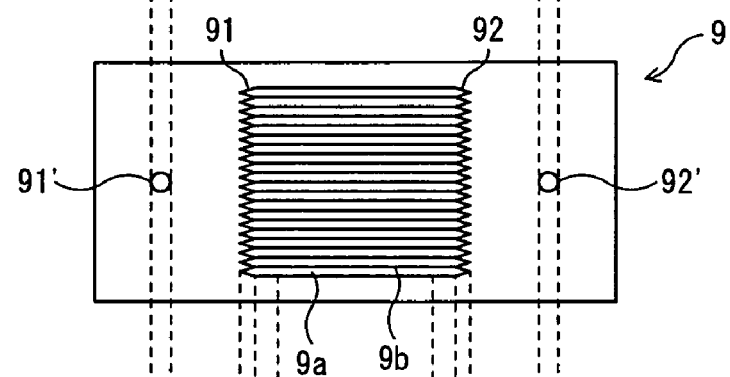
FIG. 9(b) is a diagrammatic top view of an intermediate plate according to the third modification of the first embodiment of the present invention.
Figure 9C:
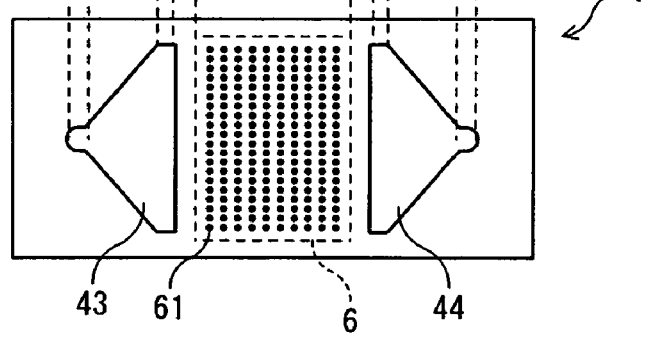
FIG. 9(c) is a diagrammatic top view of a basal plate according to the third modification of the first embodiment of the present invention.

It is also preferable that as shown in FIGS. 9(a)–(c), the openings 81, 82 of the plate 8 are incorporated into the basal plate 4 instead of using the plate 8. In the modification, the basal plate 4 has groove parts (concavity parts) 43, 44, which are directly formed on the top surface of the basal plate 4 and have the shapes corresponding to the openings 81, 82 so as to define the flow-channel confluence parts. In addition, the openings 91', 92' are formed through the plate 9 in such a manner that when the cover member 2 is laid on the plate 9, the opening 91' and the opening 92' are aligned with the injection port 21 and the drain port 22, respectively, to communicate with the injection port 21 and the drain port 22 with the groove parts. With this arrangement, since it is necessary only that the plate 9 is sandwiched between the basal plate 4 and the cover member 2, it is possible to make the chip 1 easily.

Figure 33:
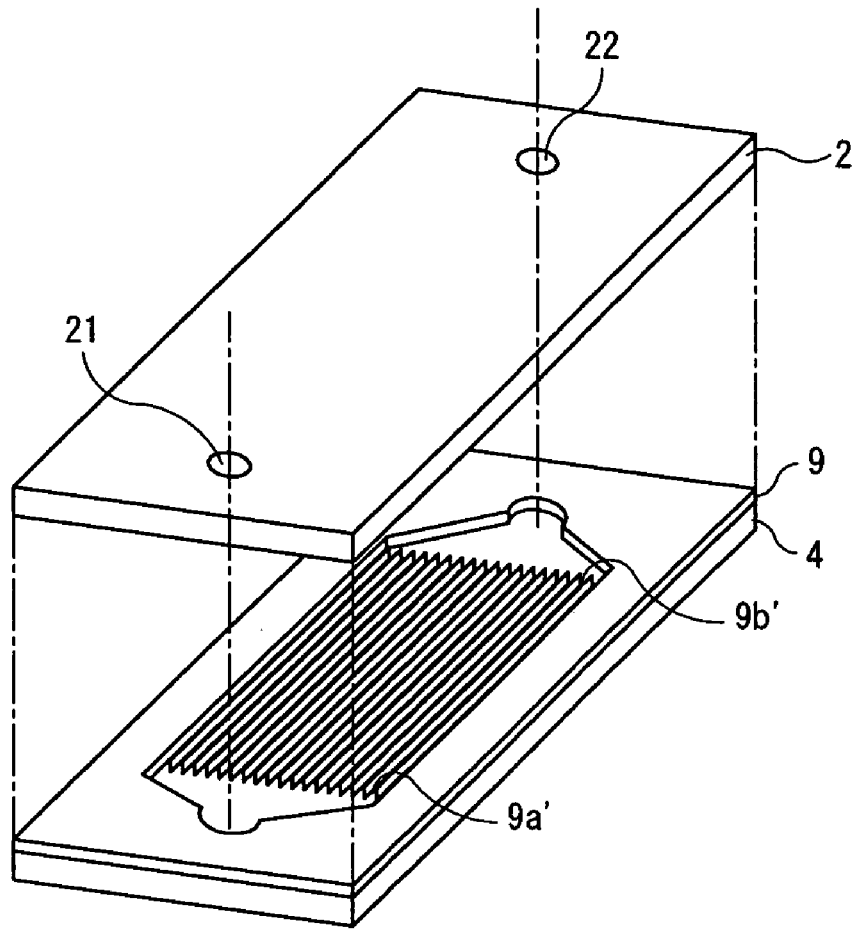
FIG. 33(a) is a diagrammatic exploded perspective view of an analytical chip according to an embodiment of the present invention.
FIG. 33(b) is a diagrammatic sectional view of substantial part of an analytical chip according to an embodiment of the present invention, being taken along a plane orthogonal to the flow direction of the flow channel.
Figure 33:
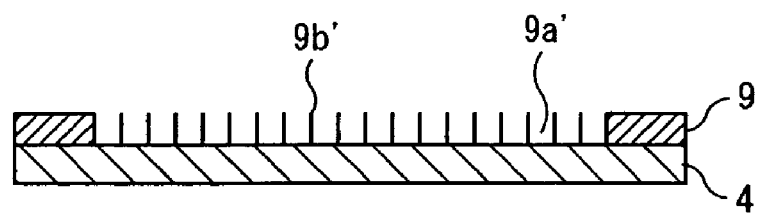

Another preferable modification is that the openings 81, 82 of the plate 8 are incorporated into the plate 9 and that the plate 9 is sandwich between the basal plate 4 and the cover member 2, thereby making the chip 1 (refer to FIG. 33(a)). The chip 1 according to the modification can be made more easily by using techniques such as screen printing, ink jet printing, and coating, as will be described later.

Figure 45:
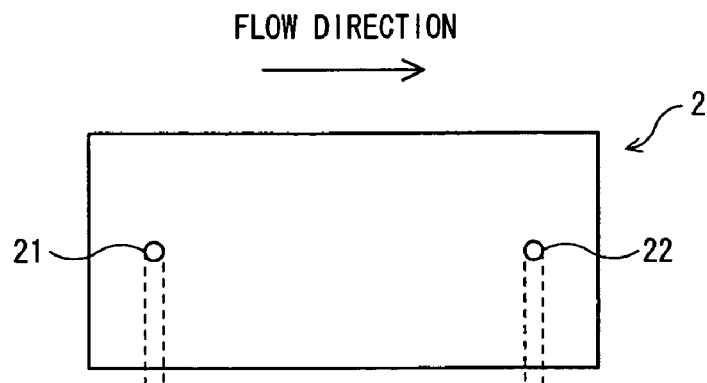
FIG. 45(a) is a diagrammatic top view of a cover member according to a modification the first embodiment of the present invention.
FIG. 45(b) is a diagrammatic top view of a plate according to a modification of the first embodiment of the present invention.
FIG. 45(c) is a diagrammatic top view of a basal plate according to a modification of the first embodiment of the present invention.
Figure 45:
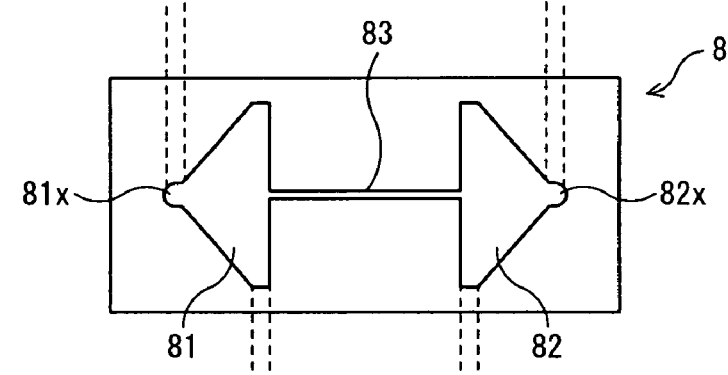
Figure 45:
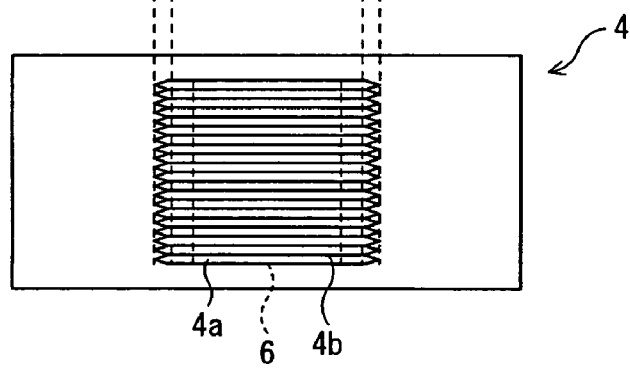

The inner flow channels can be formed also in two or three components from the cover member 2, the intermediate plate 8, and the basal plate 4. To take the modification shown in FIGS. 45(a)–(c) as an example, a slit-form opening 83 is formed through the plate 8 so as to interconnect the flow-channel confluence part 81 on the upstream side and the flow-channel confluence part 82 on the downstream side, while the slit-form grooves 4a are formed through the basal plate 4 so that the slit-form opening 83 and the slit-form grooves 4a both function as inner flow channels. Although in the modification, only the single slit-form opening 83 is formed in the plate 8, it is a matter of course that two or more slit-form openings 83 can be formed.

In FIGS. 7–9, 33, and 45, the reference characters also used in FIGS. 1–6 designate like components.

(2) Second Embodiment

An analytical chip according to the second embodiment of the present invention is constituted as an analytical chip (hereinafter called simply "the sensor chip") used for an SPR sensor, based on surface plasmon resonance (SPR: surface plasmon resonance).

The following description will be made on the SPR sensor and the sensor chip with reference to FIGS. 10 and 11.

Figure 10:
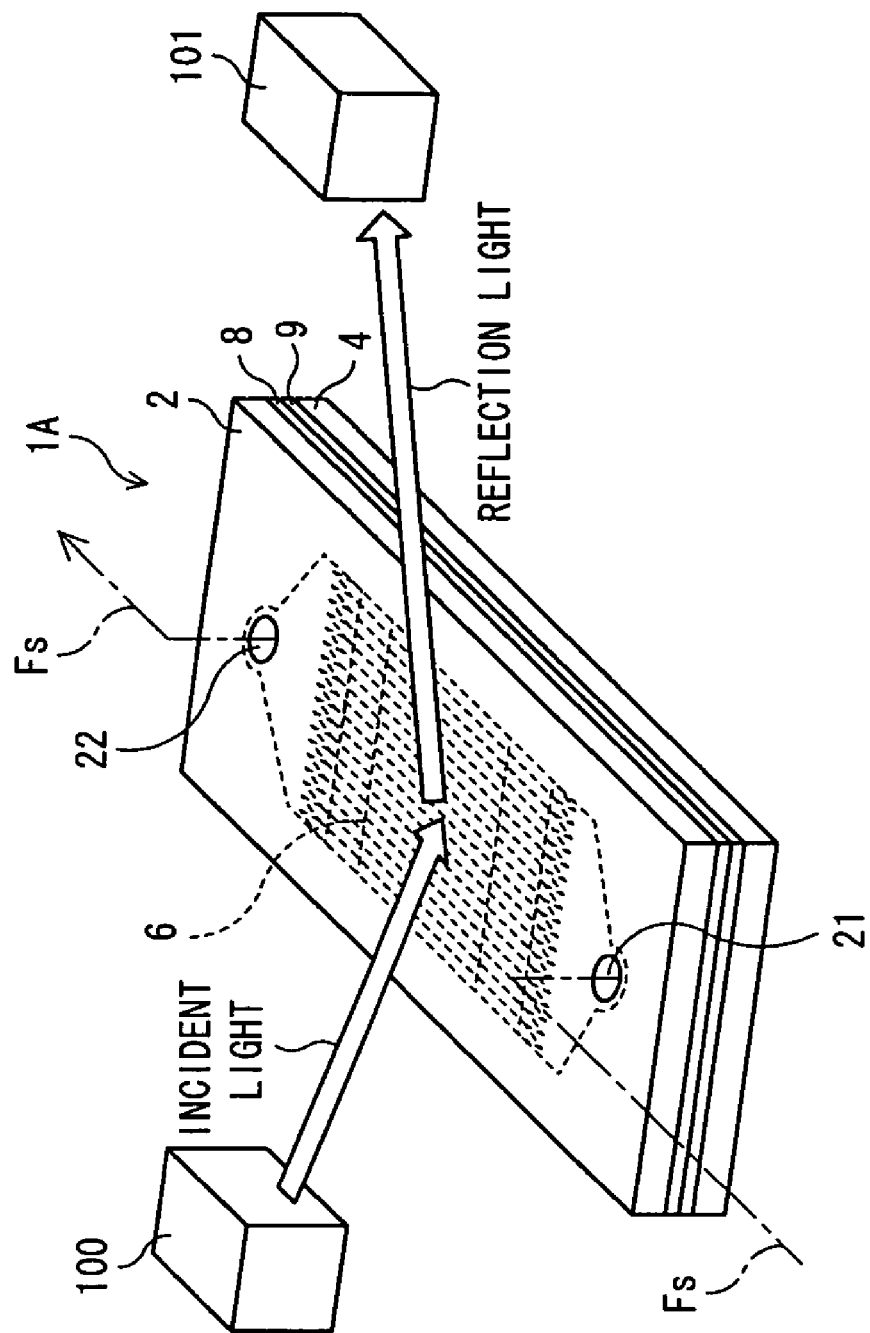
FIG. 10 is a diagrammatic perspective view of a whole constitution of an SPR sensor according to the second embodiment of the present invention.
Figure 11:
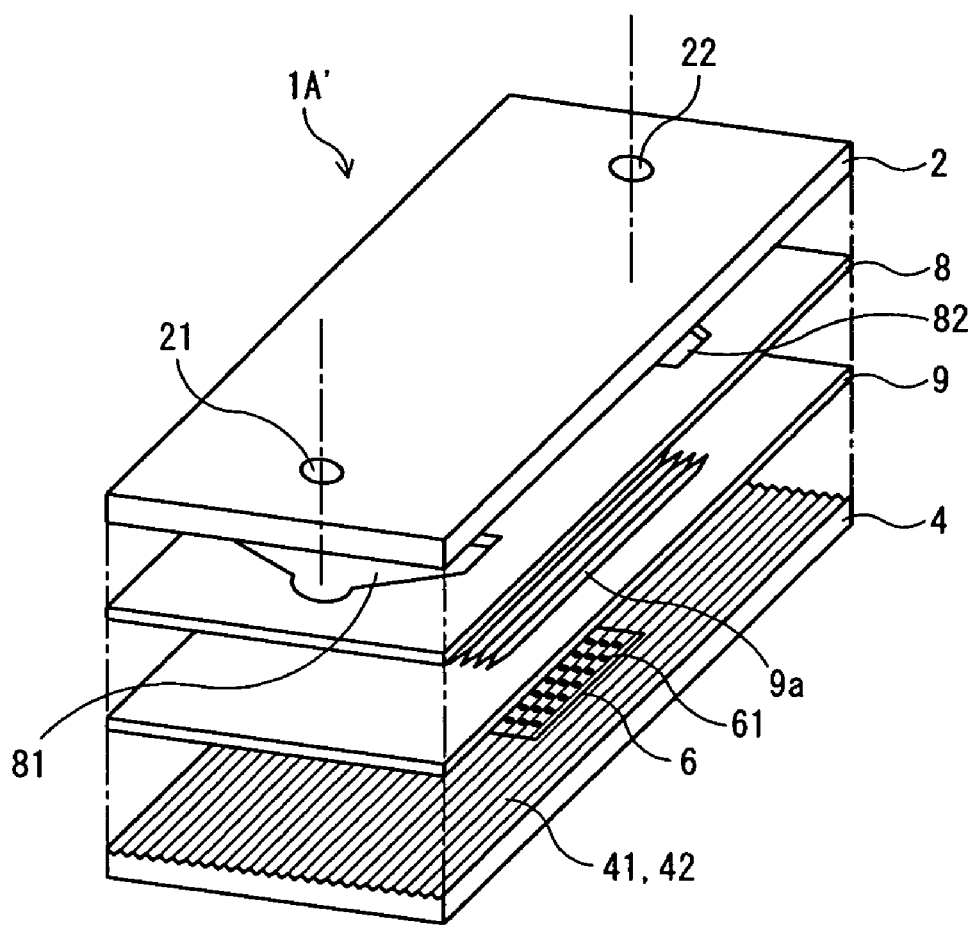
FIG. 11 is a diagrammatic exploded perspective view of the constitution of an analytical chip according to the second embodiment of the present invention.

FIGS. 10 and 11 each show the second embodiment of the present invention. Specifically, FIG. 10 is a diagrammatic system block diagram of the SPR sensor, and FIG. 11 is a diagrammatic exploded perspective view of the sensor chip for assistance in explaining the constitution of the sensor chip. In FIGS. 10 and 11, the same or similar components as already explained in the first embodiment are designated by like reference characters to omit redundant explanations.

As shown in FIG. 10, the SPR sensor is composed of sensor chip 1A, light source 100 for irradiating the sensor chip 1A with light, and detector (in the embodiment, CCD (charge coupled device) camera) 101 for detecting the reflection light from the sensor chip 1A. Although shown in FIG. 10 as both being perpendicular to the flow direction, the orientations of the optical axes for the incident light from the light source 100 and the reflection light from the sensor chip 1A are not limited to those in the drawing: for example, the optical axis for the incident light can be parallel with the flow direction, while the optical axis for the reflection light can have a different orientation from that of the incident light as a consequence of reflecting by the sensor chip 1A. The embodiment can be also modified such that the incident light is applied from the back face of the sensor chip 1 (from the side of the basal plate 4) while the reflection light is detected the back face of the sensor chip 1 (from the side of the basal plate 4) to carry out analysis. In the modification, however, it is necessary to make the basal plate 4 from a material that can transmit the incident light and the reflection light.

The sensor chip 1A, like the analytical chip 1 of the first embodiment described above (refer to FIG. 1), is composed of slit-form flow channels 9a and flow-channel confluence parts 81, 82 so that fluid sample Fs can be made flow through the slit-form flow channels 9a and the flow-channel confluence parts 81, 82 by means of an injection pump (not shown in the drawings).

As shown in FIG. 11, the sensor chip 1A is different from the analytical chip 1 of the first embodiment in that the basal plate 4 has an alternative constitution and that each of the cover member 2 and the plates 8, 9 is made from one or more transparent materials.

A metal layer 41 is coated over the surface of the basal plate 4 facing the slit-form flow channels 9a when the chip 1 is in the assembled state. Also, after the plate 9 is laid on the basal plate 4 as in the first embodiment, the surface coated with the metal layer 41 is processed to have diffraction grating 42, as an optical structure that can generate an evanescent wave, and reaction area 6 (two or more specific substances 61). The reaction area 6 is fixed directly to either the metal layer 41 or an organic film formed on the metal layer 41.

When the light is applied from the light source 100 toward the basal plate 4 through the cover member 2 and the plates 8, 9 being transparent, a surface plasmon wave is produced along the surface of the metal layer 41 while an evanescent wave is induced along the metal layer 41 due to the diffraction grating 42. These waves cause resonance to bring about energy absorption by the metal layer 41 from the optic element having a specific incident angle or a specific wavelength in the incident light applied to the metal layer 41.

As a result, in the reflection light from the metal layer 41, the energy of the optic element having a specific incident angle or a specific wavelength decreases.

The angle and the wavelength of the evanescent wave generated along the metal layer 41 varies depending on the amount of target species trapped by the specific substances 61 fixed to the metal layer 41 or the organic film formed on the metal layer 41, and the angle and the wavelength of the absorbed optical component of the reflection light also varies accordingly. The organic film in the embodiment can also be selected from conventional structures. Preferably, the organic film has the property of being able to fix the specific substance 61 to the metal layer 41 securely while preventing nonspecific absorption. Specifically, it is preferred that the organic film includes: as a functional group for binding to a biological substance, at least one group selected from amino, aldehyde, epoxy, carboxyl, carbonyl, hydrazide, hydroxyl, and vinyl group; and, for binding to the metal layer 41, one or more straight-chain macromolecules including at least one selected from isothiocyanato, isonitrile, xanthate, diselenide, sulfide, selenide, selenol, thiol, thiocarbamate, nitrile, nitro, and phosphine, and/or hydrocarbon chains having at least one double and/or triple bond. It is also preferable to use a material that forms hydrogel (agarose, alginic acid, carrageenin, cellulose, dextran, polyacrylamide, polyethylene glycol, polyvinyl alcohol, etc.) as a matrix. It is also preferable to use an organization structure such as a LB membrane, a self-assembled monolayer, or a lipid bilayer.

With this arrangement, by monitoring the light intensity of the reflection light from each of the specific substances 61 on the reaction area 6 using the CCD camera 101 to detect the change in the angle and/or the wavelength, it is possible to measure the concentration of target species contained in a test fluid in real time.

A material from which the metal layer 41 is made is not limited as long as it allows to induce surface plasmon wave, examples of which material include gold, silver, and aluminum.

The diffraction grating 42 can be embodied on the surface of the metal layer 41 by forming concavities and convexities on the surface of the basal plate 4, and then laminating on the concavities and convexities with a thin layer of a metal using a technique such as sputtering, to form the metal layer 41.

The concavities and convexities, which are formed for providing the basal plate 4 with the diffraction grating 42, can be formed by, for example, cutting the basal plate 4. The cutting method is not limited: it can be carried out mechanically, or chemically using a technique such as etching.

When making the basal plate 4 from a resin material, it is possible to form the concavities and convexities using a stumper on which the corresponding concavities and convexities are formed by means of photo lithography or the like. It can be achieved before the resin material has not solidify completely, by pressing the stumper on the basal plate 4, or by transferring the concavities and convexities from the stumper using a technique such as injection molding.

Constituted as described above, the analytical chip according to the second embodiment of the present invention (sensor chip) 1A, like the analytical chip 1 of the first embodiment, enables to inhibit the occurrence of air bubbles due to the enclosing flow of the fluid sample Fs, to prevent deformation of the analytical chip 1A, and to reduce the amount of the fluid sample Fs.

Another major feature of the analytical chip used for the SPR sensor is that it enables to detect the state of interaction in the reaction area 6 (the plural specific substances 61) optically and online.

Specifically, if an air bubble remains dwelling in the reaction area (i.e., the measurement area) 6 of the conventional chip, the dwelling air bubble may prevent not only interaction between the specific substance 61 and the target species but also optical measurement. By contrast, the present analytical chip 1A has the advantage that it prevents the occurrence of air bubbles and thereby enables to carry out analysis based on optical measurement online with stability.

Meanwhile, when carrying out analysis based on SPR as described above, it is possible not only to make a single fluid sample Fs flow into the microchannel chip for analysis, but also to make two or more fluid samples Fs flow one after another at successive intervals using a buffer and analyze a series of binding and dissociation between target substances contained in the fluid samples Fs and the specific substance.

Also, the detector 101 is not limited to a CCD camera, as is used in the present embodiment: any other kinds of detectors such as a photo diode, a photomultiplier, a photosensitive paper, etc. are also usable as the detector 101.

(3) Third Embodiment

Figure 12:
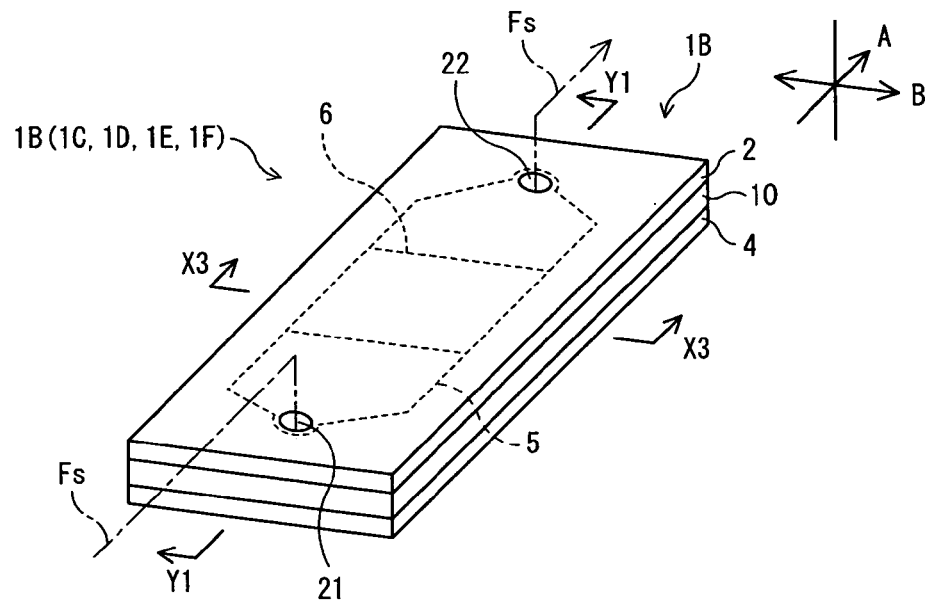
FIG. 12(a) is a diagrammatic assembled perspective view of an analytical chip according to the third embodiment of the present invention.
FIG. 12(b) is a diagrammatic exploded perspective view of the analytical chip according to the third embodiment of the present invention.
Figure 12:
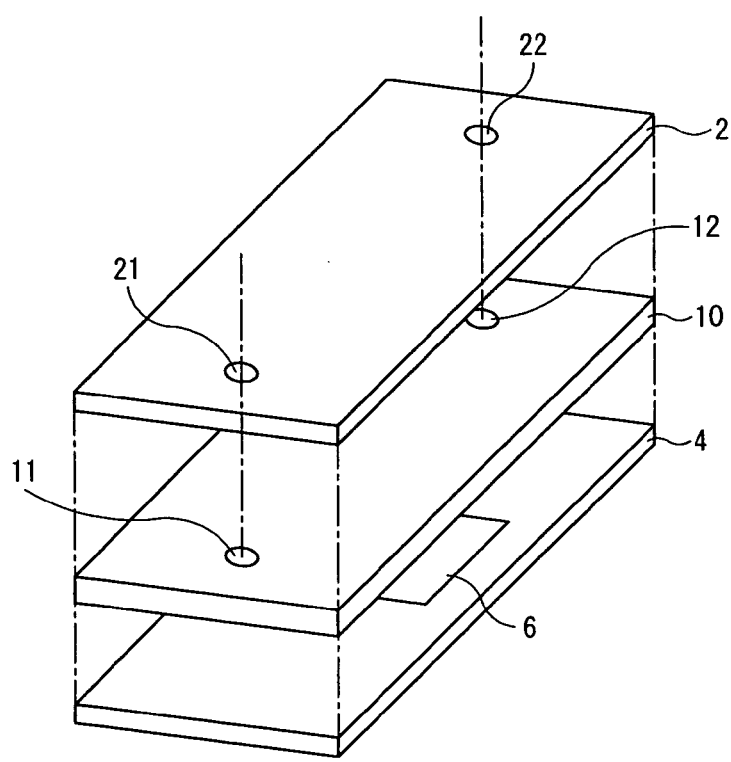
Figure 13:
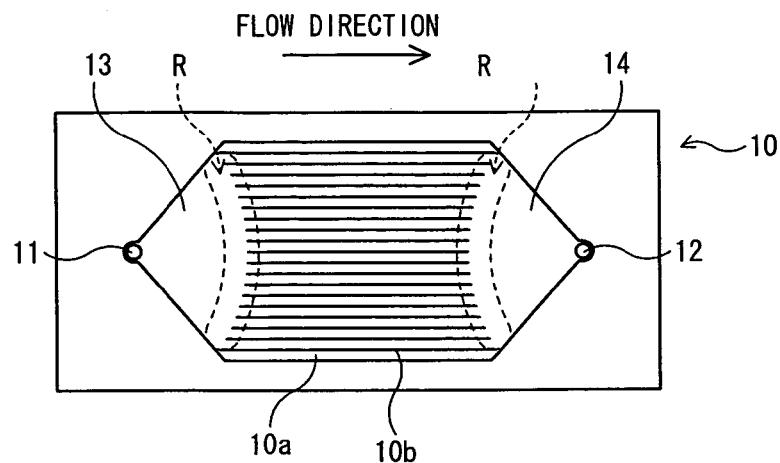
FIG. 13 is a diagrammatic bottom view of an intermediate plate provided in the analytical chip according to the third embodiment of the present invention.
Figure 14:
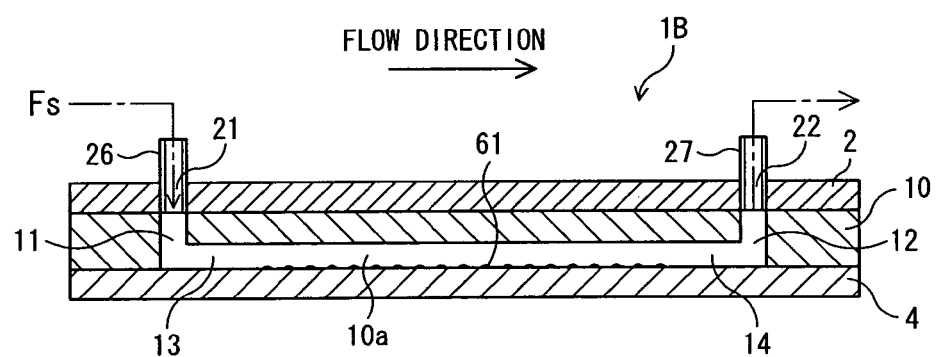
FIG. 14(a) is a diagrammatic sectional view taken on line Y1—Y1 of FIG. 12(a)
FIG. 14(b) is a diagrammatic sectional view taken on line X3—X3 of FIG. 12(a)
Figure 14:
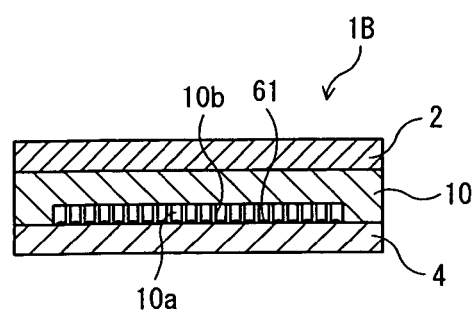

FIGS. 12 through 14 each illustrate the constitution of an analytical chip according to the third embodiment of the present invention. Specifically, FIG. 12(*a*) is a diagrammatic assembled perspective view of the chip, FIG. 12(*b*) is a diagrammatic exploded perspective view of the chip, FIG. 13 is a diagrammatic bottom view of a plate of the chip, FIG. 14(*a*) is a sectional view taken from Y1—Y1 of FIG. 12(*a*), and FIG. 14(*b*) is a sectional view taken from X3—X3 of FIG. 12(*a*). The same or similar components as already explained in the first embodiment are designated by like reference characters to omit redundant explanations.

As shown in FIGS. 12(*a*), (*b*), the present analytical chip (hereinafter also called simply "the chip") 1B is composed of cover member 2, plate 10, and basal plate 4.

A feature of the present analytical chip 1 compared to the first embodiment is that it has the plate (intermediate plate) 10 instead of the plates 8, 9. Hence, the following description will be made focusing on the plate 10 in detail.

Pipes 26, 27 (refer to FIG. 14) are put in the injection port 21 and the drain port 22 of the cover member 2, respectively, so as to facilitate the connection of tubes each leading to an external injection pump or waste liquid tank.

As shown in FIGS. 12(*a*), (*b*), the plate 10 has openings 11, 12 that can communicate with the injection port 21 and the drain port 22 of the cover member 2, respectively.

As shown in FIG. 13, the plate 10 also has concavity part 13 and concavity part 14 on the under surface (the side to be faced with the basal plate 4) of the plate 10. The concavity part 13 is formed in such a manner that its width becomes gradually broader from the opening 11 along the flow direction toward the middle part of the plate 10, while the concavity part 14 is formed in such a manner that its width becomes gradually narrower from the middle part of the plate 10 along the flow direction toward the opening 12.

When the plate 10 is laid on the basal plate 4, it blocks the openings of the concavity parts 13, 14 of the plate 10 to define parts of a flow channel in which a fluid sample Fs flows unitedly. In the following, therefore, the spaces defined by the basal plate 1 and the concavity parts 13, 14 of the plate 10 are called the flow-channel confluence parts 13, 14.

In the middle part of the plate 10 along the flow direction (an area between the concavity part 13 and the concavity part 14), two or more slit-form grooves 10*a* are formed, divided with one or more partition walls 10*b* across the width directions. When the plate 10 is laid on the basal plate 4, the concavity parts 13, 14 and the middle part of the plate 10 define a flow channel 5 through which a fluid sample Fs flows.

When the plate 10 is laid on the basal plate 4, it blocks the openings of the slit-form grooves 10a to define slit-form inner flow channels (slit-form flow channels). In the following, therefore, the slit-form grooves and the slit-form flow channels are designated by the same reference character, 10a.

It is preferable to form the individual slit-form flow channel 10a in such a manner that its cross section has an aspect ratio ([length size]/[width size]) of between 0.005 (i.e., 5 μm in length, 1 mm in width) and 100 (i.e., 1000 μm in length, 10 μm in width). Also preferably, the individual slit-form flow channel 10a is formed in such a manner as to have a cross sectional area of usually 5 mm$^2$ or below, preferably 100 μm$^2$ or above and 5 mm$^2$ or below, further preferably 2000 μm$^2$ or above and 0.3 mm$^2$ or below. With the slit-form flow channels 10a constituted as described above, it becomes possible to prevent more securely the occurrence of air bubbles in the flow channel due to running ahead of the fluid sample Fs.

For forming the concavity parts 13, 14 and the slit-form grooves 10a described above, the following methods can be selectively used: machining; various transferring techniques typified by injection molding and compression molding; dry etching (RIE, IE, IBE, plasma etching, laser etching, laser ablation, blasting, electrical discharge machining, LIGA, electron beam etching, FAB); wet etching (chemical erosion); integral molding such as optical machining or ceramic covering; Surface Micro-machining of coating with various substances in a layer and partially removing by means of vacuum evaporation, sputtering, deposition, or the like, to thereby form a microstructure; a method that includes dripping a material of the flow channel using an ink jet or a dispenser (namely, preliminary forming the concavity parts 13, 14 and the middle part of the flow direction integrally as a concavity portion, and then dripping the material of the channels onto the middle part along the flow direction flow to thereby form the partition walls 10b), optical machining method, etc.

Next, a production method of the present analytical chip 1B will be described. First, the fluid containing specific substance is dripped onto the target positions of the basal plate 4, using an injector or the like that is capable of positioning operation, so that the specific substance 61 is fixed to the basal plate 4 as spots arranged at regular intervals.

Next, as shown in FIG. 14(b), the plate 10 is mounted on the basal plate 4 in such a manner that each of the partition walls 10b of the plate 10 is aligned between adjacent rows of the specific substance 61, and the cover member 2 is set on the plate 10. Alternatively, it is also possible to use the cover member 2 and the plate 10 bonded together as a unit and set it on the basal plate 4.

Constituted as described above, when using the analytical chip according to the third embodiment of the present invention 1B, as shown in FIG. 14(a), the fluid sample Fs injected through the injection port 21 of the cover member 2 runs through the opening 11 of the plate 10 into the flow-channel confluence part 13, and then flows through each of the slit-form flow channels 10a, coming in touch with the specific substance 61 during the flowing.

Subsequently, the flows of the fluid sample Fs from the slit-form flow channels 10a run into the flow-channel confluence part 14 to join together, and the resultant flow run through the opening 12 of the plate 10 and drained from the drain port 22 of the cover member 2 to outside the chip 1.

As described above, according to the present analytical chip 1B, the width of the flow-channel confluence part 13 becomes gradually broader from the upstream end along the flow direction toward the middle part, it becomes possible to guide the fluid sample Fs smoothly toward the middle part along the flow direction. Also, since the width of the flow-channel confluence part 14 becomes gradually narrower from the middle part along the flow direction toward the downstream end, it becomes possible to guide the fluid sample Fs smoothly toward the downstream end.

Besides, providing the flow channel formed as a sheet-shaped space with the partition walls 10b to make narrow-width flow channels (slit-form flow channels) 10a, it becomes possible to prevent the occurrence of air bubbles due to enclosing flow of the fluid sample Fs.

Hence, according to the present analytical chip 1B, like the advantages of the first embodiment, it becomes possible to remove various adverse effects arising from the dwelling of air bubbles (such as the blockage of the normal flow of the fluid sample Fs, the hindering of the contact between the specific substance 61 and the fluid sample Fs, the non-uniformity of temperature in the system of measurement caused by the difference of heat transfer coefficient between the liquid Fs and the air bubble 201, the inhibition of the measurement during the analysis using an optical system because of the air bubble 201 dwelling in the optical path, etc.), resulting in the advantage that the reliability of analysis is improved. Besides, since it eliminates the need for extra work of getting rid of air bubbles, there is the advantage that analytical work can be carried out efficiently.

Moreover, even when the chip 1B fastened together with the holder is subjected to a constant pressure, like the first embodiment, since the plural partition walls 10b formed across the width directions of the chip 1B function as prop members, the pressure resistance of the chip 1B can be improved and the chip 1B can be prevented from undergoing shape distortion along the thickness direction. This feature offers the advantage that the occurrence of non-uniformity in velocity distribution due to bending of the chip 1B can be prevented. It also offers the advantage that even when the analysis is carried out using optical irradiation, since the unevenness in length of the optical paths and the alteration of the optical axis can be prevented, it becomes possible to carry out analysis under the favorable conditions, thereby the precision of analysis results being improved.

In addition, like the first embodiment, it becomes possible to reduce the necessary fluid sample Fs.

Meanwhile, although in the present embodiment the chip 1B is formed by sandwiching the plate 10 between the basal plate 4 and the cover member 2, it is also preferable, as shown in FIGS. 15(a), (b), to form directly on the under surface of the cover member 2 concavity parts 21', 22', which correspond to the concavity parts 13, 14 of the plate 10 so as to define flow-channel confluence parts, and the slit-form grooves 2a, which correspond to the slit-form grooves 10a of the plate 10 so as to define the inner flow channels. According to the modification, it is possible to make the chip 1B easily only by laying the cover member 2 on the basal plate 4, without the need of the plate 10. Meantime, reference character 2b designates the partition walls.

The analytical chip 1 made according to the above modification is thus composed of the basal plate 4 and the cover member 2, which is disposed facing the basal plate 4 so as to define, together with the basal plate 4, a sheet-shaped space having the flow channel 5 between the basal plate 4 and the cover member 2, and also having the partition walls 10b, which function as both prop members and partition members, in the flow channel 5.

Figure 16:
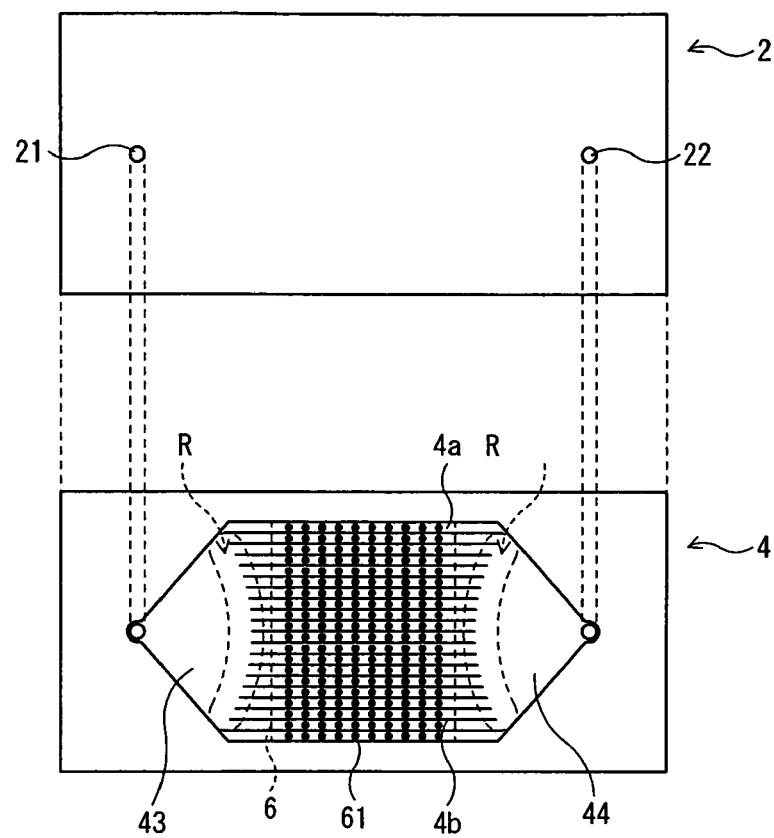
FIG. 16(a) is a diagrammatic bottom view of a cover member of the analytical chip according to the second modification of the third embodiment of the present invention.
FIG. 16(b) is a diagrammatic top view of a basal plate of the analytical chip according to the second modification of the third embodiment of the present invention.

Alternatively, it is also preferable, as shown in FIGS. 16(a), (b), to form, directly on the upper surface of the basal plate 4, concavity parts 43, 44, which correspond to the concavity parts 13, 14 of the plate 10 so as to define the flow-channel confluence parts, and the slit-form grooves 4a, which correspond to the slit-form grooves 10a of the plate 10 so as to define the inner flow channels. According to the modification, it is possible to make the chip 1B easily only by laying the cover member 2 on the basal plate 4, without the need of the plate 10. Meantime, reference character 4b designates the partition walls.

When forming the chip 1B only with the basal plate 4 and the cover member 2 as the above modifications, it is also preferable to form the injection port 21 and the drain port 22 of the fluid sample Fs on the side surface of the cover member 2 at the upstream and downstream ends, as shown in FIG. 17(a), or on the under surface of the basal plate 4, as shown in FIG. 17(b).

Figure 18:
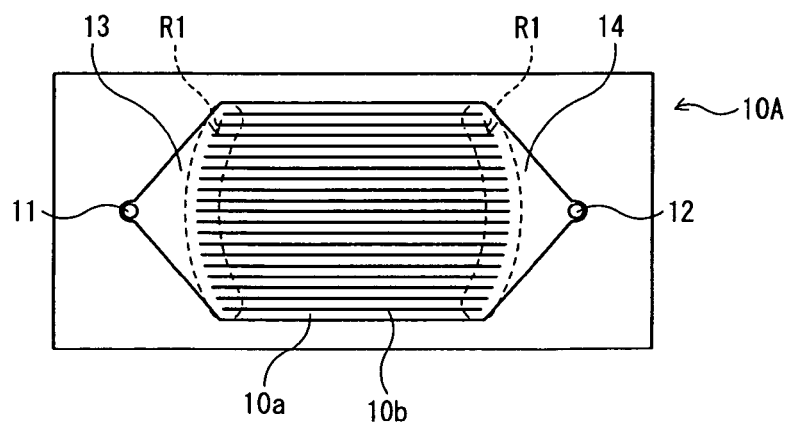
FIG. 18 is a diagrammatic bottom view of a modification of the intermediate plate according to the third embodiment of the present invention.

Besides, in the present embodiment, as indicated by reference character R of FIGS. 13, 15(a), and 16(b), the partition walls 10b, 2b, 4b are formed in such a manner that the distances between the opening 11 or the opening 12 and the ends of the individual partition walls 10b are substantially identical with each other. However, it is also preferable that, as indicated by reference character R1 of FIG. 18, the partition walls 10b are formed in such a manner that the individual partition wall 10b is longer (namely, the distance between the opening 11 or the opening 12 and the end of the individual partition wall 10b is shorter, compared to that shown in FIGS. 13, 15(a), and 16(b)) as it is closer to the center of the width directions. It is a matter of course that the modification illustrated by FIG. 18 is also applicable to the modifications illustrated by FIGS. 15(a) and 16(b).

(4) Fourth Embodiment

Figure 19:
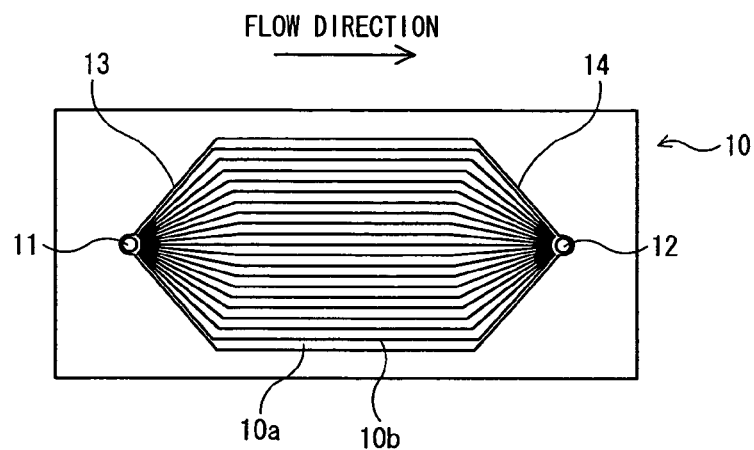
FIG. 19(a) is a diagrammatic bottom view of an intermediate plate according to the fourth embodiment of the present invention.
FIG. 19(b) is a diagrammatic bottom view of a cover member according to the fourth embodiment of the present invention.
FIG. 19(c) is a diagrammatic top view of a basal plate according to the fourth embodiment of the present invention.
Figure 19:
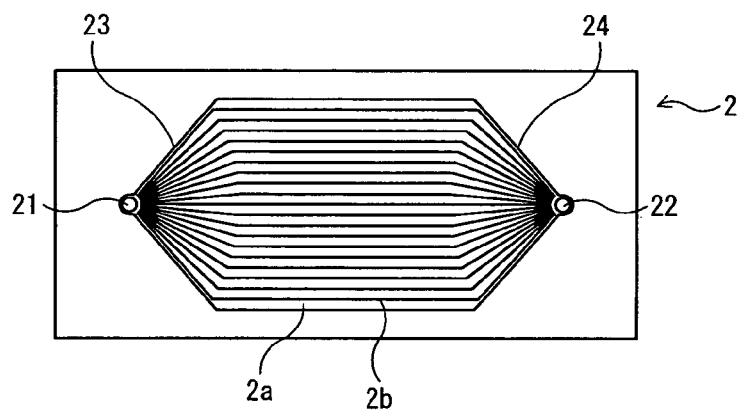
Figure 19:
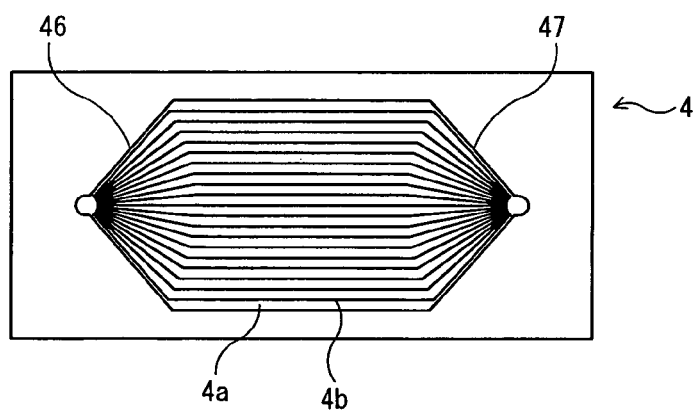

FIG. 19(a) is an explanatory bottom view of a plate (intermediate plate) according to the fourth embodiment of the present invention.

The analytical chip 1C according to the fourth embodiment of the present invention, as shown in FIG. 19(a), has the similar constitution to the above third embodiment illustrated by FIGS. 12–14, with the exception that the partition walls 10b of the intermediate plate 10 are formed so as to extend from the opening 11 being the injection port toward the opening 12 being the drain port. The same or similar components as already explained in the third embodiment are designated by like reference characters to omit redundant explanations.

Specifically, in the present embodiment, the partition walls 10b are formed not only around the middle part along the flow direction but also on the concavity parts 13, 14, and each of the inner flow channels 10a, which are divided by the partition walls 10, has the inlet port opened to the opening 11 and the outlet port opened to the opening 12. Hence, in the present embodiment, the concavity parts 13, 14 define part of the inner flow channels 10a, instead of defining part of the flow-channel confluence parts.

Since the fourth embodiment of the present invention is constituted as described above, it enables the same operations and advantageous effects as those of the third embodiment, except for the operations and advantageous effects resulted from the flow-channel confluence parts. In addition, since it is possible to form the inner flow channels so as to extend to even the concavity parts, which define the flow-channel confluence part in the third embodiment, it is possible to prevent the occurrence of air bubbles securely over a wider area in flow channel 5 and the deformation of the chip, and also to reduce the necessary amount of the fluid sample Fs further. Consequently, it becomes possible to carry out analysis more accurately and also to widen the reaction area, thereby efficient analysis being realized.

It is preferable to form the inner flow channels 10a so as to be substantially equal in length. Besides, by adjusting the pressure of the fluid sample Fs, the shapes of the partition walls 10b, the properties of the wall surface of the flow channel 5, etc., it becomes possible to form such that even if an air bubble arises, it can be easily removed with a backing pressure.

Besides, in the present embodiment, like the third embodiment, it is also preferable to, as shown in FIG. 19(b), form directly on the under surface of the cover member 2 groove parts (concavity parts) 23, 24 and slit-form grooves 2a, which correspond to the shapes of the concavity parts 13, 14 and the slit-form grooves 10a of the plate 10, respectively. Alternatively, it is also preferable to, as shown in FIG. 19(c), form directly on the upper surface of the basal plate 4 groove parts (concavity parts) 46, 47 and slit-form grooves 4a, which correspond to the shapes of the concavity parts 13, 14 and the slit-form groove 10a of the plate 10, respectively.

Excepting the points described above, the constitution of the chip of FIG. 19(b) is basically identical to that of the chip illustrated by FIGS. 15(a), (b), while the constitution of the chip of FIG. 19(c) is basically identical to that of the chip illustrated by FIGS. 16(a), (b).

(5) Fifth Embodiment

Figure 20:
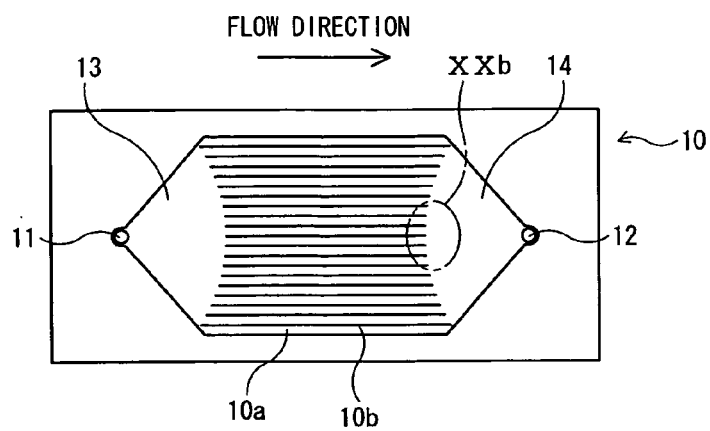
FIG. 20(a) is a diagrammatic bottom view of an intermediate plate according to the fifth embodiment of the present invention.
FIG. 20(b) is an enlarged view of the part designated by XXb in FIG. 20(a)
FIG. 20(c) is an enlarged view of the substantial part of a conventional plate.
Figure 20:
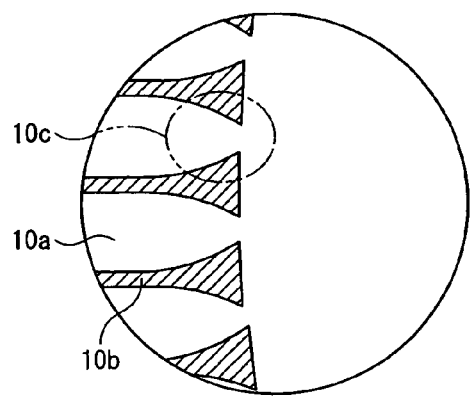
Figure 20:
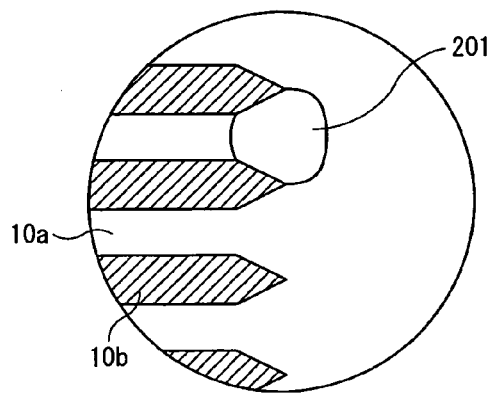

FIG. 20(a) is an explanatory bottom view of a plate (intermediate plate) according to the fifth embodiment of the present invention.

The analytical chip 1D according to the fifth embodiment of the present invention is identical in its basic constitution to the above third embodiment shown in FIG. 12(a). Namely, the chip illustrated by FIGS. 20(a), (b) has the similar constitution to that of the third embodiment except for the intermediate plate. The same or similar components as already explained in the third embodiment are designated by like reference characters to omit redundant explanations. Additional feature of the present embodiment is that, as shown in FIG. 20(b), contraction part 10c is formed at the downstream end of the individual inner flow channel 10a.

FIG. 20(b) is an enlarged view of part XXb of the FIG. 20(a). The contraction part 10c is a part of the inner flow channel 10a which is formed in such a manner that, as shown in FIG. 20(b), the inner flow channel 10a becomes gradually narrower, that is, a sectional area of the inner flow channel 10a which is perpendicular to the flow direction gradually decreases. In the drawing, it means the part formed in such a manner that the width of the inner flow channel 10a becomes gradually narrower.

With the constitution described above, the fifth embodiment of the present invention can produce, in addition to the similar advantages to those of the third embodiment, the advantage that it is possible to inhibit an air bubble from dwelling at the downstream end of the individual inner flow channel 10a.

To explain in detail, it is empirically expected that at the downstream end of the conventionally formed inner flow channel 10a, an air bubble 201 is apt to arise as illustrated by FIG. 20(c). One assumed reason is that in the inner flow channel 10a having a shape as indicated in FIG. 20(c) at the downstream end, backing pressure falls quickly at the downstream end of the inner flow channel 10a when the fluid sample Fs flows out of the inner flow channel 10a to run into the flow-channel confluence part 14 at the downstream side, causing the arising and dwelling of the air bubble 201. Although FIG. 20(c) illustrates the instance in which the inner flow channel 10a is formed in such a manner as to become gradually broader along the width directions at the downstream end (namely, in such a manner that the thickness of the partition wall 10b gradually decreases), the air bubble 201 can arise in a similar manner even when the downstream-side end of the inner flow channel 10a is formed to have a constant width along the width directions. By contrast, since the present embodiment has the contraction part 10c as described above, when the fluid sample Fs flows out of the inner flow channel 10a to run into the flow-channel confluence part 14 on the downstream side, it becomes possible to prevent the sudden drop of backing pressure, as is described in the above: since the linear velocity of the fluid sample Fs increases owing to the contraction part 10c illustrated by FIG. 20(b), it becomes possible to inhibit the air bubble 201 from remaining dwelling in the inner flow channel 10a.

It is a matter of course that the constitution of the present embodiment is also applicable to the other embodiments and their modifications.

(6) Sixth Embodiment

Figure 21:
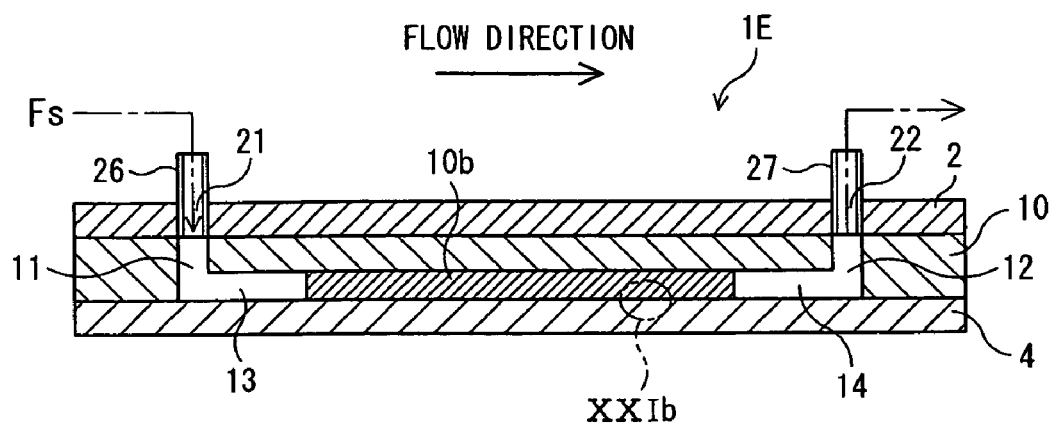
FIG. 21(a) is a diagrammatic sectional view of a part of the flow channel where the partition walls is formed in the analytical chip according to the sixth embodiment of the present invention, being taken along a plane orthogonal to the width directions of the flow channel.
FIG. 21(b) is an enlarged view of the part designated by XXIb in FIG. 21(a)
Figure 21:
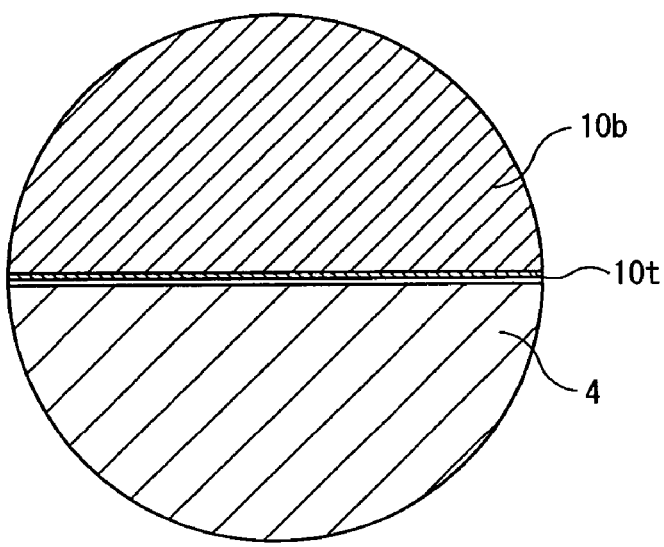

FIG. 21(a) is a sectional view of assistance in explaining the sixth embodiment of the present invention, diagrammatically showing an enlarged section taken along a plane orthogonal to the width directions of the flow channel around the area where partition walls are formed.

The analytical chip 1E according to the sixth embodiment of the present invention has a basic constitution, as shown in FIG. 21(a), identical to that of the above third embodiment. The same or similar components as already explained in the third embodiment are designated by like reference characters to omit redundant explanations. Besides, as shown in FIG. 21(a) and FIG. 21(b), which is an enlarged view of part XXIb of FIG. 21(a), the chip of the present embodiment has, on the side of the individual partition wall 10b confronting the basal plate 4, a layer (adhesion-reducing layer) lot made of a substance that can reduce adhesiveness between the partition wall 10b and the basal plate 4, for example, Teflon$^R$. The adhesiveness between the partition wall 10b and the basal plate 4 is reduced with the layer, while the partition wall 10b and the basal plate 4 are kept separated with a minute clearance.

The adhesiveness between the partition wall 10b and the basal plate 4 should be reduced to such a degree that, as a result of reduction, the fluid sample Fs being a fluid permeates through the gap between the partition wall 10b and the basal plate 4 and forms a thin liquid layer via which the partition wall 10c can support the basal plate 4. The actual adhesiveness value varies depending on the kind of the fluid sample Fs, conditions during analysis, and so forth.

In addition, the end of the individual partition wall 10b on the side of the plate 10 is formed integrally with the plate 10.

Constituted as described above, the sixth embodiment of the present invention offers, in addition to the same advantages as those of the third embodiment, an additional advantage that it can prevent the occurrence of shape deformation due to the stress between the partition wall 10b and the basal plate 4.

The following description goes into further details. When the individual partition wall 10b and the basal plate 4 are adhered to each other, or kept in highly close contact with each other, the analytical chip 1E may become deformed due to excessive stress placed on the part of the contact between the partition wall 10b and the basal plate 4. Specifically, in the production process of the analytical chip 1E, the chip can be subjected to a stress caused in adhering process of the partition walls 10b to the basal plate 4, or a stress caused because, after the adhesion, the chip deviates from its ideal shape (namely, the shape in a state where any force such as a stress or a pressure is not loaded to the chip) when the fluid sample Fs is made flow or when temperature fluctuates, which stress may bring about the shape deformation of the analytical chip 1E.

To solve the problem, the chip of the present embodiment is formed in such a manner that the adhesiveness between the individual partition wall 10b and the basal plate 4 is reduced and that when a fluid sample Fs being a liquid is made flow through the flow channel 5, the fluid sample Fs permeates partially through the gap between the partition wall 10b and the basal plate 4 and forms a thin liquid layer via which the partition wall 10c can support the basal plate 4, so that the plate 10 is supported by the basal plate 4. With this arrangement, because excessive stress is not transmitted between the partition wall 10b and the basal plate 4, it becomes possible to prevent the occurrence of stress between the partition wall 10b and the basal plate 4 and also prevent the occurrence of shape deformation due to the stress transmission.

It is preferable to reduce the size of clearance between the partition wall 10b and the basal plate 4 to a minimum as long as the partition wall 10b can support the basal plate 4 via the fluid sample 10b, which is in a state of a thin liquid layer, and as the normally expectable degree of deformation of the analytical chip 1E can be inhibit.

The adhesion-reducing layer is not limited to the layer made from Teflon$^R$, but can be made from any other substances as long as it can reduce the adhesiveness between the surface of the individual partition wall 10b and the surface of the basal plate 4.

Other methods are also available for making the partition wall 10b supported by the basal plate 4 via the fluid sample Fs between the partition wall 10b and the basal plate 4. For example, it is preferable to reduce the height of the partition wall 10b (namely, the size of the flow channel along the height direction) by an infinitesimal amount of between several through tens of nanometers, by means of a wet etching, such as chemical erosion, or a dry etching, such as reactive ion etching (Deep Reactive Ion Etching).

However, in the present embodiment, as distinct from the third embodiment, a leak of the fluid sample Fs may arise between the adjacent inner flow channels, i.e., between the adjacent slit-form grooves 10b through the gap between the partition wall 10b and the basal plate 4. It is therefore preferable to use the technique described in the present embodiment only when occurrence of such a leak arises is acceptable.

Also, although in the present embodiment the attention is focused on the part between the individual partition wall 10b and the basal plate 4, when the analytical chip 1E has a different constitution, the part to be supported by the fluid sample Fs should be selected depending on the constitution of the analytical chip 1E. Besides, when the flow channel 5 is formed so as to face the cover member 2, the gap between the partition wall 10b and the surface of the cover member 2 on the side of the flow channel 5 should be supported by the fluid sample Fs. The technique of the present embodiment can be applicable to any parts of the surface of the flow channel 5 on which a stress can be imposed.

Besides, although in the present embodiment the description was made on the instance where the fluid sample Fs is made flow through the gap between the individual partition wall 10b and the basal plate 4, the fluid to permeate through the gap between the partition wall 10c and the basal plate 4 is not limited to the present instance. For example, when a buffer, in addition to the fluid sample Fs, is made flow during analysis, it is possible to form such that the individual partition wall 10c supports the basal plate 4 via the buffer flowing through the flow channel 5. Furthermore, in the case where a gas such as air, or a mixture of a gas and a liquid, arises to dwell between the partition wall 10c and the basal plate 4, it is also allowable that the partition wall 10c support the basal plate 4 via such a gas or a mixture. However, when a gas arises to stay between the partition wall 10b and the basal plate 4, it is undesirable that the precision of analysis deteriorates due to the gas, specifically, due to the reason that the gas keeps dwelling continuously between the partition wall 10b and the basal plate 4 throughout the analysis, or due to the like reasons.

Additionally, it is not necessary that a fluid should keep staying continuously between the partition wall 10b and the basal plate 4. Even if, for example, the partition wall 10b and the basal plate 4 touch directly for an instant during analysis, it is allowable unless the touching causes excessive stress between the partition wall 10b and the basal plate 4.

(7) Seventh Embodiment

Figure 22:
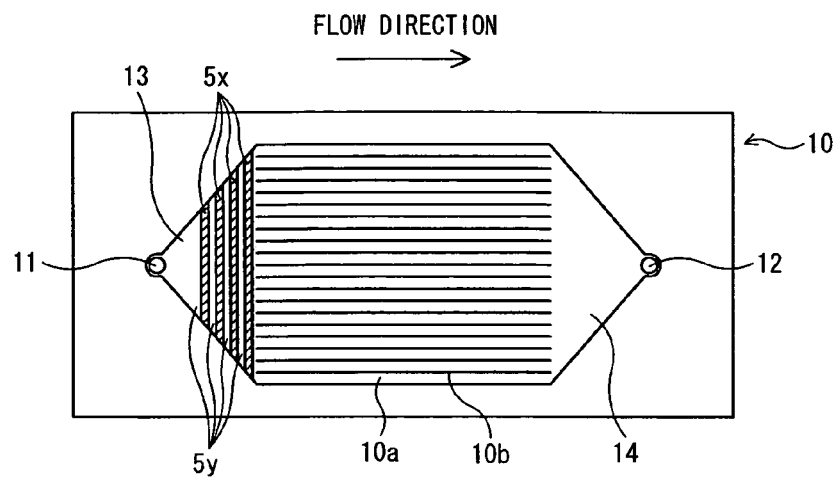
FIG. 22 is a diagrammatic bottom view of intermediate plate according to the seventh embodiment of the present invention.
Figure 23:
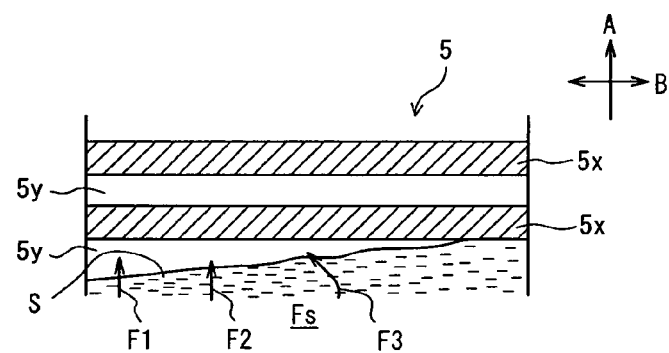
FIG. 23(a), FIG. 23(b) are diagrams of assistance in explaining the seventh embodiment of the present invention.
Figure 23:
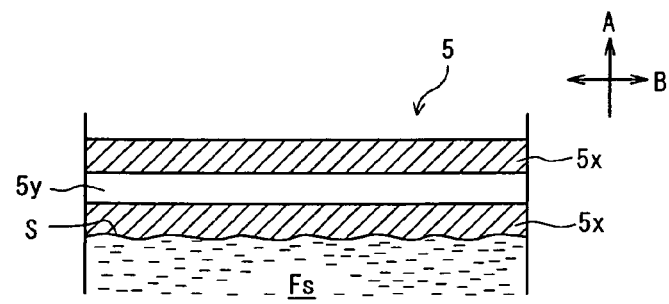

FIG. 22 is a diagrammatic bottom view of a plate (intermediate plate) for explaining the seventh embodiment of the present invention, and FIGS. 23(*a*), (*b*) are enlarged views of the plate for explaining its function.

The analytical chip 1F according to the seventh embodiment of the present invention is identical in its basic constitution to the above third embodiment. Namely, the chip illustrated by FIG. 22 and FIGS. 23(*a*), (*b*) has the same constitution as that of the third embodiment except for the plate. The same or similar components as already explained in the third embodiment are designated by like reference characters to omit redundant explanations. Besides, in the present embodiment, as shown in FIG. 22, the individual partition wall 10b is formed in such a manner that its upstream-side end and its downstream-side end are aligned in a line along the width directions, and the surface of the flow channel 5 on the side of the intermediate plate 10 is made to exhibit hydrophilicity. In addition, the flow-channel confluence part 13 on the upstream side of the flow channel 5 has, on its surface on the side of the intermediate plate 10, plural strip parts exhibiting hydrophobicity (hydrophobic parts. hereinafter called the hydrophobic parts) 5x, which are formed discretely so as to extend over the width of the flow channel 5 along the line perpendicular to the flow direction of the flow channel 5.

The flow-channel confluence part 13 thus has narrow strip parts (hydrophilic part. hereinafter called the hydrophilic parts) 5y that expose the surface of the intermediate plate 10, which is made to exhibit hydrophilicity, as first affinity parts, and the hydrophobic parts 5x as second affinity parts. As the result, in the flow-channel confluence part 13, the hydrophilic parts 5y and the hydrophobic parts 5x are arranged alternately along the flow direction. The term "affinity part" in the specification means a part that has a certain degree of affinity for a target substance. An "affinity part" therefore does not necessarily have high affinity for its target substance.

The hydrophobic parts 5x are formed to have thicknesses (the size of the flow direction of the flow channel 5) substantially identical to each other, while the hydrophilic parts 5y, separated by the hydrophobic parts 5x, are also formed to have thicknesses substantially identical to those of the hydrophobic parts 5x. The values of these thicknesses should be determined appropriately depending on various conditions and not necessarily be quite identical to each other, generally being equal to or lower than 10 µm through 1000 mm.

With the arrangement, even when a part of a fluid sample Fs exhibiting hydrophilicity precedes the remaining part to reach the hydrophobic parts 5x, as shown in FIG. 23(*a*), since the hydrophobic parts 5x are difficult to allow the fluid sample Fs to flow along, the preceding part of the fluid sample Fs falls into such a state as is braked at its contacting part with the hydrophobic parts 5x. The remaining part of the fluid sample Fs therefore flows round toward an area in which such a braking effect does not act and along which the fluid sample Fs is therefore easy to flow, i.e. the side area of the hydrophilic parts 5y which the fluid sample Fs has not reached yet, as indicated by arrows F1–F3.

Consequently, the preceding part of the fluid sample Fs is inhibited from getting over, and going beyond, the hydrophobic parts 5x until the hydrophobic parts 5x is fully reached by the fluid sample Fs along the whole width of the flow channel 5. It thus becomes possible to align the front edge (air-liquid interface) S of the flow of the fluid sample Fs along the width directions B, as shown in FIG. 23(*b*).

Although in the present embodiment the hydrophobic parts 5x are formed only on the intermediate plate 10 as described above, the hydrophobic parts 5x can be formed on any area of the surface of the flow channel 5, for example, on the side of the flow channel 5 along the surface of the basal plate 4. In addition, although it is most preferable that the hydrophobic parts 5x are formed all around the whole circumference along a cross section of the flow channel 5, since the distance across the flow channel 5 is so infinitesimal that the fluid sample Fs meets with high resistance from the wall surface of the flow channel 5, so long as the hydrophobic parts 5x are formed only on the intermediate plate 10 as in the present embodiment, it is possible to inhibit non-uniform flow of the fluid sample Fs to thereby align the front line of the fluid sample Fs.

Constituted as described above, the analytical chip according to the seventh embodiment of the present invention offers, in addition to the same advantages as those of the third embodiment, an additional advantage that it becomes possible to prevent the occurrence of air bubbles due to enclosing flow of the fluid sample Fs more securely owing to the hydrophilic parts 5y and the hydrophobic parts 5x and to thereby carry out analysis accurately with greater efficiency.

Besides, since the hydrophilic parts 5y and the hydrophobic parts 5x are form in the flow-channel confluence part 13, which is located upstream of the reaction area 6 along the flow direction, it becomes possible to prevent securely the occurrence of air bubbles before the fluid sample Fs fully reaches the reaction area 6, thereby accurate analysis being realized.

Besides, although in the present embodiment the first affinity parts 5y are formed to exhibit hydrophilicity while the second affinity parts 5x are formed to exhibit hydrophobicity, it is not necessary that both the hydrophilic parts and the hydrophobic parts are formed: it is also allowable to form the flow channel 5 in such a manner that, for example, hydrophobicity is imparted partially to the surface of the flow channel 5 or that, in contrast, hydrophilicity is imparted to only the remaining areas along the surface of the flow channel 5 other than predetermined areas (areas corresponding to the hydrophobic parts 5x), so that the second affinity parts exhibit lower affinity (in the present modification, a lower degree of hydrophilicity) for a liquid fluid Fs than that of the first affinity parts. However, equipped with both the hydrophilic parts 5y and the hydrophobic parts 5x, as is the present embodiment, it is possible to inhibit the occurrence of air bubbles more efficiently.

As the method for imparting hydrophilicity and hydrophobicity, various known methods are available. Specifically, when the surface of the flow channel 5 is made from hydrophobic materials with relatively low affinity, such as acrylic resins, polycarbonates, polystyrenes, silicones, polyurethanes, polyolefins, polytetrafluoroethylenes, polypropylenes, polyethylenes, and thermoplastic elastomers, examples of the method for imparting hydrophilicity to the surface include surface coating, wet chemical reforming, gas reforming, surface treatment using an active agent, corona discharge, rough surfacing, vacuum evaporation of metal, sputtering of metal, ultraviolet rays processing, and methods in which hydrophilic functional groups or hydrophilic molecules are added to the surface depending on the atmosphere during processing (plasma method, ion injection method, laser processing, etc.).

On the other hand, when the surface of the flow channel 5 is made from hydrophilic materials with relatively high affinity, such as glasses, metals, and ceramics, examples of the method for imparting hydrophobicity to the surface include surface coating and surface graft method of hydrophobic substances, such as adhesive agents and waxes, and methods in which hydrophilic functional groups or hydrophobic molecules are added to the surface depending on the atmosphere during processing (plasma method, ion injection method, laser processing, etc.).

When reforming (imparting hydrophilicity or hydrophobicity) the wall surface of the flow channel 5 as described above, it is possible to carry out any of the methods exemplified above selectively, for the local areas of the wall surface of the flow channel 5 which are to be reformed or, alternatively, wholly for the entire wall surface of the flow channel 5 with masking the local areas which are not to be reformed.

In addition, it is also possible to use additional hydrophilic or hydrophobic materials to thereby form partial patterns. For example, it is possible to paste hydrophobic materials on the wall surface of the flow channel 5 exhibiting hydrophilicity to thereby form the hydrophobic parts.

Besides, although in the present embodiment the hydrophilic parts 5y and the hydrophobic parts 5x are formed in strip shapes so as to extend all over the width of the flow channel 5, it is possible to adjust their size in width, their number to be arranged along the flow direction, their mutual intervals, their shapes, etc. suitably.

Figure 24:
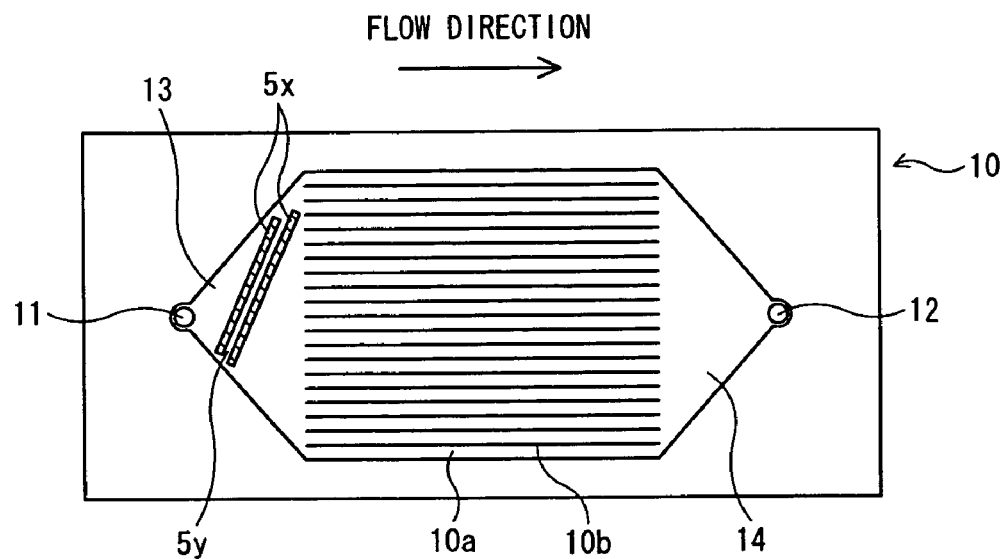
FIG. 24 is a diagrammatic bottom view of intermediate plate according to the first modification of the seventh embodiment of the present invention.

Besides, it is not necessary to form the hydrophilic parts 5y and the hydrophobic parts 5x always in strip shapes orthogonal to the flow direction of the flow channel 5. For example, as shown in FIG. 24, it is also possible to form them in strip shapes extending to slantingly cross the flow direction of the flow channel 5. Also, it is not necessary to form the hydrophobic parts 5x so as to range over the whole width of the flow channel 5. It is possible to adjust the angles, lengths, and so forth, of the hydrophilic parts 5y and the hydrophobic parts 5x, i.e., the first and second affinity parts, suitably depending on the constitution of the analytical chip 1F.

Figure 25:
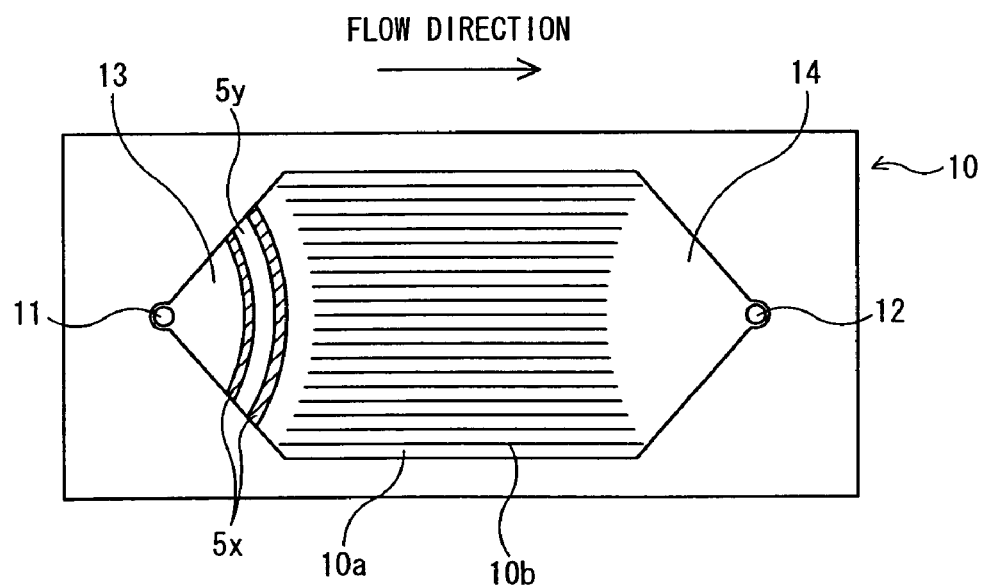
FIG. 25 is a diagrammatic bottom view of intermediate plate according to the second modification of the seventh embodiment of the present invention.

Also, it is possible to form the hydrophilic parts 5y and the hydrophobic parts 5x in non-linear shapes. For example, when setting the distances from the openings 11, 12 to the ends of the partition walls 10b so as to be substantially identical to each other as shown in FIG. 25, it is preferable to form the hydrophobic parts 5x in arc shapes in such a manner that their distances from the opening 11 are substantially uniform.

Besides, although in the present embodiment more than one first affinity part and more than one second affinity part are formed, it is allowable so long as at least one first affinity part and at least one second affinity part are formed. It is still preferable, however, to arrange the plural first affinity parts and the plural second affinity parts along the flow direction. If the front line of the fluid sample Fs is non-uniform the moment it reaches the hydrophobic parts 5x, it is difficult to sufficiently reduce the non-uniformity. Even in such a case, by arranging the plural hydrophobic parts 5x along the flow direction, it is possible to repeatedly align the front line of the fluid sample Fs and to thereby prevent the enclosing of air securely.

The first affinity parts 5y and the second affinity parts 5x can be disposed to any areas in the flow channel 5. For example, it is possible to form the first affinity parts 5y and the second affinity parts 5x on the middle part of the flow channel 5 as shown in FIG. 26(a), to form the first affinity parts 5y and the second affinity parts 5x on the flow-channel confluence part 14 at the downstream side as shown in FIG. 26(b), and to arrange the first affinity parts 5y and the second affinity parts 5x alternately along the whole length of the flow channel 5 as shown in FIG. 26(c).

Meantime, the chip illustrated by each of FIG. 24, FIG. 25, and FIGS. 26(a)–(c) is identical in its basic constitution to that of the above third embodiment except for the points described above.

Although the above embodiment was explained assuming that the fluid sample Fs is hydrophilic, the fluid sample Fs can also be hydrophobic. In the case, the hydrophobic parts are to be replaced with lyophilic parts (parts exhibiting relatively low lyophilicity), while the hydrophilic parts are to be replaced with lyophilic parts, which exhibit higher lyophilicity than the lyophobic parts.

Although in the above embodiment the first affinity parts 5y are formed as hydrophilic parts while the second affinity parts 5x are formed as hydrophobic parts, it is also possible to form the first affinity parts 5x as rough-surfaced parts and the second affinity parts 5y as smooth-surfaced parts, where the smooth-surfaced parts means parts having smoother surface than that of the rough-surfaced parts. Directing the wettability of the surface of the flow channel 5, the face with smooth surface generally exhibits a lower affinity for the fluid sample Fs than the face with rough surface. Hence, in the embodiment described above, it becomes possible to prevent the dwelling of air bubbles. Incidentally, although it was described in the above first embodiment that the flow channel 5 having rough surface causes increase in pressure loss of the fluid sample Fs flowing through the flow channel 5, the description of the first embodiment can be consistent with the description of the present modification because the "pressure loss" and the "wettability" at the interface between the three phases of solid-gas-liquid (the property when the fluid sample Fs begins to flow into the flow channel 5 through which the fluid sample Fs has not yet flowed) are conceptually different from each other.

Moreover, although the above embodiment is based on the instance in which only the first affinity parts 5y and the second affinity parts 5x are formed on the flow channel 5, the chip according to the present embodiment can have, in addition to the necessary first and second affinity parts, additional affinity parts that have a different affinity for the fluid sample Fs from those of the first affinity parts $5y$ and the second affinity parts $5x$.

(8) Eighth Embodiment

Figure 27:
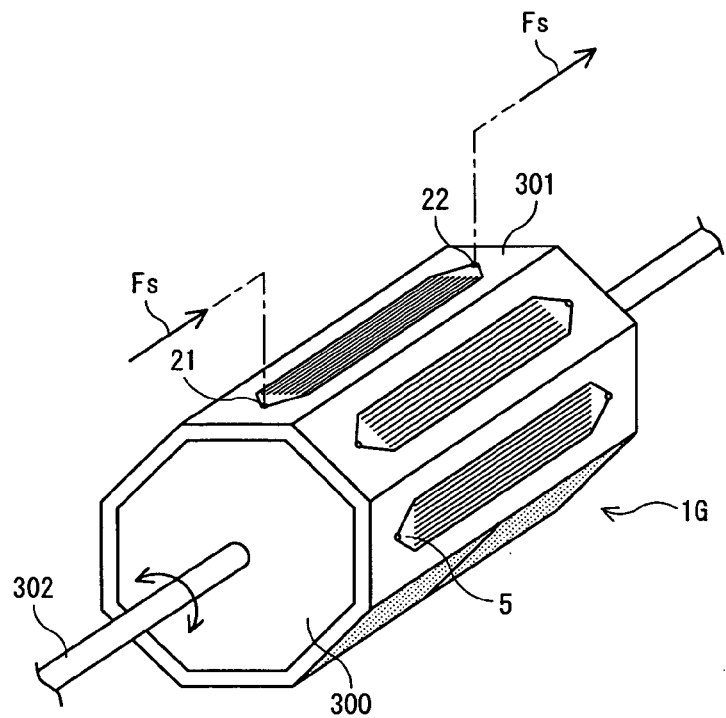
FIG. 27 is a diagrammatic perspective view of an analytical-chip unit according to the eighth embodiment of the present invention.

FIG. 27 is a perspective view diagrammatically showing the eighth embodiment of the present invention.

As shown in FIG. 27, the analytical-chip unit 1G according to the eighth embodiment of the present invention has unit base 300, which is formed in the shape of an equilateral octagonal prism, and rotation support shaft 302, which is attached to the unit base so as to pass through the centers of both ends of the equilateral octagonal prism. In addition, each side of the equilateral octagonal prism of the unit base 300 supports unit chip 301, which has the same constitution of the analytical chip according to any one of the first and third through seventh embodiments. The unit base 300 is rotatable about the support shaft 301 as the rotation axis. The unit chip 301, which was described in the first embodiment, has the same constitution as already described in the above first and third through seventh embodiments, so that redundant explanation is omitted. In FIG. 27 the flow channel 5 of the unit chip 301 is exposed for the sake of explanation, although it is actually covered with the cover member 2 and the plates 8, 9, 10.

Using the analytical-chip unit 1G according to the eighth embodiment of the present invention, which is constituted as described above, analysis is carried out with a unit chip 301 of the analytical-chip unit 1G at a predetermined position. Namely, the fluid sample Fs is first injected from the injection port 21 into the flow channel 5 of the unit chip 301 at the certain position, then flows through the flow channel 5 during analysis, and, after the analysis, is drained from the drain port 22 to outside the unit chip 301. After the analysis using the certain unit chip 301 is completed, the unit base 300 is rotated a predetermined angle (e.g., an integral multiple of 45°) about the rotation support shaft 302 so as to place another unit chip 301 at the predetermined position, and analysis is again carried out now using the unit chip 301 placed at the predetermined position. The series of operations is repeated while analysis with the analytical-chip unit 1G is carried out.

Fixing a different kind of specific substance 61 to each unit chip 301 previously, it becomes possible to detect different kinds of predetermined substances without difficulty simply by rotating the analytical-chip unit 1G, and to thereby carry out analysis of the fluid sample Fs efficiently.

Although in the present embodiment the unit base 300 is formed in the shape of an equilateral octagonal prism, the shape of the unit base 300 is not limited to the above mentioned shape but also can be other possible shapes.

It is not necessary to dispose the unit chip 301 to all the sides of the unit base 300, but it is also possible to dispose the unit chip 301 only to some of the sides of the unit base 300.

Figure 28:
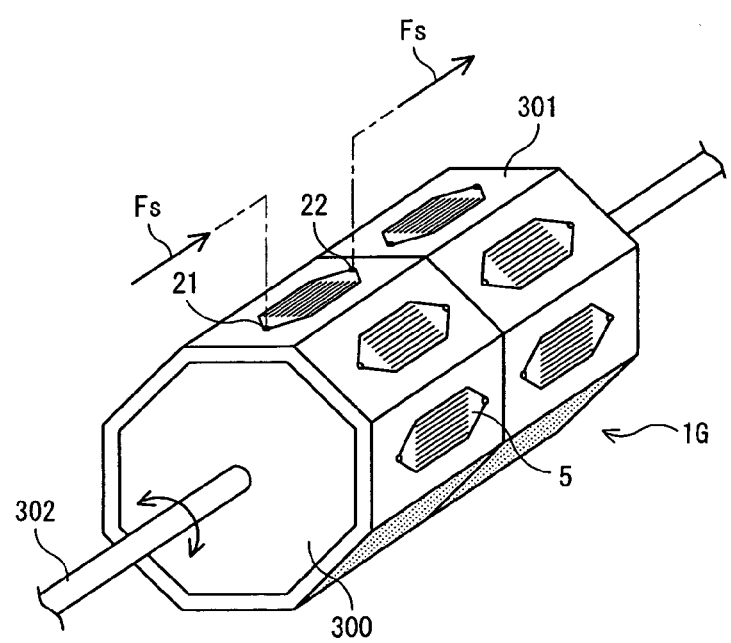
FIG. 28 is a diagrammatic perspective view of an analytical-chip unit according to a modification of the eighth embodiment of the present invention.

Also, it is not necessary that a side of the unit base 300 supports only one unit chip 301, but it is also possible that, as shown in FIG. 28, a side of the unit base 300 supports two or more unit chips 301.

It is a matter of course that the unit chip 301 is not limited to the one having the same constitution as any of the first and third through seventh embodiments, and that any analytical chips having other constitutions also can be used as the unit chip.

(9) Ninth Embodiment

Figure 29:
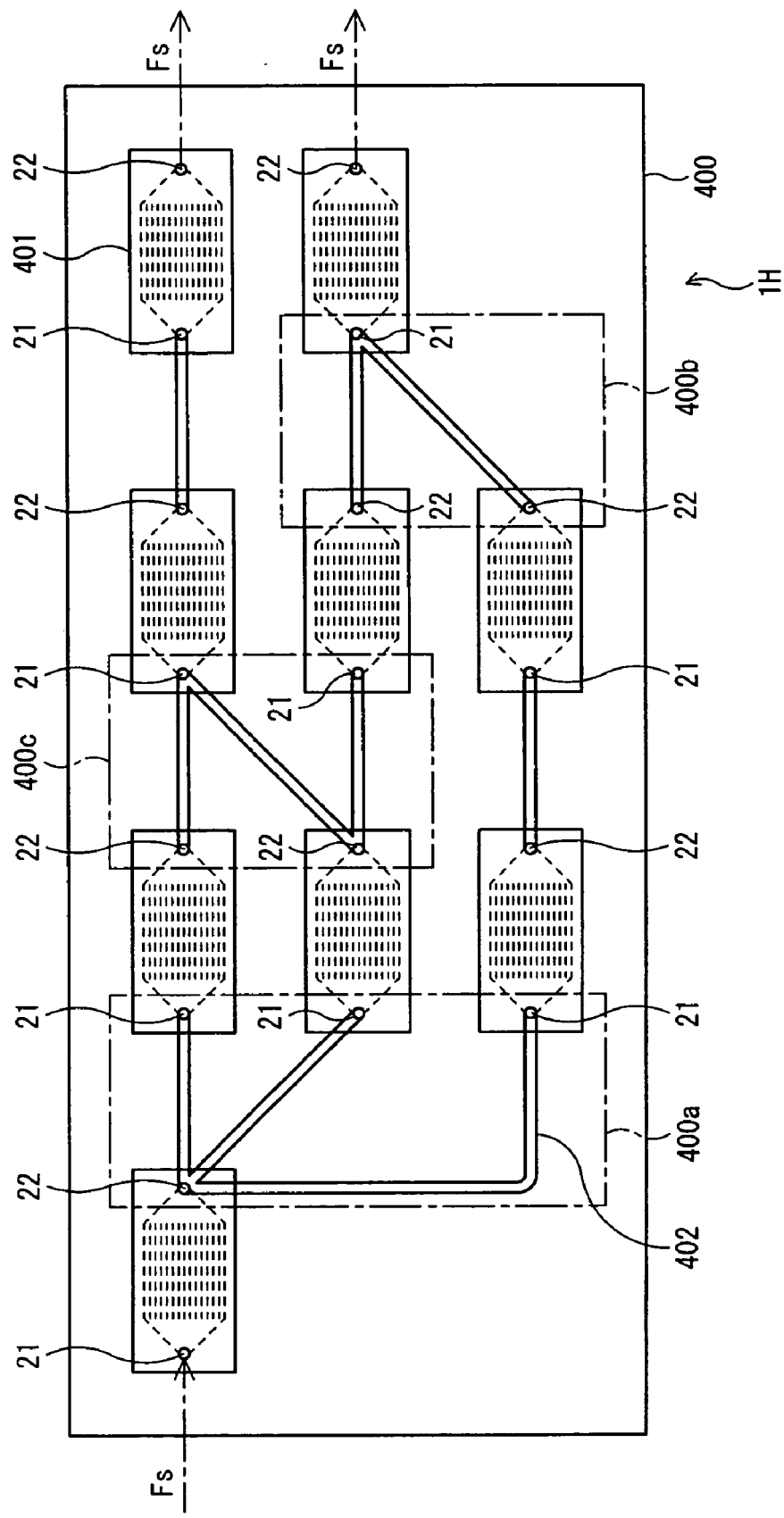
FIG. 29 is a diagrammatic plan view of assistance in explaining an analytical-chip unit according to the ninth embodiment of the present invention.

FIG. 29 is a diagram of assistance in explaining the ninth embodiment of the present invention.

As shown in FIG. 29, the analytical-chip unit 1H according to the ninth embodiment of the present invention has unit base 400, which is formed in a flat-plate shape, and plural unit chips 401, each of which has the same constitution as that of the analytical chip according to any one of the first and third through seventh embodiments. The constitution of the individual unit chip 401 has been already described above in detail in the first and third through seventh embodiments, so that redundant explanation is omitted.

Also, with the exception of the injection port 21 of the unit chip 401 positioned most upstream and the drain port 22 of the unit chip 401 positioned most downstream, as shown in FIG. 29, the injection port 21 of each unit chip 401 is connected with the drain port 22 of another unit chip 401, which is to be associated with the injection port 21 of the aforesaid unit chip 401, by connection flow channel 402, which is disposed to the unit base 401. In the instance, one connection flow channel 402 interconnects the drain port 22 of one unit chip 401 and the injection ports 21 of other plural unit chips 401 (reference character 400a of FIG. 29), another connection flow channel 402 interconnects the drain ports 22 of plural unit chips 401 and the injection port 21 of another one unit chip 401 (reference character 400b of FIG. 29), and still another connection flow channel 402 interconnects the drain ports 22 of plural unit chips 401 and the injection ports 21 of other plural unit chips 401 (reference character 400c of FIG. 29).

When using the analytical-chip unit 1H according to the ninth embodiment of the present invention, constituted as described above, the fluid sample Fs is injected from the injection port 21 at the upstream end and flows through each of the unit chips 401 and the connection flow channels 402 while analysis is carried out. After flowing through the unit chips 401 and the connection flow channels 402, the fluid sample Fs is drained from the drain port 22 of the unit chip 401 at the downstream end.

Using the above analytical-chip unit 1H with interconnected unit chips 401, it becomes possible to carry out analysis of the fluid sample Fs efficiently.

Specifically, fixing different kinds of specific substance 61 to plural unit chips 401, it is possible to detect plural kinds of predetermined substances simultaneously through a single analysis operation, so that analysis of the fluid sample Fs can be carried out efficiently.

On the contrast, fixing a single kind of specific substance 61 to plural unit chips 401, since observation and measurement can be carried out for each reaction area of the unit chips 401, it is possible to obtain multiple data through a single analysis operation and to thereby improve the reliability of the analysis results.

Besides, since the plural unit chips 401 are integrated in the single analytical-chip unit 1H, it is possible to reduce the dead volume of the sample, which becomes large when conventional separate analytical chips are used. In addition, since the need for the installation of piping or the like, which is necessary when conventional separate analytical chips are used, can be negated, it becomes possible to reduce costs for the arrangement and inspection of such equipment and, also, to eliminate various hindrances to precise and efficient analysis, such as the possibility of leakage, fluctuations in temperature and humidity outside the chip, blockage in pipes, tubes, connectors, etc., and absorption by materials of tubes or connectors.

In the meantime, the combination and arrangement of the unit chips 401 supported by the unit base 400 are not restricted particularly but can be determined freely depending on the purpose.

Also, it is a matter of course that the unit chip 401 is not limited to the one having the same constitution as any of the first and third through seventh embodiments, and that any analytical chips having other constitutions also can be used as the unit chip.

(10) Tenth Embodiment

Figure 30:
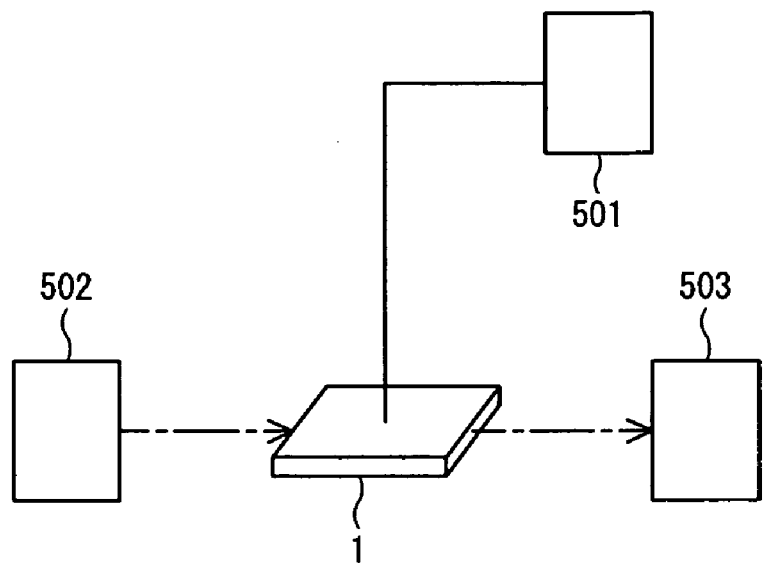
FIG. 30 is a diagrammatic view of assistance in explaining an analysis apparatus according to the tenth embodiment of the present invention.

FIG. 30 is a diagram of assistance in explaining an analysis apparatus according to the tenth embodiment of the present invention. As shown in FIG. 30, the analysis apparatus according to the tenth embodiment of the present invention has the analytical chip 1, 1B, 1C, 1D, 1E, 1F, which is explained in each of the first and third through seventh embodiments (hereinafter, the analytical chip is designated by reference character 1), analysis section 501, which is for carrying out analysis of the fluid sample Fs flowing through the analytical chip 1, separation section (hereinafter also called the "separation apparatus") 502, which is disposed upstream of the analytical chip 1 for separating the fluid sample Fs by physical and/or chemical action prior to the introduction of the fluid sample Fs to the analytical chip 1, and after-analysis section (hereinafter also called the "after-analysis apparatus") 503, which is for analyzing the fluid sample Fs drained from the analytical chip. The constitution of the analytical chip has been already described above in detail in the first and third through seventh embodiments, so that redundant explanation is omitted.

The constitution of the analysis section 501 is not restricted particularly, although it is generally preferable to use, as the analysis section 501, an apparatus which carries out analysis using at least one analytical technique selected surface plasmon resonance, chemiluminescence, bioluminescence, electrochemiluminescence, fluorescence, and RI (radioactive isotope analysis). It is possible to use either an analysis section carrying out analysis using one of the above-exemplified techniques or an analysis section carrying out analysis using two or more of the techniques in combination.

When using the analysis section 501 which carries out analysis based on surface plasmon resonance, it is possible to configure the analysis section 501 specifically in the same constitution as that of the second embodiment. Also, when using the analysis section 501 which carries out analysis based on surface plasmon resonance, it is also possible to carry out analysis under light irradiation from the back face of the analytical chip 1. Specifically, a light beam is applied from the side of the basal plate 4 of the analytical chip 1 into the reaction area 6, which is formed in the flow channel 5 of the analytical chip 1, and the light beam reflected by the reaction area 6 is observed at the side of the basal plate 4 of the analytical chip 1 while analysis is carried out. In the case, however, since it is necessary that the applied light beam reaches the reaction area 6 of the analytical chip 1, it is required as a matter of course that the basal plate 4 is formed in such a manner that it allows the incident light to pass through. Hence, when analysis is carried out under light application from the back face the analytical chip 1, the basal plate 4 is usually made from materials that can transmit light having the same wavelengths as those of the incident light.

When using the analysis section 501 which carries out analysis based on fluorescence, in general, the cover member 2 of the analytical chip is formed to be transparent, and excitation light is applied from the side of the cover member 2 while fluorescence is also detected also from the side of the cover member 2. However, it is also possible, just as in the case where analysis is carried out based on surface plasmon resonance, to apply excitation light from the side of the back face of the analytical chip 1, i.e., the side of the basal plate 4 and detect fluorescence from the side of the basal plate 4 to carry out analysis. In the latter case, it is necessary to form the basal plate 4 to be transparent. In addition, it is also possible to apply excitation light from the side of the cover member 2 of the analytical chip 1 and detect fluorescence from the side of the basal plate 4 or, in contrast, to apply excitation light from the side of the basal plate 4 and detect fluorescence from the side of the cover member 2.

When using the analysis section 501 that carries out analysis based on chemiluminescence or bioluminescence, as in the case the analysis is carried out based on surface plasmon resonance or fluorescence, it is possible to detect chemiluminescence from a desired direction through a transparent part (part formed to be transparent) of the analytical chip 1. Specifically, when the cover member 2 of the analytical chip 1 is formed to be transparent, for example, it is possible to carry out the application and detection of light from the side of the cover member 2, and when the basal plate 4 is formed to be transparent, it is possible to carry out the application and detection of light from the side of the basal plate 4. Incidentally, when using chemiluminescence or bioluminescence, there is usually no necessity for applying excitation light.

When using the analysis section 501 that carries out analysis based on electrochemiluminescence, it is possible to carry out analysis basically in the same manner as in the case of chemiluminescence. As an exception, however, it is to be noted that it is necessary to dispose an electrode to the basal plate 4 in the case of electrochemiluminescence. Hence, so long as the electrode is made from a non-transparent material, even if the basal plate 4 is made from a transparent material, it is difficult to detect electrochemiluminescence from the side of the basal plate 4. On the other hand, when the electrode is made from a transparent material (i.e., ITO), or when the electrode is made from a non-transparent material but formed in such a extremely thin film that it can transmit light, it is also possible to carry out the application and detection of light from the side of the basal plate 4.

Besides, the analysis apparatus according to the present embodiment has separation apparatus 502, which is disposed upstream of the analytical chip 1 and is for separating the fluid sample Fs by physical and/or chemical action prior to the introduction of the fluid sample Fs into the analytical chip 1.

The constitution of the separation apparatus 502 is not restricted particularly, although it is generally preferable to use the techniques such as: liquid chromatography and HPLC (high performance liquid chromatography), which carry out separation based on the adsorptivity or the distribution coefficient of samples; capillary electrophoresis, micro chip electrophoresis, and microchannel electrophoresis, which carry out separation based on the electronegativity of samples; and flow injection. Also, it is naturally possible to equip the analysis apparatus with any other types of apparatus as the separation apparatus 502, either alone or in combination with the above-exemplified types of apparatus.

The "microchannel" means a groove which is formed on a chip surface and through which a sample flows, and the "microchannel electrophoresis" means the technique of carrying out separation by filling a part of the groove with substances corresponding to column fillers used for HPLC or fixing functional groups to the groove surface.

The "flow injection" is a method of bringing about various kinds of reactions in the state where a sample is flowing. According to the method, it is possible to, for example, bring about complex formation reaction, carry out solvent extraction, and so forth, thereby removing substances other than target species in the sample to achieve separation.

As a matter of course, it is also possible to equip the analysis apparatus with any apparatus other than those exemplified above as the separation apparatus 502.

Besides, the analysis apparatus according to the present embodiment has after-analysis apparatus 503, which carries out analysis of the fluid sample Fs drained from the analytical chip. The constitution of the after-analysis apparatus 503 is not restricted particularly, and various types of analysis apparatus can be used as the after-analysis apparatus 503. Specifically, examples include MS (mass spectrograph), protein sequencer, DNA sequencer, SEM, SPM, STM, AFM, etc.

In addition, the after-analysis apparatus 503 can also have a pretreatment mechanism, which make the fluid sample Fs in the state of allowing analysis. Also, it can have any of the above-exemplified types of apparatus in combination.

When using the analysis apparatus according to the tenth embodiment of the present invention, which is constituted as described above, during analysis, the fluid sample Fs is made flow through in turn the separation apparatus 502, the analytical chip 1, and the after-analysis apparatus 503 while analysis is carried out.

Since the analytical chip 1 is used for carrying out analysis in the analysis section 501, it is possible to carry out analysis of the fluid sample Fs efficiently with high precision.

Besides, since the analysis apparatus has the separation apparatus 502, it is possible to preliminary a sample containing separate predetermined substances, such as enzymes and proteins, into fractions each containing pure substances, using the separation apparatus. It becomes thus possible to analyze predetermined substances in the state of being fractioned into pure substances, so that it is possible to carry out analysis more accurately.

In addition, since the analysis apparatus has the after-analysis apparatus 503, it is possible to obtain multiple data through a single analysis operation and to thereby analyze the fluid sample Fs from various points of view.

In the meantime, although in the present embodiment the analytical chip 1 explained in the first embodiment is used as the analytical chip, it is a matter of course that the analytical chip is not limited to the same one as described above. It is also possible to use the analytical chips that have any other constitutions, for example, the constitutions according to the third through seventh embodiments.

Figure 31:
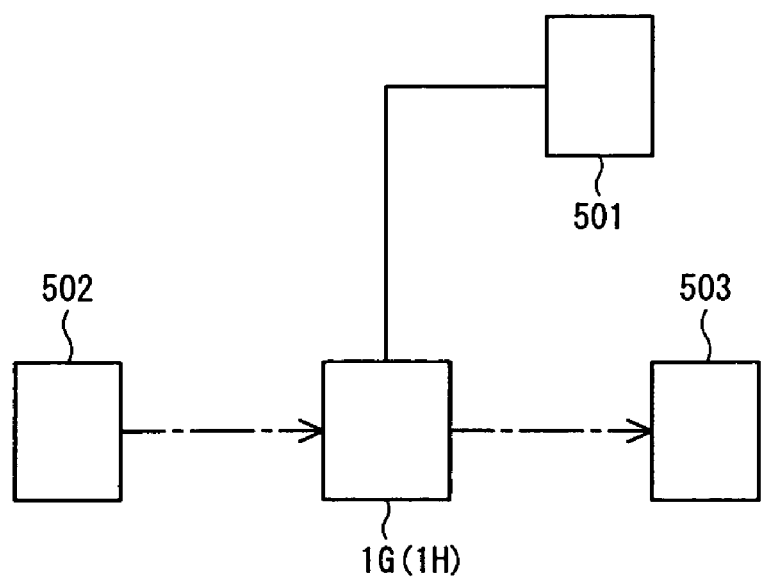
FIG. 31 is a diagrammatic view of assistance in explaining an analysis apparatus according to a modification of the tenth embodiment of the present invention.
Figure 32:
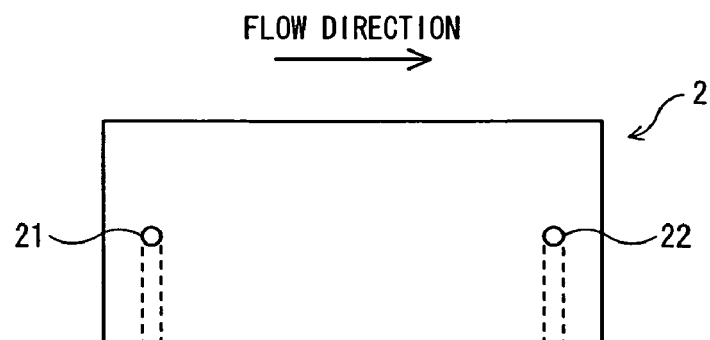
FIG. 32(a) is a diagrammatic top view of a cover member according to an embodiment of the present invention.
FIG. 32(b) is a diagrammatic top view of a first plate according to an embodiment of the present invention.
FIG. 32(c) is a diagrammatic top view of a second plate according to an embodiment of the present invention.
FIG. 32(d) is a diagrammatic top view of basal plate according to an embodiment of the present invention.
Figure 32:
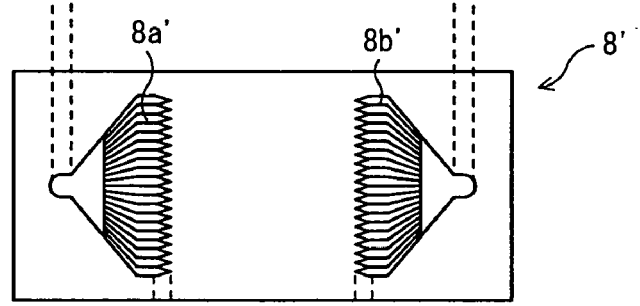
Figure 32:
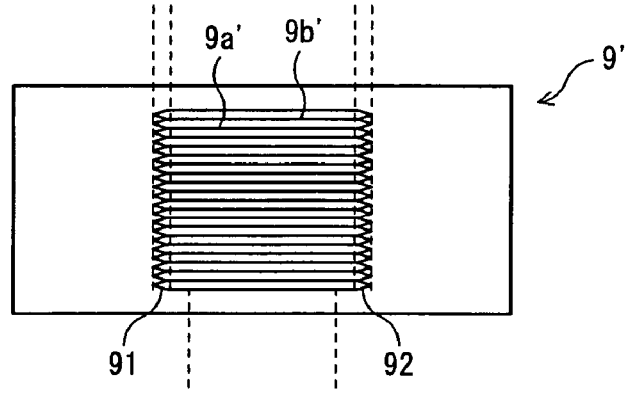
Figure 32:
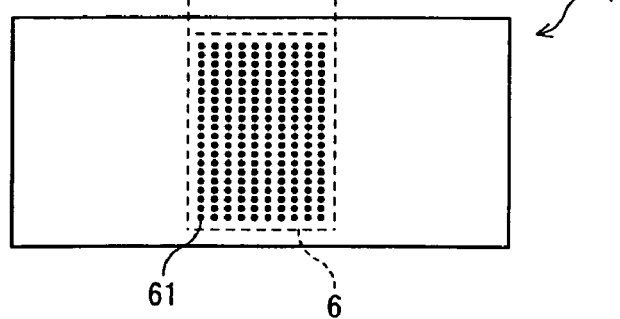

Also, instead of the analytical chip used in the present embodiment, it is also possible to use, as shown in FIG. 31, the analytical-chip unit 1G, 1H according to the eighth embodiment or the ninth embodiment. In FIG. 30 and FIG. 31, like reference characters designate like components.

With the constitution, since the analytical-chip unit 1G, 1H is used for carrying out analysis in the analysis section 501, it is possible to carry out analysis of the fluid sample Fs efficiently with high precision.

In addition, since the analysis apparatus has the separation apparatus 502, it is possible to preliminary a sample containing separate predetermined substances, such as enzymes and proteins, into fractions each containing pure substances, using the separation apparatus. It becomes thus possible to analyze predetermined substances in the state of being fractioned into pure substances, so that it is possible to carry out analysis more accurately.

Besides, since the analysis apparatus has the after-analysis apparatus 503, it is possible to obtain multiple data through a single analysis operation and to thereby analyze the fluid sample Fs from various points of view.

(11) Eleventh Embodiment

Figure 4:
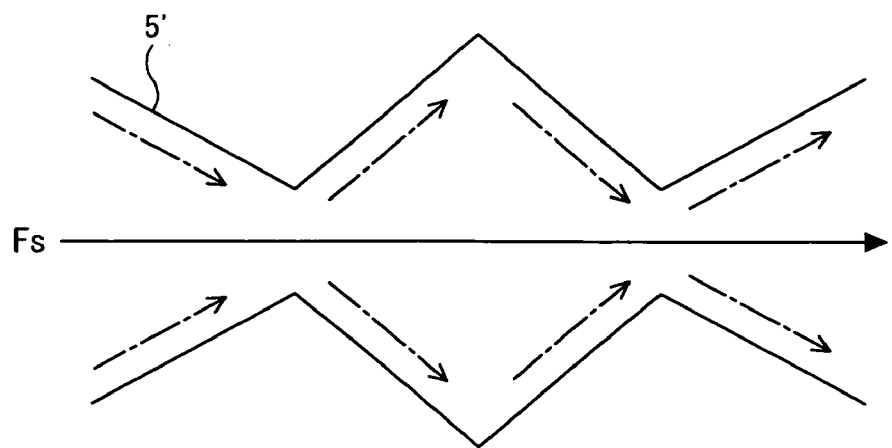
FIG. 4 is a diagram of assistance in explaining the definition of a flow direction of the fluid sample.
Figure 48:
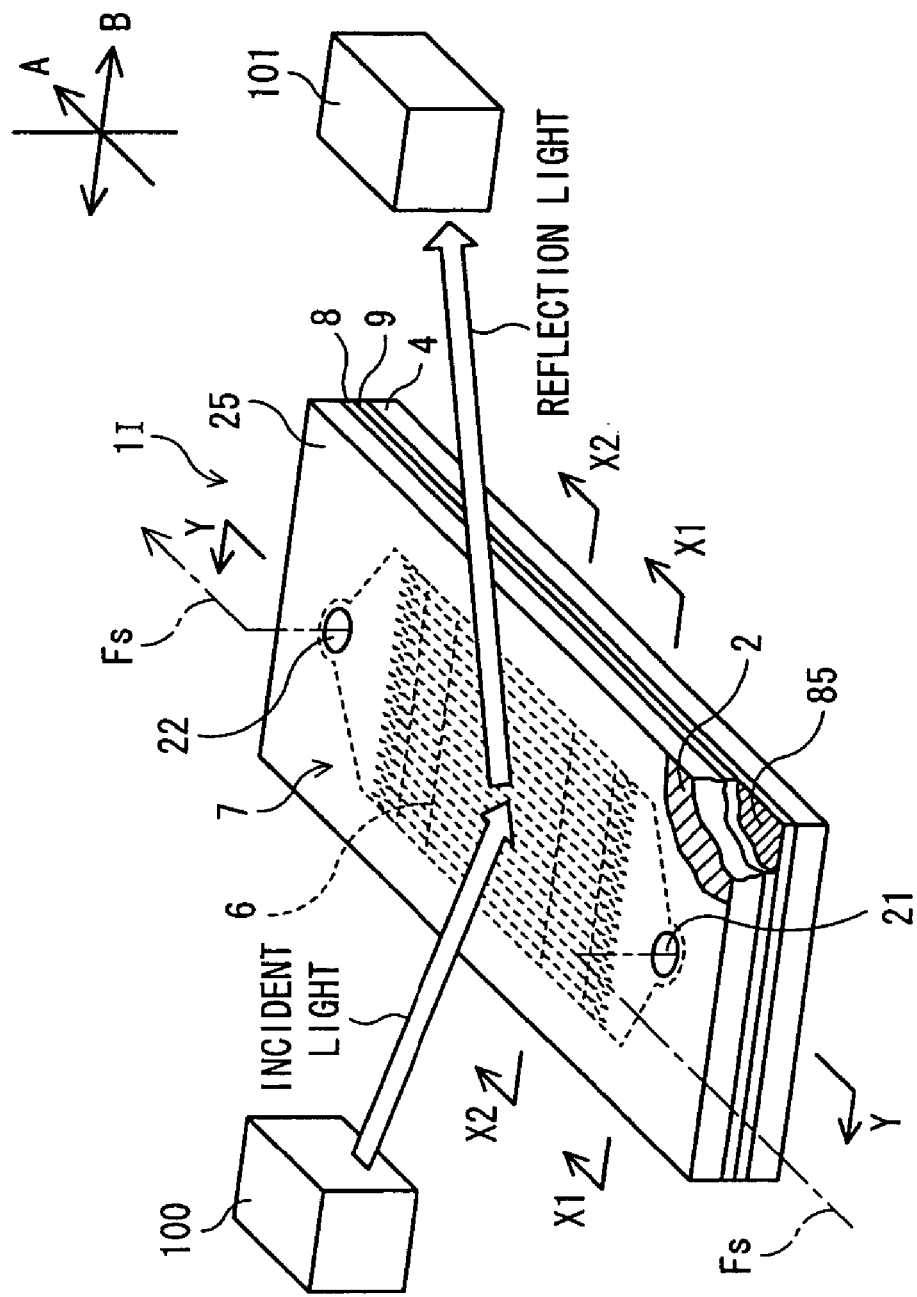
FIG. 48 is a block diagram illustrating an SPR sensor system using an analytical chip according to the eleventh embodiment of the present invention, the analytical chip being partially broken away.
Figure 49:
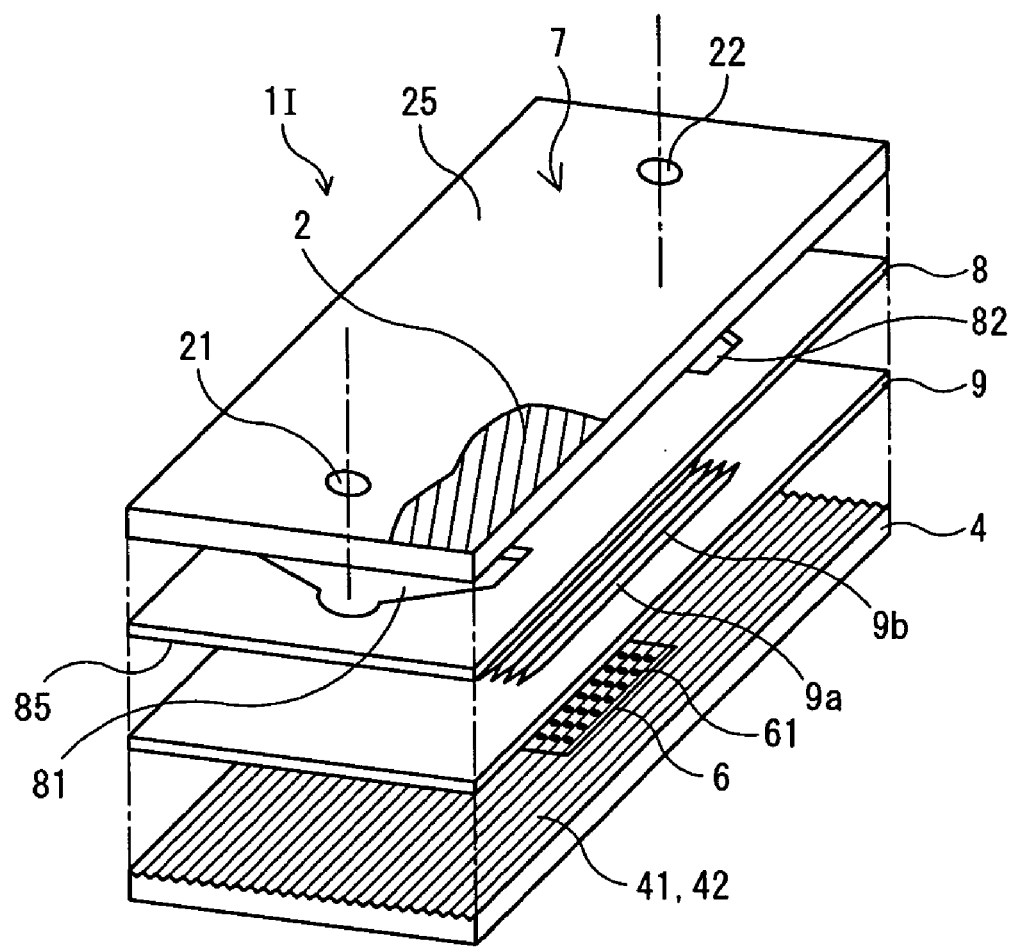
FIG. 49 is a diagrammatic exploded perspective view of an analytical chip according to the eleventh embodiment of the present invention, a cover member of the analytical chip being partially broken away.
Figure 50:
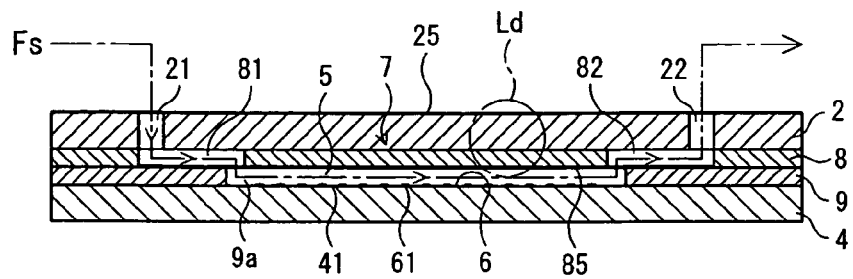
FIG. 50(a) is a diagrammatic sectional view taken on line Y—Y of FIG. 48.
FIG. 50(b) is a diagrammatic sectional view taken on line X1—X1 of FIG. 48.
FIG. 50(c) is a diagrammatic sectional view taken on line X2—X2 of FIG. 48.
FIG. 50(d) is an enlarged view of the part designated by Ld in FIG. 50(a)
Figure 50:
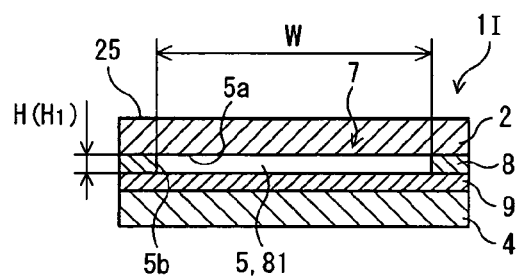
Figure 50:
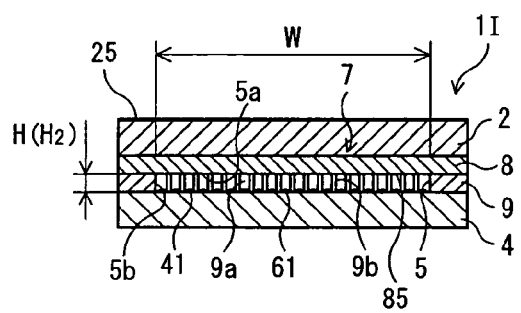
Figure 50:
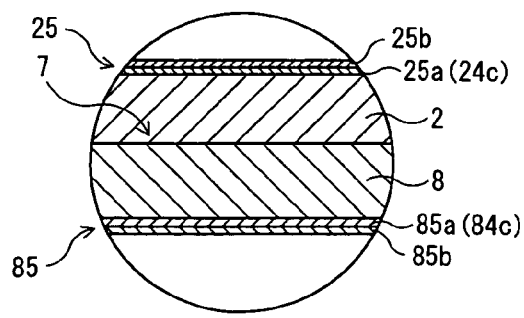

FIGS. 48 through 51 each show an analytical chip according to the eleventh embodiment of the present invention. Specifically, FIG. 48 is a block diagram illustrating an SPR sensor system using an analytical chip according to the eleventh embodiment of the present invention, the analytical chip being partially broken away; FIG. 49 is a diagrammatic exploded perspective view of an analytical chip according to the eleventh embodiment of the present invention, a cover member of the analytical chip being partially broken away; FIG. 50(a) is a diagrammatic sectional view taken on line Y—Y of FIG. 48, FIG. 50(b) is a diagrammatic sectional view taken on line X1—X1 of FIG. 48, FIG. 50(c) is a diagrammatic sectional view taken on line X2—X2 of FIG. 48, and FIG. 50(d) is an enlarged view of the part designated by Ld in FIG. 50(a); and FIG. 51(a) is a diagrammatic top view of a cover member of an analytical chip according to the eleventh embodiment of the present invention, FIG. 51(b) is a diagrammatic bottom view of a first plate of an analytical chip according to the eleventh embodiment of the present invention, FIG. 51(c) is a diagrammatic top view of a second plate of an analytical chip according to the eleventh embodiment of the present invention, and FIG. 51(d) is a diagrammatic top view of a basal plate of an analytical chip according to the eleventh embodiment of the present invention. In the following description, the "flow direction A" of the fluid sample Fs means the direction of the main flow through the flow channel: for example, the flow direction of the flow channel 5' as shown in FIG. 4 is the direction indicated by the arrow in solid line. Besides, the components that are substantially identical to those of the conventional techniques and the other embodiments are designated by like reference characters.

As shown in FIG. 48, the SPR sensor is composed of SPR sensor chip (hereinafter called the "chip") 1I, which is an analytical chip, light source 100, which is for irradiating the chip 1I with light, and detector (in the present embodiment, CCD (charge coupled device) camera) 101, which is for detecting the reflection light from the chip 1I. The chip 1I has cover member 2, first plate (intermediate plate. hereinafter called simply as the "plate") 8, second plate (intermediate plate. hereinafter called simply as the "plate") 9, and basal plate 4, each of which components is made from a transparent quartz glass, as will be described later. The cover member 2 and the plate 8 is formed in such a manner as to transmit the light emitted from the light source 100 and the reflection light to be detected by the detector 101, and thus each have optically transparent parts 7. Incidentally, although in FIG. 48 both the optical axis for the incident light from the light source 100 and the optical axis for the reflection light from the sensor chip 1I are perpendicular to the flow direction, the optical axes for the incident light and the reflection light are not limited to those of the drawing: for example, the optical axis for the incident light can be parallel with the flow direction, while the optical axis for the reflection light can have a different orientation from that of the incident light as a consequence of reflecting by the sensor chip 1I. The embodiment can be also modified such that the incident light is applied from the back face of the sensor chip 1 (from the side of the basal plate 4) while the reflection light is detected the back face of the sensor chip 1 (from the side of the basal plate 4) to carry out analysis. In the modification, however, it is necessary to make the basal plate 4 from a material that can transmit the incident light and the reflection light.

In the following, the chip 1I will be explained in detail.

As shown in FIG. 49, the chip 1I is composed of cover member 2, which is in a flat-plate shape, plate 8, which is of small thickness, plate 9, which is also of small thickness as with the plate 8, and basal plate 4. In carrying out analysis, as shown in FIG. 48, these components 2, 8, 9, 4 are piled up in the listed order from above downward, and fastened together as a unit by a joining holder, not shown in the drawings. The plates 8, 9 are thus interposed between the cover member 2 and the basal plate 4. It is preferable that the holder has a protection device for securing accurate alignment and preventing scratches. Examples of the protection device include a locking part, attached to the holder so as to lock the analytical chip 1I, and a hollow, formed on the holder so that an observation part (reaction area 6, which will be described later) of the analytical chip 1I does not touch the holder.

As shown in FIG. 50(a), fluid sample Fs is to be injected into opening 21 (an injection port at the upstream end of flow channel 5, which will be described later) of the cover member 2, and to flow through opening 81 (a flow-channel confluence part on the upstream side) of the plate 8, then through each of slit-form openings 9a (inner flow channels) of the plate 9. Subsequently, the fluid sample Fs is to flow through opening 82 (a flow-channel confluence part on the downstream side) of the plate 8, and to be finally drained from opening 22 (a drain port at the downstream end of flow channel 5, which will be described later) of the cover member 2. While passing through the slit-form openings 9a of the plate 9, the fluid sample Fs is to be in contact with one or more specific substances 61, which are fixed to reaction area 6 of the basal plate 4.

Specific substance 61 is fixed to the chip 1I as plural spots arranged at intervals long enough to prevent each of the spots from being contaminated by adjacent spots of the specific substance 61.

It is not necessary to use different kinds of specific substances 61 at different spots; the same specific substance 61 can be used at two or more different spots. In any event, what kinds of specific substances 61 are used should be determined as appropriate, depending on the object of analysis.

In order to fix the specific substance 61 securely to the basal plate 4, it is preferable to previously form on the surface of the basal plate 4 an immobilized film (organic film) that can bind with the specific substance 61. The immobilized film in the embodiment may be one or more selected from conventional structures. Preferably, the immobilized film has the property of being able to fix the specific substance 61 to the metal layer 41 securely while preventing nonspecific absorption. Specifically, it is preferred that the immobilized film includes: as a functional group for binding to a biological substance, at least one group selected from amino, aldehyde, epoxy, carboxyl, carbonyl, hydrazide, hydroxyl, and vinyl group; and, for binding to the metal layer 41, one or more straight-chain macromolecules including at least one selected from isothiocyanato, isonitrile, xanthate, diselenide, sulfide, selenide, selenol, thiol, thiocarbamate, nitrile, nitro, and phosphine, and/or hydrocarbon chains having at least one double and/or triple bond. It is also preferable to use a material that forms hydrogel (agarose, alginic acid, carrageenin, cellulose, dextran, polyacrylamide, polyethylene glycol, polyvinyl alcohol, etc.) as a matrix. It is also preferable to use an organization structure such as a LB membrane, a self-assembled monolayer, or a lipid bilayer.

The following description is made on a production method of the present analytical chip 1I. The plate 9 is bonded to the basal plate 4, after which the specific substance 61 is fixed to the basal plate 4. Specifically, the specific substance 61 is dispersed or dissolved in a liquid to form a dispersion liquid or solution of the specific substance 61. The dispersion liquid or solution is dripped through the slit-form openings 9a of the plate 9 in such a manner that the drops are aligned at regular intervals, as shown in FIG. 5, using a injector or a spotter (not shown in the drawings) that is capable of positioning operation. In the following description, the above dispersion liquid or solution, which is obtained by dispersing or dissolving the specific substance 61 into a liquid, is called the "fluid containing specific substance". Although not limiting the kind of the liquid in which the specific substance 61 is dispersed or dissolved, it is assumed that in the present embodiment, the fluid containing specific substance is an aqueous solution obtained by dissolving the specific substance 61 in water. FIG. 5 is a top view of the chip, illustrating the state where the plate 9 is bonded to the basal plate 4 and the fluid containing specific substance is dripped so that the specific substance 61 is fixed.

Subsequently, the plate 8 is mounted on the plate 9, and the cover member 2 is further mounted on the plate 8, so that the analytical chip 1I is produced.

Also, The fluid sample Fs is to flow through the flow channel 5, whose section (orthogonal to the flow direction A of the fluid sample Fs) is in a slit shape elongated horizontally, as shown in FIGS. 50(b), (c). Put another way, the flow channel 5 is formed as a sheet-shaped space having closed-section structure. In the present invention, the "flow channel formed as a sheet-shaped space" generally means a flow channel whose long side 5a has a size W of between 500 μm and 100 mm inclusive, and whose short side 5b has a size H of between 5 μm and 2 mm inclusive. The "long side" means the longest side among all the sides of both sections orthogonal to the flow direction of the flow channel 5 and sections orthogonal to width directions, generally being a side along either the width of the flow channel 5 or the length of the flow channel 5 in the flow direction (in the present embodiment, a side along the width of the flow channel 5). The "short side" means a side along the height of flow channel 5. The size ratio between the long side 5a and the short side 5b (=[long side size W]/[short side size H]) is generally 1.5 or above, preferably 10 or above, and generally 20000 or below, preferably 100 or below. When the flow channel 5 is, as will be described later, divided into two or more inner flow channels 9a with one or more partition walls 9b (which serve as projection member, partition members, or prop members), at least the sizes of the whole flow channel 5 (the sizes of the whole of the plural inner flow channels 9a joined together) have to meet the above range of size ratio. In the present embodiment, the length W of the long side 5a is set at 20 mm, while the length of the short side 5b of each of the plates 8, 9 (in X1—X1 section, thickness $H_1$ of the plate 8; in X2—X2 section, thickness $H_2$ of the plate 9) is set at 250 μm.

Hereafter, each of the above components of the present analytical chip 1I will be described in detail.

Each of the cover member 2, the plate 8, the plate 9, and the basal plate 4 can be made from any kinds of materials, examples of which include, but are not limited to, resins, ceramics, glasses, and metals. However, when measuring any interaction (such as reaction or binding) between target species and the specific substances 61 optically based on fluorescence, luminescence, color change, or phosphorescence, etc., it is desired to make each of the cover member 2 and the plates 8, 9 from one or more transparent materials; as an exception, when measurement can be carried out with the analytical chip 1 being disassembled, the cover member 2 and the plates 8, 9 are not necessarily required to have transparency. Examples of transparent materials are: resins, such as acrylic resin, polycarbonate, polystyrene, polydimethylsiloxane, and polyolefin; and glasses, such as Pyrex$^R$ (i.e., borosilicate glass) and quartz glass. In the present embodiment, it is assumed that each of the cover member 2, the plates 8, 9 and the basal plate 4 is made from quartz glass. Hence, each of the cover member 2 and the plates 8, 9 of the chip 1I can transmit light. In the present embodiment, especially the cover member 2 and the plate 8 each have optically transparent parts 7. On the other hand, the basal plate 4 has metal layer 41 formed thereon, which will be described later, and there does not allow light transmission.

As shown in FIG. 51(a), opening (injection port) 21 is formed at the upstream end of the cover member 2, while another opening (drain port) 22 is formed at the downstream end of the cover member 2.

The injection port 21 is connected to an injection pump (e.g. syringe pump) using a connector and a tube (not shown in the drawings), while the drain port 22 is connected to a waste liquid tank using a connector and a tube (not shown in the drawings). Operating the above injection pump, it is possible to inject the fluid sample Fs via the injection port 21 into the chip 1I and drained from the chip 1I.

Also, as shown in FIGS. 48 and 51(a), protective layer 25 is formed over the whole top surface of the cover member 2, namely, the surface that is exposed outside when the chip 1I is in the assembled state. The protective layer 25 will be explained later in full detail.

As shown in FIG. 51(b), opening 81 is formed at the upstream side of the plate 8, while opening 82 is formed at the downstream side of the plate 8.

The upstream end 81x of the opening 81 is located in such a manner as to be aligned, and communicate, with the injection port 21 of the cover member 2 when the chip 1I is in the assembled state. The opening 81 is also formed in such a manner that its width gradually becomes broader from the upstream end 81x along the flow direction toward a middle part of the plate 8 (toward the downstream side along the flow direction of the fluid sample Fs).

On the other hand, the downstream end 82x of the opening 82 is located in such a manner as to be aligned, and communicate, with the drain port 22 of the cover member 2 when the chip 1I is in the assembled state. The opening 82 is also formed in such a manner that its width gradually becomes narrower from the middle part of the plate 8 along the flow direction toward the downstream end 82x (toward the downstream side along the flow direction of the fluid sample Fs).

When the chip 1I is in the assembled state, the top and under faces of the plate 8 are blocked by the cover member 2 and the plate 9, respectively, and each of the openings 81, 82 forms a part of the flow channel in which the fluid sample Fs flows unitedly. The part of the flow channel, formed by each the openings 81, 82 of the plate 8, is also called flow-channel confluence part 81, 82. Although in FIG. 48 the whole top surface and the whole under surface of the plate 8 are blocked by the cover member 2 and the plate 9, respectively, yet it is acceptable that at least the parts of the top and under surfaces of the plate 8 corresponding to the openings 81, 82 is blocked.

According to the chip 1I, since the flow-channel confluence part 81 becomes gradually broader from the upstream end 81x toward the middle part along the flow direction, the fluid sample Fs can be guided smoothly toward the middle part of the flow direction. On the other hand, since the flow-channel confluence part 82 becomes gradually narrow from the middle part toward the downstream end 82x along the flow direction, the fluid sample Fs can be guided smoothly toward the downstream end 82x.

Besides, as shown in FIGS. 48 and 51(b), protective layer 85 is formed over the whole under surface of the plate 8, namely, the surface that confronts to flow channel 5 when the chip 1I is in the assembled state. The protective layer 85 will be explained later in full detail.

As shown in FIG. 51(c), around the middle part of the plate 9 along the flow direction, projection member is formed as one or more partition walls (partition members) 9b, dividing two or more slit-form openings 9a or inner openings (hereinafter called the slit-form openings) one from another across the width directions. When the chip 1I is in the assembled state, the slit-form openings 9a form slit-form inner flow channels (hereinafter also called slit-form flow channels), which are divided with the partition walls 9b one from another around the middle part of the flow channel 5. The term "inner flow channels" means flow channels that are divided with the partition members across the width directions. The partition walls 9b adjoin directly the basal plate 4 and the plate 8 so that the fluid sample Fs is shut out from both between the partition walls 9b and the basal plate 4 and between the partition walls 9b and the plate 8, thereby the flow channel 5 being divided into plural inner flow channels. Meanwhile, when the chip 1I is in the assembled state, the top and under faces of the slit-form openings are blocked by the plate 8 and the basal plate 4 to thereby define the slit-form flow channels. Since the slit-form openings, the slit-form flow channels, and the inner flow channels are thus equivalent to each other, they are all designated by the same reference character 9a.

With the arrangement, as shown in FIGS. 50(a) and 51(a)–(d), the fluid sample Fs injected via the injection port 21 of the cover member 2 flows into the flow-channel confluence part 81 of the plate 8. After then, the fluid sample Fs flows from the upstream ends 91 of the slit-form flow channels 9a into the individual slit-form flow channels 9a, and comes into touch with the specific substance 61. Subsequently, the flows of the fluid sample Fs run out of the downstream ends 92 of the slit-form flow channels 9a to join together in the flow-channel confluence part 82 and be drained from the drain port 22 of the cover member 2 toward outside the chip 1I.

It is usually preferable to form each of the slit-form flow channels 9a such that its cross section has an aspect ratio {[length size]/[width size]} of between 0.005 (e.g., 5 µm in length and 1 mm in width) and 100 (e.g., 10 mm in length and 100 µm in width) inclusive. Also, it is generally preferred that each of the slit-form flow channels 9a has a cross sectional area of 5 mm$^2$ or below. Specifically, the sectional area of each slit-form flow channel 9a is usually 100 µm$^2$ or above, preferably 2000 µm² or above, and usually 5 mm² or below, preferably 0.3 mm² or below.

Also, when the chip 1I is in the assembled state, the upstream end 91 of each slit-form opening 9a is located such as to communicate with the opening 81 at the downstream end of the plate 8, while the downstream end 92 of each slit-form opening 9a is located such as to communicate with the opening 82 at the upstream end of the plate 8.

With the above arrangement, the fluid sample Fs injected from the flow-channel confluence part 81 of the plate 8 flows through the upstream end 91 of each slit-form flow channel 9a into each slit-form flow channel 9a of the plate 9, finally going out of the downstream end 92 of each slit-form flow channel 9a of the plate 8 to gather into one volume in the flow-channel confluence part 82.

According to the present analytical chip 1I as described above, it becomes possible to prevent running ahead of the fluid sample Fs by providing the conventionally-formed, sheet-shaped flow channel 5 with one or more partition walls 9b to divide the flow channel 5 into two or more inner flow channels 9a with minute section (namely, by decreasing the cross sectional area of the individual flow channel).

Besides, as shown in FIGS. 49 and 51(d), a metal layer 41 is coated over the surface of the basal plate 4 facing the slit-form flow channels 9a when the chip 1I is in the assembled state. Also, the surface coated with the metal layer 41 is processed to have diffraction grating 42, as an optical structure that can generate an evanescent wave.

When the light is applied from the light source 100 toward the basal plate 4 through the cover member 2 and the plates 8, 9 being transparent, a surface plasmon wave is produced along the surface of the metal layer 41 while an evanescent wave is induced along the metal layer 41 due to the diffraction grating 42. These waves cause resonance to bring about energy absorption by the metal layer 41 from the optic element having a specific incident angle or a specific wavelength in the incident light applied to the metal layer 41. As a result, in the reflection light from the metal layer 41, the energy of the optic element having a specific incident angle or a specific wavelength decreases.

The angle and the wavelength of the evanescent wave generated along the metal layer 41 varies depending on the amount of target species trapped by the specific substances 61 fixed to the metal layer 41, and the angle and the wavelength of the absorbed optical component of the reflection light also varies accordingly. Hence, by monitoring the light intensity of the reflection light from each of the specific substances 61 on the reaction area 6 using the CCD camera 101 to detect the change in the angle and/or the wavelength, it is possible to measure the concentration of target species contained in a test fluid in real time.

A material from which the metal layer 41 is made is not limited as long as it allows to induce surface plasmon wave, examples of which material include gold, silver, and aluminum.

The diffraction grating 42 can be embodied on the surface of the metal layer 41 by forming concavities and convexities on the surface of the basal plate 4, and then laminating on the concavities and convexities with a thin layer of a metal using a technique such as sputtering, to form the metal layer 41.

The concavities and convexities, which are formed for providing the basal plate 4 with the diffraction grating 42, can be formed by, for example, cutting the basal plate 4. The cutting method is not limited: it can be carried out mechanically, or chemically using a technique such as etching. When making the basal plate 4 from a resin material, it is possible to form the concavities and convexities using a stumper on which the corresponding concavities and convexities are formed by means of photo lithography or the like. It can be achieved before the resin material has not solidify completely, by pressing the stumper on the basal plate 4, or by transferring the concavities and convexities from the stumper using a technique such as injection molding.

In the meanwhile, reaction area 6 is disposed around the middle part of the basal plate 4 along the flow direction so as to face the flow channel 5.

As shown in FIG. 51(d), the reaction area 6 is an area where, as shown in FIG. 3(d), at least one specific substance 61 that can cause interaction specifically or nonspecifically with one or more predetermined substances (target species) is fixed, as plural spots, to the surface of the basal plate 4 on the side of the flow channel 5.

The sizes {[length size]×[width size]} of the reaction area 6 are usually between 3 mm×3 mm through 20 mm×20 mm inclusive. In the area, the specific substance 61 are disposed as generally 9 through 40000 spots in such a matrix that 3 through 200 spots are aligned along every row of each direction at intervals of between 100 µm and 1 mm inclusive.

It is assumed that as the specific substance 61, the embodiment uses plural kinds of specific substances (different from each other) each of which can cause any interaction, such as reaction or binding, specifically or nonspecifically with different kinds of substances.

Each of the predetermined substance and the specific substance can be selected from substances that can cause any interaction, such as antigen-antibody reaction, complementary DNA binding, receptor-ligand interaction, enzyme-substrate interaction, etc., and is selectable from various substances, for examples, protein, nucleic acid, DNA, RNA, PNA, peptide, hormone, antigen, antibody, ligand, receptor, enzyme, substrate, low molecular organic compound, cell, etc., and complex thereof. These substances may be labeled, if necessary, with any other substance such as a fluorescence substance, luminescence substance, radioactive substance, etc.

When the present analytical chip 1I is assembled, the plate 9 is first fixed on the basal plate 4, after which the specific substances 61 are fixed to the basal plate 4 from above the plate 9 through the slit-form openings 9a of the plate 9. Hence, the reaction area 6 (the area where the plural specific substances 61 are fixed) shown in FIGS. 49 and 51(d) is not actually formed in the early stage of assembling: in FIGS. 49 and 51(d), the specific substances 61 fixed to the basal plate 4 are illustrated for convenience in explaining the arrangement of the spots of the specific substances 61 with respect to the basal plate 4 intelligibly. Accordingly, FIGS. 49 and 51(d) illustrate the positions and the number of the spots of the specific substances 61 along the width directions in such a manner that they correspond to the positions and the number of the slit-form openings 9a of the intermediate plate 9 along the width directions.

The fluid sample Fs flowing through the slit-form flow channels 9a comes into contact with these specific substances 61 during the process of the flowing, after which analysis is carried out regarding the fluid sample Fs, based on the state of reaction at each spot of the specific substances 61.

Specifically, if the occurrence of reaction is detected at any spot of the specific substances 61, it is possible to determine that the fluid sample Fs contains a kind of substance corresponding to the specific substance 61 fixed at the spot where the reaction is detected.

The specific substances 61 are fixed to the chip 1 as plural spots arranged at regular intervals so as not to be contaminated with the specific substance 61 at the neighboring spots. The term "regular intervals" means the intervals between the centers of the spots where the specific substances are fixed, to which intervals the pitch of the partition walls 9b is set to be substantially identical. In the present invention, it is not necessary to reduce the number of spots of the specific substance 61 per unit area than in the conventional chip in return for disposing the partition walls 9b; on the contrary, since the disposition of the partition walls 9b enables to prevent the contamination as described above, the pitch of the specific substances 61 along the width directions (the directions orthogonal to the flow direction) can be minimized, so that it becomes possible to rather increase the number of spots per unit area.

It is not necessary to use different kinds of specific substances 61 at different spots; the same specific substance 61 can be used at two or more different spots. In any event, what kinds of specific substances 61 are used should be determined as appropriate, depending on the object of analysis.

Hereafter, the description will be made on the protective layers 25, 85, which are characteristics of the present embodiment.

As described above, the protective layer 25 is formed over the whole top surface of the cover member 2, namely, the surface that is exposed outside when the chip 1I is in the assembled state. Also, the protective layer 85 is formed over the whole under surface of the plate 8, namely, the surface that confronts to flow channel 5 when the chip 1I is in the assembled state. In the present embodiment, each of the protective layers 25, 85 is a layer that protects the surface of the optically transparent part 7 with allowing light transmission.

As shown in FIG. 50(d), the protective layer 25 is composed of anti-reflection layer 25a, which is formed on the surface of the cover member 2, and abrasion resistance layer 25b, which is formed over the surface of the anti-reflection layer 25a (hereinafter also called the "outermost surface" of the cover member 2). Also, the protective layer 85 is composed of anti-reflection layer 85a, which is formed over the surface of the plate 8, and abrasion resistance layer 85b, which is formed over the surface of the anti-reflection layer 85a (hereinafter also called the "outermost surface" of the plate 8).

Each of the anti-reflection layers 25a, 85a is not limited particularly so long as it can allow light transmission through either the outer surface of the cover member 2 or the surface of the plate 8 on the side of the flow channel 5 and prevent the reflection of light transmitted through either the outer surface of the cover member 2 or the surface of the plate 8 on the side of the flow channel 5. Specifically, the individual anti-reflection layer 25a, 85a can be made from any desired substances, such as magnesium fluoride, silicas, and resins, and also can be formed in any thickness depending on the kind of the light to be detected. The thickness of each anti-reflection layer 25a, 85a is usually between several tens of Å and several hundreds of Å. In the present embodiment, each of the anti-reflection layers 25a, 85a is formed in a single-layered AR layer (single-layered anti-reflection layer) made from a magnesium fluoride. Magnesium fluoride has a refractive index different from that of quartz glass, which forms the cover member 2 and the plate 8. To form the anti-reflection layers 25a, 85a, known methods such as vacuum evaporation and sputtering are available.

Each of the abrasion resistance layers 25b, 85b is provided for protecting either the outer surface of the cover member 2 forming the optically transparent part 7 or the surface of the plate 8 on the side of the flow channel 5 while allowing light transmission, and can be made from any desired substances and formed in any desired thickness. Specifically, it should be made preferably from high-strength substances, such as BK7™, fused silica, magnesium fluoride, and Pyrex$^R$. However, since at least either of the abrasion resistance layers 25b, 85b must be positioned so as to cross the optical path during analysis, it is preferable to form the individual abrasion resistance layers 25b, 85b in a thickness small enough not to cause any adverse effect on the light passing through the individual abrasion resistance layer 25b, 85b, such as the decrease of light volume or the shift of the plane of polarization. Specifically, the thickness of each abrasion resistance layer 25b, 85b is usually between several Å through several hundreds of Å. Even if the decrease of the light volume or the shifting of the plane of polarization arises when the light passes through either of the abrasion resistance layers 25b, 85b, so long as the thickness of the abrasion resistance layer 25b, 85b is small enough, the decrease of the light volume or the shift of the plane of polarization can be lessened to a negligible degree. Incidentally, in the present embodiment the abrasion resistance layer 8 is made from silicas.

Using the analytical chip 1I according to the eleventh embodiment of the present invention, which is constituted as described above, when the chip 1I is irradiated with light from the light source 100, it is possible to prevent the reflection of the incident light, which passes through the outer surface and the surface on the side of the flow channel 5 of the optically transparent part 7. Also, it is possible to protect the surface of the optically transparent part 7 of the analytical chip 1I against scratches.

In the following description, advantages offered by the present embodiment will be explained in contrast with conventional problems.

Although various techniques have been already suggested, there is still a large demand for techniques of reducing the amount of fluid sample necessary for analysis so as to carry out analysis efficiently. Reducing the amount of fluid sample, as mentioned above, is required in many cases, especially when only a very small amount of fluid sample is available, when it is undesirable to obtain plenty of fluid sample from man or other organisms due to the physical or mental state of the subject organism, when it needs a large cost to obtain plenty of fluid sample, when multiple kinds of, or multiple times of, analysis must be made on a fluid sample, when a reexamination of a fluid sample is necessary, etc.

When using a conventional analytical chip such as a DNA chip or a protein chip, a biological substance is generally fixed to a two-dimensional plane (the bottom face of the flow channel) as plural spots arranged in the form of a matrix. Hence, the bottom face of the flow channel of such a conventional analytical chip inevitably has an area large so that the reaction area of the flow channel can be fixed within it. In order to reduce the amount of fluid sample for such a chip, it is necessary to make the height of the flow channel still smaller.

In the meantime, many of the conventional analytical chips as described above use light for detecting the interaction of specific substances. Examples of the chips include the ones that use excitation light as described above, such as SPR and fluorescence, and the ones that carry out detection based on light, such as chemiluminescence, bioluminescence, and electrochemiluminescence.

When analysis is carried out using light as described above, the reflection of light may occur in an optical path, through which a light beam passes, and cause a decline in the efficiency or precision of analysis.

Figure 64:
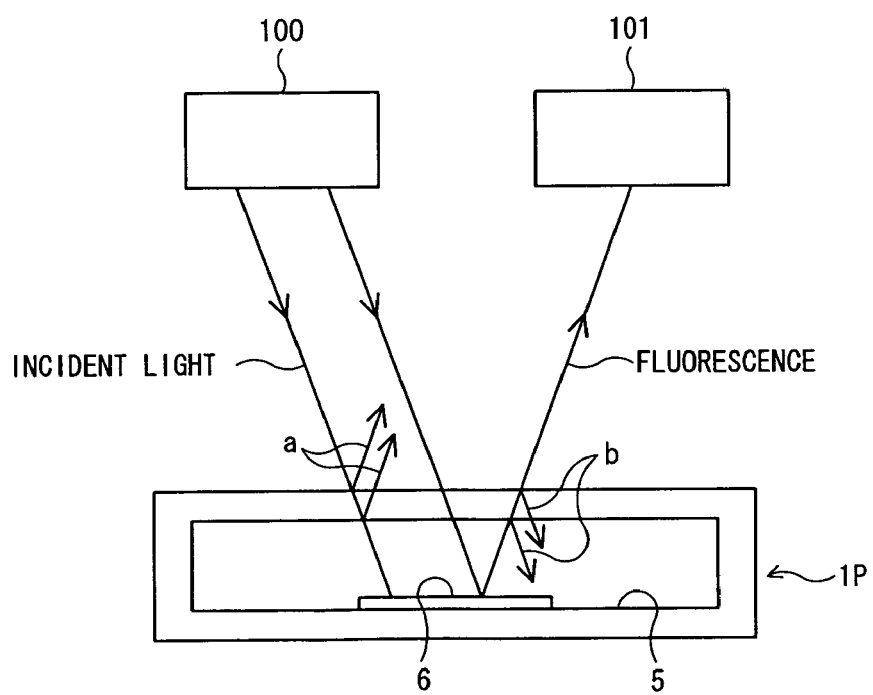
FIG. 64 is a diagram of assistance in explaining an example of the conventional fluorescence analysis.

Hereafter, the state of such a decline is explained with taking, as an example, the case illustrated by FIG. 64, where fluorescence analysis is carried out. In the example, the flow channel 5 is formed in analytical chip 1P, and the reaction area 6 is disposed to the bottom face of the flow channel 5. A specific substance is fixed to the reaction area 6, which substance can be excited by incident light from the light source 100 to generate fluorescence, and the generated fluorescence is to be detected by the detect section 101.

When analysis is carried out using the analytical chip 1P, the analytical chip 1P is irradiated with a incident light beam from the light source 100. As indicated by reference character a, a part of the incident light beam is reflected by the outer surface of the analytical chip 1P or the inner surface of the analytical chip 1P (the ceiling surface of the flow channel 5). Also, as indicated by reference character b, a part of the fluorescence generated in the reaction area 6, which is on the bottom face of the flow channel 5, is reflected by the inner surface of the analytical chip 1P (the ceiling surface of the flow channel 5) or the outer surface of the analytical chip 1P. The occurrence of such a reflection may bring about a decline in the intensity of fluorescence, although it may be initially high enough, or the interference between the fluorescence to be detected and the reflection light from the surface of the analytical chip 1P, causing errors in the detection results of fluorescence.

Thus, when analysis is carried out based on light, the reflection of light may occur in the optical path and cause a decline in the efficiency or precision of analysis. Besides, especially when the flow channel is made to have a small height in order to reduce the amount of fluid sample used for analysis, the incident light, the reflection light, or the fluorescence may be reflected repeatedly by other surfaces of the analytical chip to cause multi reflection, so that the effect of interference of light may increase. It is therefore difficult to carry out analysis efficiently using a small amount of fluid sample with minimizing the effect of the reflection of light according to the conventional art.

Also, there are cases where a number of specific substances are fixed to an analytical chip while a fluid sample is analyzed under the same conditions (temperature, flow mode, light volume, optical axis, conditions of light detection, fixing method of specific substances, the kinds and number of fluid samples, etc.) to thereby detect the difference in the state of interaction between the specific substances, the difference between each specific substance and a non-interaction area (an area of the surface of the analytical chip to which any specific substance is not fixed), or the difference between the states of each specific substance before and after reaction. In the cases, when any error occurs in the detection results as described above, even if the error relates to only the detection results of some specific substances, all the differences to be detected are involved and become impossible to be analyzed.

Besides, in the case where analysis is carried out based on light, when the surface of the analytical chip that serves as the optical path has flaws or the like, such flaws may cause reflection, dispersion, or deviation of the optical axis. Hence, it may become impossible to analyze the fluid sample precisely, or some of the specific substances may partially become undetectable. Such flaws can occur during various processes the analytical chip undergoes, such as manufacturing, assembling, packing, transferring for distribution, unsealing, pretreating for experiment, cleaning, experiment, etc., and are therefore difficult to be expected and prevented.

As described above, in the cases where an error occur due to reflections or flaws on the optical path, or in any similar cases, since it is necessary to prepare the analytical chip and carry out experiments again, the time and cost for analysis increase, and it is required to prepare a new fluid sample again even if it is valuable.

By contrast, using the analytical chip 1I according to the present embodiment, since the anti-reflection layer 25a is formed over the outer surface the cover member 2, it is possible to prevent the reflection of light transmitted through the outer surface of the cover member 2. Besides, since the anti-reflection layer 85 is formed over the surface of the plate 8 on the side of the flow channel 5, it is also possible to prevent the reflection of light transmitted through the surface of the plate 8 on the side of the flow channel 5. Also, regarding the light reflected from the reaction area 6 toward outside the analytical chip 1I, as in the case of the incident light, it is possible to prevent the light from being reflected by the outer surface of the cover member 2 and the surface on the side of the flow channel 5. It thereby becomes possible to inhibit the occurrence of errors due to the reflection of light on the surface of the optically transparent part 7.

Besides, since the abrasion resistance layer 25b, 85b is formed over the outermost surface of each of the cover member 2 and the plate 8, which serves as the optically transparent part 7, it is possible to protect the surface of the optically transparent part 7 of the analytical chip 1I against flaws or scratches. Hence, when analysis is carried out using the analytical chip 1I, since there arise no flaws on the optical path, it is possible to prevent the occurrence of reflection or dispersion of light, or deviation of the optical axis, due to such flaws on the optical path.

Incidentally, the anti-reflection layers 25a, 85a and the abrasion resistance layers 25b, 85b do not block the optical path for the incident light from the light source 100 nor that for the reflection light from the reaction area to outside.

As described above, since the analytical chip 1I has the anti-reflection layers 25a, 85a and the abrasion resistance layers 85a, 85b, by using the analytical chip 1I to carry out analysis, it is possible to obtain precise results securely, without being affected by the reflection of light on the surface of the optically transparent part 7 or the dispersion of light due to flaws on the optical path. It becomes therefore possible to carry out analysis efficiently, negating the necessity for carrying out analysis repeatedly.

Besides, in the present embodiment, since the protective layers 25, 85 are formed over both the outer surface of the optically transparent part 7 and the surface of the optically transparent part 7 on the side of the flow channel 5, it is possible to carry out analysis more precisely compared with the case the protective layer 25, 85 is formed on either the outer surface or the surface on the side of the flow channel 5.

In addition, in the case where the anti-reflection films 25a, 85a are formed, as is the present embodiment, even when the flow channel 5 is made to have a small height (depth) and is in a sheet shape thinner than that of the conventional chip, there does not arise such a multi reflection as described above. It becomes therefore possible to make the height (depth) of the flow channel 5 much smaller and to thereby reduce the amount of fluid sample Fs even further.

Also, according to the present analytical chip 1I, the plural slit-form flow channels 9a share the single injection port 21 and the single drain port 22. Hence, compared to the above-described conventional technique, in which plural flow channels are simply arranged in parallel and the fluid is injected into and drained from each of the flow channels separately, the present analytical chip has the advantage that it needs fewer connectors and tubes for injection and drainage, simplifying the installation work of such connectors and tubes to the chip 1I. As a matter of course, it is also possible to provide plural injection ports 21 and plural drain ports 22.

Besides, since the flow channel 5 formed as a sheet-shaped space is divided into the minute (narrow-width) inner flow channels (slit-form flow channels) 9a with the partition walls 9b, it becomes possible to prevent the occurrence of air bubbles due to enclosing flow of the fluid sample Fs.

Specifically speaking, in the conventional sheet-shaped flow channel, since the interface between the three phases of solid-gas-liquid has a long front line as shown in FIG. 6(a), part of the fluid sample Fs runs ahead due to non-uniformity of wettability, so that enclosing flow of the fluid sample Fs occurs to result in generation of the enclosure of gas (air bubble 201). In the present invention, since the flow channel 5 is divided into the separate, minute inner flow channels (the slit-form flow channels 9a), the length of line segment L (flow channel width) perpendicular to the main flow in the flow channel becomes small as shown in FIG. 6(b), so that the occurrence rate of the enclosing flow decreases significantly. Besides, since the cross sectional area of the flow channel becomes small, it is possible to apply backing pressure efficiently to the interior of each slit-form flow channel 9a, thereby making air bubbles hard to remain dwelling.

Consequently, according to the present analytical chip 1I, it becomes possible to remove various adverse effects arising from the dwelling of air bubbles (such as the blockage of the normal flow of the fluid sample Fs, the hindering of the contact between the specific substance 61 and the fluid sample Fs, the non-uniformity of temperature in the system of measurement caused by the difference of heat transfer coefficient between the liquid Fs and the air bubble 201, the inhibition of the measurement during the analysis using an optical system because of the air bubble 201 dwelling in the optical path, etc.), resulting in the advantage that the reliability of analysis is improved. Besides, since it eliminates the need for extra work of getting rid of air bubbles 201, there is the advantage that analytical work can be carried out efficiently.

Moreover, even when the chip 1I fastened together with the holder is subjected to a pressure, since it is provided with the plural partition walls 9b formed across the width directions of the chip 1I, the pressure resistance of the chip 1I can be improved and the chip 1I can be prevented from undergoing shape distortion, specifically shape distortion along the thickness direction. This feature offers the advantage that the occurrence of non-uniformity in velocity distribution due to bending of the chip 1I can be prevented. It also offers the advantage that even when the analysis is carried out using an optical system, since the unevenness in length of the optical paths and the alteration of the optical axis can be prevented, it becomes possible to carry out analysis under the favorable conditions, thereby the precision of analysis results being improved.

Meantime, a major feature of the analytical chip used for the SPR sensor is that it enables to detect the state of interaction in the reaction area 6 (the plural specific substances 61) optically and online. Specifically, if an air bubble remains dwelling in the reaction area (i.e., the measurement area) 6 of the conventional chip, the dwelling air bubble may prevent not only interaction between the specific substance 61 and the target species but also optical measurement. By contrast, the present analytical chip 1A has the advantage that it prevents the occurrence of air bubbles and thereby enables to carry out analysis based on optical measurement online with stability.

Figure 52:
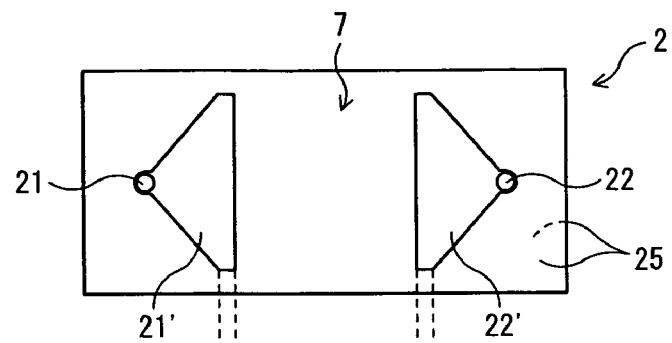
FIG. 52(a) is a diagrammatic bottom view of a cover member according to the first modification of the eleventh embodiment of the present invention.
FIG. 52(b) is a diagrammatic top view of an intermediate plate according to the first modification of the eleventh embodiment of the present invention.
FIG. 52(c) is a diagrammatic top view of a basal plate according to the first modification of the eleventh embodiment of the present invention.
Figure 52:
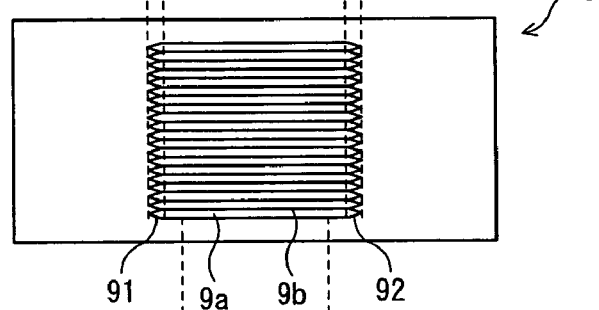
Figure 52:
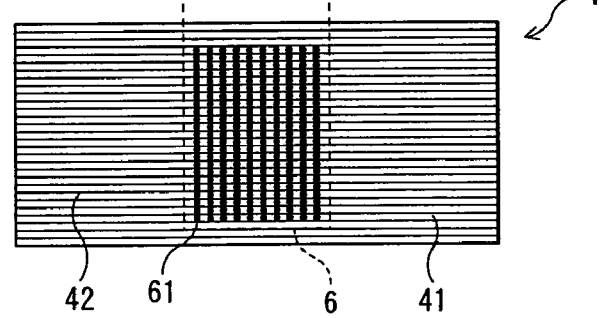

Incidentally, although in the present embodiment the plate 8 and the plate 9 are sandwiched between the basal plate 4 and the cover member 2 to thereby form the chip 1I, it is also preferable that as shown in FIGS. 52(a)–FIG. 52(c), the openings 81, 82 of the plate 8 defining the flow-channel confluence parts are incorporated into the cover member 2. In the modification, the cover member 2 has groove parts (concavity parts) 21', 22', which are formed directly on the under surface of the cover member 2 and have the shapes corresponding to the openings 81, 82 so as to define the flow-channel confluence parts. With this arrangement, since it is necessary only that the plate 9 is be sandwiched between the basal plate 4 and the cover member 2, it is possible to make the chip 1 easily. In the modification, since the optically transparent part 7 is formed by the cover member 2 alone, as shown in FIG. 52(a), the protective layers 25 is formed over each of the upper surface and the under surface of the cover member 2. As in the eleventh embodiment, each of the protective layers 25 can allow light transmission while protecting the surface of the optically transparent part 7, and is composed of the anti-reflection layer 25a and the abrasion resistance layer 25b. The plate 9 and the basal plate 4 are identical to the plate 9 and the basal plate 4 shown in FIGS. 51(c), (d), so that redundant explanation is omitted.

Alternatively, it is also preferable that as shown in FIGS. 53(a), (b), in addition to the groove parts (concavity parts) 21', 22' formed directly on the under surface of the cover member 2 and having the shapes corresponding to the openings 81, 82 so as to define the flow-channel confluence parts, the slit-form grooves are formed directly on the basal plate 4 the slit-form flow channels 4a so as to eliminate the need for the plate 9. Incidentally, the slit-form grooves 4a, the slit-form flow channels 4a, and the inner flow channels mean the same components. With this arrangement, since it is necessary only that the cover member 2 is laid on the basal plate 4, it is possible to make the chip 1I more easily. Also in the modification, since the optically transparent part 7 is formed by the cover member 2 alone, as shown in FIG. 53(a) the protective layers 25 is formed over each of the upper surface and the under surface of the cover member 2. As in the eleventh embodiment, each of the protective layers 25 can allow light transmission while protecting the surface of the optically transparent part 7, and is composed of the anti-reflection layer 25a and the abrasion resistance layer 25b. In FIG. 53, the reference characters also used in FIGS. 48–52 designate like components.

It is also preferable that as shown in FIGS. 54(a)–(c), the openings 81, 82 of the plate 8 are incorporated into the basal plate 4 instead of using the plate 8. In the modification, the basal plate 4 has groove parts (concavity parts) 43, 44, which are directly formed on the top surface of the basal plate 4 and have the shapes corresponding to the openings 81, 82 so as to define the flow-channel confluence parts. In addition, the openings 91', 92' are formed through the plate 9 in such a manner that when the cover member 2 is laid on the plate 9, the opening 91' and the opening 92' are aligned with the injection port 21 and the drain port 22, respectively, to communicate with the injection port 21 and the drain port 22 with the groove parts. With this arrangement, since it is necessary only that the plate 9 is sandwiched between the basal plate 4 and the cover member 2, it is possible to make the chip 1I easily. Also in the modification, since the optically transparent part 7 is formed by the cover member 2 alone, as shown in FIG. 54(*a*), the protective layers 25 is formed over each of the upper surface and the under surface of the cover member 2. As in the eleventh embodiment, each of the protective layers 25 can allow light transmission while protecting the surface of the optically transparent part 7, and is composed of the anti-reflection layer 25*a* and the abrasion resistance layer 25*b*. In FIG. 54, the reference characters also used in FIG. 51 designate like components.

Figure 55:
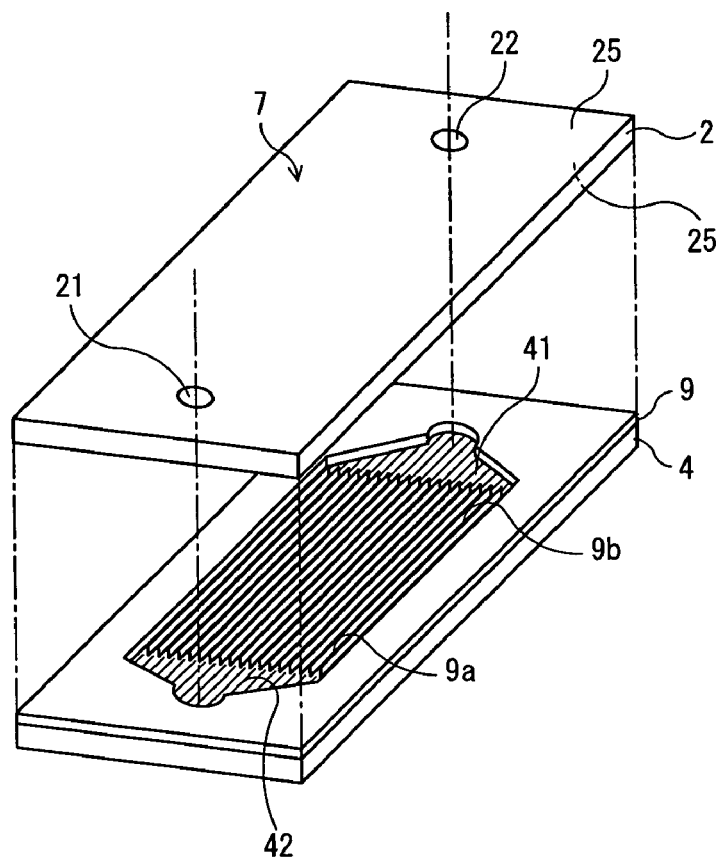
FIG. 55 is a diagrammatic exploded perspective view of an analytical chip according to an embodiment of the present invention.

Another preferable modification is that as shown in FIG. 55, the openings 81, 82 of the plate 8 are incorporated into the plate 9 and that the plate 9 is sandwich between the basal plate 4 and the cover member 2, thereby making the chip 1I. Although in the modification the partition walls 9*b* are separated from the plate 9, the chip 1I can be made more easily by using techniques such as screen printing, ink jet printing, and coating. Also in the modification, since the optically transparent part 7 is formed by the cover member 2 alone, as shown in FIG. 55, the protective layers 25 is formed over each of the upper surface and the under surface of the cover member 2. As in the eleventh embodiment, each of the protective layers 25 can allow light transmission while protecting the surface of the optically transparent part 7, and is composed of the anti-reflection layer 25*a* and the abrasion resistance layer 25*b*. In FIG. 55, the reference characters also used in FIG. 51 designate like components.

For forming the concavity parts 21', 22', 46, 47 and the slit-form grooves 9*a*, the following methods can be selectively used: machining; various transferring techniques typified by injection molding and compression molding; dry etching (RIE, IE, IBE, plasma etching, laser etching, laser ablation, blasting, electrical discharge machining, LIGA, electron beam etching, FAB); wet etching (chemical erosion); integral molding such as optical machining or ceramic covering; Surface Micro-machining of coating with various substances in a layer and partially removing by means of vacuum evaporation, sputtering, deposition, or the like, to thereby form a microstructure; a method that includes dripping a material of the flow channel using an ink jet or a dispenser (namely, preliminary forming the concavity parts 21', 22', 46, 47 and the middle part of the flow direction integrally as a concavity portion, and then dripping the material of the channels onto the middle part along the flow direction flow to thereby form the partition walls 9*a*), optical machining method, etc.

Besides, although in the present embodiment the components are joined together by fastening physically with a holder so that the chip 1I can be disassembled, it is also possible to use any other measures for joining the components. Examples of the joining measures include, although not limited thereto, adhesion with an adhesive agent, resin bonding with a primer, diffusion bonding, anodic bonding, eutectic bonding, heat sealing, ultrasonic bonding, laser fusing, dissolution with a resolvent or a solvent, etc. It is also possible to use a sticky tape, an adhesive tape, or a self-adsorbent. Alternatively, it is also preferable to adopt pressure bonding, or form concavities and convexities on the components so as to be engageable with each other. With these measures, the components can be easily assembled. It is also allowable to use any two or more of the above joining measures in combination.

Meanwhile, when carrying out analysis based on SPR as described above, it is possible not only to make a single fluid sample Fs flow into the microchannel chip for analysis, but also to make two or more fluid samples Fs flow one after another at successive intervals using a buffer and analyze a series of binding and dissociation between target substances contained in the fluid samples Fs and the specific substance.

Besides, although in the present embodiment it is not possible that light passes through the basal plate 4 due to the metal layer 41 formed over the basal plate 4, if the metal layer 41 is formed in quite a small thickness, there may be a case where light can pass through the basal plate 4 due to the metal layer 41 formed over the basal plate 4. Even in such a case, however, the metal layer 41 is usually not transparent.

Also, the detector 101 is not limited to a CCD camera, as is used in the present embodiment: any other kinds of detectors such as a photo diode, a photomultiplier, a photosensitive paper, etc. are also usable as the detector 101.

(12) Twelfth Embodiment

Figure 56:
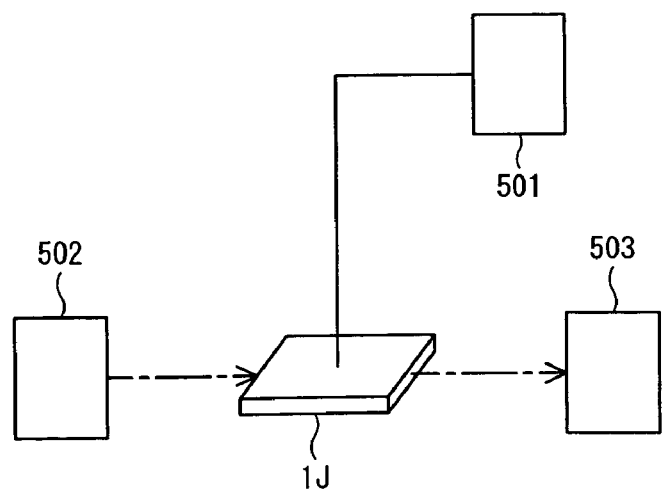
FIG. 56 is a diagram of assistance in explaining an analysis apparatus according to the twelfth embodiment of the present invention.

FIG. 56 is a diagram of assistance in explaining an analysis apparatus according to the twelfth embodiment of the present invention. As shown in FIG. 56, the analysis apparatus according to the twelfth embodiment of the present invention has analytical chip 1J, which has the same constitution of that of analytical chip 1I described in the eleventh embodiment, analysis section 501, which is for carrying out analysis of fluid sample Fs flowing through the analytical chip 1J, separation apparatus 502, which is disposed upstream of the analytical chip 1J for separating the fluid sample Fs by physical and/or chemical action prior to the introduction of the fluid sample Fs to the analytical chip 1J, and after-analysis apparatus 503, which is for analyzing the fluid sample Fs drained from the analytical chip 1J. The constitution of the analytical chip 1J is identical to that of the analytical chip 1I, so that redundant explanation is omitted.

The analysis section 501 is for carrying out analysis based on surface plasmon resonance, and it is possible to configure the analysis section 501 specifically in the same constitution as that of the eleventh embodiment. Specifically, when using the analysis section 501 which carries out analysis based on surface plasmon resonance, it is also possible to carry out analysis under light irradiation from the back face of the analytical chip 1J. Namely, a light beam is applied from the side of the basal plate 4 of the analytical chip 1J into the reaction area 6, which is formed in the flow channel 5 of the analytical chip 1J, and the light beam reflected by the reaction area 6 is observed at the side of the basal plate 4 of the analytical chip 1J while analysis is carried out. In the case, however, since it is necessary that the applied light beam reaches the reaction area 6 of the analytical chip 1J, it is required as a matter of course that the basal plate 4 is formed in such a manner that it allows the incident light to pass through. Hence, when analysis is carried out under light application from the back face the analytical chip 1J, the basal plate 4 is usually made from materials that can transmit light having the same wavelengths as those of the incident light.

Figure 57:
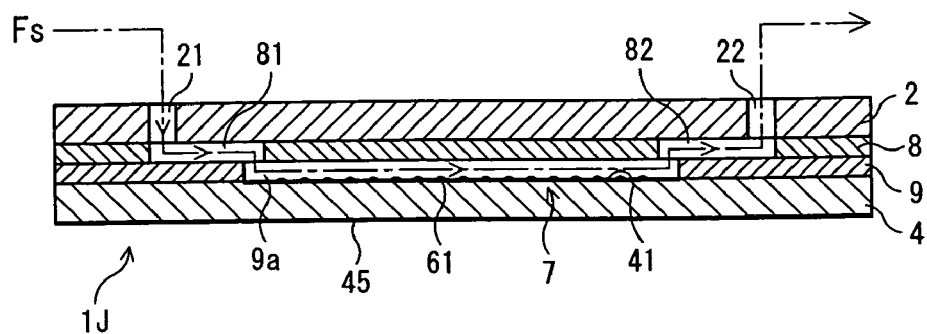
FIG. 57 is a diagrammatic sectional view of assistance in explaining the first modification of the twelfth embodiment of the present invention.

Also, when analysis is carried out while light is applied from the back face of the analytical chip 1J, namely, from the side of the basal plate 4, the basal plate 4 forms the optically transparent part 7. Specifically, the light passes through the basal plate 4 to reach the reaction area 6, and is reflected by the reaction area 6, then the reflection light passes through the basal plate 4 to outside the analytical chip 1J and is detected. It is therefore necessary that, as shown in FIG. 57, the protective layer 45 (the protective layer 45 is composed of the anti-reflection layer and the abrasion resistance layer) can protect the surface of the optically transparent part 7 while allowing light transmission, as in the eleventh embodiment, and hence must be formed over the outer surface of the basal plate 4, through which the incident light and the reflection light are to pass through. In FIG. 57, the same reference characters as used in FIGS. 48–56 designate the same components.

Besides, the analysis apparatus according to the present embodiment has separation apparatus 502, which is disposed upstream of the analytical chip 1J and is for separating the fluid sample Fs by physical and/or chemical action prior to the introduction of the fluid sample Fs into the analytical chip 1J.

The constitution of the separation apparatus 502 is not restricted particularly, although it is generally preferable to use the techniques such as: liquid chromatography and HPLC (high performance liquid chromatography), which carry out separation based on the adsorptivity or the distribution coefficient of samples; capillary electrophoresis, micro chip electrophoresis, and microchannel electrophoresis, which carry out separation based on the electronegativity of samples; and flow injection. Also, it is naturally possible to equip the analysis apparatus with any other types of apparatus as the separation apparatus 502, either alone or in combination with the above-exemplified types of apparatus.

The "microchannel" means a groove which is formed on a chip surface and through which a sample flows, and the "microchannel electrophoresis" means the technique of carrying out separation by filling a part of the groove with substances corresponding to column fillers used for HPLC or fixing functional groups to the groove surface.

The "microchannel" means a groove which is formed on a chip surface and through which a sample flows, and the "microchannel electrophoresis" means the technique of carrying out separation by filling a part of the groove with substances corresponding to column fillers used for HPLC or fixing functional groups to the groove surface.

As a matter of course, it is also possible to equip the analysis apparatus with any apparatus other than those exemplified above as the separation apparatus 502.

In addition, the analysis apparatus according to the present embodiment has after-analysis apparatus 503, which carries out analysis of the fluid sample Fs drained from the analytical chip. The constitution of the after-analysis apparatus 503 is not restricted particularly, and various types of analysis apparatus can be used as the after-analysis apparatus 503. Specifically, examples include MS (mass spectrograph), protein sequencer, DNA sequencer, SEM, SPM, STM, AFM, etc.

In addition, the after-analysis apparatus 503 can also have a pretreatment mechanism, which make the fluid sample Fs in the state of allowing analysis. Also, it can have any of the above-exemplified types of apparatus in combination.

When using the analysis apparatus according to the tenth embodiment of the present invention, which is constituted as described above, during analysis, the fluid sample Fs is made flow through in turn the separation apparatus 502, the analytical chip 1J, and the after-analysis apparatus 503 while analysis is carried out.

When analysis is carried out by the analysis section 501, since the analytical chip 1J has the anti-reflection films 25a, 85a, it is possible to prevent the reflection of light that passes through the surface of the optically transparent part 7 of the analytical chip 1J. Also, since the analytical chip 1J has the anti-reflection films 25b, 85b, it is possible to protect the surface of the optically transparent part 7 of the analytical chip 1J against flaws. It becomes therefore possible to carry out analysis of the fluid sample Fs efficiently with high precision.

Besides, since the analysis apparatus has the separation apparatus 502, it is possible to preliminary a sample containing separate predetermined substances, such as enzymes and proteins, into fractions each containing pure substances, using the separation apparatus. It becomes thus possible to analyze predetermined substances in the state of being fractioned into pure substances, so that it is possible to carry out analysis more accurately.

In addition, since the analysis apparatus has the after-analysis apparatus 503, it is possible to obtain multiple data through a single analysis operation and to thereby analyze the fluid sample Fs from various points of view.

In the meantime, although in the present embodiment the analytical chip 1I explained in the eleventh embodiment is used as the analytical chip 1J, it is a matter of course that the analytical chip is not limited to the same one as described above. It is also possible to use the analytical chips that have any other constitutions.

Besides, the analysis section 501 can also use any analytical techniques other than surface plasmon resonance, such as chemiluminescence, bioluminescence, electrochemiluminescence, fluorescence, or RI (radioactive isotope analysis), so long as analysis is carried out based on the detection and measurement from the reaction area 6 through the optically transparent part 7. Also, the analysis section 501 carries out analysis using one of the above-exemplified techniques or carries out analysis using two or more of the techniques in combination. Even when the analysis section 501 carries out analysis using any analytical technique other than surface plasmon resonance, it is also possible to combine the analysis section 501 with the separation apparatus 502 and the after-analysis apparatus 503 in a similar manner as the analysis apparatus described above.

For example, when using the analysis section 501 which carries out analysis based on fluorescence, it is possible to use the analytical chip 1J with the same constitution as that of the analytical chip 1I, as described in the eleventh embodiment, with the exception that the metal layer 41 and the diffraction grating 42 are not formed on the basal plate 4. Also, as described above, the separation apparatus 502 is disposed at the upstream side of the analytical chip 1J, while the after-analysis apparatus 503 is disposed at the downstream side of the analytical chip 1J. With the arrangement, since the analytical chip 1J has the anti-reflection films 25a, 85a, it is possible to prevent the reflection of light that passes through the surface of the optically transparent part 7 of the analytical chip 1J. Also, since the analytical chip 1J has the anti-reflection films 25b, 85b, it is possible to protect the surface of the optically transparent part 7 of the analytical chip 1J against flaws. It becomes therefore possible to carry out analysis of the fluid sample Fs efficiently with high precision. Besides, since it has the separation apparatus 502 and the after-analysis apparatus 503, it is possible to carry out analysis accurately from multiple points of view, as in the case of the analysis section 501 that carries out analysis based on surface plasmon resonance.

Figure 58:
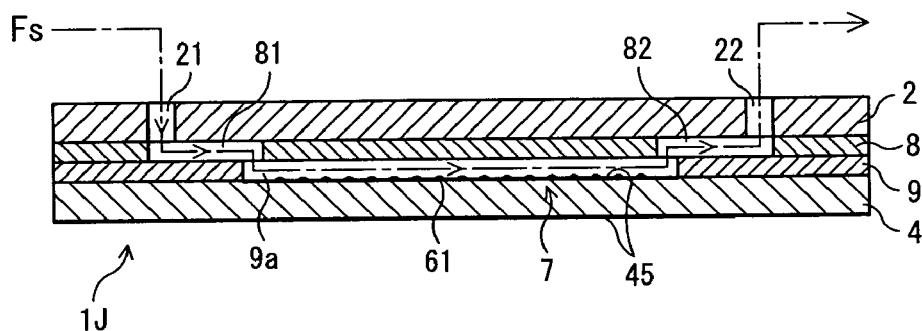
FIG. 58 is a diagrammatic sectional view of assistance in explaining the second modification of the twelfth embodiment of the present invention.

When analysis is carried out, excitation light is applied from the side of the cover member 2 while fluorescence is also detected also from the side of the cover member 2. However, it is also possible, just as in the case where analysis is carried out based on surface plasmon resonance, to apply excitation light from the side of the back face of the analytical chip 1, i.e., the side of the basal plate 4 and detect fluorescence from the side of the basal plate 4 to carry out analysis. In the case, the basal plate 4 forms the optically transparent part 7. Hence in this case, as shown in FIG. 58, it is necessary to form the protective layer 45 (the protective layer 45 is composed of the anti-reflection layer and the abrasion resistance layer), which can protect the surface of the optically transparent part 7 while allowing light transmission as in the eleventh embodiment, on both the outer surface of the basal plate 4 and the surface of the basal plate 4 on the side of the flow channel 5. In FIG. 58, the same reference characters as used in FIGS. 48–57 designate the same components.

Figure 59:
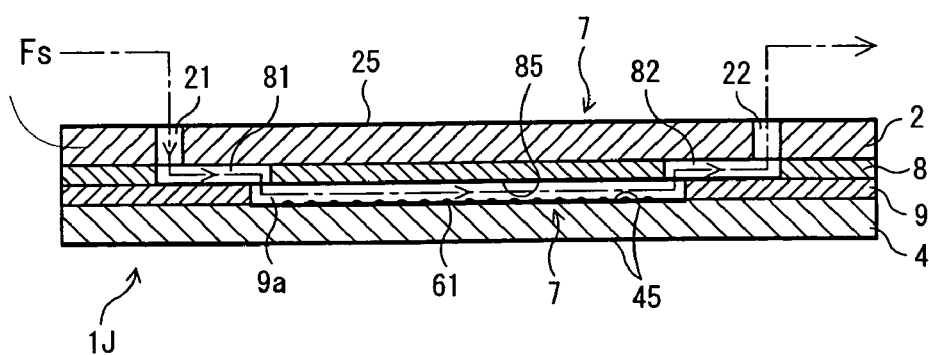
FIG. 59 is a diagrammatic sectional view of assistance in explaining the third modification the twelfth embodiment of the present invention.

In addition, it is also possible to apply excitation light from the side of the cover member 2 of the analytical chip 1J and detect fluorescence from the side of the basal plate 4 or, in contrast, to apply excitation light from the side of the basal plate 4 and detect fluorescence from the side of the cover member 2. In the case, each of the cover member 2, the plate 8, and the basal plate 4 forms the optically transparent part 7. Hence in this case, as shown in FIG. 59, it is necessary to form the protective layers 25, 85, 45 (each of the protective layers 25, 85, 45 is composed of the anti-reflection layer and the abrasion resistance layer), which can protect the surface of the optically transparent part 7 while allowing light transmission as in the eleventh embodiment, on the outer surface of the cover member 2, the surface of the plate 8 on the side of the flow channel 5, the outer surface of the basal plate 4, and the surface of the basal plate 4 on the side of the flow channel 5. In FIG. 59, the same reference characters as used in FIGS. 48–58 designate the same components.

When using the analysis section 501 that carries out analysis based on chemiluminescence or bioluminescence, as in the case the analysis is carried out based on fluorescence, it is possible to use the analytical chip 1J with the same constitution as that of the analytical chip 1I, as described in the eleventh embodiment, with the exception that the metal layer 41 and the diffraction grating 42 are not formed on the basal plate 4. Also, as described above, the separation apparatus 502 is disposed at the upstream side of the analytical chip 1J, while the after-analysis apparatus 503 is disposed at the downstream side of the analytical chip 1J. Incidentally, when using chemiluminescence or bioluminescence, there is usually no necessity for applying excitation light. With the arrangement, since the analytical chip 1J has the anti-reflection films 25a, 85a, it is possible to prevent the reflection of light that passes through the surface of the optically transparent part 7 of the analytical chip 1J. Also, since the analytical chip 1J has the anti-reflection films 25b, 85b, it is possible to protect the surface of the optically transparent part 7 of the analytical chip 1J against flaws. It becomes therefore possible to carry out analysis of the fluid sample Fs efficiently with high precision. Besides, since it has the separation apparatus 502 and the after-analysis apparatus 503, it is possible to carry out analysis accurately from multiple points of view, as in the case of the analysis section 501 that carries out analysis based on surface plasmon resonance.

When analysis is carried out in the analysis section 501 based on electrochemiluminescence, the analysis apparatus has the same analytical chip 1J as that of the analysis apparatus having the analysis section 501 for carrying out analysis based on fluorescence or chemiluminescence, except for the basal plate 4 has an electrode. Also, as described above, the separation apparatus 502 is disposed at the upstream side of the analytical chip 1J, while the after-analysis apparatus 503 is disposed at the downstream side of the analytical chip 1J. With the arrangement, since the analytical chip 1J has the anti-reflection films 25a, 85a, it is possible to prevent the reflection of light that passes through the surface of the optically transparent part 7 of the analytical chip 1J. Also, since the analytical chip 1J has the anti-reflection films 25b, 85b, it is possible to protect the surface of the optically transparent part 7 of the analytical chip 1J against flaws. It becomes therefore possible to carry out analysis of the fluid sample Fs efficiently with high precision. Besides, since it has the separation apparatus 502 and the after-analysis apparatus 503, it is possible to carry out analysis accurately from multiple points of view, as in the case of the analysis section 501 that carries out analysis based on surface plasmon resonance.

It is to be noted, however, that it is necessary to dispose the electrode to the basal plate 4 in the case of electrochemiluminescence. Hence, so long as the electrode is made from a non-transparent material, even if the basal plate 4 is made from a transparent material, it is difficult to detect electrochemiluminescence from the side of the basal plate 4. On the other hand, when the electrode is made from a transparent material (i.e., ITO), or when the electrode is made from a non-transparent material but formed in such a extremely thin film that it can transmit light, it is also possible to carry out the application and detection of light from the side of the basal plate 4.

(13) Thirteenth Embodiment

Figure 65:
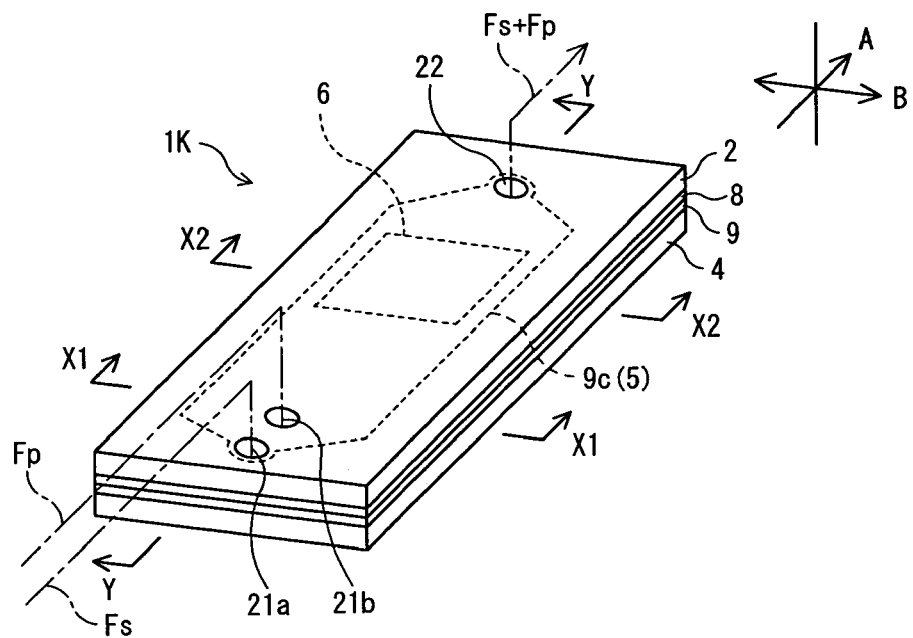
FIG. 65(a) is a diagrammatic assembled perspective view of an analytical chip according to the thirteenth embodiment of the present invention.
FIG. 65(b) is a diagrammatic exploded perspective view of an analytical chip according to the thirteenth embodiment of the present invention.
Figure 65:
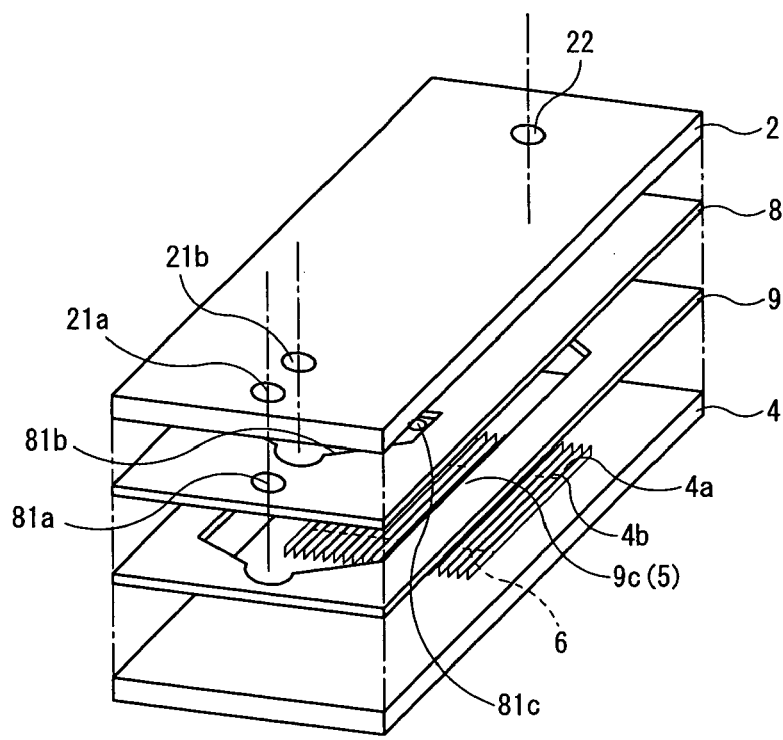
Figure 67:
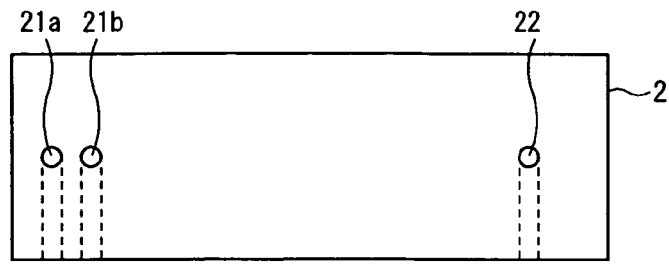
FIG. 67(a) is a diagrammatic top view of a cover member of an analytical chip according to the thirteenth embodiment of the present invention.
FIG. 67(b) is a diagrammatic top view of a plate of an analytical chip according to the thirteenth embodiment of the present invention.
FIG. 67(c) is a diagrammatic top view of a plate of an analytical chip according to the thirteenth embodiment of the present invention.
FIG. 67(d) is a diagrammatic top view of a basal plate of an analytical chip according to the thirteenth embodiment of the present invention.
Figure 67:
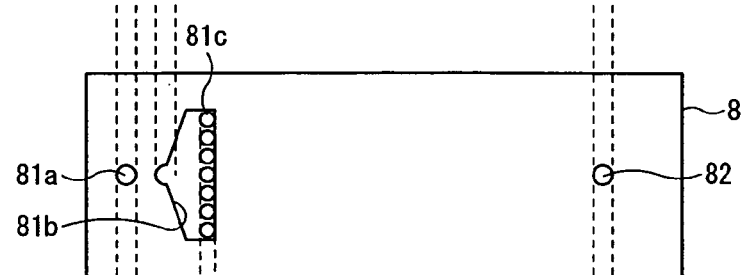
Figure 67:
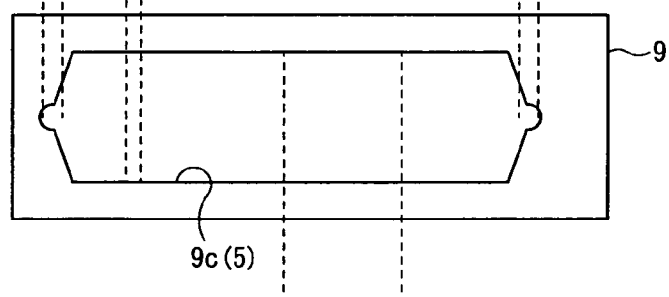
Figure 67:
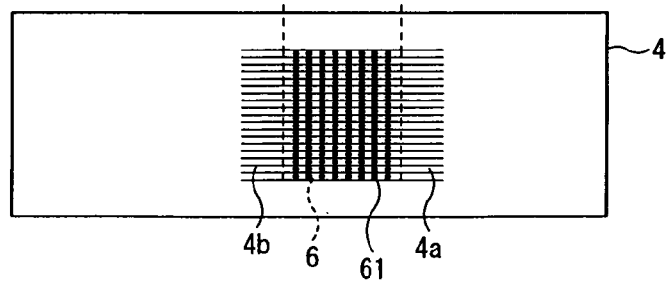

FIGS. 65 through 67 each show an analytical chip 1K according to the thirteenth embodiment of the present invention. Specifically, FIG. 65(a) is a diagrammatic assembled perspective view of an analytical chip according to the thirteenth embodiment of the present invention, and FIG. 65(b) is a diagrammatic exploded perspective view of an analytical chip according to the thirteenth embodiment of the present invention; FIG. 66(a) is a diagrammatic sectional view taken on line Y—Y of FIG. 65(a), FIG. 66(b) is a diagrammatic sectional view taken on line X1—X1 of FIG. 65(a), and FIG. 66(c) is a diagrammatic sectional view taken on line X2—X2 of FIG. 65(a); and FIG. 67(a) is a diagrammatic top view of a cover member of an analytical chip according to the thirteenth embodiment of the present invention, FIG. 67(b) is a diagrammatic top view of a plate of an analytical chip according to the thirteenth embodiment of the present invention, FIG. 67(c) is a diagrammatic top view of a plate of an analytical chip according to the thirteenth embodiment of the present invention, and FIG. 67(d) is a diagrammatic top view of a basal plate of an analytical chip according to the thirteenth embodiment of the present invention. In the following description, flow direction A of fluid sample Fs is defined as the major direction in which most of the fluid sample Fs flows through the flow channel. To take FIG. 4 as an example, the flow direction of flow channel 5' is defined as the direction indicated by the arrow in solid line. In the following, the thirteenth embodiment of the present invention is explained with taking, as an instance, the case where analysis is carried out while the fluid sample Fs is mixed with a pH adjuster solution Fp for pH adjusting.

As shown in FIGS. 65(a), (b) and FIGS. 66(a)–(c), the present analytical chip (hereinafter called simply "the chip") 1K is composed of cover member 2, which is flat-plate shaped, first plate (hereinafter called simply "the plate") 8, which is of small thickness, second plate (an intermediate plate, hereinafter called simply "the plate") 9, which is of small thickness as with the plate 8, and basal plate 4. In carrying out analysis, as shown in FIG. 65(a), these components 2, 8, 9, 4 are piled in the listed order from above downward, and fastened together as a unit by a joining holder, not shown in the drawings. The plates 8, 9 are thus interposed between the cover member 2 and the basal plate 4. It is preferable that the holder has a protection device for securing accurate alignment and preventing scratches. Examples of the protection device include a locking part, which is attached to the holder so as to lock the analytical chip 1K, and a hollow, formed on the holder so that an observation part (reaction area 6, which will be described later) of the analytical chip 1 does not touch the holder.

As shown in FIG. 66(*a*), fluid sample Fs is to be injected into opening 21*a* (an injection port at the upstream end of flow channel 5, which will be described later) of the cover member 2, and to flow through opening 81 (a flow-channel confluence part on the upstream side) of the plate 8, then through each of slit-form openings 9*c* (inner flow channels) of the plate 9. Subsequently, the fluid sample Fs is to flow through opening 82 (a flow-channel confluence part on the downstream side) of the plate 8, and to be finally drained from opening 22 (a drain port at the downstream end of flow channel 5, which will be described later) of the cover member 2. While passing through the slit-form openings 9*c* of the plate 9, the fluid sample Fs is to be in contact with one or more specific substances 61, which are fixed to reaction area 6 of the basal plate 4.

On the other hand, the pH adjuster solution Fp injected from the opening 21*b* of the cover member 2 passes through concavity parts (groove parts) 81*b*, which are formed on the plate 8, and then through plural openings (injection port group for the pH adjuster solution) 81*c*, which are formed at the downstream end of the concavity parts 81*b*, and flows into the openings 9*c* of the plate 9. In the openings 9*c*, the pH adjuster solution joins the fluid sample Fs to be mixed with fluid sample Fs together, and the mixture liquid flows through the opening 82 of the plate 8 and then flows out from the opening 22 of the plate 2. In the drawings, reference character Fs+Fp designates the mixture liquid of the fluid sample Fs and the pH adjuster solution Fp to be drained from the drain port 22.

As shown in FIGS. 65(*b*) and 66(*b*), the concavity parts 81*b* formed on the plate 8 are opened only to the side of the cover member 2. Also, as shown in FIG. 66(*c*), the openings 9*c* formed on the plate 9 are opened to both sides of the plate 9. The plate 8 blocks the openings 9*c* from one side of the plate 9 while the basal plate 4 blocks the other side, thereby defining the flow channel 5 formed as a sheet-shaped space. Thus the openings 9*c* define the flow channel 5.

In the present invention, the "flow channel formed as a sheet-shaped space" generally means a flow channel whose long side 5*a* has a size W of between 500 μm and 100 mm inclusive, and whose short side 5*b* has a size H of between 5 μm and 2 mm inclusive. The "long side" means the longest side among all the sides of both sections orthogonal to the flow direction of the flow channel 5 and sections orthogonal to width directions, generally being a side along either the width of the flow channel 5 or the length of the flow channel 5 in the flow direction (in the present embodiment, a side along the width of the flow channel 5). The "short side" means a side along the height of flow channel 5. The size ratio between the long side 5*a* and the short side 5*b* (=[long side size W]/[short side size H]) is generally 1.5 or above, preferably 10 or above, and generally 20000 or below, preferably 100 or below. When the flow channel 5 is, as will be described later, divided into two or more inner flow channels 4*a* with one or more partition walls 4*b* (which serve as projection member, partition members, or prop members), at least the sizes of the whole flow channel 5 (the sizes of the whole of the plural inner flow channels 4*a* joined together) have to meet the above range of size ratio. In the present embodiment, the length W of the long side 5*a* is set at 20 mm, while the length of the short side 5*b* of each of the plates 8, 9 (in X1—X1 section, height $H_3$ of the concavity parts 81*b*; in X2—X2 section, thickness $H_2$ of the plate 9) is set at 250 μm.

Hereafter, each of the above components of the present analytical chip 1K will be described in detail.

Each of the cover member 2, the plate 8, the plate 9, and the basal plate 4 can be made from any kinds of materials, examples of which include, but are not limited to, resins, ceramics, glasses, and metals. However, when measuring any interaction (such as reaction or binding) between target species and the specific substances 61 optically based on fluorescence, luminescence, color change, or phosphorescence, etc., it is desired to make each of the cover member 2 and the plates 8, 9 from one or more transparent materials; as an exception, when measurement can be carried out with the analytical chip 1 being disassembled, the cover member 2 and the plates 8, 9 are not necessarily required to have transparency. Examples of transparent materials are: resins, such as acrylic resin, polycarbonate, polystyrene, polydimethylsiloxane, and polyolefin; and glasses, such as Pyrex$^R$ (i.e., borosilicate glass) and quartz glass. In the present embodiment, it is assumed that the cover member 2 is made from a transparent glass, the plates 8, 9 from resins, and the basal plate 4 from a metal.

As shown in FIG. 67(*a*), opening 21*a* through which the fluid sample Fs is to be injected is formed at the upstream end of the cover member 2, opening 21*b* through which the pH adjuster solution Fp is to be injected is formed the downstream side of the opening 21*a*, and single opening (drain port) 22 is formed at the downstream end of the cover member 2.

Each of the openings 21*a*, 21*b* is connected to an injection pump (e.g. a syringe pump) via a connector or a tube, which is omitted in the drawings, and the drain port 22 is connected to a waste liquid tank via a connector or a tube, which is omitted in the drawings. Operating the above injection pump, it is possible to inject the fluid sample Fs via the injection port 21*a*, and the pH adjuster solution Fp via the injection port 21*b*, into the chip 1 and drain them from the chip 1.

As shown in FIG. 67(*b*), at the upstream end of the plate 8, opening (injection port) 81*a* through which the fluid sample Fs is to be injected into the flow channel 5 is formed so as to pierce both sides of the plate 8. The opening 81*a* is located in such a manner that when the chip 1K is in the assembled state, it aligns with, and communicates with, the opening 21*a* of the cover member 2.

Also, concavity parts 81*b* are formed on the downstream side of the opening 81*a* of the plate 8. The upstream end of the concavity parts 81*b* is located in such a manner that when the chip 1K is in the assembled state, it aligns with, and communicates with, the opening 21*b* of the cover member 2. The concavity parts 81*b* are formed in such a manner that their widths become gradually broader from the upstream end toward the downstream side (toward the downstream side of the flowing direction of the fluid sample Fp), and the wall surface at the downstream end is formed such as to be orthogonal to the flow direction.

In addition, at the downstream end of the concavity parts 81*b*, plural openings (a group of injection ports arranged in a line) 81*c* through which the pH adjuster solution is to be injected into the flow channel 5 are formed so as to align along the width directions. Each of the openings 81*c* passes through from the concavity parts 81*b* to the surface of the plate 8 facing the plate 9.

Besides, at the downstream end of the plate 8, opening 82 is formed so as to pass through both sides of the plate 8. The opening 82 is located in such a manner that when the chip 1K is in the assembled state, it aligns with, and communicates with, the opening 22 of the cover member 2.

As shown in FIG. 67(*c*), openings 9*c* is formed through the plate 9. the upstream end and the downstream end of the openings 9*c* are located in such a manner that when the chip 1K is in the assembled state, they aligns with, and communicate with, the opening 81*a* and the opening 82 of the plate 8, respectively. As described above, when the chip 1K is in the assembled state, the openings 9*c* forms the flow channel 5, so that the openings 9*c* of the plate 9 corresponds to the flow channel 5.

As shown in FIG. 65(*b*), FIG. 66(*c*), and, FIG. 67(*d*), around the middle part of the basal plate 4 along the flow direction, plural upright partition walls 4*b* are formed facing the flow channel 5. When the chip 1K is in the assembled state, the partition walls 4*b* divides the middle part of the flow channel 5 to form the slit-form inner flow channels (hereinafter called the "slit-form flow channels") 4*a*. The "slit-form flow channel 4*a*" means flow channels that are divided with the partition walls 4*b* across the width directions. Also, when the chip 1K is in the assembled state, the partition walls 4*b* adjoin directly the basal plate 4 and the plate 8 so that the fluid sample Fs is shut out from both between the partition walls 4*b* and the basal plate 4 and between the partition walls 4*b* and the plate 8, thereby the flow channel 5 being divided into plural slit-form flow channel 4*a*.

It is usually preferable to form each of the slit-form flow channel 4*a* such that its cross section has an aspect ratio {[length size]/[width size]) of between 0.005 (e.g., 5 μm in length and 1 mm in width) and 100 (e.g., 10 mm in length and 100 μm in width) inclusive. Also, it is generally preferred that each of the slit-form flow channel 4*a* has a cross sectional area of 5 mm$^2$ or below. Specifically, the sectional area of each slit-form flow channel 4*a* is usually 100 μm$^2$ or above, preferably 2000 μm$^2$ or above, and usually 5 mm$^2$ or below, preferably 0.3 mm$^2$ or below.

According to the present analytical chip 1K as described above, it becomes possible to inhibit the enclosing flow of the fluid sample Fs by providing the conventionally-formed, sheet-shaped flow channel 5 with the partition walls 4*b*, to divide the flow channel 5 into the inner flow channels 4*a* with minute section (namely, by decreasing the cross sectional area of the individual flow channel).

In the meanwhile, as shown in FIGS. 65(*a*), (*b*) and FIG. 67(*d*), reaction area 6 is disposed around the middle part of the basal plate 4 along the flow direction so as to face the flow channel 5.

Illustrated in a simplified form in FIGS. 65(*a*), (*b*), the reaction area 6 is an area where, as shown in FIG. 67(*d*), at least one specific substance 61 that can cause interaction specifically or nonspecifically with one or more predetermined substances (target species) is fixed, as plural spots, to the surface of the basal plate 4 on the side of the flow channel 5. In order to fix the specific substance 61 securely to the basal plate 4, it is preferable to previously form on the surface of the basal plate 4 an immobilized film (organic film) that can bind with the specific substance 61.

The sizes ([length size]×[width size]) of the reaction area 6 are usually between 3 mm×3 mm through 20 mm×20 mm inclusive. In the area, the specific substance 61 are disposed as generally 9 through 40000 spots in such a matrix that 3 through 200 spots are aligned along every row of each direction at intervals of between 100 μm and 1 mm inclusive.

It is assumed that as the specific substance 61, the embodiment uses plural kinds of specific substances (different from each other) each of which can cause any interaction, such as reaction or binding, specifically or nonspecifically with different kinds of substances.

Each of the predetermined substance and the specific substance can be selected from substances that can cause any interaction, such as antigen-antibody reaction, complementary DNA binding, receptor-ligand interaction, enzyme-substrate interaction, etc., and is selectable from various substances, for examples, protein, nucleic acid, DNA, RNA, PNA, peptide, hormone, antigen, antibody, ligand, receptor, enzyme, substrate, low molecular organic compound, cell, etc., and complex thereof. These substances may be labeled, if necessary, with any other substance such as a fluorescence substance, luminescence substance, radioactive substance, etc.

The fluid sample Fs flowing through the flow channel 5 comes to touch with these spots 61 during the flowing process, after which it is possible to carry out analysis of the fluid sample Fs based on the reaction status of each of the spots 61. Specifically, if the occurrence of reaction is detected at any spot 61 of the plural spots 61, it is possible to determine that the fluid sample Fs contains a predetermined substance associated with the spot (specific substance) 61 at which the reaction occurs.

Meanwhile, in the present analytical chip 1K the reaction area 6 (the area where the plural specific substances 61 are fixed) shown in FIG. 67(*d*) is not actually formed in the early stage of assembling: in FIG. 67(*d*), the specific substances 61 fixed to the basal plate 4 are illustrated for convenience in explaining the arrangement of the spots of the specific substances 61 with respect to the basal plate 4 intelligibly. Accordingly, FIG. 67(*d*) illustrates the positions and the number of the spots of the specific substances 61 along the width directions in such a manner that they correspond to the positions and the number of the slit-form flow channels 4*a* of the basal plate 4 along the width directions.

The fluid sample Fs flowing through the slit-form flow channels 4*a* comes into contact with these specific substances 61 during the process of the flowing, after which analysis is carried out regarding the fluid sample Fs, based on the state of reaction at each spot of the specific substances 61.

Specifically, if the occurrence of reaction is detected at any spot of the specific substances 61, it is possible to determine that the fluid sample Fs contains a kind of substance corresponding to the specific substance 61 fixed at the spot where the reaction is detected.

The specific substances 61 are fixed to the chip 1K as plural spots arranged at regular intervals so as not to be contaminated with the specific substance 61 at the neighboring spots. The term "regular intervals" means the intervals between the centers of the spots where the specific substances are fixed, to which intervals the pitch of the partition walls 4*b* is set to be substantially identical. In the present invention, it is not necessary to reduce the number of spots of the specific substance 61 per unit area than in the conventional chip in return for disposing the partition walls 4*b*; on the contrary, since the disposition of the partition walls 4*b* enables to prevent the contamination as described above, the pitch of the specific substances 61 along the width directions (the directions orthogonal to the flow direction)

can be minimized, so that it becomes possible to rather increase the number of spots per unit area.

It is not necessary to use different kinds of specific substances 61 at different spots; the same specific substance 61 can be used at two or more different spots. In any event, what kinds of specific substances 61 are used should be determined as appropriate, depending on the object of analysis.

In the analytical chip 1K according to the thirteenth embodiment of the present invention, which is constituted as described above, the opening 81a is assigned as an injection port via which the fluid sample Fs is injected to the flow channel 5, and the fluid sample Fs is injected from the opening 21a via the opening 81a to the flow channel 5. Also, the openings 81c is assigned as an injection port via which the pH adjuster solution Fp is injected to the flow channel 5, and the pH adjuster solution Fp is injected from the opening 21 via the concavity part 81b and the openings 81c to the analytical chip 1K. With the arrangement, the fluid sample Fs and the pH adjuster solution Fp join together at the connection part of the openings 81c and the flow channel 5.

After the fluid sample Fs and the pH adjuster solution Fp join together, the merged flow of the fluid sample Fs and the pH adjuster solution Fp is mixed together to be uniform by diffusion phenomenon during the flowing process until it flows into the reaction area 6, so that the pH value of the fluid sample Fs is adjusted depending on the amount of the pH adjuster solution injected from the opening 21b. Namely, by introducing the pH adjuster solution from the opening (injection port) 81c to the flow channel 5 through which the fluid sample Fs is flowing, it is possible to adjust the pH of the fluid sample Fs.

After its pH is adjusted, the fluid sample Fs flows through the flow channel 5 and reaches the reaction area 6, where it comes into contact with the specific substance 61. With the arrangement, it becomes possible to carry out analysis of the fluid sample Fs using the specific substance 61 under a desired pH value.

Hence, using the analytical chip 1K, it is possible to adjust the pH value of the fluid sample Fs easily. Also, since the fluid sample Fs and the pH adjuster solution Fp are mixed through the flow, it becomes possible to carry out analysis continuously with adjusting pH.

The following description is given on an advantage of the present embodiment compared with a conventional problem.

When analysis is carried out using a conventional analytical chip, there are several cases where fluid samples are to be mixed with other liquids before analysis: the case where a fluid sample is to be mixed with a solvent for adjusting the concentration of the fluid sample before analysis, the case where a fluid sample is to be mixed with a pH adjuster liquid for adjusting the pH value of the fluid sample before analysis, the case where a fluid sample is to be mixed with another fluid sample before analysis, etc.

In such a case, before the fluid sample is made flow into the analytical chip, the fluid sample is usually mixed with some liquid or solid in advance as a separate process to prepare the sample (the fluid sample after the mixing process). However, in such a case, the mixing process often causes the reduction of efficiency. For example, in order to analyze a sample in different mixing ratios, it is necessary to prepare different samples according to the mixing ratios to be analyzed, so that the operation becomes complicated. In another case, when the fluid sample obtained from the mixing process, for example, becomes denatured over time, a considerable duration of time may pass after the advance mixing process until analysis, so that it is difficult to analyze the denaturation over time with precision.

In addition to the above-mentioned method in which a sample is prepared in advance through a separate process, it is also conceivable that, for example, a component such a pipe or a mixing vessel is disposed at the upstream side of the analytical chip so that mixing is carried out during the flow in the component such a pipe or a mixing vessel before the fluid sample is introduced to the analytical chip. However, when mixing is carried out during the flow, there is a possibility that the properties of the fluid sample, such as the concentration and the pH, change during the period after the mixing until it reaches the analytical chip. For example, when different kinds of liquid are made flow successively, there is a possibility that the different kinds of liquid are mixed by diffusion and that it thereby becomes impossible to carry out analysis accurately. Additionally, when the different kinds of liquid can react with each other, there is a possibility that a reaction which is not intended arises during analysis and that that the object analysis thereby becomes impossible. Besides, when measurement is carried out while the pH of flowing liquid is varied continuously, there is a possibility that the mixing of the liquid along the flow direction may arise by diffusion along the flow direction during the liquid is flowing through pipes or the like, and that the pH of the liquid thereby deviates from the intended pH at the point of time that the liquid reaches the analytical chip.

In addition, when mixing is carried out through a component such a pipe or a mixing vessel at the upstream side of the analytical chip, a lot of dead volume arises. Many fluid samples that can be subjected to analysis using a microchannel chip are limited in amount usable for analysis. For example, in analysis using a chip such as a DNA chip or a protein chip, a fluid sample can be taken from all kinds of products (DNA, RNA, PNA, peptide, protein, etc.), including both natural products extracted from diverse creatures and various biochemically synthetic products. Some of these products can be extracted or synthesized only in a restricted amount, or require a great deal of labor for extraction or synthesis. It is therefore strongly desired to reduce the amount of a sample used for analysis to a minimum. It is therefore undesirable to use a mixing method that involves the occurrence of dead volume for analytical chips such as the above-mentioned microchannel chips. Besides, when using a component such as a piping or a mixing vessel, considerable costs are needed for the arrangement and inspection of such equipment. In addition, there are many problems that hinder precise and efficient analysis, such as the possibility of leakage, fluctuations in temperature and humidity outside the chip, blockage in pipes, tubes, connectors, etc., and absorption by materials of tubes or connectors.

By contrast, using the analytical chip 1K according to the present embodiment, it is possible to adjust the pH of the fluid sample Fs easily. Besides, the fluid sample Fs and the pH adjuster solution Fp are mixed during the flow, it becomes possible to carry out analysis continuously with adjusting pH. As a result, it becomes possible to eliminate additional operations for preparing the chip 1K or the analysis apparatus over again, so that the extra labor needed for analysis can be saved.

Moreover, according to the analytical chip 1K, since the fluid sample Fs and the pH adjuster solution Fp are mixed immediately before the reaction area 6, it becomes possible to carry out analysis of the fluid sample Fs immediately after the fluid sample Fs and the pH adjuster solution Fp are mixed (usually within 1 minute after mixing, preferably within 1 second after mixing). Hence, even when the fluid sample Fs becomes denatured over time after being mixed with the pH adjuster solution Fp, it becomes possible to carry out analysis with precision without being affected by the denaturation over time.

In addition, since the mixing is carried out in the flow channel 5 formed to have minute sections, it becomes possible to avoid wasting the fluid sample Fs due to the occurrence of dead volume or the like, so that analysis can be carried out efficiently with a minimum volume of fluid sample Fs.

Also, since the openings 81c are arranged in a line along the width directions of the flow channel 5, it is possible to realize uniform mixing in the flow channel 5.

In the meantime, as is evident from the above description, the upstream portion of the flow channel 5 in which the openings (injection ports) 81a, 81c should be disposed are not limited so long as they are located upstream to the area of the flow channel 5 where detection or measurement is carried out, so that the openings (injection ports) 81a, 81c can be formed at any positions upstream of the flow channel 5. However, since in most cases, such detection or measurement is carried out in the reaction area 6 during analysis, the injection ports 81a, 81c are usually formed at positions upstream of the reaction area 6 of the flow channel 5. Hence, in the present embodiment, the upstream portion of the flow channel 5 in which the injection ports 81a, 81c are formed means a portion in the flow channel 5 upstream of the reaction area 6. Incidentally, in the case where the fluid sample Fs is detected or observed downstream of the reaction area 6 for any reasons, the injection ports can be disposed on the downstream side of the reaction area 6 along the flow direction.

Besides, since the flow channel 5 is divided with the partition walls 4b into the minute (narrow-width) slit-form flow channels 4a, it becomes possible to prevent the occurrence of air bubbles due to enclosing flow of the fluid sample Fs.

Specifically speaking, in the conventional sheet-shaped flow channel, since the interface between the three phases of solid-gas-liquid has a long front line as shown in FIG. 6(a), part of the fluid sample Fs runs ahead due to non-uniformity of wettability, so that enclosing flow of the fluid sample Fs occurs to result in generation of the enclosure of gas (air bubble 201). In the present invention, since the flow channel 5 is divided into the separate, minute inner flow channels (the slit-form flow channels 4a), the length of line segment L (flow channel width) perpendicular to the main flow in the flow channel becomes small as shown in FIG. 6(b), so that the occurrence rate of the enclosing flow decreases significantly. Besides, since the cross sectional area of the flow channel becomes small, it is possible to apply backing pressure efficiently to the interior of each slit-form flow channel 4a, thereby making air bubbles hard to remain dwelling.

Consequently, according to the present analytical chip 1K, it becomes possible to remove various adverse effects arising from the dwelling of air bubbles (such as the blockage of the normal flow of the fluid sample Fs, the hindering of the contact between the specific substance 61 and the fluid sample Fs, the non-uniformity of temperature in the system of measurement caused by the difference of heat transfer coefficient between the liquid Fs and the air bubble 201, the inhibition of the measurement during the analysis using an optical system because of the air bubble 201 dwelling in the optical path, etc.), resulting in the advantage that the reliability of analysis is improved. Besides, since it eliminates the need for extra work of getting rid of air bubbles, there is the advantage that analytical work can be carried out efficiently.

In the conventional flow channel formed in the sheet-shaped space, the non-uniformity of flow occurs over a wide area. Specifically, when a liquid fluid is fed at a flow rate within the normal range, the velocity of the liquid fluid is zero at the wall surface of the flow channel while being the highest at the center of the flow channel, and becomes lower as being closer to the wall surface both longitudinally and latitudinally, thus causing the non-uniformity.

By contrast, according to the present analytical chip 1K, the separate, minute inner flow channels (slit-form flow channels 4a) are formed. When the spots of the specific substance 61 are aligned, for example, in two rows along the width directions of the slit-form flow channels 4a, it becomes possible to make the fluid sample Fs be in contact with the spots of the specific substance 61 aligned in each row along the width directions during the same period, thereby improving the precision of the analysis results.

Moreover, even when the chip 1K fastened together with the holder is subjected to a pressure, since it is provided with the plural partition walls 4b formed across the width directions of the chip 1K, the pressure resistance of the chip 1K can be improved and the chip 1K can be prevented from undergoing shape distortion, specifically shape distortion along the thickness direction. This feature offers the advantage that the occurrence of non-uniformity in velocity distribution due to bending of the chip 1K can be prevented. It also offers the advantage that even when the analysis is carried out using an optical system, since the unevenness in length of the optical paths and the alteration of the optical axis can be prevented, it becomes possible to carry out analysis under the favorable conditions, thereby the precision of analysis results being improved.

The present embodiment also offers the advantage that it enables to reduce various wastes resulting from the occurrence of air bubbles 201, such as the number of times analytical work must be carried out and the amount of fluid sample Fs to be used accordingly, thereby enabling efficient analysis.

Then, after passing along the reaction area 6, the fluid sample Fs and the pH adjuster solution Fp, which is mixed with the fluid sample Fs, flow through, in turn, the downstream ends of the slit-form flow channels 4a, the opening 82 of the plate 8, and the drain port 22 of the cover member 2 and drained outside the chip 1K.

Meanwhile, although in the present embodiment, the fluid sample Fs and the pH adjuster solution Fp are mixed, the kinds and combination of liquid to be injected via the injection ports into the flow channel 5 are not particularly limited, and it is also possible to mix the fluid sample Fs with any other kinds of liquid, in addition to those used in the present embodiment. For example, by mixing the fluid sample Fs with a salt-concentration adjuster solution, such as its solvent or the solution of the predetermined substance whose concentration is different from that of the fluid sample Fs, it is possible to carry out analysis with varying the concentration of the predetermined substance in the fluid sample Fs. As another example, it is also possible to carry out analysis with mixing fluid sample Fs1 with another fluid sample Fs2. For still another example, it is also possible to inject the same kind of fluid sample Fs from different injection ports and carry out the diffusion mixing (mixing by diffusion) of the fluid sample Fs efficiently.

Figure 68:
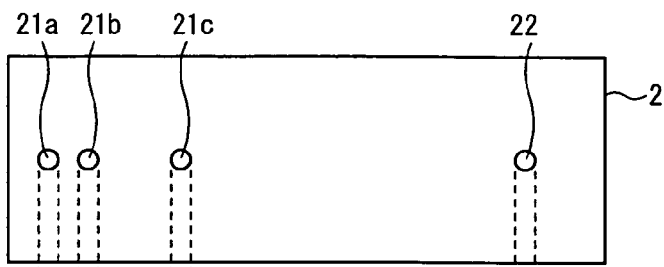
FIG. 68(a) is a diagrammatic top view of a cover member of an analytical chip according to the thirteenth embodiment of the present invention.
FIG. 68(b) is a diagrammatic top view of a plate of an analytical chip according to the thirteenth embodiment of the present invention.
FIG. 68(c) is a diagrammatic top view of a plate of an analytical chip according to the thirteenth embodiment of the present invention.
FIG. 68(d) is a diagrammatic top view of a basal plate of an analytical chip according to the thirteenth embodiment of the present invention.
Figure 68:
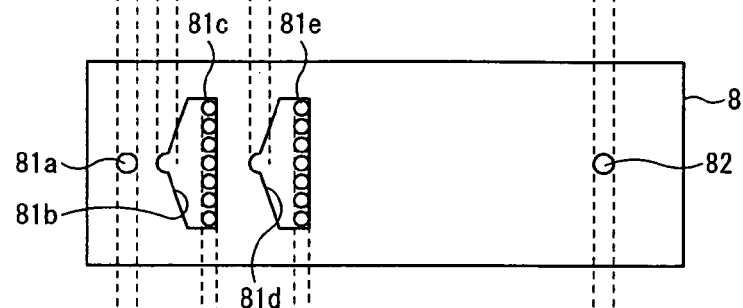
Figure 68:
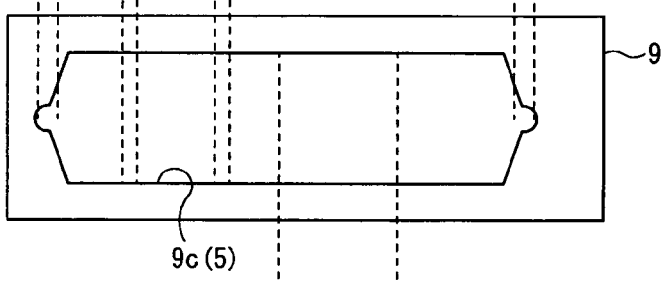
Figure 68:
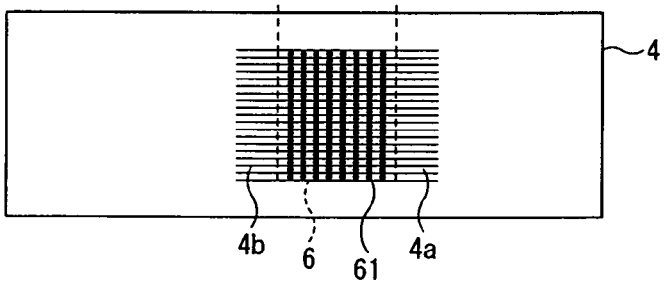

Also, although in the present embodiment, the analytical chip 1K is constituted in such a manner that it allows the mixing of two different kinds of liquid, namely, the fluid sample Fs and the pH adjuster solution Fp, the analytical chip 1K can be also constituted in such a manner that three or more kinds of liquid can be mixed. For example, as shown in FIGS. 68(*a*)–(*d*), by forming the openings 21*c* downstream of the opening 21*b* of the cover member 2, and by forming the concavity parts 81*d* that have plural openings 81*e* formed downstream of the concavity parts 81*b* of the plate 8 in such a manner that their upstream-side ends align with, and communicate with, the openings 21*c* and that their downstream-side ends communicate with the flow channel 5, in addition to the fluid sample Fs and the pH adjuster solution Fp, it becomes possible to inject still another kind of liquid to the flow channel 5 to be involved in the mixing. In FIG. 68, the reference characters also used in FIGS. 65–67 designate the same components.

Figure 69:
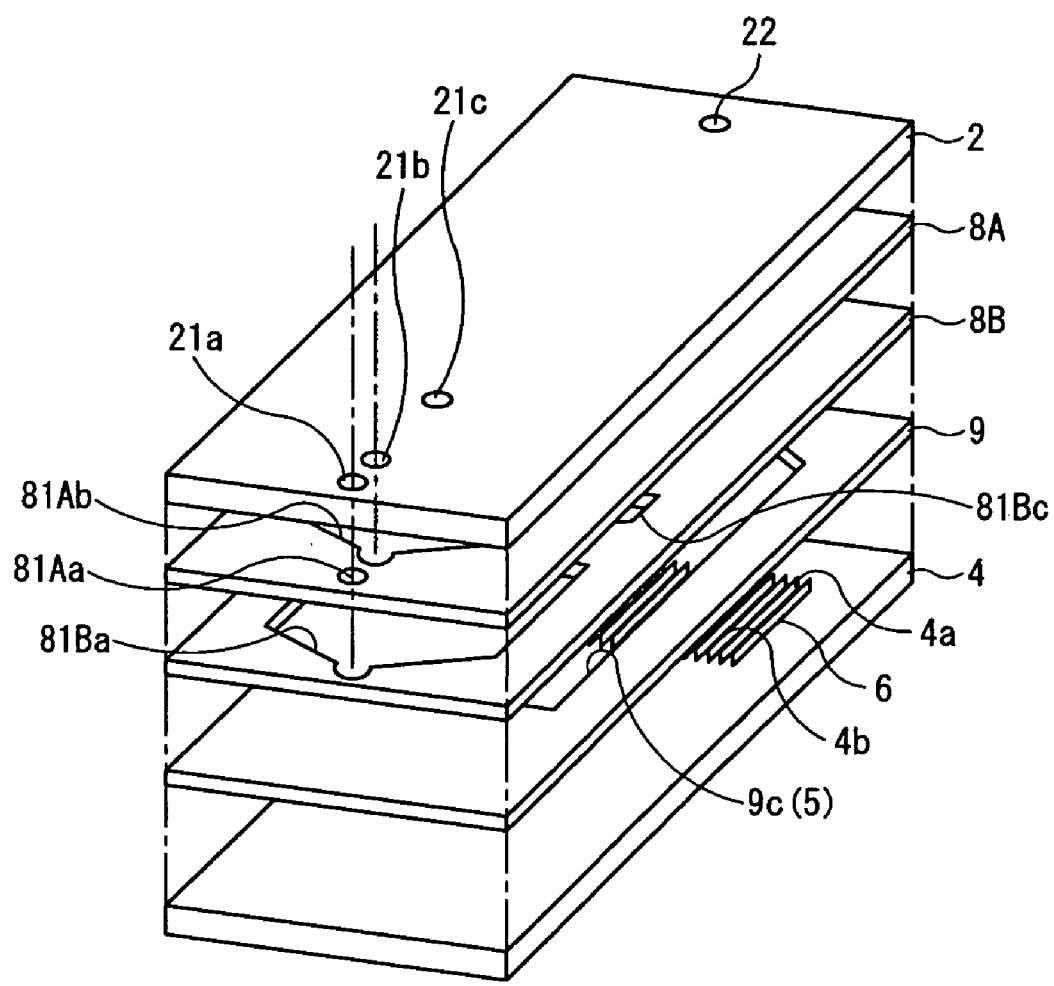
FIG. 69 is a diagrammatic exploded perspective view of an analytical chip according to the second modification of the thirteenth embodiment of the present invention.

It is also possible to increase the number of plates to be interposed between the cover member 2 and the basal plate 4. For example, as shown in FIG. 69 and FIGS. 70(*a*)–(*e*), it is possible to use plate 8A and plate 8B instead of the plate 8 to form the analytical chip 1K. The embodiment will be explained hereinafter.

The cover member 2 and the basal plate 4 are identical to those used in the above thirteenth embodiment, so that redundant explanation is omitted. The plate 8A has opening 81Aa, which aligns with and communicates with the opening 21*a*, concavity part 81Ab, whose upstream end aligns with and communicates with the opening 21*b*, plural openings 81Ac, which are formed at the downstream end of the concavity part 81Ab, opening 81Ad, which aligns with and communicates with the opening 21*c*, and opening 82A, which aligns with and communicates with the opening 22.

The plate 8B has concavity part 81Ba, whose upstream end aligns with and communicates with the opening 81Aa, plural openings 81Bb, which are formed at the downstream end of the concavity part 81Ba, concavity part 81Bc, whose upstream end aligns with and communicates with the opening 81Ad, plural openings 81Bd, which are formed at the downstream end of the concavity part 81Bc, and opening 82B, which aligns with and communicates with the opening 82A. Although the plate 9 has the openings 9*c* as in the above thirteenth embodiment, the upstream end of the openings 9*c* aligns with and communicates with the openings 81Bb, and the downstream ends of the openings 9*c* aligns with and communicates with the opening 82B. In addition, the openings 81Bd aligns with and communicates with the openings 9*c*. As in the analytical chip 1K according to the above thirteenth embodiment, the openings 9*c* define the flow channel 5.

Using the analytical chip 1K as constituted above, the fluid sample Fs injected via the opening 21*a* and a liquid injected via the opening 21*b* join together and mixed in the concavity part 81Bb. After the mixing in the concavity part 81Ba, the fluid sample Fs flows through the openings 81Bb into the flow channel 5. On the other hand, a liquid injected via the opening 21*c* flow through, in turn, the opening 81Ad, the concavity part 81Bc, and the openings 81Bd to run into the flow channel 5, in which it join with the fluid sample Fs.

It is thus possible to dispose a number of plates between the cover member 2 and the basal plate 4 to thereby make the analytical chip 1K. In FIGS. 69 and 70, the reference characters also used in FIGS. 65–68 designate the same components.

Figure 71:
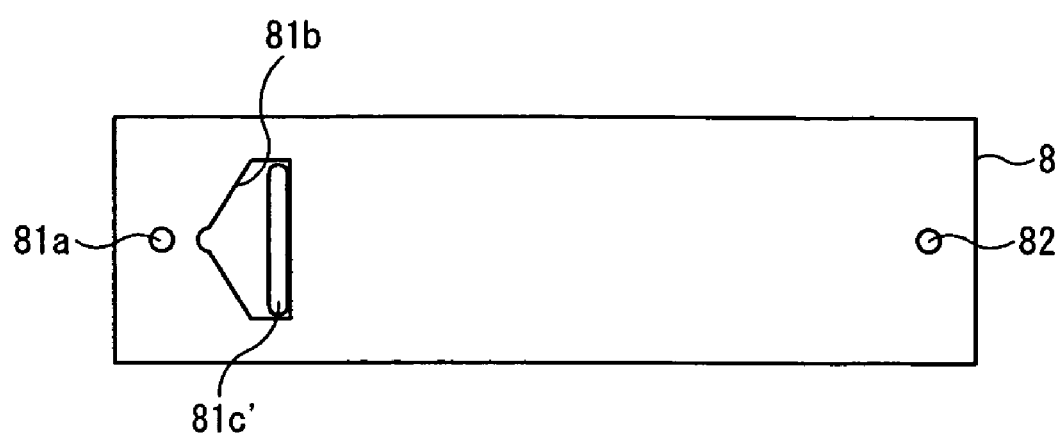
FIG. 71(a) is a diagrammatic top view of a plate of an analytical chip according to the third modification of the thirteenth embodiment of the present invention, and FIG.
Figure 71:
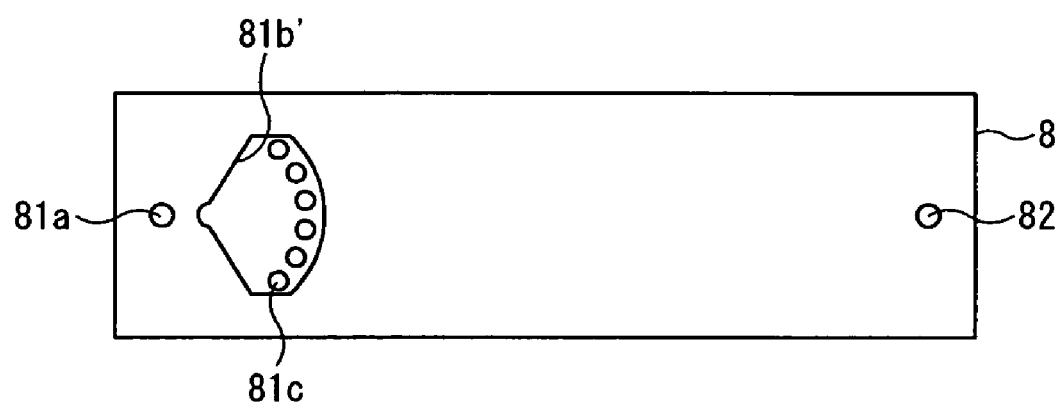

Besides, the openings 81*c*, which serve as injection ports, can be formed in any arrangement and in any shaped, for example, in such a manner as to be aligned along the width directions as in the present embodiment. For example, as shown in FIG. 71(*a*), they can be unitedly formed as slotted hole 81*c*'. As another example, as shown in FIG. 71(*b*), it is also possible to make distances from the injection port 81*a* of the fluid sample Fs toward the ends of the concavity parts 81*b*' identical to each other and arrange the openings 81*c*, which are formed at the downstream ends of the concavity parts 81*b*', in an arc shape so that the distances toward the openings 81*c* are identical to each other.

In FIG. 71, the reference characters also used in FIGS. 65–67 designate the same components.

For forming the concavity parts 81*b*, 81*a*, 81Ab, 81Ba, 81Bc, 81*b*' described above, the following methods can be selectively used: machining; various transferring techniques typified by injection molding and compression molding; dry etching (RIE, IE, IBE, plasma etching, laser etching, laser ablation, blasting, electrical discharge machining, LIGA, electron beam etching, FAB); wet etching (chemical erosion); integral molding such as optical machining or ceramic covering; Surface Micro-machining of coating with various substances in a layer and partially removing by means of vacuum evaporation, sputtering, deposition, or the like, to thereby form a microstructure; a method that includes dripping a material of the flow channel using an ink jet or a dispenser, optical machining method, etc.

(14) Fourteenth Embodiment

The analytical chip 1L according to the fourteenth embodiment of the present invention is constituted as an analytical chip (hereinafter called the "sensor chip") used for an SPR, which is based on sensor surface plasmon resonance (SPR: Surface Plasmon Resonance).

Hereinafter, the SPR sensor and the sensor chip 1L are explained with reference to FIGS. 72 and 73.

FIG. 72 and FIG. 73 illustrate the fourteenth embodiment of the present invention. FIG. 72 is a diagrammatic system block diagram of the SPR sensor, and FIG. 73 is a diagrammatic exploded perspective view of assistance in explaining the sensor chip 1L. Like components also explained in the above thirteenth embodiment are designated by like reference characters, so that redundant explanation is omitted.

As shown in FIG. 72, the SPR sensor has sensor chip 1L, which is an analytical chip, light source 100, which is for irradiating the sensor chip 1L with light, and detector (in the embodiment, a CCD (charge coupled device) camera) 101, which is for detecting the reflection light from the sensor chip 1L. Although shown in FIG. 72 as both being perpendicular to the flow direction, the orientations of the optical axes for the incident light from the light source 100 and the reflection light from the sensor chip 1L are not limited to those in the drawing: for example, the optical axis for the incident light can be parallel with the flow direction, while the optical axis for the reflection light can have a different orientation from that of the incident light as a consequence of reflecting by the sensor chip 1L. The embodiment can be also modified such that the incident light is applied from the back face of the sensor chip 1L (from the side of the basal plate 4) while the reflection light is detected the back face of the sensor chip 1L (from the side of the basal plate 4) to carry out analysis. In the modification, however, it is necessary to make the basal plate 4 from a material that can transmit the incident light and the reflection light.

In the sensor chip 1L, each of the cover member 2 and the plates 8, 9 is made from one or more transparent materials. In addition, a metal layer 41 is coated over the surface of the basal plate 4 facing the plate 9 when the chip 1L is in the assembled state. In the surface of the basal plate 4 on which the metal layer 41 is coated, the diffraction grating 42 is formed as an optical structure that can generate an evanescent wave. The other constitution of the sensor chip 1L is identical to that of the analytical chip 1K, which was already explained in the thirteenth embodiment.

The metal layer 41 can be made from any material without limitation so long as it can induce a surface plasmon wave, examples of which material include gold, silver, and aluminum.

In reaction area 6, the specific substance 61 can be fixed either directly to the metal layer 41 or to an immobilized film (organic film) formed on the metal layer 41. The immobilized film in the embodiment may be one or more selected from conventional structures. Preferably, the immobilized film has the property of being able to fix the specific substance 61 to the metal layer 41 securely while preventing nonspecific absorption. Specifically, it is preferred that the immobilized film includes: as a functional group for binding to a biological substance, at least one group selected from amino, aldehyde, epoxy, carboxyl, carbonyl, hydrazide, hydroxyl, and vinyl group; and, for binding to the metal layer 41, one or more straight-chain macromolecules including at least one selected from isothiocyanato, isonitrile, xanthate, diselenide, sulfide, selenide, selenol, thiol, thiocarbamate, nitrile, nitro, and phosphine, and/or hydrocarbon chains having at least one double and/or triple bond. It is also preferable to use a material that forms hydrogel (agarose, alginic acid, carrageenin, cellulose, dextran, polyacrylamide, polyethylene glycol, polyvinyl alcohol, etc.) as a matrix. It is also preferable to use an organization structure such as a LB membrane, a self-assembled monolayer, or a lipid bilayer.

The diffraction grating 42 can be embodied on the surface of the metal layer 41 by forming concavities and convexities on the surface of the basal plate 4, and then laminating on the concavities and convexities with a thin layer of a metal using a technique such as sputtering, to form the metal layer 41.

The concavities and convexities, which are formed for providing the basal plate 4 with the diffraction grating 42, can be formed by, for example, cutting the basal plate 4. The cutting method is not limited: it can be carried out mechanically, or chemically using a technique such as etching.

When making the basal plate 4 from a resin material, it is possible to form the concavities and convexities using a stumper on which the corresponding concavities and convexities are formed by means of photo lithography or the like. It can be achieved before the resin material has not solidify completely, by pressing the stumper on the basal plate 4, or by transferring the concavities and convexities from the stumper using a technique such as injection molding.

When analysis is carried out using the analytical chip (sensor chip) 1A according to the fourteenth embodiment of the present invention, which is constituted as described above, as in the thirteenth embodiment, since the fluid sample Fs is injected via the opening 21a while the pH adjuster solution Fp is injected via the opening 21b, and the fluid sample Fs and the pH adjuster solution Fp are mixed, it becomes possible to carry out analysis based on surface plasmon resonance with adjusting pH precisely.

When light is applied from the light source 100 via the cover member 2 and the plates 8, 9, which are transparent, to the basal plate 4, under the action of the incident light, a surface plasmon wave is generated along the surface of the metal layer while an evanescent wave is induced along the metal layer 41 by the diffraction grating 42, and the resonance between the surface plasmon wave and the evanescent wave occurs, resulting in the absorption by the metal layer 41 the energy of an optic element with a specific incident angle or a specific wavelength in the incident light to the metal layer 41. Hence, in the reflection light from the metal layer 41, the energy of the optic element with the specific incident angle or the specific wavelength declines.

The angle and the wavelength of the evanescent wave generated along the metal layer 41 varies depending on the amount of target species trapped by the specific substances 61 fixed to the metal layer 41 or the organic film formed on the metal layer 41, and the angle and the wavelength of the absorbed optical component of the reflection light also varies accordingly.

With this arrangement, by monitoring the light intensity of the reflection light from each of the specific substances 61 on the reaction area 6 using the CCD camera 101 to detect the change in the angle and/or the wavelength, it is possible to measure the concentration of target species contained in a test fluid in real time.

According to the analytical chip (sensor chip) 1L of the fourteenth embodiment of the present invention, as described above, as in the above thirteenth embodiment of the present invention, since the fluid sample Fs and the pH adjuster solution Fp are mixed rapidly and accurately in the upstream portion of the flow channel 5, it becomes possible to carry out analysis accurately and efficiently. Also, when analysis based on surface plasmon resonance is carried out using the chip 1L, it is possible to achieve the same advantageous effects as those of the thirteenth embodiment.

Another major feature of the analytical chip used for the SPR sensor is that it enables to detect the state of interaction in the reaction area 6 (the plural specific substances 61) optically and online.

Besides, when carrying out analysis based on SPR as described above, it is possible not only to make a single fluid sample Fs flow into the microchannel chip for analysis, but also to make two or more fluid samples Fs flow one after another at successive intervals using a buffer and analyze a series of binding and dissociation between target substances contained in the fluid samples Fs and the specific substance.

Also, the detector 101 is not limited to a CCD camera, as is used in the present embodiment: any other kinds of detectors such as a photo diode, a photomultiplier, a photosensitive paper, etc. are also usable as the detector 101.

(15) Fifteenth Embodiment

FIGS. 74–76 show the constitution of an analytical chip 1M according to the fifteenth embodiment of the present invention. Specifically, FIG. 74(a) is a diagrammatic assembled perspective view of the chip 1M, FIG. 74(b) is a diagrammatic exploded perspective view of the analytical chip 1M, FIG. 75 is a sectional view taken along line Y—Y of FIG. 74(a), FIG. 76(a) is a top view of the cover member of the analytical chip 1M, FIG. 76(b) is a top view of the intermediate plate of the analytical chip 1M, and FIG. 76(c) is a top view of the body of the analytical chip 1M. Like components also explained in the above thirteenth embodiment are designated by like reference characters, so that redundant explanation is omitted.

As shown in FIGS. 74(a), (b), the present analytical chip (hereinafter also called simply the "chip") 1B is constituted as having cover member 2, intermediate plate (hereinafter called simply the "chip") 10, and basal plate 4.

The present analytical chip 1M has the same constitution as that of the analytical chip 1K of the thirteenth embodiment with the exception that it has plate 10, which defines a sheet-shaped space, instead of the plates 8, 9. The following description will be therefore focused on the plate 10 in full detail.

Pipes (not shown in the drawings) are put in the injection ports 21a, 21b and the drain port 22 of the cover member 2, respectively, so as to facilitate the connection of tubes each leading to an external injection pump or waste liquid tank.

As shown in FIGS. 74(a), (b), through the plate 10, opening 10d is formed so as to be opened to both sides of the plate 10. As shown in FIG. 75, when the chip 1M is in the assembled state, an aperture of the opening 10d is blocked by the cover member 2 while the other aperture of the opening 10d is blocked by the basal plate 4 so that the sheet-shaped flow channel 5 is defined. Thus, the opening 10d forms flow channel 5. Besides, the opening 10d is formed in such a manner that its upstream-side end aligns with and communicates with the opening 21a while its downstream-side end aligns with and communicates with the opening 22.

As a main feature of the present embodiment, as shown in FIGS. 76(a)–(c), narrow flow channel portion (upstream portion) 10e is disposed upstream of the opening 10d, namely, upstream of the flow channel 5. In the narrow flow channel portion 10e, the width of the flow channel 5 (i.e., the size of the opening 10d along the width directions) is smaller than in the remaining portion of the opening 10d, so that the sectional area orthogonal to the flow direction is smaller than that of the flow channel 5. The openings 21a, 21b, which serve as injection ports, are located such as to communicate with the narrow flow channel portion 10e.

Using the analytical chip 1M according to the fifteenth embodiment of the present invention, which is constituted as above, the fluid sample Fs injected via the injection port 21a of the cover member 2 flows into the narrow flow channel portion 10e. On the other hand, the pH adjuster solution Fp injected via the opening 21b flows into the narrow flow channel portion 10e to join with the fluid sample Fs, so that the fluid sample Fs and the pH adjuster solution Fp are mixed in the narrow flow channel portion 10e. The fluid sample Fs mixed with the pH adjuster solution Fp flows through the flow channel 5 and passes along the reaction area 6, and then is drained from the opening 22.

According to the analytical chip 1M of the present embodiment, it is possible to achieve the same advantageous effects as those of the analytical chip 1K of the thirteenth embodiment.

Also, when using the analytical chip 1M, as in the thirteenth embodiment, diffusion phenomenon occurs while the fluid sample Fs and the pH adjuster solution Fp are mixed. Since the narrow flow channel portion 10e is formed such as to have a narrow width, its sectional area orthogonal to the flow direction becomes small accordingly, so that diffusion is completed more quickly. As a result, the fluid sample Fs and the pH adjuster solution Fp become mixed uniform within a shorter time, thereby efficient analysis being realized.

Although in the present embodiment the fluid sample Fs is mixed with the pH adjuster solution Fp, it is also possible to mix the fluid sample Fs with another kind of liquid.

Besides, although in the present embodiment the analytical chip 1M is formed so as to enable the mixing of two kinds of liquid, namely, the fluid sample Fs and the pH adjuster solution Fp, it is also possible, as in the thirteenth embodiment, to increase the number of the injection ports of the analytical chip 1M [in the instance illustrated by FIG. 77(a), three openings 21a, 21b, 21c] so that three or more kinds of liquid can be mixed.

In addition, although in the present embodiment the narrow flow channel portion 10e is formed by reducing the width of the narrow flow channel portion 10e, it is also possible to form the narrow flow channel portion 10e by, as shown in FIG. 77(b), reducing the height of the flow channel 5. In FIG. 77, like reference characters also used in FIGS. 65–76 designate like components.

Besides, although in the present embodiment the narrow flow channel portion 10e is formed by reducing the width of the flow channel 5 throughout the whole upstream portion of the flow channel 5, it is also possible to form the narrow flow channel portion 10e by, for example, reducing the width of the injection port on the downstream side (in the present embodiment, the opening 21b) in, as shown in FIGS. 78(a)–(c), only a part downstream along the flow direction so that a part of the upstream portion of the flow channel 5, which is located upstream of the reaction area 6, becomes narrow. With the modification it is possible to achieve the same advantageous effects as those of the present embodiment.

In FIG. 78, like reference characters also used in FIGS. 65–77 designate like components.

When, as in the present embodiment, plural liquid samples (in the modification, the fluid sample Fs and the pH adjuster solution Fp) are made flow from above the flow channel 5 (from the side of the cover member 2), these liquid samples form layered flows, as shown in FIG. 86(a), along the height direction under a normal Reynolds number (Re<100) unless diffusion occurs. However, in the flow channel formed as a sheet-shaped space 5, since the height of the flow channel 5 is small, as shown in FIG. 86(b), it is possible to cause diffusion along the height direction of the flow channel 5, along which direction concentration distribution is formed, within a very short time. The occurrence of diffusion also depends on a residence time: in a region the liquid have not been mixed uniform yet, the degree of diffusion increases with the length of the residence time. For example, when the flow rate of the liquid flowing through the flow channel 5 is constant, the linear velocity of the liquid becomes lower as the width of the flow channel is larger. Based on the fact, by enlarging the width of the flow channel 5 while keeping the height constant to thereby reduce the linear velocity of the liquid flowing through the flow channel 5 (the fluid sample Fs and the pH adjuster solution Fp), so that it becomes possible to cause diffusion more efficiently. It is also possible to cause diffusion more efficiently by, for example, reducing the flow rate of the liquid. Hence, as shown in FIGS. 87(a), (b), more effect can be achieved in the narrow flow channel portion 10e by increasing the width of the flow channel 5 while reducing the height of the flow channel 5. Even in the case, however, it is preferable to form the narrow flow channel portion 10e, whose sectional area orthogonal to the flow direction is smaller than that of the flow channel 5, in the upstream portion of the flow channel 5, as described above, so that concentration distribution along the width directions becomes uniform before the liquid flows into a part of the flow channel 5 with larger width. The signs appeared in FIGS. 86(a), (b) and FIGS. 87(a), (b) are used same as in FIGS. 65–77.

In the meanwhile, diffusion depends on various parameters, such as the solvents of the liquid samples to be mixed together (in the modification, the fluid sample Fs and the pH adjuster solution Fp), the molecular weight of the dissolved substance, diffusion coefficient, viscosity, kinetic viscosity, density, the amount of flow, linear velocity, temperature, or the shape and size of the flow channel. Derived from these parameters, dimensionless quantities, Reynolds number Re and Péclet number Pe, can be used for basic indices for diffusion mixing.

(16) Sixteenth Embodiment

FIGS. 79–81 show the constitution of an analytical chip 1N according to the sixteenth embodiment of the present invention. Specifically, FIG. 79(*a*) is a diagrammatic assembled perspective view of the chip 1N, FIG. 79(*b*) is a diagrammatic exploded perspective view of the chip 1N, FIG. 80 is a sectional view taken along line Y—Y of FIG. 79(*a*), FIG. 81(*a*) is a top view of the cover member of the analytical chip 1N, FIG. 81(*b*) is a top view of the first plate of the analytical chip 1N, FIG. 81(*c*) is a top view of the second plate of the analytical chip 1N, and FIG. 81(*d*) is a top view of a body of the analytical chip 1N. Like components also explained in the above thirteenth through fifteenth embodiments are designated by like reference characters, so that redundant explanation is omitted.

The analytical chip 1N according to the sixteenth embodiment of the present invention has the basic constitution identical to that of the analytical chip 1K of the thirteenth embodiment with the exception that it has, as shown in FIGS. 79(*a*), (*b*), first intermediate plate (hereinafter called simply the "chip") 16 and second intermediate plate (hereinafter called simply the "chip") 17, instead of the plates 8, 9 of the analytical chip 1K according to the thirteenth embodiment. The following explanation will be therefore focused on the plates 16, 17.

As shown in FIGS. 81(*a*)–(*d*), opening 16*d* is formed at the downstream part of the plate 16 in such a manner that when the analytical chip 1N is in the assembled state, it aligns with and communicates with the opening 22 of the cover member 2, while opening 17*c* is formed at the downstream part of the plate 17 in such a manner that when the analytical chip 1N is in the assembled state, it aligns with and communicates with the opening 16*d*.

When the analytical chip 1N is in the assembled state, as shown in FIG. 80, one aperture of the opening 17*c* is blocked by the plate 16 while the other aperture of the opening 17*c* is blocked by the basal plate 4, so that a part of the sheet-shaped flow channel 5 (the downstream section) is defined. Besides, the other aperture of the opening 17*c* is also located that when the analytical chip 1N is in the assembled state, it can communicate with the reaction area 6.

Besides, upstream of the opening 17*c*, narrow flow channel portion 17*d* is formed, in which portion the width of the opening 17*c* (i.e., the size of the opening 17*c* along the width directions) is made small.

In the plate 16, U-shaped opening 16*b* and U-shaped opening 16*c* are formed in such a manner that each of them bends in a U shape [FIG. 81(*b*)], bulging out toward a direction along the width of the flow channel 5 [the upward direction in FIG. 81(*b*)]. Although, in the plate 17, U-shaped opening 17*a* and U-shaped opening 17*b* are formed in such a manner that each of them bulges out toward the other direction along the width of the flow channel 5 (the downward direction in FIG. 81(*c*)).

The U-shaped openings 16*b*, 16*c*, 17*a*, 17*b* are arranged in such a manner that when the analytical chip 1N is in the assembled state, the downstream end of the U-shaped opening 16*c* aligns with and communicates with the upstream end of the narrow flow channel portion 17*d* (this corresponds to the upstream end of the opening 17*c*), the downstream end of the U-shaped opening 17*b* aligns with and communicates with the upstream end of the U-shaped opening 16*c*, the downstream end of the U-shaped opening 16*b* aligns with and communicates with the upstream end of the U-shaped opening 17*b*, and the downstream end of the U-shaped opening 17*a* aligns with and communicates with the upstream end of the U-shaped opening 16*b*.

The opening 16*a* is formed at the upstream end of the plate 16 in such a manner that its downstream-side part bends in a U shape bulging out toward a direction along the width of the flow channel 5 and that its upstream-side part extends in parallel with the flow direction. The opening 16*a* is also located in such a manner that when the analytical chip 1N is in the assembled state, the downstream end of the opening 16*a* aligns with and communicates with the upstream end of the U-shaped opening 17*a*, the upstream end the opening 16*a* aligns with and communicates with the opening 21*a*, and the upstream-side part of the opening 16*a* aligns with and communicates with the opening 21*b*.

Besides, as will be described later, the opening 16*a*, the U-shaped openings 17*a*, 16*b*, 17*b*, 16*c*, and the opening 17*c* define the flow channel 5 of the chip 1N of the present embodiment, and the opening 16*a* and the U-shaped openings 17*a*, 16*b*, 17*b*, 16*c* define chaotic mixer (chaotic mixer) 18 of the chip 1N of the present embodiment.

Each of the opening 16*a* and the U-shaped openings 17*a*, 16*b*, 17*b*, 16*c* is formed to have the same width as that of the narrow flow channel portion 17*d*.

When using the analytical chip 1N according to the sixteenth embodiment of the present invention, which is constituted as described above, the fluid sample Fs injected via the opening 21*a*, which serves as an injection port, flows through, in turn, the opening 16*a*, the U-shaped opening 17*a*, the U-shaped opening 16*b*, the U-shaped opening 17*b*, the U-shaped opening 16*c*, and the opening 17*c*, and then flows out via the opening 16*d* to be drained from opening 22, which serves as a drain port. Thus, the opening 16*a*, the U-shaped openings 17*a*, 16*b*, 17*b*, 16*c*, and the opening 17*c* define the flow channel 5 of the present embodiment, while the opening 16*a* and the U-shaped openings 17*a*, 16*b*, 17*b*, 16*c* define the chaotic mixer 18 of the chip 1N of the present embodiment as the upstream portion of the flow channel 5.

Also, the pH adjuster solution Fp injected via the opening 21*b*, which serves as an injection port, flows is then injected into the flow channel 5 at a part of the opening 16*a* on the downstream side of the opening 21*a* to join with the fluid sample Fs.

After joining with each other, the fluid sample Fs and the pH adjuster solution Fp flow together through the opening 16*a* and the U-shaped openings 17*a*, 16*b*, 17*b*, 16*c*, which define the chaotic mixer 18. As shown in FIGS. 81(*b*), (*c*), the route through the opening 16*a* and the U-shaped openings 17*a*, 16*b*, 17*b*, 16*c* is formed in such a manner that as it goes from the upstream side toward the downstream side, it winds alternately from one direction to the other along the width of the flow channel. Moreover, as shown in FIG. 80, the route through the opening 16*a* and the U-shaped openings 17*a*, 16*b*, 17*b*, 16*c* is formed in such a manner that as it goes from the upstream side toward the downstream side, it winds alternately from one direction to the other along the thickness of the flow channel. Namely, when passing through the opening 16*a* and the U-shaped openings 17*a*, 16*b*, 17*b*, 16*c*, which form the chaotic mixer 18, the fluid sample Fs and the pH adjuster solution Fp come to flow through the narrow flow channel portion that winds repeatedly both in up-and-down directions and in side-to-side directions as it goes toward the flow direction. Since the windings impede the flowing of the fluid sample Fs, the interface area between the fluid sample Fs and the pH adjuster solution Fp increases with the fluid sample Fs, so that diffusion mixing is expedited markedly with efficiency.

Besides, as indicated in FIGS. 81(b), (c), in the narrow flow channel portion 17d composed of the opening 16a, the U-shaped openings 17a, 16b, 17b, 16c, and the opening 17c, which define the chaotic mixer 18, the flow channel has a small width. With the arrangement, as explained in the fifteenth embodiment, compared with the case where the flow channel has a large width, diffusion is expeditiously completed, so that the efficiency of diffusion mixing is improved.

After thus joining together and being mixed efficiently in the opening 16a, the mixture of the fluid sample Fs and the pH adjuster solution Fp then flows into the reaction area 6, in which the detection and measurement of the fluid sample Fs are carried out, and finally flows through the opening 16d and is drained via the opening 22.

As described above, using the analytical chip 1N of the present embodiment, it is possible to carry out mixing efficiently with the chaotic mixer, in addition to achieving the same advantageous results as those of the thirteenth embodiment.

Although in the present embodiment the fluid sample Fs is mixed with the pH adjuster solution Fp, it is also possible to mix the fluid sample Fs with another kind of liquid in a different combination.

Besides, although in the present embodiment the analytical chip 1N is formed in such a manner as to enable the mixing of two kinds of liquid, namely, the fluid sample Fs and the pH adjuster solution Fp, it is also possible to form three or more openings (in the instance illustrated by FIG. 82, three openings 21a, 21b, 21c) on the cover member 2, for example, to form opening 21c, which communicates with the opening 16a, in addition to the above two openings, so that the analytical chip 1N can mix three or more kinds of liquid. In FIG. 82, like reference characters also used in FIGS. 65–81 designate like components.

Also, as in the thirteenth embodiment, the number and the shapes of the openings 21a, 21b, which serve as injection ports, are not limited particularly and can be selected appropriately according to the analysis method.

Besides, although in the present embodiment the chaotic mixer is formed by varying, in three dimensions, the arrangements of the opening 16a and the U-shaped openings 17a, 16b, 17b, 16c, which the upstream portion of the flow channel 5, the constitution of the chaotic mixer is not limited to the above embodiment.

If the flow route through the chaotic mixer is complicated to an appropriate degree, liquid particles that are once adjacent to each other keep moving around independently during flowing through the chaotic mixer to such a degree that the distance between these particles after the flowing during a certain period of time is unpredictable. This phenomenon is called "chaotic mixing". The present embodiment is based on the chaotic mixing. Namely, by making a liquid with an appropriate Reynolds number flow through a nonlinear flow channel (the chaotic mixer 18), as shown in FIGS. 80 and 81(b), (c), the liquid is mixed in the chaotic mixer 18 after a certain period of time. Hence, the chaotic mixer applied to the present embodiment is not limited to the one explained in the present embodiment but is selectable as appropriate from various known chaotic mixers.

(17) Seventeenth Embodiment

FIG. 83 is a diagram of assistance in explaining the seventeenth embodiment of the present invention.

The analysis apparatus according to the seventeenth embodiment of the present invention has, as shown in FIG. 83, one of the analytical chips 1K, 1M, 1N explained in the thirteenth, fifteenth, and sixteenth embodiments (hereinafter, reference character 1K is used for designating the analytical chip), analysis section 501, which is for carrying out analysis of the fluid sample Fs flowing through the analytical chip 1K, separation apparatus 502, which is disposed upstream of the analytical chip 1K for separating the fluid sample Fs by physical and/or chemical action prior to the introduction of the fluid sample Fs to the analytical chip 1K, after-analysis apparatus 503, which is for analyzing the fluid sample Fs drained from the analytical chip 1K. The analytical chip 1K was already explained in each of the above embodiments, so that redundant explanation is omitted.

The constitution of the analysis section 501 is not restricted particularly, although it is generally preferable to use, as the analysis section 501, an apparatus which carries out analysis using at least one analytical technique selected surface plasmon resonance, chemiluminescence, bioluminescence, electrochemiluminescence, fluorescence, and RI (radioactive isotope analysis). It is possible to use either an analysis section carrying out analysis using one of the above-exemplified techniques or an analysis section carrying out analysis using two or more of the techniques in combination.

When using the analysis section 501 which carries out analysis based on surface plasmon resonance, it is possible to configure the analysis section 501 specifically in the same constitution as that of the second embodiment. Also, when using the analysis section 501 which carries out analysis based on surface plasmon resonance, it is also possible to carry out analysis under light irradiation from the back face of the analytical chip 1K. Specifically, a light beam is applied from the side of the basal plate 4 of the analytical chip 1K into the reaction area 6, which is formed in the flow channel 5 of the analytical chip 1K, and the light beam reflected by the reaction area 6 is observed at the side of the basal plate 4 of the analytical chip 1K while analysis is carried out. In the case, however, since it is necessary that the applied light beam reaches the reaction area 6 of the analytical chip 1K, it is required as a matter of course that the basal plate 4 is formed in such a manner that it allows the incident light to pass through. Hence, when analysis is carried out under light application from the back face the analytical chip 1K, the basal plate 4 is usually made from materials that can transmit light having the same wavelengths as those of the incident light.

When using the analysis section 501 which carries out analysis based on fluorescence, in general, the cover member 2 of the analytical chip is formed to be transparent, and excitation light is applied from the side of the cover member 2 while fluorescence is also detected also from the side of the cover member 2. However, it is also possible, just as in the case where analysis is carried out based on surface plasmon resonance, to apply excitation light from the side of the back face of the analytical chip 1K, i.e., the side of the basal plate 4 and detect fluorescence from the side of the basal plate 4 to carry out analysis. In the latter case, it is necessary to form the basal plate 4 to be transparent. In addition, it is also possible to apply excitation light from the side of the cover member 2 of the analytical chip 1K and detect fluorescence from the side of the basal plate 4 or, in contrast, to apply excitation light from the side of the basal plate 4 and detect fluorescence from the side of the cover member 2. Incidentally, when carrying out analysis based on chemiluminescence or bioluminescence, it is generally unnecessary for the application of excitation light.

When using the analysis section 501 that carries out analysis based on chemiluminescence or bioluminescence, as in the case the analysis is carried out based on surface plasmon resonance or fluorescence, it is possible to detect chemiluminescence from a desired direction through a transparent part (part formed to be transparent) of the analytical chip 1K. Specifically, when the cover member 2 of the analytical chip 1K is formed to be transparent, for example, it is possible to carry out the application and detection of light from the side of the cover member 2, and when the basal plate 4 is formed to be transparent, it is possible to carry out the application and detection of light from the side of the basal plate 4.

When using the analysis section 501 that carries out analysis based on electrochemiluminescence, it is possible to carry out analysis basically in the same manner as in the case of chemiluminescence. As an exception, however, it is to be noted that it is necessary to dispose an electrode to the basal plate 4 in the case of electrochemiluminescence. Hence, so long as the electrode is made from a non-transparent material, even if the basal plate 4 is made from a transparent material, it is difficult to detect electrochemiluminescence from the side of the basal plate 4. On the other hand, when the electrode is made from a transparent material (i.e., ITO), or when the electrode is made from a non-transparent material but formed in such a extremely thin film that it can transmit light, it is also possible to carry out the application and detection of light from the side of the basal plate 4.

Besides, the analysis apparatus according to the present embodiment has separation apparatus 502, which is disposed upstream of the analytical chip 1K and is for separating the fluid sample Fs by physical and/or chemical action prior to the introduction of the fluid sample Fs into the analytical chip 1K.

The constitution of the separation apparatus 502 is not restricted particularly, although it is generally preferable to use the techniques such as: liquid chromatography and HPLC (high performance liquid chromatography), which carry out separation based on the adsorptivity or the distribution coefficient of samples; capillary electrophoresis, micro chip electrophoresis, and microchannel electrophoresis, which carry out separation based on the electronegativity of samples; and flow injection. Also, it is naturally possible to equip the analysis apparatus with any other types of apparatus as the separation apparatus 502, either alone or in combination with the above-exemplified types of apparatus.

The "microchannel" means a groove which is formed on a chip surface and through which a sample flows, and the "microchannel electrophoresis" means the technique of carrying out separation by filling a part of the groove with substances corresponding to column fillers used for HPLC or fixing functional groups to the groove surface.

The "flow injection" is a method of bringing about various kinds of reactions in the state where a sample is flowing. According to the method, it is possible to remove substances other than target species in the sample to achieve separation by, for example, bringing about complex formation reaction, carrying out solvent extraction, and so forth.

As a matter of course, it is also possible to equip the analysis apparatus with any apparatus other than those exemplified above as the separation apparatus 502.

Besides, the analysis apparatus according to the present embodiment has after-analysis apparatus 503, which carries out analysis of the fluid sample Fs drained from the analytical chip 1K. The constitution of the after-analysis apparatus 503 is not restricted particularly, and various types of analysis apparatus can be used as the after-analysis apparatus 503. Specifically, examples include MS (mass spectrograph), protein sequencer, DNA sequencer, SEM, SPM, STM, AFM, etc.

The after-analysis apparatus 503 can also have a pretreatment mechanism, which make the fluid sample Fs in the state of allowing analysis. Also, it can have any of the above-exemplified types of apparatus in combination.

When using the analysis apparatus according to the seventeenth embodiment of the present invention, which is constituted as described above, during analysis, the fluid sample Fs is made flow through in turn the separation apparatus 502, the analytical chip 1K, and the after-analysis apparatus 503 while analysis is carried out.

Also, since analysis is carried out in the analysis section 501 using the analytical chip 1K, it is possible to mix the fluid sample Fs with another kind of liquid easily and efficiently, so that it becomes possible to carry out analysis efficiently with high precision and to achieve the same advantages as those of the thirteenth embodiment.

In addition, since the analysis apparatus according to the present embodiment has the after-analysis apparatus 503, it is possible to obtain multiple data through a single analysis operation and to thereby analyze the fluid sample Fs from various points of view.

Although the analytical chip 1K explained in the thirteenth embodiment is used in the present embodiment, it is a matter of course that the analytical chip 1 is not limited to the one used in the above embodiment but can be any other analytical chip 1 having a different constitution.

(18) Others

In the above description, the first through seventeenth embodiments of the present invention were explained, although the present invention should not be limited to these embodiments but can be carried out in various embodiments unless departing from the scope of the invention.

For example, it is also possible to carry out two or more of the first through seventeenth embodiments in combination. Specifically, the explanations of the above fourth through seventh embodiments were made mainly based on the constitution of the analytical chip of the third embodiment, it is also possible to carry out one or more of the other embodiments such as the first embodiment and the second embodiment.

Also, it is possible to carry out the third embodiment in combination with the second embodiment, for example. Specifically, the cover member 2 and the plate 10 according to the analytical chip 1B of the third embodiment are made from a transparent material while the diffraction grating 42 and the metal layer 41 are formed the surface of the basal plate 4 to which the specific substance 61 is to be fixed, thereby the sensor chip being formed. With the arrangement, by irradiating the basal plate 4 with light via the cover member 2 and the plate 10 and detecting the intensity of the light reflected from each spot of the specific substance 61 on the reaction area 6, in addition to the same advantageous effects as those of the second embodiment, it becomes possible to measure the concentration of target species in the test fluid in real time.

Besides, although being an injection pump in each of the above embodiments, means for transmitting the fluid sample Fs is not limited to the injection pump. Not to mention a pressure-type pump, it is also possible to use the method in which an electric field is applied to the slit-form flow channels 9a (the first and second embodiments), 10a (the third embodiment) and the flow-channel confluence parts 81, 82 (the first and second embodiments), 13, 14 (the third embodiment) to thereby generate the flow of the fluid sample Fs (electroendosmotic flow). The method can be also carried out in combination with transmission by capillary phenomenon.

Besides, although in the above embodiments explanation is made using the instance where the fluid sample Fs is water-soluble, the fluid sample Fs can also be oleaginous.

It is also preferable to arrange plural flow channels, each of which has a cross section with aspect ratio ([length size]/[width size]) of between 0.005 (e.g., 5 μm in length and 1 mm in width) and 100 (e.g., 10 mm in length and 100 μm in width) inclusive and a cross sectional area of 5 mm$^2$ or below, in parallel between a single injection port and a single drain port, and to place a specific substance that can cause specifically or nonspecifically interaction with a predetermined substance in each of the flow channels. It is also preferred that the cross sectional area is usually 100 μm$^2$ or above, preferably 2000 μm$^2$ or above, and usually 5 mm$^2$ or below, preferably 0.3 mm$^2$ or below. With the constitution, since the occurrence of air bubbles in the flow channels can be inhibited, it is possible to carry out analysis under an optimal condition in which air bubbles do not occur, so that the precision of analysis results is improved.

Besides, it is also possible to form inner flow channels so as to extend over plural intermediate plates. Specifically, for example, as shown in FIGS. 32(a)–(d), it is possible to interpose between the cover member 2 and the basal plate 4 the first plate 8', which has the slit-form openings 8a' divided with the partition walls 8b', and the second plate 9', which has the slit-form openings 9a' divided with the partition walls 9b', in such a manner that the slit-form openings 8a', 8b' and the slit-form openings 9a' define the inner flow channels.

In addition, it is also possible to form the partition walls (projection member) 9b', as shown in FIG. 33(a), directly on the basal plate 4 using a technique such as printing (e.g., screen printing, ink jet printing) or coating. When the projection member is formed using the intermediate plate 9', as is explained in the first embodiment, there is a case where, as shown in FIG. 33(b), the projection member 9b' separates from the intermediate plate 9' due to the slit-form openings 9a' or the like, so that it is difficult to form the analytical chip. In contrast, by forming the projection member 9b' directly on the basal plate 2, it is possible to form the projection member 9b' easily. Further, this technique is applicable to other embodiments, including the above first and third embodiments.

Figure 17:
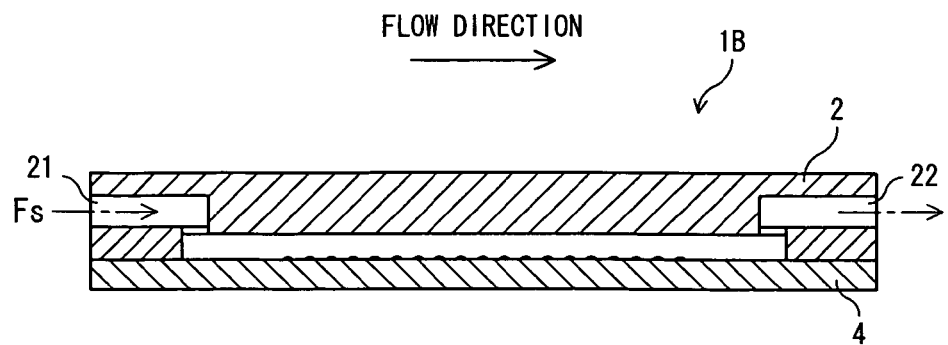
FIG. 17(a), FIG. 17(b) are diagrammatic sectional views of analytical chips according to the third modification of the third embodiment of the present invention.
Figure 17:
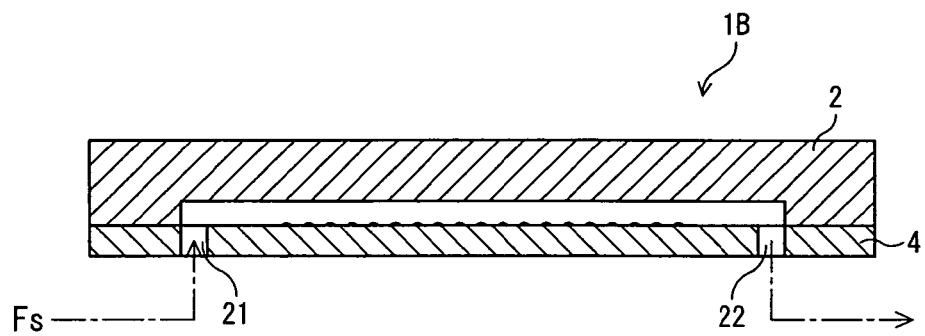
Figure 34:
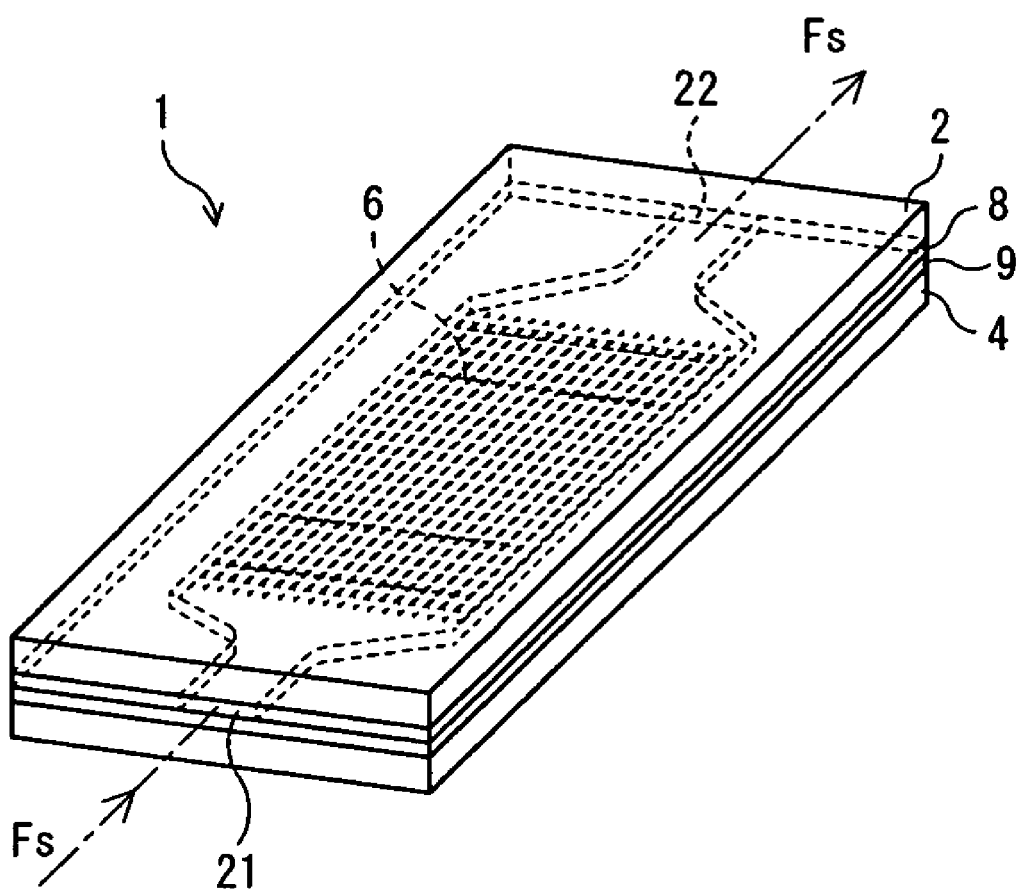
FIG. 34 is a diagrammatic assembled perspective view of an analytical chip according to an embodiment of the present invention.

Besides, although already mentioned in FIG. 17, it is also possible to form the injection port 21 and the drain port 22 on a side surface of the analytical chip 1, as shown in FIG. 34. In the drawing, the opening 21 is formed as the injection port on one of the opposite side surfaces of the plate 8, while the opening 22 is formed as the drain port on the other side surface. With the modification, when analysis is carried out using, for example, a surface plasmon resonance sensor, it is possible to negate the need to dispose a connector for introducing or draining the fluid sample Fs to or from an upper part of the analytical chip 1 through which light passes, so that the reaction area 6 can be extended. It is also possible to achieve other advantages, one of which is that it is possible to arrange an optical system component such as a light source or a detector nearer the analytical chip.

Besides, the shape and arrangement of the projection member is not limited to those explained in the embodiments and is selectable as appropriate. Concrete examples are explained hereafter with reference to FIGS. 35(a)–(f), diagrams each showing various shapes of the flow channel 5.

Figure 35:
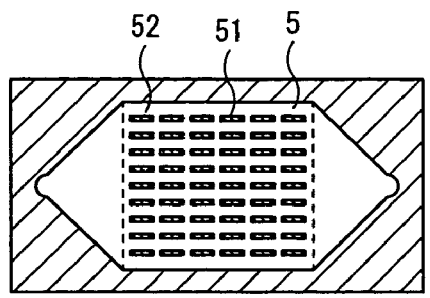
FIG. 35(a) through FIG. 35(f) are diagrammatic views of assistance in explaining an example of a flow channel of an analytical chip according to the present invention.
Figure 35:
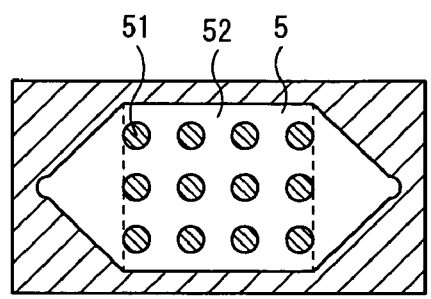
Figure 35:
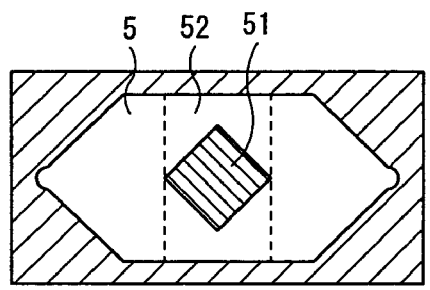
Figure 35:
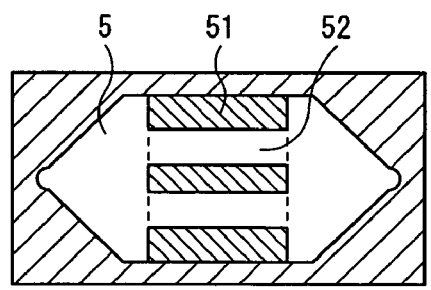
Figure 35:
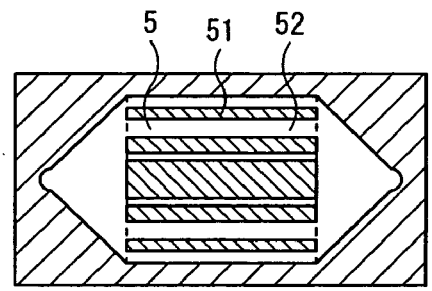
Figure 35:
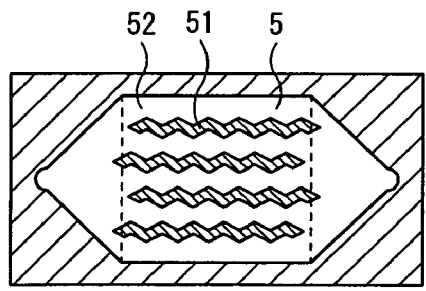

For example, it is possible to form the projection member 51, as shown in FIG. 35(a), in the shapes of separate rows of discrete walls, and also possible to form the projection member 51, as shown in FIG. 35(b), in the shapes of multiple circular cylinders. Also, it is possible to form the projection member 51, as shown in FIG. 35(c), as a single member disposed at the center of the flow channel 5, and also possible to form the projection members (wall-shape members) 51, as shown in FIG. 35(d), so as to adjoin the wall surfaces of the flow channel 5. Besides, it is possible to form the projection members (wall-shape members) 51 in such a manner that, as shown in FIG. 35(e), the sizes of the members and the widths of the inner flow channel 52 are varied, and also possible to form the projection members (wall-shape members) 51 in the manner that, as shown in FIG. 35(f), their widths are not uniform along the flow direction of the inner flow channels 52, and that they have not any regularity.

Although in the above embodiments the projection member is formed in the form of the partition walls serving as the prop members, it is also possible that the projection members also have any functions other than the prop members or the partition walls. For example, the projection member can be a micro fluid element such as a micro mixer, a micro pump, a heat exchanger (heater, cooler), a micro injector, etc., made by a technique such as micro-fabrication technique, MEMS technique, and semiconductor manufacturing technique.

Besides, although in each of the above-mentioned embodiments, explanations were made assuming that the flow channel 5 of the analytical chip is in a substantially hexagonal sheet shape, it is also possible to form the flow channel 5 in any other shapes. For example, it can be formed in a shape defined simply by curved lines or in a shape other than a hexagon. Moreover, it is also possible to form the flow channel in a shape other than a sheet shape (the flow channel having a shape formed as a non-sheet-shaped space), for example, a cylindrical shape.

Based on the above embodiments, it is possible to consider the projection member (partition walls) as forming, if focusing on its function of inhibiting the occurrence of air bubbles 201, air-bubble inhibiting means while as forming, if focusing on its function of dividing the flow channel 5 into the plural inner flow channels, flow-channel dividing means that divides the flow channel 5. Also, it is possible to consider the projection member (partition walls) as forming, if focusing on its function of preventing of deformation of the analytical chip 1, 1A–1H, deformation preventing means while as forming, if focusing on its function of reducing the amount of fluid sample Fs to be used, fluid-sample saving means.

Besides, although in the eleventh and twelfth embodiments, for example, the protective layers 25, 85, 45, which can protect the surface of the optically transparent part 7 while allowing light transmission (each of the protective layers 25, 85, 45 is composed of an anti-reflection layer and an abrasion resistance layer) are formed on both surfaces of the optically transparent part 7 (i.e., the outer surface of the optically transparent part 7 and the surface of the optically transparent part 7 on the side of the flow channel 5), it is also possible to form either of the surfaces.

Figure 60:
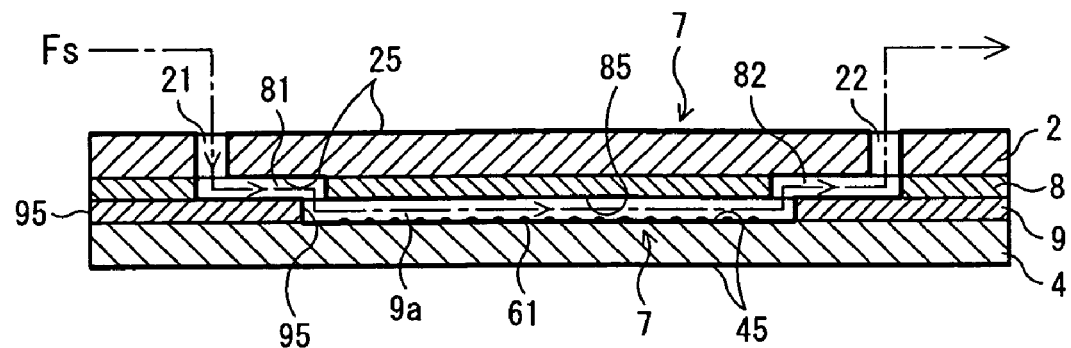
FIG. 60 is a diagrammatic sectional view of assistance in explaining another embodiment of the present invention.

It is also possible to form, as shown in FIG. 60, the protective layers 25, 85, 95, 45 (each of the protective layers 25, 85, 95, 45 is composed of the anti-reflection layer and the abrasion resistance layer), which can protect the surfaces of the optically transparent part 7 while allowing light transmission, on the whole surface of the analytical chip 1I, namely, the whole surfaces of the cover member 2, the plates 8, 9, and the basal plate 4. In FIG. 60, the reference characters also used in FIGS. 48–59 designate the same components.

Figure 61:
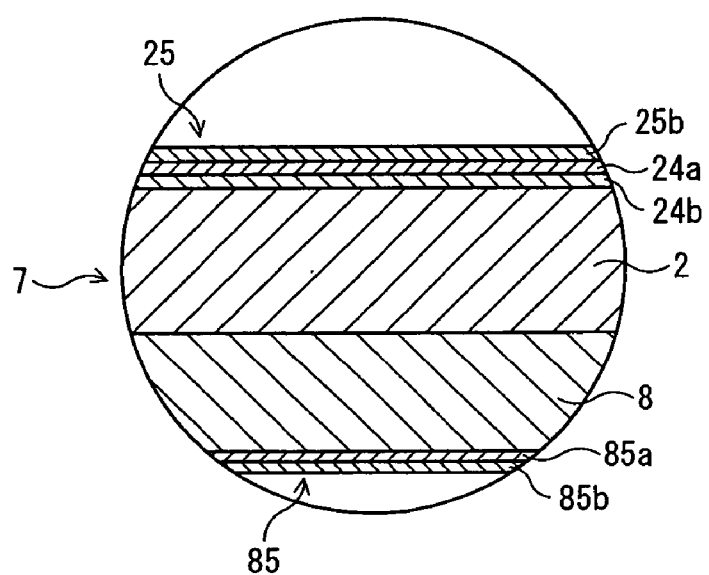
FIG. 61 is a diagrammatic sectional view of assistance in explaining another embodiment of the present invention, whose substantial part is shown with enlarged.

In addition, although in the above eleventh and twelfth embodiments the anti-reflection layers 25a, 85a are formed as single-layered AR layers, it is possible to form the anti-reflection layers 25a, 85a in different structures. For example, it is also possible, as shown in FIG. 61, to form each of the anti-reflection layers 25a as a multi-layered AR layer, composed of plural layers 24a, 24b with different refractive indexes. In such a case where there is not any material having an appropriate refractive index as a single layer, by combining plural layers 24a, 24b with different refractive indexes to form a multi-layered AR layer, as described above, it is possible to adjust the refractive index of the whole multi-layered AR layer to the appropriate value. In FIG. 61, the reference characters also used in FIGS. 48–60 designate the same components.

It is also possible to form the anti-reflection layers 25a, 85a as nonglare layers, instead of single-layered AR layers (refer to the nonglare layers 24c, 84c of FIG. 50(d)).

Besides, it is also possible to form each of the protective layers 25, 85, 45, which can protect a surface of the optically transparent part 7 while allowing light transmission, so as to be composed of either the anti-reflection layer 25a, 85a or the abrasion resistance layer 25b, 85b.

Figure 62:
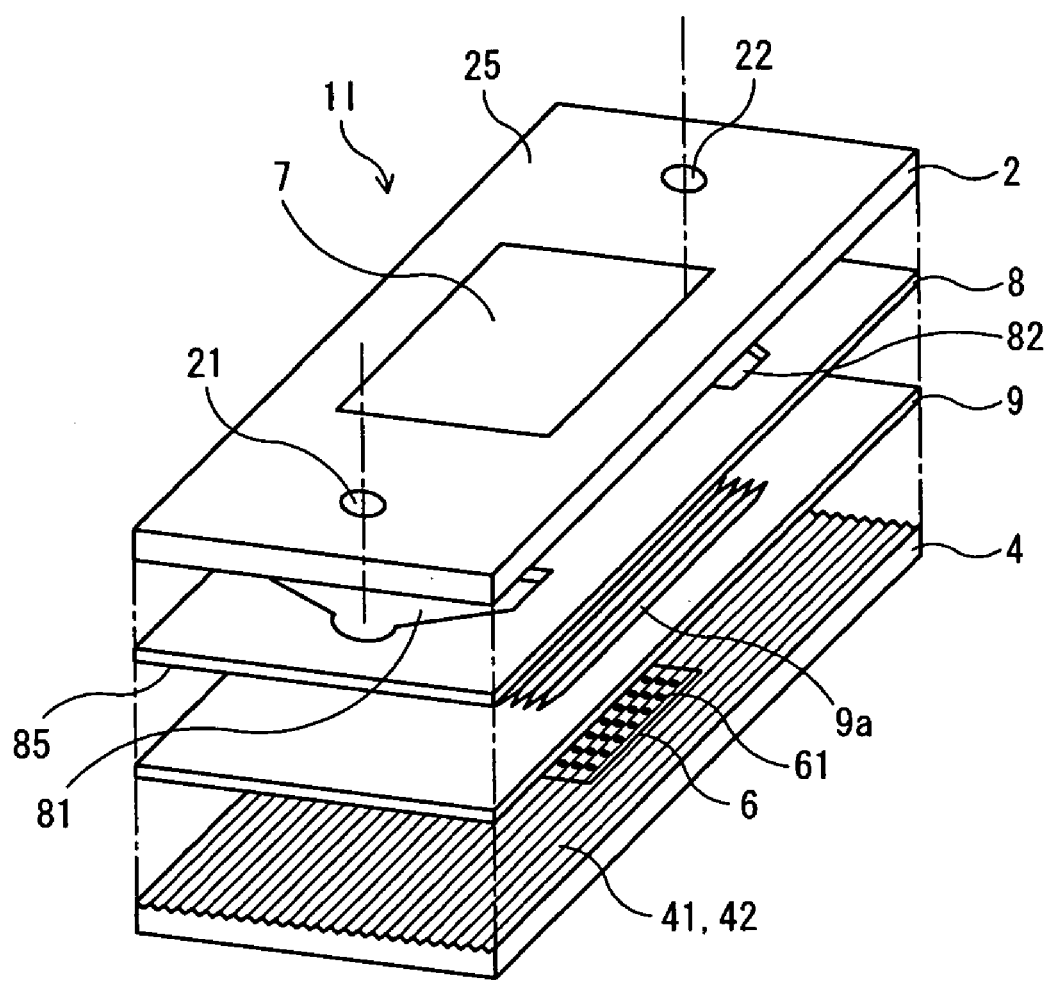
FIG. 62 is a diagrammatic exploded perspective view of an analytical chip according to another embodiment of the present invention.

Also, the position and the shape of the optically transparent part 7 can be selected as appropriate. For example, it is also possible, as shown in FIG. 62, to form a transparent window part in each of the cover member 2 and the plate 8 so as to use the window part as the optically transparent part 7. In FIG. 62, like reference characters also used in FIGS. 48–61 designate like components.

It is not necessary to form the optically transparent part as being transparent. It is allowable so long as the optically transparent part can transmit the light of predetermined wavelengths used for analysis.

Although in the above eleventh and twelfth embodiments, the flow channel 5 is formed by interposing the plate 9 with openings between the cover member 2 and the basal plate 4, it is also possible to form the flow channel 5 directly on the cover member 2 and/or the basal plate 4 (refer to FIG. 53). For forming the flow channel directly on the cover member 2 and/or the basal plate 4, the following methods can be selectively used: machining; various transferring techniques typified by injection molding and compression molding; dry etching (RIE, IE, IBE, plasma etching, laser etching, laser ablation, blasting, electrical discharge machining, LIGA, electron beam etching, FAB); wet etching (chemical erosion); and optical machining method.

Figure 63:
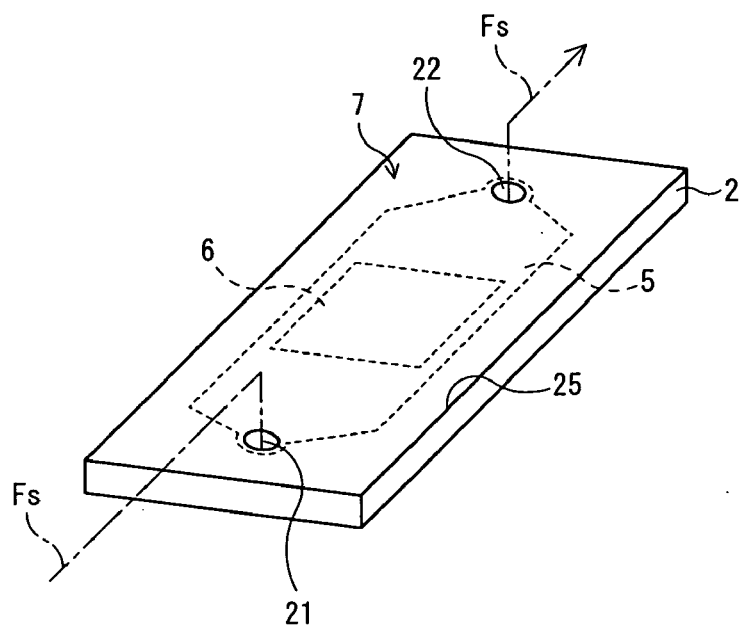
FIG. 63 is a diagrammatic perspective view of an analytical chip according to another embodiment of the present invention.

It is also possible to form the body of the chip 1I, as shown in FIG. 63, integrally as a unit having the flow channel 5, not a structure that can be disassembled into the cover member 2 and the basal plate 4, by using: an integral molding such as optical machining or ceramic covering; Surface Micro-machining of coating with various substances in a layer and partially removing by means of vacuum evaporation, sputtering, deposition, or the like, to thereby form a microstructure; or the like. In FIG. 63, the reference characters also used in FIGS. 48–62 designate the same components. In addition, in FIG. 64, the flow channel 5 and the reaction area 6 are both formed in the cover member 2.

Besides, although being an injection pump in the above eleventh and twelfth embodiments, means for transmitting the fluid sample Fs is not limited to the injection pump. Not to mention a pressure-type pump, it is also possible to use the method in which an electric field is applied to the flow channels 5. The method can be also carried out in combination with transmission by capillary phenomenon.

Also, the explanations of the eleventh and twelfth embodiments of the present invention were made based on the analytical chips 1I, 1J, in which components such as the slit-form flow channels 9a and the flow-channel confluence parts 81, 82 are formed in the flow channel 5. However, the protective layers 25, 45, 85 as one of the features of the present invention is also applicable to the analytical chips in which neither the slit-form flow channels 9a nor the flow-channel confluence parts 81, 82 are formed.

Further, it is also possible to carry out two or more of the thirteenth through seventeenth embodiments in combination. For example, it is possible to carry out the fifteenth embodiment in combination with the fourteenth embodiment. Specifically, the cover member 2 and the plate 10 of the analytical chip of 1M according to the fifteenth embodiment are made from transparent materials, and the diffraction grating 42 and the metal layer 41 are formed on the surface of the basal plate 4 to which the specific substance 61 is to be fixed, to thereby form the sensor chip. With the arrangement, by irradiating the basal plate 4 with light via the cover member 2 and the plate 10 while detecting the intensity of light reflected from each spot of specific substance 61 on the reaction area 6, as in the fourteenth embodiment, it becomes possible to measure the concentration of target species in the fluid sample in real time.

Besides, although being an injection pump in each of the thirteenth through seventeenth embodiments, means for transmitting the fluid sample Fs is not limited to the injection pump. Not to mention a pressure-type pump, it is also possible to use the method in which an electric field is applied to the flow channel 5 to thereby generate the flow of the fluid sample Fs (electroendosmotic flow). The method can be also carried out in combination with transmission by capillary phenomenon.

Also, it is possible to form, as shown in FIG. 84, the components other than the basal plate to which the specific substance is to be fixed (in the above thirteenth-seventeenth embodiments, the cover member 2 and the plates 8–10, 16, 17) integrally as a unit structure using a method such as optical machining. In FIG. 84, the reference characters also used in FIGS. 65–83 designate the same components.

It is also possible to form the plates 8–10, 16, 17, explained in the above embodiments, directly on the basal plate 4 using a technique such as printing (e.g., screen printing, ink jet printing) or coating Besides, as shown in FIG. 85, it is also possible to form a part or all of the injection ports and the drain ports on a side surface of the analytical chip 1. In FIG. 85, the injection port 21a, through which the fluid sample Fs is injected, and the drain port 22 are formed on one of the side surfaces of the plate 8, while the injection port 21b, through which the pH adjuster solution Fp is injected, is formed on the upper surface of the cover member 2. With the modification, when analysis is carried out using, for example, a surface plasmon resonance sensor, it is possible to negate the need to dispose a connector for introducing or draining the fluid sample Fs to or from an upper part of the analytical chip 1 through which light passes, so that the reaction area 6 can be extended. It is also possible to achieve other advantages, one of which is that it is possible to arrange an optical system component such as a light source or a detector nearer the analytical chip. In FIG. 85, the reference characters also used in FIGS. 65–84 designate the same components.

Although each of the analytical chips 1K–1N, used for the explanations of the thirteenth through seventeenth embodiments, is formed in such a manner that the flow channel 5 is divided into the inner flow channels (slit-form flow channels) 4a in the reaction area 6, when embodying the present invention, it is also possible to form the analytical chip with a flow channel not having any slit-form flow channel.

Besides, although in the above thirteenth through seventeenth embodiments explanations were made based on the instance where the fluid sample Fs is mixed with the pH adjuster solution Fp, the liquid to be mixed with the fluid sample Fs can be selected as appropriate. Examples include, besides such a pH adjuster solution, a salt-concentration adjuster solution, a concentration adjuster solution, a reaction accelerator solution, a reaction inhibitor solution, a reaction terminator solution, and a liquid that reacts the fluid sample Fs.

(Experimental Embodiment 1)

The present invention will now be described in detail with reference to the following experimental embodiment, although the present invention should not be limited to the experimental embodiment but can be carried out in various embodiments unless departing from the scope of the invention.

On the surface of a flat plate resin, an uneven area was formed with grooves whose pitch is of about 870 nm and whose depth is of about 40 nm, serving as a diffraction grating. On the uneven area of the flat plate resin, gold was deposited through vacuum evaporation, thereby a thin film layer with a thickness of about 80 nm being formed. From the resultant flat plate resin, two sections of the 25 mm×25 mm size were cut out and used as basal plates.

Figure 46:
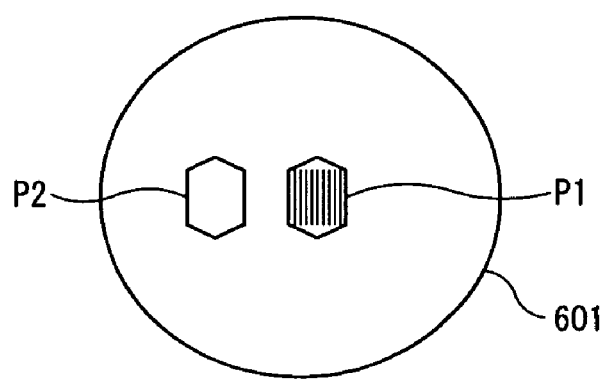
FIG. 46 is a diagram of assistance in explaining an experimental embodiment of the present invention.

A 4-inch silicon wafer (available from Furuuchi Chemical Co.) was coated with a photoresist Nano XP SU-8 (50) (available from MicroChem Co.) by spin coating. The solvent was removed by a 30 minutes application of heat. The resultant wafer was cooled down to ambient temperature and then exposed to ultraviolet rays through a photo film mask (available from Falcom Co.). As shown in FIG. 46, the photo film mask has two patterns P1, P2 formed thereon in such a manner that they are to be printed on the same silicon wafer 601. Pattern P1, having slit forms, is used for producing an analytical chip with projection member, while pattern P2, not having any slit forms, is used for producing a conventional analytical chip. Each of the patterns P1, P2 is shaped in such a manner that when used for producing the respective analytical chip, it provides a form corresponding to the flow channel. Specifically, its maximum length along the flow direction is 10 mm, and its maximum length along the width directions is 21 mm. In addition, the pattern P1 includes a pattern of slits (slit forms) shaped in such a manner that the flow channel can be divided into plural inner flow channels each having a width of 0.5 mm.

After the exposure, the resultant wafer was subjected to after-baking for 30 minutes, then to developing for 15 minutes by a developer (Nano XP SU-8 Developer, available from MicroChem Co.), and finally to cleaning with isopropyl alcohol and water.

PDMS (polydimethylsiloxane) Sylgard184 Kit (available from Dow Corning Toray Silicone Co.) was used as a silicone elastomer. A base agent and a curing agent in the ratio of 10:1 were mixed with being agitated, and the resultant mixture was deaerated under a vacuum of −630 Torr for 15 minutes.

Figure 47:
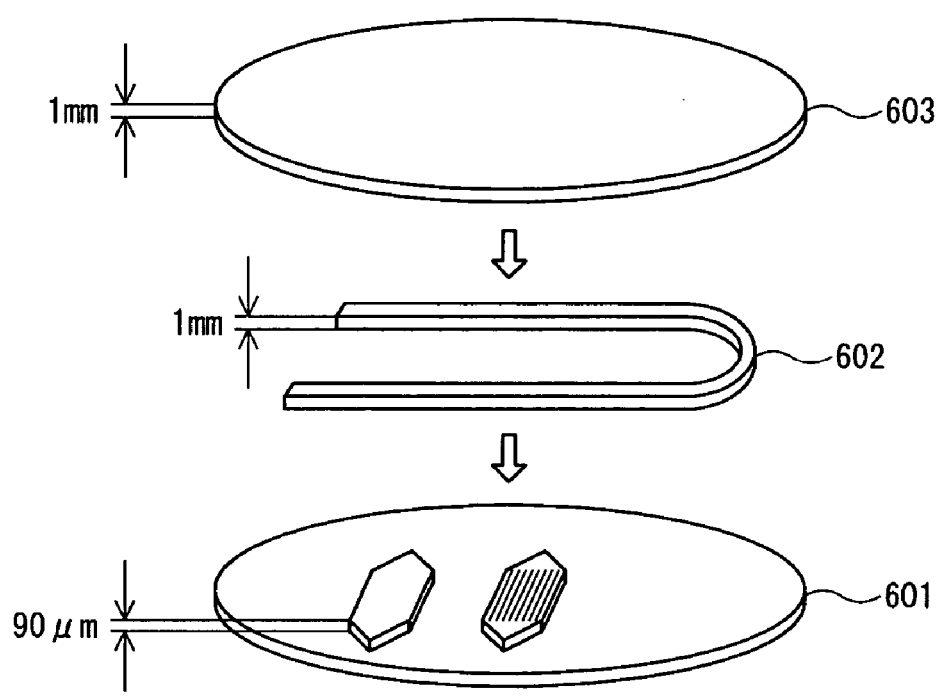
FIG. 47 is a diagram of assistance in explaining an experimental embodiment of the present invention.

On the silicon wafer 601, as shown in FIG. 47, a U-shaped mold 602 of PMMA with a thickness of 1 mm and a resin flat plate 603 with a thickness of 1 mm were laid in turn, so that a mold cavity for elastomer was defined. The above elastomer mixture was filled through an opening of the mold cavity, and then cured under the condition of 80° C. for 3 hours. After the curing process, the silicon wafer 601 and the U-shaped mold 602 were taken off from the cured elastomer. A part of the product where each of the patterns P1, P2 was printed was cut off as a section having a sheet-shaped flow channel. Through the resin flat plate 603 of each of the cut sections, a pair of pass-through holes corresponding to injection and drain ports were formed. For each of the cut sections, a Pyrex$^R$ glass plate with the thickness of 1 mm was prepared as a cover member, having a pair of pass-through holes also corresponding to injection and drain ports. Each of the cover members was laid on, and registered with respect to, their respective cut section in such a manner that the pass-through holes of the cover member are aligned one to each of the pass-through holes of the flow cell of the cut section. The cover member and the respective cut section being in register were then pasted together, and joined with the basal plate to finally form an analytical chip. Of the resultant analytical chips, the one includes the cut section having a printed pattern P1 with slit forms, being used as an analytical chip with projection member. The other includes the cut section having a printed pattern P2 without slit forms, being used as a conventional analytical chip. In each of the analytical chips, the flow channel has the depth of 90 μm.

Prepared according to the above-mentioned process, both the analytical chip with projection member and the conventional analytical chip were subjected to SPR analysis using an SPR measuring equipment, FLEX CHIPT™ Kinetic Analysis System (available from HTS Biosystems). At the temperature of 30° C., purified water was made flow through the flow channel of each of the analytical chips at the constant velocity of 500 μl/min for 60 minutes. During the flow, angle scan was carried out to obtain data of 512 different angles at intervals of about 7 seconds for determining fluctuant resonance angles. A detection area of 10 mm×10 mm was divided into 8×20=160 unit regions of interest (ROI), and data was obtained at each of the unit regions. The difference between the maximum value and the minimum value in the range of measuring time (60 minutes) was obtained for each unit region and determined as a drift amount. The resultant drift amounts were compared between the analytical chip with projection member and the conventional analytical chip. FIG. 88(*a*) shows the drift amounts (angle differences) obtained using the analytical chip with projection member, while FIG. 88(*b*) shows the drift amounts (angle differences) obtained using the conventional analytical chip. Table 1 shows the average value of the drift amounts of all unit regions for each analytical chip.

TABLE 1

| Analytical Chip | Analytical Chip with Projection Member | Conventional Analytical Chip |
|---|---|---|
| Drift Amount (mdeg) | 7.22 | 12.77 |

It is apparent from Table 1 that the analytical chip with projection member has an average drift amount smaller than that of the conventional analytical chip. It is therefore demonstrated that using the analytical chip with projection member enables to carry out analysis with high precision while restraining both the repetitions of analysis operations to be carried out and the accompanying increase in amount of the fluid sample to be used, so that efficient analysis becomes possible.

(Supplementary Note)

According to the analytical chip, analytical-chip unit, and analysis apparatus of the present invention, it becomes possible to analyze a fluid sample efficiently with high precision, as mentioned above. In addition, one or more of the following advantages can be obtained.

(1) The occurrence of air bubbles due to running ahead of the fluid sample can be avoided.
(2) The deformation of the analytical chip can be prevented.
(3) When analysis is carried out with an optical system, the occurrence of reflection in the optical path can be avoided, which reflection may adversely affect the analysis.
(4) When analysis is carried out with an optical system, the dispersion of light due to defect flaws in the optical path can be prevented.
(5) Mixing can be carried out quickly and easily while the analytical chip remains in simple and compact constitution.
(6) The amount of fluid sample required for analysis can be reduced.

INDUSTRIAL APPLICABILITY

As mentioned above, an analytical chip according to the present invention, in addition to an analytical-chip unit, an analysis apparatus, an analysis method, and a method of making an analytical chip according to the present invention, is applicable to various areas such as chemical analysis, biological analysis, and biochemical analysis. Among others, it is suitable for a combined use with another device or apparatus, such as a clinical device of small size or a detector for HPLC. It is also suitable especially for the cases where it is desired to reduce the amount of a fluid sample used for analysis, such as the analysis of blood or urine, the analysis of nutritive substances in food, and the analysis of chemical substances in drainage water.

The invention claimed is:

1. An analytical chip comprising:
 a flow channel (5), whose section is in a closed shape and through which a fluid sample (Fs) is made to flow, for carrying out analysis regarding the fluid sample (Fs) based on interaction between a predetermined substance and a specific substance (61), which is fixed facing said flow channel (5); and
 a projection member (9b) attached to said flow channel (5).

2. An analytical chip as defined in claim 1, wherein said flow channel (5) is formed as a sheet-shaped space.

3. An analytical chip as defined in claim 2, further comprising:
 an injection port (21) connected to the upstream end of said flow channel (5), through which port the fluid sample (Fs) is to be injected; and
 a drain port (22) connected to the downstream end of said flow channel (5), through which port the fluid sample (Fs) is to be drained.

4. An analytical chip as defined in claim 2, wherein said projection member (9b) is in the form of one or more partition members (9b) dividing said flow channel (5) across the width directions, and
said flow channel (5) has two or more inner flow channels (9a) divided by said one or more partition members (9b).

5. An analytical chip as defined in claim 4, further comprising:
 a basal plate (4);
 a cover member (2); and
 at least one intermediate plate (8, 9) being interposed between said basal plate (4) and said cover member (2) and, together with at least either of said basal plate (4) and said cover member (2), defining a sheet-shaped space that has said flow channel (5).

6. An analytical chip as defined in claim 5, wherein one or more inner openings (9a) are formed through said intermediate plate (9), and
said cover member (2) is overlaid on said basal plate (4) with said intermediate plate (9) between in such a manner that the inner openings (9a) form said inner flow channels (9a).

7. An analytical chip as defined in claim 6, wherein the surface of said intermediate plate (9) on the side opposite to said basal plate (4) is made from a material having a lower affinity for a fluid containing the specific substance than that of at least either of the wall surface of the inner openings (9a) in said intermediate plate (9) and the surface of said basal plate (4) on the side facing said flow channel (5).

8. A method of making an analytical chip, wherein a specific substance (61) is placed on an analytical chip as defined in claim 7 to thereby make an analytical chip with a fixed specific substance (61), comprising the steps of:
 fixing the intermediate plate (9) on the basal plate (4);
 dropping a fluid containing the specific substance on the basal plate (4) through the inner openings (9a) of the intermediate plate (9) to thereby fix the specific substance (61) on the basal plate (4) as spots; and
 fixing the cover member (2) on the intermediate plate (9).

9. An analytical chip as defined in claim 4, further comprising:
 a basal plate (4); and
 a cover member (2) being disposed so as to face said basal plate (4) and, together with said basal plate (4), defining a sheet-shaped space that has said flow channel (5).

10. An analytical chip as defined in claim 9, wherein said cover member (2) is overlaid on said basal plate (4), and
said inner flow channels (4a) are formed on at least either of the confronting surfaces of said basal plate (4) and said cover member (2).

11. An analytical chip as defined in claim 4, wherein each of said inner flow channels (10a) has a contraction part (10c) on the downstream end, in which part each said inner flow channel (10a) contracts gradually.

12. An analytical chip as defined in claim 4, wherein said inner flow channels (10a) extend from said injection port (11) to said drain port (12).

13. An analytical chip as defined in claim 4, wherein
said partition members (9b) are in the form of partition walls (9b),
said inner flow channels (9a) are slit-form flow channels (9a) divided from each other by said partition walls (9b) around a middle part of said flow channel (5) along a flow direction, and
said analytical chip further comprises a flow-channel confluence part (81, 82) disposed at each of the upstream and downstream ends of said flow channel (5) along the flow direction, in which part the fluid sample (Fs) flows unitedly.

14. An analytical chip as defined in claim 13, wherein
the flow-channel confluence part (81) at the upstream end is formed in such a manner as to become gradually broad from said injection port (21) toward the middle part, and
the flow-channel confluence part (82) at the downstream end is formed in such a manner as to become gradually narrow from the middle part toward said drain port (22).

15. An analytical chip as defined in claim 14, wherein the flow-channel confluence part (21, 22, 43, 44) at each of the upstream and downstream ends is formed on either of said basal plate (4) and said cover member (2).

16. An analytical chip as defined in claim 13, wherein each of said slit-form flow channels (9a) has a cross sectional area of 5 mm$^2$ or smaller.

17. An analytical chip as defined in claim 16, wherein the cross section of each said slit-form flow channel has an aspect ratio of between 0.005 and 100.

18. An analytical chip as defined in claim 4, wherein the specific substance (61) is fixed as a plurality of spots, which are arranged with regular intervals, in such a manner as to face said inner flow channels (9a).

19. An analytical chip as defined in claim 1, wherein said projection member (9b) is in the form of a prop member (9b) interposed between the confronting interior surfaces of said flow channel (5).

20. An analytical chip as defined in claim 19, further comprising:
a basal plate (4);
a cover member (2); and
at least one intermediate plate (8, 9) being interposed between said basal plate (4) and said cover member (2) and, together with at least either of said basal plate (4) and said cover member (2), defining a sheet-shaped space that has said flow channel (5);
wherein, in said flow channel (5) of the sheet-shaped space, said prop member (9b) is interposed between the confronting surfaces of said intermediate plate (8) and at least either of said basal plate (4) and said cover member (2).

21. An analytical chip as defined in claim 20, wherein
the sheet-shaped space is defined by the floor surface, the ceiling surface, the left-side surface, the right-side surface, the upstream-end surface, and the downstream-end surface of said flow channel (5), and
said prop member (9b) is interposed at least either of between the left-side and right-side surfaces and between the upstream-end and downstream-end surfaces.

22. An analytical chip as defined in claim 19, wherein said prop member (9b) adjoins directly each of the confronting surfaces.

23. An analytical chip as defined in claim 19, wherein
a part of said prop member (10b) adjoins directly one of the confronting surfaces, and
the opposite end of said prop member (10b) is joined by a fluid (Fs) with the other of the confronting surfaces when the fluid (Fs) is made to flow through said flow channel (5).

24. An analytical chip as defined in claim 23, wherein an adhesion-reducing layer (10t) is formed on the surface of said prop member (10b).

25. An analytical chip as defined in claim 19, further comprising:
a basal plate (4); and
a cover member (2) being disposed so as to face said basal plate (4) and, together with said basal plate (4), defining a sheet-shaped space that has said flow channel (5);
wherein, in said flow channel (5) of the sheet-shaped space, said prop member (4b) is interposed between the confronting surfaces of said basal plate (4) and said cover member (2).

26. An analytical chip as defined in claim 1, wherein said flow channel (5) has a first affinity part (5y) and a second affinity part (5x), whose affinity for the fluid sample (Fs) is lower than that of the first affinity part (5y).

27. An analytical chip as defined in claim 26, wherein the specific substance (61) is fixed to a part of the surface of said flow channel (5), and
both of the first affinity part (5y) and the second affinity part (5x) are disposed upstream, along the flow direction, of the part to which the specific substance (61) is fixed.

28. An analytical chip as defined in claim 26, wherein each of the first affinity part (5y) and the second affinity part (5x) is in a belt shape that spreads along a line crossing the flow direction of said flow channel (5).

29. An analytical chip as defined in claim 26, wherein more than one first affinity part (5y) and more than one second affinity part (5x) are provided and arranged alternately.

30. An analytical chip as defined in claim 26, wherein the first affinity part (5y) is a hydrophilic part, and the second affinity part (5x) is a hydrophobic part.

31. An analytical chip as defined in claim 26, wherein the first affinity part (5y) is a rough-surfaced part, and the second affinity part (5x) is a smooth-surfaced part.

32. An analytical chip as defined in claim 1, wherein
said flow channel (5) has an area to which the specific substance (61) is fixed, and
said area has
a diffraction grating (42) that can generate an evanescent wave upon light irradiation, and
a metal layer (41) along which a surface plasmon wave can be induced.

33. An analytical chip as defined in claim 1, wherein said analytical chip is made from a material having a Young's modulus that is not lower than 60GPa and not higher than 1000 GPa.

34. An analytical chip as defined in claim 25, wherein
the sheet-shaped space is defined by the floor surface, the ceiling surface, the left-side surface, the right-side surface, the upstream-end surface, and the downstream-end surface of said flow channel (5), and
said prop member (9b) is interposed at least either of between the left-side and right-side surfaces and between the upstream-end and downstream-end surfaces.

* * * * *